US008318757B2

United States Patent
Mita et al.

(10) Patent No.: US 8,318,757 B2
(45) Date of Patent: *Nov. 27, 2012

(54) SUBSTITUTED ISOXAZOLINE COMPOUND AND PEST CONTROL AGENT

(75) Inventors: Takeshi Mita, Funabashi (JP); Kazushige Maeda, Funabashi (JP); Youko Yamada, Funabashi (JP); Eitatsu Ikeda, Funabashi (JP); Ken-ichi Toyama, Funabashi (JP); Mitsuaki Komoda, Minami Saitama-gun (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 213 days.

This patent is subject to a terminal disclaimer.

(21) Appl. No.: 12/677,197

(22) PCT Filed: Sep. 10, 2008

(86) PCT No.: PCT/JP2008/066345
§ 371 (c)(1),
(2), (4) Date: Mar. 9, 2010

(87) PCT Pub. No.: WO2009/035004
PCT Pub. Date: Mar. 19, 2009

(65) Prior Publication Data
US 2011/0009438 A1 Jan. 13, 2011

(30) Foreign Application Priority Data

Sep. 10, 2007 (JP) ................................. 2007-234527
Dec. 19, 2007 (JP) ................................. 2007-327111

(51) Int. Cl.
*A61K 31/42* (2006.01)
*A61K 31/506* (2006.01)
*C07D 413/12* (2006.01)
*A01N 43/54* (2006.01)
*A01N 43/80* (2006.01)

(52) U.S. Cl. ......... 514/274; 514/378; 544/316; 548/240
(58) Field of Classification Search .................. 514/274, 514/378; 544/316; 548/240
See application file for complete search history.

(56) References Cited

U.S. PATENT DOCUMENTS 7,662,972 B2 * 2/2010 Mita et al. ..................... 548/240
8,022,089 B2 * 9/2011 Mita et al. ..................... 514/378

FOREIGN PATENT DOCUMENTS

| WO | WO 97/48395 A1 | 12/1997 |
| WO | WO 2005/085216 A1 | 9/2005 |
| WO | WO 2007/026965 A1 | 3/2007 |
| WO | WO 2007/070606 A2 | 6/2007 |
| WO | WO 2007/105814 A1 | 9/2007 |
| WO | WO 2008/122375 A2 | 10/2008 |

OTHER PUBLICATIONS

Extended European Search Report issued in European Application No. 08830131.2 on Mar. 30, 2011.
International Search Report issued in PCT/P2008/066345, on Oct. 7, 2008 (with translation).

* cited by examiner

*Primary Examiner* — Sabiha Qazi
(74) *Attorney, Agent, or Firm* — Oliff & Berridge, PLC

(57) ABSTRACT

There is provided a novel pest control agent, particularly an insecticide or miticide. A substituted isoxazoline compound of General Formula (1):

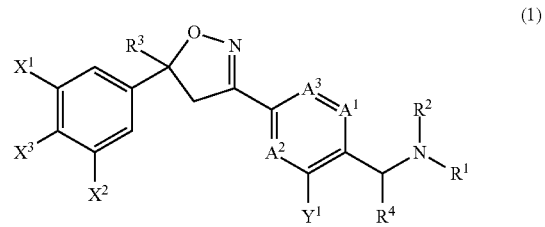

where $A^1$, $A^2$ and $A^3$ independently are CH or N, etc., $X^1$, $X^2$ and $X^3$ are independently are H, a halogen atom, etc., $Y^1$ is H, etc., $R^1$ is —C(O)$R^{1a}$, —C(S)$R^{1a}$, $R^{1a}$ is —C($R^9$)($R^{9a}$)—S(O)$_r R^{10}$, —C($R^9$)($R^{9a}$)—S(O)$_t$($R^{10}$)=N$R^{11}$, etc., $R^2$ is H, etc., $R^3$ is $CF_3$, $CClF_2$, etc., $R^4$ is H, etc., $R^9$ is H, etc., $R^{9a}$ is H, etc., $R^{10}$ is $C_{1-2}$ alkyl, etc., $R^{11}$ is H, etc., r is an integer of 0-2, t is an integer of 0 or 1; and a pest control agent comprising the compound or the salt thereof.

9 Claims, No Drawings

SUBSTITUTED ISOXAZOLINE COMPOUND AND PEST CONTROL AGENT

TECHNICAL FIELD

The present invention relates to a novel substituted isoxazoline compound and a salt thereof, and a pest control agent containing the compound as an active ingredient. The pest control agent in the present invention means insect pest control agents aimed at harmful arthropods in the agricultural and horticultural fields, in the livestock and sanitation fields (internal or external parasites of mammals or birds as domestic animals or pet animals and sanitary insects and discomfort insects at home and at business sites), or the like. In addition, the agricultural chemicals in the present invention mean insecticides and miticides, nematicides, herbicides, fungicides and the like in the agricultural and horticultural fields.

BACKGROUND ART

In the related art, with respect to substituted isoxazoline compounds, a 4-(5-substituted-5-substituted aryl-4,5-dihydroisoxazole-3-yl)benzoic acid amide compound (see Patent Documents 1 and 2) and an N-[4-(5-substituted-5-substituted aryl-4,5-dihydroisoxazole-3-yl)phenylmethyl]carboxamide compound (see Patent Document 3) are known to exhibit pest control activity, particularly insecticidal and miticidal activity. However, nothing is disclosed with respect to a specific N-[4-(5-substituted-5-substituted aryl-4,5-dihydroisoxazole-3-yl)phenylmethyl]sulfur-containing alkylamide compound according to the present invention and the like.

In addition, there is known that a 3-(5-substituted carbamoyl-5-substituted alkyl-4,5-dihydroisoxazole-3-yl)benzylamine derivative has a blood platelet glycoprotein IIb/IIIa fibrinogen receptor complex antagonistic activity, a factor Xa inhibiting activity, or the like and is used as a thrombolytic drug and a curative drug for thromboembolic diseases (for example, see Patent Document 4), or the like. However, nothing is disclosed with respect to a specific N-[4-(5-substituted-5-substituted aryl-4,5-dihydroisoxazole-3-yl)phenylmethyl] sulfur-containing alkylamide compound according to the present invention or the like and further, nothing is known with respect to the usefulness of the compound as a pest control agent.

[Patent Document 1]
International Publication No. WO 2005/085216 pamphlet
[Patent Document 2]
International Publication No. WO 2007/026965 pamphlet
[Patent Document 3]
International Publication No. WO 2007/105814 pamphlet
[Patent Document 4]
International Publication No. WO 97/048395 pamphlet

DISCLOSURE OF THE INVENTION

Problems to be Solved by the Invention

The development of pest control agents for the purpose of controlling various pests such as agricultural and horticultural pests, forest pests or sanitary pests has been progressed and until today, various agents have been practically applied.

However, due to the use of such agents for a long period, recently, pests have acquired drug resistance and there has been increased the number of situations in which the control with related art insecticides and fungicides which have been used becomes difficult. In addition, a part of the related art pest control agents has high toxicity or some of them remain in the environment for a long period to disturb the ecosystem, which is becoming a significant problem. Under such a situation, the development of a novel pest control agent having not only high pest control activity, but also low toxicity and a low residual property is constantly expected.

Means for Solving the Problems

As a result of assiduous research intended to overcome these disadvantages, the inventors of the present invention have found that a novel substituted isoxazoline compound of the following General Formula (1) according to the present invention exhibits excellent pest control activity, particularly excellent insecticidal and miticidal activity and is extremely useful compounds having substantially no adverse effect on non-target organisms such as mammals, fish and beneficial insects to complete the present invention.

That is, the present invention relates to [1] to [9].
[1] A substituted isoxazoline compound of General Formula (1):

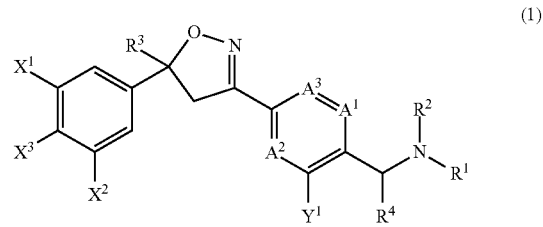

[where $A^1$, $A^2$ and $A^3$ independently are C—$Y^2$ or N,
$X^1$ is a halogen atom, —$SF_5$, $C_{1-6}$ haloalkyl, hydroxy ($C_{1-4}$)haloalkyl, $C_{1-4}$ alkoxy($C_{1-4}$)haloalkyl, $C_{1-6}$ haloalkoxy, $C_{1-4}$ haloalkoxy($C_{1-4}$)haloalkoxy or $C_{1-6}$ haloalkylthio,
$X^2$ is a hydrogen atom, a halogen atom, cyano, nitro, $C_{1-6}$ alkyl, $C_{1-6}$ haloalkyl, —$OR^5$ or —S(O)$_r R^5$,
$X^3$ is a hydrogen atom, a halogen atom, $C_{1-6}$ haloalkoxy or —$NH_2$, or $X^3$ together with $X^1$ or $X^2$ may form —$CF_2OCF_2$—, —$OCF_2O$—, —$CF_2OCF_2O$— or —$OCF_2CF_2O$— to form together with a carbon atom to which each of $X^3$ and $X^1$ or $X^2$ is bonded, a 5- or 6-membered ring, with the proviso that when $X^1$ and $X^2$ are simultaneously a chlorine atom, $X^3$ is a halogen atom, $C_{1-6}$ haloalkoxy or —$NH_2$,
$Y^1$ is a hydrogen atom, a halogen atom, cyano, nitro, $C_{1-6}$ alkyl, $C_{1-6}$ haloalkyl, ($C_{1-4}$)alkyl substituted with $R^6$, $C_{2-6}$ alkenyl, $C_{2-6}$ alkynyl, —$OR^5$, —S(O)$_r R^5$, —$N(R^8)R^7$, —$C(S)NH_2$, D-1 to D-4, D-8 or D-10,
$Y^2$ is a hydrogen atom, a halogen atom or methyl and further, when two $Y^2$s are adjacent to each other, the two $Y^2$s adjacent to each other may form —$CH_2CH_2CH_2$—, —$CH_2CH_2O$—, —$CH_2OCH_2$—, —$OCH_2O$—, —$CH_2CH_2S$—, —$CH_2SCH_2$—, —$SCH_2S$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$OCH_2CH_2S$—, —$SCH_2CH_2S$—, —OCH=N—, —SCH=N—, —CH=CHCH=CH—, —CH=CHCH=N—, —CH=CHN=CH—, —CH=NCH=CH— or —N=CHCH=CH— to form together with carbon atoms to which each of the two $Y^2$s is bonded, a 5-membered ring or a 6-membered ring,
$R^1$ is —C(O)$R^{1a}$ or —C(S)$R^{1a}$,
$R^{1a}$ is —C($R^9$)($R^{9a}$)—S(O)$_r$—$R^{10}$, —C($R^9$)($R^{9a}$)—S(O)$_t$($R^{10}$)=$NR^{11}$ or E-1 to E-6, where E-1 to E-6 individually are a sulfur-containing saturated heterocycle of Structural Formulae:

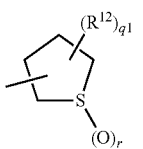
E-1

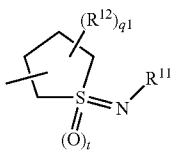
E-2

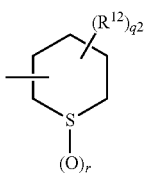
E-3

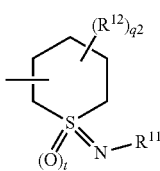
E-4

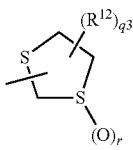
E-5

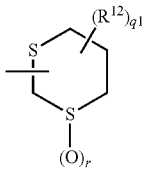
E-6

$R^2$ is a hydrogen atom, cyano, $C_{1-6}$ alkyl, $(C_{1-4})$alkyl optionally substituted with $R^{13}$, $C_{3-6}$ cycloalkyl, $C_{3-6}$ alkenyl, $C_{3-6}$ alkynyl, $C_{1-6}$ alkylcarbonyl, $C_{1-6}$ alkoxycarbonyl or $C_{1-6}$ alkoxy, $R^3$ is $C_{1-6}$ haloalkyl or $C_{3-8}$ halocycloalkyl, $R^4$ is a hydrogen atom, cyano, $C_{1-6}$ alkyl, $C_{1-6}$ haloalkyl, $C_{3-6}$ cycloalkyl, $C_{2-6}$ alkynyl, —C(O)NH$_2$, —C(S)NH$_2$, phenyl, D-6 or D-7, $R^5$ is $C_{1-6}$ alkyl or $C_{1-6}$ haloalkyl, $R^6$ is —OH, $C_{1-4}$ alkoxy, $C_{1-4}$ alkylthio, $C_{1-4}$ alkylsulfinyl or $C_{1-4}$ alkylsulfonyl, $R^7$ is a hydrogen atom, $C_{1-6}$ alkyl, —CHO, $C_{1-6}$ alkylcarbonyl or $C_{1-6}$ alkoxycarbonyl, $R^8$ is a hydrogen atom or $C_{1-6}$ alkyl, $R^9$ is a hydrogen atom, a halogen atom, $C_{1-6}$ alkyl, $C_{1-6}$ alkoxy, $C_{1-6}$ alkylthio, $C_{1-6}$ alkylsulfinyl or $C_{1-6}$ alkylsulfonyl, $R^{9a}$ is a hydrogen atom, a halogen atom or $C_{1-6}$ alkyl, or $R^{9a}$ together with $R^9$ may form an ethylene chain to form together with an atom to which $R^9$ and $R^{9a}$ are bonded, a cyclopropyl ring, $R^{10}$ is cyano, $C_{1-6}$ alkyl, $(C_{1-4})$alkyl optionally substituted with $R^{14}$, $C_{3-6}$ cycloalkyl, $C_{2-6}$ alkenyl, $C_{2-6}$ haloalkenyl, $C_{2-6}$ alkynyl, $C_{2-6}$ haloalkynyl, —C(O)R$^{15}$, —C(O)OR$^{16}$, —C(O)SR$^{16}$, —C(O)N(R$^{17}$)R$^{16}$, —C(S)R$^{15}$, —C(S)OR$^{16}$, —C(S)SR$^{16}$, —C(S)N(R$^{17}$)R$^{16}$, M-1 to M-6, phenyl, D-6, D-7, D-9, D-11 or D-12 to D-14, where M-1 to M-6 individually are a partially saturated heterocycle of Structural Formulae:

M-1

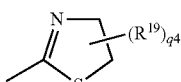
M-2

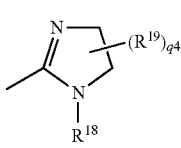
M-3

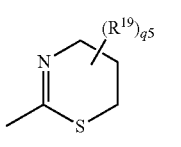
M-4

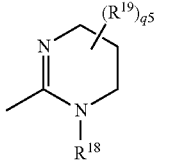
M-5

M-6

$R^{11}$ is a hydrogen atom, cyano, nitro, $C_{1-6}$ alkyl, $C_{1-6}$ haloalkyl, $C_{1-6}$ alkylcarbonyl, $C_{1-6}$ haloalkylcarbonyl, $C_{1-6}$ alkoxycarbonyl, $C_{1-6}$ haloalkoxycarbonyl, $C_{1-6}$ alkylsulfonyl or $C_{1-6}$ haloalkylsulfonyl, $R^{12}$ is a fluorine atom, nitro, —OH, $C_{1-4}$ alkyl or $C_{1-4}$ haloalkyl, $R^{13}$ is a halogen atom, cyano, $C_{3-6}$ cycloalkyl, —OR$^{20}$, —S(O)$_r$R$^{21}$, —N(R$^{23}$)R$^{22}$, —C(O)R$^{24}$, —C(O)OR$^{25}$, —C(O)SR$^{25}$, —C(O)NH$_2$, —C(O)N(R$^{26}$)R$^{25}$, —C(S)OR$^{25}$, —C(S)SR$^{25}$, —C(S)NH$_2$, —C(S)N(R$^{26}$)R$^{25}$ or phenyl, $R^{14}$ is a halogen atom, cyano, $C_{3-6}$ cycloalkyl, —OR$^{20}$, —S(O)$_r$R$^{21}$, —C(O)R$^{24}$, —C(O)OR$^{25}$, —C(O)NH$_2$, —C(O)N(R$^{26}$)R$^{25}$, —C(S)NH$_2$, phenyl or D-11, $R^{15}$ is $C_{1-6}$ alkyl, $C_{1-6}$ haloalkyl, $C_{3-6}$ cycloalkyl, phenyl, phenyl substituted with $(Z)_{p1}$, D-1, D-2, D-4, D-5, D-7, D-8, D-10 or D-11, where D-1 to D-14 individually are an aromatic heterocycle of Structural Formulae:

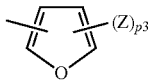
D-1

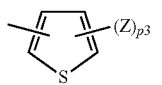
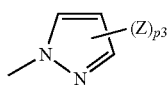
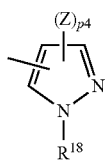
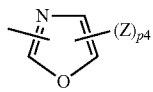
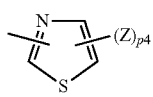
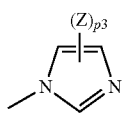
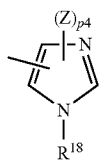
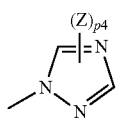
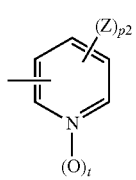
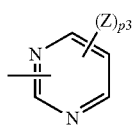
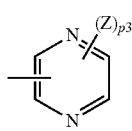

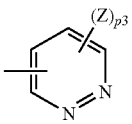

Z is a halogen atom, cyano, nitro, $C_{1-6}$ alkyl, $C_{1-6}$ haloalkyl, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, $C_{1-4}$ haloalkylthio, $C_{1-4}$ haloalkylsulfinyl or $C_{1-4}$ haloalkylsulfonyl, where when p1 and p2 are an integer of 2 or more, more than one such Z may be the same as or different from each other, $R^{16}$ is $C_{1-6}$ alkyl or $C_{1-6}$ haloalkyl, $R^{17}$ is a hydrogen atom or $C_{1-6}$ alkyl, or $R^{17}$ together with $R^{16}$ may form a $C_{3-5}$ alkylene chain to form together with a nitrogen atom to which $R^{16}$ and $R^{17}$ are bonded, a 4- to 6-membered ring, and at this time, the alkylene chain may contain one oxygen atom, sulfur atom or nitrogen atom and may be optionally substituted with a $C_{1-4}$ alkyl group, a —CHO group, a $C_{1-4}$ alkylcarbonyl group, a $C_{1-4}$ alkoxycarbonyl group or an oxo group, $R^{18}$ is a hydrogen atom, $C_{1-4}$ alkyl or $C_{1-4}$ haloalkyl, $R^{19}$ is a fluorine atom, $C_{1-4}$ alkyl or $C_{1-4}$ haloalkyl, $R^{20}$ is $C_{1-4}$ alkyl, $C_{1-4}$ haloalkyl, —C(O)$R^{27}$ or —C(O)O$R^{28}$, $R^{21}$ is $C_{1-4}$ alkyl or $C_{1-4}$ haloalkyl, $R^{22}$ is $C_{1-4}$ alkyl, —C(O)$R^{27}$ or —C(O)O$R^{28}$, $R^{23}$ is a hydrogen atom or $C_{1-4}$ alkyl, $R^{24}$ is $C_{1-4}$ alkyl or $C_{1-4}$ haloalkyl, $R^{25}$ is $C_{1-4}$ alkyl, $C_{1-4}$ haloalkyl or $C_{3-6}$ cycloalkyl, $R^{26}$ is a hydrogen atom or $C_{1-4}$ alkyl, or $R^{26}$ together with $R^{25}$ may form a $C_{3-5}$ alkylene chain to form together with a nitrogen atom to which $R^{25}$ and $R^{26}$ are bonded, a 4- to 6-membered ring, and at this time, the alkylene chain may contain one oxygen atom, sulfur atom or nitrogen atom and may be optionally substituted with a $C_{1-4}$ alkyl group, a —CHO group, a $C_{1-4}$ alkylcarbonyl group, a $C_{1-4}$ alkoxycarbonyl group or an oxo group, $R^{27}$ is $C_{1-4}$ alkyl, $C_{1-4}$ haloalkyl, $C_{3-6}$ cycloalkyl, phenyl, phenyl substituted with $(Z)_{p1}$, D-1, D-2, D-5, D-7 or D-11, $R^{28}$ is $C_{1-4}$ alkyl or $C_{1-4}$ haloalkyl, p1 is an integer of 1 to 3,
p2 is an integer of 0 to 2,
p3 and p4 are an integer of 0 or 1,
q1 is an integer of 0 to 7,
q2 is an integer of 0 to 9,
q3 is an integer of 0 to 5,
q4 and q5 are an integer of 0 to 2,
r is an integer of 0 to 2, and
t is an integer of 0 or 1]; or a salt of the substituted isoxazoline compound,

[2] The substituted isoxazoline compound or the salt of the substituted isoxazoline compound according to [1], in which $A^1$ is CH or N, $A^2$ and $A^3$ are CH, $X^1$ is a halogen atom, —SF$_5$, $C_{1-4}$ haloalkyl, $C_{1-4}$ haloalkoxy or $C_{1-4}$ haloalkylthio, $X^2$ is a hydrogen atom, a halogen atom, cyano, nitro, $C_{1-4}$ alkyl, $C_{1-4}$ haloalkyl, $C_{1-4}$ alkoxy, $C_{1-4}$ haloalkoxy, $C_{1-4}$ alkylthio or $C_{1-4}$ haloalkylthio, $X^3$ is a hydrogen atom, a halogen atom or $C_{1-4}$ haloalkoxy, with the proviso that when $X^1$ and $X^2$ are simultaneously a chlorine atom, $X^3$ is a halogen atom or $C_{1-4}$ haloalkoxy, Y$^1$ is a hydrogen atom, a halogen atom, cyano, nitro, C$_{1-4}$ alkyl, C$_{1-4}$ haloalkyl, C$_{2-4}$ alkynyl, C$_{1-4}$ alkoxy, C$_{1-4}$ haloalkoxy, C$_{1-4}$ alkylthio, C$_{1-4}$ haloalkylthio or —C(S)NH$_2$, R$^{1a}$ is —C(R$^9$)(R$^{9a}$)—S(O)$_r$—R$^{10}$, —C(R$^9$)(R$^{9a}$)—S(O)$_t$(R$^{10}$)=NR$^{11}$, E-1 to E-3 or E-5, R$^2$ is a hydrogen atom, C$_{1-4}$ alkyl, C$_{1-4}$ haloalkyl, (C$_{1-2}$) alkyl substituted with R$^{13}$, C$_{3-4}$ alkenyl, C$_{3-4}$ alkynyl or C$_{1-4}$ alkoxy, R$^3$ is C$_{1-4}$ haloalkyl, R$^4$ is a hydrogen atom, cyano, C$_{1-2}$ alkyl, C$_{1-2}$ haloalkyl, ethynyl, —C(S)NH$_2$ or D-7, R$^9$ is a hydrogen atom, a fluorine atom, C$_{1-4}$ alkyl, C$_{1-4}$ alkoxy, C$_{1-4}$ alkylthio or C$_{1-4}$ alkylsulfinyl, R$^{9a}$ is a hydrogen atom, a fluorine atom or methyl, R$^{10}$ is C$_{1-4}$ alkyl, C$_{1-4}$ haloalkyl, (C$_{1-2}$)alkyl substituted with R$^{14}$, (C$_{1-2}$) haloalkyl substituted with R$^{14}$, C$_{3-4}$ cycloalkyl, C$_{3-4}$ alkenyl, C$_{3-4}$ alkynyl, —C(O)R$^{15}$, —C(O)OR$^{16}$ or —C(O)N(R$^{17}$)R$^{16}$, R$^{11}$ is a hydrogen atom, cyano or C$_{1-4}$ haloalkylcarbonyl, R$^{13}$ is cyano, C$_{3-4}$ cycloalkyl, —OR$^{20}$, C$_{1-2}$ alkylthio, —N(R$^{23}$)R$^{22}$, —C(O)OR$^{25}$, —C(O)NH$_2$, —C(O)N(R$^{26}$)R$^{25}$, —C(S)NH$_2$ or phenyl, R$^{14}$ is cyano or —C(O)N(R$^{26}$)R$^{25}$, R$^{15}$ is C$_{1-4}$ alkyl, D-4, D-8 or D-10, R$^{16}$ is C$_{1-4}$ alkyl, R$^{17}$ is a hydrogen atom or C$_{1-4}$ alkyl, R$^{20}$ is C$_{1-2}$ alkyl or C$_{1-2}$ haloalkyl, R$^{22}$ is C$_{1-2}$ alkylcarbonyl or C$_{1-2}$ alkoxycarbonyl, R$^{23}$ is a hydrogen atom, R$^{25}$ is C$_{1-2}$ alkyl or C$_{1-2}$ haloalkyl, R$^{26}$ is a hydrogen atom or C$_{1-2}$ alkyl, p3 and p4 are 0, and q1, q2 and q3 are 0.

[3] The substituted isoxazoline compound or the salt of the substituted isoxazoline compound according to [2], in which X$^1$ is a halogen atom, —SF$_5$, C$_{1-2}$ haloalkyl, C$_{1-2}$ haloalkoxy or C$_{1-2}$ haloalkylthio, X$^2$ is a hydrogen atom, a halogen atom, cyano, C$_{1-2}$ haloalkyl, C$_{1-2}$ haloalkoxy or C$_{1-2}$ haloalkylthio, X$^3$ is a hydrogen atom, a halogen atom or C$_{1-2}$ haloalkoxy, with the proviso that when X$^1$ and X$^2$ are simultaneously a chlorine atom, X$^3$ is a halogen atom or C$_{1-2}$ haloalkoxy, Y$^1$ is a hydrogen atom, a halogen atom, cyano, nitro, C$_{1-2}$ alkyl, C$_{1-2}$ haloalkyl, C haloalkoxy, C$_{1-2}$ haloalkylthio or —C(S)NH$_2$, R$^{1a}$ is —C(R$^9$)(R$^{9a}$)—S(O)$_r$R$^{10}$, —C(R$^9$)(R$^{9a}$)—S(O)$_t$(R$^{10}$)=NR$^{11}$ or E-1, R$^2$ is a hydrogen atom, C$_{1-2}$ alkyl, methyl substituted with R$^{13}$, allyl or propargyl, R$^3$ is C$_{1-2}$ haloalkyl, R$^4$ is a hydrogen atom, cyano, methyl, ethynyl or —C(S)NH$_2$, R$^9$ is a hydrogen atom, a fluorine atom, C$_{1-2}$ alkyl, C$_{1-2}$ alkylthio or C$_{1-2}$ alkylsulfinyl, R$^{9a}$ is a hydrogen atom or a fluorine atom, R$^{10}$ is C$_{1-2}$ alkyl, C$_{1-2}$ haloalkyl or cyanomethyl, R$^{11}$ is a hydrogen atom or C$_{1-2}$ haloalkylcarbonyl, R$^{13}$ is cyano, cyclopropyl, C$_{1-2}$ alkoxy, —C(O)OR$^{25}$, —C(O)NH$_2$, —C(O)N(R$^{26}$)R$^{25}$ or —C(S)NH$_2$, R$^{25}$ is C$_{1-2}$ alkyl, and R$^{26}$ is a hydrogen atom or methyl.

[4] The substituted isoxazoline compound or the salt of the substituted isoxazoline compound according to [3], in which A$^1$ is CH, X$^1$ is a chlorine atom, a bromine atom or trifluoromethyl, X$^2$ is a fluorine atom, a chlorine atom, a bromine atom, an iodine atom or trifluoromethyl, X$^3$ is a hydrogen atom, a fluorine atom or a chlorine atom, with the proviso that when X$^1$ and X$^2$ are simultaneously a chlorine atom, X$^3$ is a fluorine atom or a chlorine atom, Y$^1$ is a hydrogen atom, a halogen atom, nitro or methyl, R$^{1a}$ is —C(R$^9$)(R$^{9a}$)—S(O)$_r$—R$^{10}$ or E-1, R$^2$ is a hydrogen atom, C$_{1-2}$ alkyl or propargyl, R$^3$ is trifluoromethyl or chlorodifluoromethyl, R$^4$ is a hydrogen atom or methyl, R$^9$ is a hydrogen atom, C$_{1-2}$ alkyl, C$_{1-2}$ alkylthio or C$_{1-2}$ alkylsulfinyl, R$^{9a}$ is a hydrogen atom, and R$^{10}$ is C$_{1-2}$ alkyl or C$_{1-2}$ haloalkyl,

[5] The substituted isoxazoline compound or the salt of the substituted isoxazoline compound according to [4], in which Y$^1$ is a halogen atom, R$^{1a}$ is —CH(R$^9$)—S(O)$_r$—R$^{10}$, R$^2$ is a hydrogen atom, R$^4$ is a hydrogen atom, R$^9$ is a hydrogen atom or C$_{1-2}$ alkylthio, and R$^{10}$ is C$_{1-2}$ alkyl.

[6] A pest control agent containing as active ingredient(s), one or two or more selected from the substituted isoxazoline compounds and the salts of the substituted isoxazoline compounds as described in [1] to [5].

[7] An agricultural chemical containing as active ingredient(s), one or two or more selected from the substituted isoxazoline compounds and the salts of the substituted isoxazoline compounds as described in [1] to [5].

[8] A control agent against internal or external parasites of mammals or birds containing as active ingredient(s), one or two or more selected from the substituted isoxazoline compounds and the salts of the substituted isoxazoline compounds as described in [1] to [5].

[9] An insecticide or a miticide containing as active ingredient(s), one or two or more selected from the substituted isoxazoline compounds and the salts of the substituted isoxazoline compounds as described in [1] to [5].

Effects of the Invention

The compound of the present invention has excellent insecticidal and miticidal activity with respect to a number of agricultural insect pests, spider mites and internal or external parasites of mammals or birds, and also exerts satisfactory control effect on insect pests which have acquired resistance to related art pesticides. Furthermore, the compound has substantially no adverse effect on mammals, fish and beneficial insects, and has a low residual property to have the least effect on the environment.

Accordingly, the present invention can provide a useful novel pest control agent.

BEST MODES FOR CARRYING OUT THE INVENTION

In the compounds included in the present invention, although geometric isomers of an E form and a Z form may exist depending on a substituent type, the present invention includes the E form, the Z form or a mixture containing the E form and the Z form at any ratio. Furthermore, although the compounds included in the present invention include optically active substances due to the presence of one or more asymmetric carbon atom(s), the present invention includes all of the optically active substances or racemates.

Among the compounds included in the present invention, compounds capable of being converted into acid addition salts by a common method may be converted into, for example, salts of hydrohalic acids such as hydrofluoric acid, hydrochloric acid, hydrobromic acid and hydriodic acid; salts of inorganic acids such as nitric acid, sulfuric acid, phosphoric acid, chloric acid and perchloric acid; salts of sulfonic acids such as methanesulfonic acid, ethanesulfonic acid, trifluoromethanesulfonic acid, benzenesulfonic acid and p-toluenesulfonic acid; salts of carboxylic acids such as formic acid, acetic acid, propionic acid, trifluoroacetic acid, fumaric acid, tartaric acid, oxalic acid, maleic acid, malic acid, succinic acid, benzoic acid, mandelic acid, ascorbic acid, lactic acid, gluconic acid and citric acid; or salts of amino acids such as glutamic acid and aspartic acid.

In addition, among the compounds included in the present invention, compounds capable of being converted into metal salts by a common method may be converted into, for example, salts of alkali metals such as lithium, sodium and potassium; salts of alkaline earth metals such as calcium, barium and magnesium; or salts of aluminum.

Next, specific examples of each substituent shown in the present specification are shown below. Here, n-, s- and t- (or tert-) mean normal, iso, secondary and tertiary, respectively, and Ph means phenyl.

Examples of halogen atoms in the compound of the present invention include a fluorine atom, a chlorine atom, a bromine atom and an iodine atom. Here, the expression "halo" in the present specification also represents these halogen atoms.

The expression "$C_{a-b}$ alkyl" in the present specification is a linear or branched $C_{a-b}$ hydrocarbon group. Specific examples of the "$C_{a-b}$ alkyl" include a methyl group, an ethyl group, an n-propyl group, an i-propyl group, an n-butyl group, an i-butyl group, an s-butyl group, a tert-butyl group, an n-pentyl group, a 1,1-dimethylpropyl group and an n-hexyl group, and each of the alkyl groups is selected from the range of the specified number of carbon atoms.

The expression "$C_{a-b}$ haloalkyl" in the present specification is a linear or branched $C_{a-b}$ hydrocarbon group in which a hydrogen atom bonded to a carbon atom is optionally substituted with a halogen atom. At this time, when hydrogen atoms are substituted with two or more halogen atoms, these halogen atoms may be the same as or different from each other. Specific examples of "$C_{a-b}$ haloalkyl" include a fluoromethyl group, a chloromethyl group, a bromomethyl group, an iodomethyl group, a difluoromethyl group, a dichloromethyl group, a trifluoromethyl group, a chlorodifluoromethyl group, a trichloromethyl group, a bromodifluoromethyl group, a 2-fluoroethyl group, a 2-chloroethyl group, a 2-bromoethyl group, a 2,2-difluoroethyl group, a 2,2,2-trifluoroethyl group, a 2-chloro-2,2-difluoroethyl group, a 2,2,2-trichloroethyl group, a 2-bromo-2,2-difluoroethyl group, a 1,1,2,2-tetrafluoroethyl group, a 2-chloro-1,1,2-trifluoroethyl group, a pentafluoroethyl group, a 3,3,3-trifluoropropyl group, a 3-bromo-3,3-difluoropropyl group, a 2,2,3,3,3-pentafluoropropyl group, a 1,1,2,3,3,3-hexafluoropropyl group, a heptafluoropropyl group, a 2,2,2-trifluoro-1-(trifluoromethyl) ethyl group, a 1,2,2,2-tetrafluoro-1-(trifluoromethyl)ethyl group, a 2,2,3,3,4,4,4-heptafluorobutyl group and a nonafluorobutyl group. Each of the haloalkyl groups is selected from the range of the specified number of carbon atoms.

The expression "$C_{a-b}$ cycloalkyl" in the present specification is a cyclic $C_{a-b}$ hydrocarbon group, and the "$C_{a-b}$ cycloalkyl" can form a monocyclic or composite ring structure having a 3-membered ring to a 6-membered ring. Furthermore, each ring may be optionally substituted with an alkyl group within the range of the specified number of carbon atoms. Specific examples of the "$C_{a-b}$ cycloalkyl" include a cyclopropyl group, a 1-methylcyclopropyl group, a 2-methylcyclopropyl group, a 2,2-dimethylcyclopropyl group, a cyclobutyl group, a cyclopentyl group and a cyclohexyl group, and each of the cycloalkyl groups is selected from the range of the specified number of carbon atoms.

The expression "$C_{a-b}$ halocycloalkyl" in the present specification is a cyclic $C_{a-b}$ hydrocarbon group in which a hydrogen atom bonded to a carbon atom is optionally substituted with a halogen atom, and the "$C_{a-b}$ halocycloalkyl" can form a monocyclic or composite ring structure having a 3-membered ring to a 6-membered ring. Furthermore, each ring may be optionally substituted with an alkyl group within the range of the specified number of carbon atoms, and the substitution with a halogen atom may be on the ring structure part, the side chain part or both of them. In addition, when hydrogen atoms are substituted with two or more halogen atoms, these halogen atoms may be the same as or different from each other. Specific examples of the "$C_{a-b}$ halocycloalkyl" include a 2,2-difluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group and a 2,2,3,3-tetrafluorocyclobutyl group, and each of the halocycloalkyl groups is selected from the range of the specified number of carbon atoms, The expression "$C_{a-b}$ alkenyl" in the present specification is a linear or branched $C_{a-b}$ unsaturated hydrocarbon group having one or more double bond(s) in the molecule. Specific examples of the "$C_{a-b}$ alkenyl" include a vinyl group, a 1-propenyl group, a 2-propenyl group, a 1-methylethenyl group, a 2-butenyl group, a 2-methyl-2-propenyl group, a 3-methyl-2-butenyl group and a 1,1-dimethyl-2-propenyl group, and each of the alkenyl groups is selected from the range of the specified number of carbon atoms.

The expression "$C_{a-b}$ haloalkenyl" in the present specification is a linear or branched $C_{a-b}$ unsaturated hydrocarbon group having one or more double bond(s) in the molecule in which a hydrogen atom bonded to a carbon atom is optionally substituted with a halogen atom. At this time, when hydrogen atoms are substituted with two or more halogen atoms, these halogen atoms may be the same as or different from each other. Specific examples of the "$C_{a-b}$ haloalkenyl" include a 2-fluorovinyl group, a 2-chlorovinyl group, a 1,2-dichlorovinyl group, a 2,2-dichlorovinyl group, a 2-fluoro-2-propenyl group, a 2-chloro-2-propenyl group, a 3-chloro-2-propenyl group, a 2-bromo-2-propenyl group, a 3,3-difluoro-2-propenyl group, a 3-chloro-2-propenyl group, a 3,3-dichloro-2-propenyl group, a 2,3,3-trifluoro-2-propenyl group, a 2,3,3-trichloro-2-propenyl group, a 1-(trifluoromethyl)ethenyl group, a 4,4-difluoro-3-butenyl group, a 3,4,4-trifluoro-3-butenyl group and a 3-chloro-4,4,4-trifluoro-2-butenyl group, and each of the haloalkenyl groups is selected from the range of the specified number of carbon atoms.

The expression "$C_{a-b}$ alkynyl" in the present specification is a linear or branched $C_{a-b}$ unsaturated hydrocarbon group having one or more triple bond(s) in the molecule. Specific examples of the "$C_{a-b}$ alkynyl" include an ethynyl group, a 1-propynyl group, a 2-propynyl group, a 1-butynyl group, a 2-butynyl group and a 3-butynyl group, and each of the alkynyl groups is selected from the range of the specified number of carbon atoms.

The expression "$C_{a-b}$ haloalkynyl" in the present specification is a linear or branched $C_{a-b}$ unsaturated hydrocarbon group having one or more triple bond(s) in the molecule in which a hydrogen atom bonded to a carbon atom is optionally substituted with a halogen atom. At this time, when hydrogen atoms are substituted with two or more halogen atoms, these halogen atoms may be the same as or different from each other. Specific examples of the "$C_{a-b}$ haloalkynyl" include a 2-chloroethynyl group, a 2-bromoethynyl group, a 2-iodoethynyl group, a 3-chloro-2-propynyl group, a 3-bromo-2-propynyl group and a 3-iodo-2-propynyl group, and each of the haloalkynyl groups is selected from the range of the specified number of carbon atoms.

The expression "$C_{a-b}$ alkoxy" in the present specification is a $C_{a-b}$ alkyl-O-group in which the alkyl is as defined above. Specific examples of the "$C_{a-b}$ alkoxy" include a methoxy group, an ethoxy group, an n-propyloxy group, an i-propyloxy group, an n-butyloxy group, an i-butyloxy group, an s-butyloxy group and a tert-butyloxy group, and each of the alkoxy groups is selected from the range of the specified number of carbon atoms.

The expression "$C_{a-b}$ haloalkoxy" in the present specification is a $C_{a-b}$ haloalkyl-O— group in which the alkyl is as defined above. Specific examples of the "$C_{a-b}$ haloalkoxy" include a difluoromethoxy group, a trifluoromethoxy group, a chlorodifluoromethoxy group, a bromodifluoromethoxy group, a 2-fluoroethoxy group, a 2-chloroethoxy group, a 2,2,2-trifluoroethoxy group, a 1,1,2,2-tetrafluoroethoxy group, a 2-chloro-1,1,2-trifluoroethoxy group and a 1,1,2,3,3,3-hexafluoropropyloxy group, and each of the haloalkoxy groups is selected from the range of the specified number of carbon atoms.

The expression "$C_{a-b}$ alkylthio" in the present specification is a $C_{a-b}$ alkyl-S-group in which the alkyl is as defined above. Specific examples of the "$C_{a-b}$ alkylthio" include a methylthio group, an ethylthio group, an n-propylthio group, an i-propylthio group, an n-butylthio group, an i-butylthio group, an s-butylthio group and a tert-butylthio group, and each of the alkylthio groups is selected from the range of the specified number of carbon atoms.

The expression "$C_{a-b}$ haloalkylthio" in the present specification is a $C_{a-b}$ haloalkyl-S— group in which the alkyl is as defined above. Specific examples of the "$C_{a-b}$ haloalkylthio" include a difluoromethylthio group, a trifluoromethylthio group, a chlorodifluoromethylthio group, a bromodifluoromethylthio group, a 2,2,2-trifluoroethylthio group, a 1,1,2,2-tetrafluoroethylthio group, a 2-chloro-1,1,2-trifluoroethylthio group, a pentafluoroethylthio group, a 1,1,2,3,3,3-hexafluoropropylthio group, a heptafluoropropylthio group, a 1,2,2,2-tetrafluoro-1-(trifluoromethyl)ethylthio group and a nonafluorobutylthio group, and each of the haloalkylthio groups is selected from the range of the specified number of carbon atoms.

The expression "$C_{a-b}$ alkylsulfinyl" in the present specification is a $C_{a-b}$ alkyl-S(O)— group in which the alkyl is as defined above. Specific examples of the "$C_{a-b}$ alkylsulfinyl" include a methylsulfinyl group, an ethylsulfinyl group, an n-propylsulfinyl group, an i-propylsulfinyl group, an n-butylsulfinyl group, an i-butylsulfinyl group, an s-butylsulfinyl group and a tert-butylsulfinyl group, and each of the alkylsulfinyl groups is selected from the range of the specified number of carbon atoms.

The expression "$C_{a-b}$ haloalkylsulfinyl" in the present specification is a $C_{a-b}$ haloalkyl-S(O)— group in which the alkyl is as defined above. Specific examples of the "$C_{a-b}$ haloalkylsulfinyl" include a difluoromethylsulfinyl group, a trifluoromethylsulfinyl group, a chlorodifluoromethylsulfinyl group, a bromodifluoromethylsulfinyl group, a 2,2,2-trifluoroethylsulfinyl group, a 1,2,2,2-tetrafluoro-1-(trifluoromethyl)ethylsulfinyl group and a nonafluorobutylsulfinyl group, and each of the haloalkylsulfinyl groups is selected from the range of the specified number of carbon atoms.

The expression "$C_{a-b}$ alkylsulfonyl" in the present specification is a $C_{a-b}$ alkyl-S(O)$_2$-group in which the alkyl is as defined above. Specific examples of the "$C_{a-b}$ alkylsulfonyl" include a methylsulfonyl group, an ethylsulfonyl group, an n-propylsulfonyl group, an i-propylsulfonyl group, an n-butylsulfonyl group, an i-butylsulfonyl group, an s-butylsulfonyl group and a tert-butylsulfonyl group, and each of the alkylsulfonyl groups is selected from the range of the specified number of carbon atoms.

The expression "$C_{a-b}$ haloalkylsulfonyl" in the present specification is a $C_{a-b}$ haloalkyl-S(O)$_2$— group in which the alkyl is as defined above. Specific examples of the "$C_{a-b}$ haloalkylsulfonyl" include a difluoromethylsulfonyl group, a trifluoromethylsulfonyl group, a chlorodifluoromethylsulfonyl group, a bromodifluoromethylsulfonyl group, a 2,2,2-trifluoroethylsulfonyl group, a 1,1,2,2-tetrafluoroethylsulfonyl group and a 2-chloro-1,1,2-trifluoroethylsulfonyl group, and each of the haloalkylsulfonyl groups is selected from the range of the specified number of carbon atoms.

The expression "di($C_{a-b}$ alkyl)amino" in the present specification is an amino group in which both of the hydrogen atoms are substituted with $C_{a-b}$ alkyl groups as defined above and the alkyl groups may be the same as or different from each other.

Specific examples of the "di($C_{a-b}$ alkyl)amino" include a dimethylamino group, a diethylamino group, a di(n-propyl)amino group and a di(n-butyl)amino group, and each of the dialkylamino groups is selected from the range of the specified number of carbon atoms.

The expression "$C_{a-b}$ alkylcarbonyl" in the present specification is a $C_{a-b}$ alkyl-C(O)— group in which the alkyl is as defined above. Specific examples of the "$C_{a-b}$ alkylcarbonyl" include an acetyl group, a propionyl group, a butyryl group, an isobutyryl group, a valeryl group, an isovaleryl group, a 2-methylbutanoyl group and a pivaloyl group, and each of the alkylcarbonyl groups is selected from the range of the specified number of carbon atoms.

The expression "$C_{a-b}$ haloalkylcarbonyl" in the present specification is a $C_{a-b}$ haloalkyl-C(O)— group in which the alkyl is as defined above. Specific examples of the "$C_{a-b}$ haloalkylcarbonyl" include a fluoroacetyl group, a chloroacetyl group, a difluoroacetyl group, a dichloroacetyl group, a trifluoroacetyl group, a chlorodifluoroacetyl group, a bromodifluoroacetyl group, a trichloroacetyl group, a pentafluoropropionyl group, a heptafluorobutanoyl group and a 3-chloro-2,2-dimethylpropanoyl group, and each of the haloalkylcarbonyl groups is selected from the range of the specified number of carbon atoms.

The expression "$C_{a-b}$ alkoxycarbonyl" in the present specification is a $C_{a-b}$ alkyl-O—C(O)— group in which the alkyl is as defined above. Specific examples of the "$C_{a-b}$ alkoxycarbonyl" include a methoxycarbonyl group, an ethoxycarbonyl group, an n-propyloxycarbonyl group, an i-propyloxycarbonyl group, an n-butoxycarbonyl group, an i-butoxycarbonyl group and a tert-butoxycarbonyl group, and each of the alkoxycarbonyl groups is selected from the range of the specified number of carbon atoms.

The expression "$C_{a-b}$ haloalkoxycarbonyl" in the present specification is a $C_{a-b}$ haloalkyl-O—C(O)— group in which the alkyl is as defined above. Specific examples of the "$C_{a-b}$ haloalkoxycarbonyl" include a chloromethoxycarbonyl group, a 2-chloroethoxycarbonyl group, a 2,2-difluoroethoxycarbonyl group, a 2,2,2-trifluoroethoxycarbonyl group and a 2,2,2-trichloroethoxycarbonyl group, and each of the haloalkoxycarbonyl groups is selected from the range of the specified number of carbon atoms.

The expression "$C_{a-b}$ alkylcarbonyloxy" in the present specification is a $C_{a-b}$ alkylcarbonyl-O— group as defined above. Specific examples of the "$C_{a-b}$ alkylcarbonyloxy"

include a pivaloyloxy group, and each of the alkylcarbonyloxy groups is selected from the range of the specified number of carbon atoms.

The expression "$C_{a-b}$ alkoxycarbonyloxy" in the present specification is a $C_{a-b}$ alkoxycarbonyl-O— group in which the alkyl is as defined above. Specific examples of the "$C_{a-b}$ alkoxycarbonyloxy" include an isobutyloxycarbonyloxy group, and each of the alkoxycarbonyloxy groups is selected from the range of the specified number of carbon atoms.

Each expression "($C_{a-b}$)alkyl substituted with $R^6$", "($C_{a-b}$)alkyl substituted with $R^{13}$", "($C_{a-b}$)alkyl substituted with $R^{14}$" or the like in the present specification is a $C_{a-b}$ alkyl group as defined above in which a hydrogen atom bonded to a carbon atom is substituted with any of $R^6$, $R^{13}$ or $R^{14}$, and each of the alkyl groups is selected from the range of the specified number of carbon atoms.

The expression "($C_{a-b}$)alkyl optionally substituted with $R^{13}$", "($C_{a-b}$)alkyl optionally substituted with $R^{14}$" or the like in the present specification is a $C_{a-b}$ alkyl group as defined above in which a hydrogen atom bonded to a carbon atom is optionally substituted with any of $R^{13}$ or $R^{14}$, and each of the alkyl groups is selected from the range of the specified number of carbon atoms. At this time, when the number of substituents $R^{13}$ or $R^{14}$ on each ($C_{a-b}$)alkyl group is two or more, $R^{13}$s or $R^{14}$s may be the same as or different from each other.

Each expression "hydroxy($C_{d-e}$)haloalkyl" or "$C_{a-b}$ alkoxy ($C_{d-e}$)haloalkyl" in the present specification is a $C_{d-e}$ haloalkyl group as defined above in which a hydrogen atom or a halogen atom bonded to a carbon atom is substituted with any of a hydroxy group or a $C_{a-b}$ alkoxy group as defined above, and each of the haloalkyl groups is selected from the range of the specified number of carbon atoms.

The expression "($C_{a-b}$)haloalkyl substituted with $R^{14}$" in the present specification is a $C_{a-b}$ haloalkyl group as defined above in which a hydrogen atom or a halogen atom bonded to a carbon atom is substituted with any of $R^{14}$, and each of the haloalkyl groups is selected from the range of the specified number of carbon atoms.

The expression "$C_{a-b}$ haloalkoxy($C_{d-e}$)haloalkoxy" in the present specification is a $C_{d-e}$ haloalkoxy group as defined above in which a hydrogen atom or a halogen atom bonded to a carbon atom is substituted with any of $C_{a-b}$ haloalkoxy group as defined above, and each of the haloalkoxy groups is selected from the range of the specified number of carbon atoms.

Specific examples of the expressions in the present specification of ($R^{17}$ together with $R^{16}$ may form a $C_{3-5}$ alkylene chain to form together with a nitrogen atom to which $R^{16}$ and $R^{17}$ are bonded, a 4- to 6-membered ring, and at this time, the alkylene chain may contain one oxygen atom, sulfur atom or nitrogen atom), ($R^{26}$ together with $R^{25}$ may form a $C_{3-5}$ alkylene chain to form together with a nitrogen atom to which $R^{25}$ and $R^{26}$ are bonded, a 4- to 6-membered ring, and at this time, the alkylene chain may contain one oxygen atom, sulfur atom or nitrogen atom) and the like include azetidine, pyrrolidine, oxazolidine, thiazolidine, imidazolidine, piperidine, morpholine, thiomorpholine, thiomorpholine-1-oxide, thiomorpholine-1,1-dioxide, piperazine, homopiperidine and heptamethyleneimine. Each of the rings is selected from the range of the specified number of carbon atoms.

In the compounds included in the present invention, examples of the preferred combination of atoms of $A^1$, $A^2$ and $A^3$ include the following groups.

That is, A-I: $A^1$, $A^2$ and $A^3$ are CH.
A-II: $A^1$ is N, and $A^2$ and $A^3$ are CH.
A-III: $A^2$ is N, and $A^1$ and $A^3$ are CH.
A-IV: $A^3$ is N, and $A^1$ and $A^2$ are CH.

Among them, more preferred combinations of atoms of $A^1$, $A^2$ and $A^3$ are A-I and A-II, and specifically preferred is A-I.

In the compounds included in the present invention, examples of the preferred combination range of the substituents of $X^1$, $X^2$ and $X^3$ include the following groups.

That is, X-I: $X^1$ is a chlorine atom, $X^2$ is a chlorine atom, and $X^3$ is a fluorine atom or a chlorine atom.

X-II: $X^1$ is a bromine atom, $X^2$ is a chlorine atom or a bromine atom, and $X^3$ is a hydrogen atom or a fluorine atom.

X-III: $X^1$ is trifluoromethyl, $X^2$ is a fluorine atom, a chlorine atom, a bromine atom, an iodine atom or trifluoromethyl, and $X^3$ is a hydrogen atom, a fluorine atom or a chlorine atom.

X-IV: $X^1$ is a halogen atom, —$SF_5$, $C_{1-2}$ haloalkyl, $C_{1-2}$ haloalkoxy and $C_{1-2}$ haloalkylthio, and $X^2$ and $X^3$ are hydrogen atoms.

X-V: $X^1$ is a halogen atom and $C_{1-2}$ haloalkyl, $X^2$ is a hydrogen atom, and $X^3$ is a halogen atom.

X-VI: $X^1$ is a halogen atom and $C_{1-2}$ haloalkyl, $X^2$ is a fluorine atom, a bromine atom, an iodine atom, cyano, $C_{1-2}$ haloalkyl, $C_{1-2}$ haloalkoxy or $C_{1-2}$ haloalkylthio, and $X^3$ is a hydrogen atom.

X-VII: $X^1$ and $X^2$ are halogen atoms and $C_{1-2}$ haloalkyls, and $X^3$ is a halogen atom or $C_{1-2}$ haloalkoxy.

X-VIII: $X^1$ is $C_{1-4}$ haloalkyl, $C_{1-4}$ haloalkoxy and $C_{1-4}$ haloalkylthio, and $X^2$ and $X^3$ are hydrogen atoms.

X-IX: $X^1$ is a halogen atom and $C_{1-4}$ haloalkyl, $X^2$ is a fluorine atom, a bromine atom, an iodine atom, cyano, nitro, $C_{1-4}$ alkyl, $C_{1-4}$ haloalkyl, $C_{1-4}$ alkoxy, $C_{1-4}$ haloalkoxy, $C_{1-4}$ alkylthio or $C_{1-4}$ haloalkylthio, and $X^3$ is a hydrogen atom.

X-X: $X^1$ and $X^2$ are halogen atoms and $C_{1-4}$ haloalkyls, and $X^3$ is a halogen atom or $C_{1-4}$ haloalkoxy.

In the compounds included in the present invention, examples of the preferred range of the substituent of $Y^1$ include the following groups.

That is, $Y^1$-I: a hydrogen atom.
$Y^1$-II: a halogen atom.
$Y^1$-III: a halogen atom, nitro and methyl.
$Y^1$-IV: a halogen atom, cyano, nitro, $C_{1-2}$ alkyl, $C_{1-2}$ haloalkyl, $C_{1-2}$ haloalkoxy, $C_{1-2}$ haloalkylthio and —C(S)NH$_2$.
$Y^1$-V: a halogen atom, cyano, nitro, $C_{1-4}$ alkyl, $C_{1-4}$ haloalkyl, $C_{2-4}$ alkynyl, $C_{1-4}$ alkoxy, $C_{1-4}$ haloalkoxy, $C_{1-4}$ alkylthio, $C_{1-4}$ haloalkylthio and —C(S)NH$_2$.

In the compounds included in the present invention, examples of the preferred range of the substituent of $R^{1a}$ include the following groups.

That is, $R^{1a}$-I: —CH($R^9$)—S(O)$_r$—$R^{10}$ (where $R^9$ is a hydrogen atom or $C_{1-2}$ alkylthio, $R^{10}$ is $C_{1-2}$ alkyl, and r is an integer of 0 to 2).

$R^{1a}$-II: —C($R^9$)($R^{9a}$)—S(O)$_r$—$R^{10}$ (where $R^9$ is a hydrogen atom, $C_{1-2}$ alkyl, $C_{1-2}$ alkylthio or $C_{1-2}$ alkylsulfinyl, $R^{9a}$ is a hydrogen atom, $R^{10}$ is $C_{1-2}$ alkyl or $C_{1-2}$ haloalkyl, and r is an integer of 0 to 2) and E-1 (where q1 is 0, and r is an integer of 0 to 2).

$R^{1a}$-III: —C($R^9$)($R^{9a}$)—S(O)$_r$—$R^{10}$ (where $R^9$ is a hydrogen atom, a fluorine atom, $C_{1-2}$ alkyl, $C_{1-2}$ alkylthio or $C_{1-2}$ alkylsulfinyl, $R^{9a}$ is a hydrogen atom or a fluorine atom, $R^{10}$ is $C_{1-2}$ alkyl, $C_{1-2}$ haloalkyl or cyanomethyl, and r is an integer of 0 to 2).

$R^{1a}$-IV: —C($R^9$)($R^{9a}$)—S(O)$_r$($R^{10}$)=$NR^{11}$ (where $R^9$ is a hydrogen atom or $C_{1-2}$ alkyl, $R^{9a}$ is a hydrogen atom, $R^{10}$ is $C_{1-2}$ alkyl or $C_{1-2}$ haloalkyl, $R^{11}$ is a hydrogen atom or $C_{1-2}$ haloalkylcarbonyl, and t is an integer of 0 or 1).

$R^{1a}$-V: E-1 (where q1 is 0, and r is an integer of 0 to 2).

$R^{1a}$-VI: —C($R^9$)($R^{9a}$)—S(O)$_r$—$R^{10}$ (where $R^9$ is a hydrogen atom, a fluorine atom, $C_{1-4}$ alkyl, $C_{1-4}$ alkoxy, $C_{1-4}$ alkylthio or $C_{1-4}$ alkylsulfinyl, $R^{9a}$ is a hydrogen atom, a fluorine atom or methyl, $R^{10}$ is $C_{1-4}$ alkyl, $C_{1-4}$ haloalkyl, $(C_{1-2})$alkyl substituted with $R^{14}$, $(C_{1-2})$haloalkyl substituted with $R^{14}$, $C_{3-4}$ cycloalkyl, $C_{3-4}$ alkenyl, $C_{3-4}$ alkynyl, —C(O)$R^{15}$, —C(O)O$R^{16}$ or —C(O)N($R^{17}$)$R^{16}$, $R^{14}$ is cyano or —C(O)N($R^{26}$)$R^{25}$, $R^{15}$ is $C_{1-4}$ alkyl, D-4, D-8 or D-10, $R^{16}$ is $C_{1-4}$ alkyl, $R^{17}$ is a hydrogen atom or $C_{1-4}$ alkyl, $R^{25}$ is $C_{1-2}$ alkyl or $C_{1-2}$ haloalkyl, $R^{26}$ is a hydrogen atom or $C_{1-2}$ alkyl, p3 and p4 are 0, and r is an integer of 0 to 2).

$R^{1a}$-VII: —C($R^9$)($R^{9a}$)—S(O)$_t$($R^{10}$)=N$R^{11}$ (where $R^9$ is a hydrogen atom, a fluorine atom or $C_{1-2}$ alkyl, $R^{9a}$ is a hydrogen atom or a fluorine atom, $R^{10}$ is $C_{1-2}$ alkyl, $C_{1-2}$ haloalkyl or cyanomethyl, $R^{11}$ is a hydrogen atom, cyano or $C_{1-4}$ haloalkylcarbonyl, and t is an integer of 0 or 1), E-2 (where $R^{11}$ is a hydrogen atom or $C_{1-2}$ haloalkylcarbonyl, q1 is 0, and t is an integer of 0 or 1).

$R^{1a}$-VIII: E-1 (where q1 is 0, and r is an integer of 0 to 2), E-3 (where q2 is 0, and r is an integer of 0 to 2) and E-5 (where q3 is 0).

In the compounds included in the present invention, examples of the preferred range of the substituent of $R^2$ include the following groups.

That is, $R^2$-I: a hydrogen atom.

$R^2$-II: $C_{1-2}$ alkyl and propargyl.

$R^2$-III: $C_{1-2}$ alkyl, cyclopropylmethyl, allyl and propargyl.

$R^2$-IV: $C_{1-2}$ alkoxymethyl.

$R^2$-V: methyl substituted with $R^{13}$ (where $R^{13}$ is cyano, —C(O)O$R^{25}$, —C(O)NH$_2$, —C(O)N($R^{26}$)$R^{25}$ or —C(S)NH$_2$, $R^{25}$ is $C_{1-2}$ alkyl, and $R^{26}$ is a hydrogen atom or a methyl).

$R^2$-VI: $C_{1-4}$ alkyl, $C_{1-4}$ haloalkyl, $(C_{1-2})$alkyl substituted with $R^{13}$ (where $R^{13}$ is $C_{3-4}$ cycloalkyl or phenyl), $C_{3-4}$ alkenyl, $C_{3-4}$ alkynyl and $C_{1-4}$ alkoxy.

$R^2$-VII: $(C_{1-2})$alkyl substituted with $R^{13}$ (where $R^{13}$ is —O$R^{20}$ or $C_{1-2}$ alkylthio, and $R^{20}$ is $C_{1-2}$ alkyl or $C_{1-2}$ haloalkyl).

$R^2$-VIII: $(C_{1-2})$alkyl substituted with $R^{13}$ (where $R^{13}$ is —N($R^{23}$)$R^{22}$, $R^{22}$ is $C_{1-2}$ alkylcarbonyl or $C_{1-2}$ alkoxycarbonyl, and $R^{23}$ is a hydrogen atom).

$R^2$-IX: $(C_{1-2})$alkyl substituted with $R^{13}$ (where $R^{13}$ is cyano, —C(O)O$R^{25}$, —C(O)NH$_2$, —C(O)N($R^{26}$)$R^{25}$ or —C(S)NH$_2$, $R^{25}$ is $C_{1-2}$ alkyl or $C_{1-2}$ haloalkyl, and $R^{26}$ is a hydrogen atom or $C_{1-2}$ alkyl).

Among them, a more preferred range of the substituent of $R^2$ is $R^2$-I, $R^2$-II, $R^2$-III, $R^2$-IV and $R^2$-V, and specifically preferred is $R^2$-I and $R^2$-II.

In the compounds included in the present invention, examples of the preferred range of the substituent of $R^3$ include the following groups.

That is, $R^3$-I: trifluoromethyl and chlorodifluoromethyl.

$R^3$-II: difluoromethyl, trifluoromethyl, chlorodifluoromethyl, bromodifluoromethyl and 1,1,2,2-tetrafluoroethyl.

$R^3$-III: $C_{1-2}$ alkyl optionally substituted with two or more of any halogen atoms.

$R^3$-IV: $C_{1-4}$ haloalkyl.

Among them, a more preferred range of the substituent of $R^3$ is $R^3$-I and $R^3$-II, and specifically preferred is $R^3$-I.

In the compounds included in the present invention, examples of the preferred range of the substituent of $R^4$ include the following groups.

That is, $R^4$-I: a hydrogen atom.

$R^4$-II: methyl.

$R^4$-III: cyano, methyl, ethynyl and —C(S)NH$_2$.

$R^4$-IV: cyano, $C_{1-2}$ alkyl, $C_{1-2}$ haloalkyl, ethynyl, —C(S)NH$_2$ and D-7 (where p4 is 0).

These groups representing the preferred range of each substituent in the compounds included in the present invention may be optionally combined, each of which represents the range of the preferred compound of the present invention. Examples of the combination of $X^1$, $X^2$, $X^3$, $Y^1$, $R^{1a}$ and $R^4$ in the preferred range include combinations shown in Table 1. However, the combinations in Table 1 are only for exemplification, and the present invention is not intended to be limited to these combinations.

TABLE 1

| X | $Y^1$ | $R^{1a}$ | $R^4$ |
|---|---|---|---|
| X-I | $Y^1$-I | $R^{1a}$-I | $R^4$-I |
| X-I | $Y^1$-I | $R^{1a}$-I | $R^4$-II |
| X-I | $Y^1$-I | $R^{1a}$-I | $R^4$-III |
| X-I | $Y^1$-I | $R^{1a}$-I | $R^4$-IV |
| X-I | $Y^1$-I | $R^{1a}$-II | $R^4$-I |
| X-I | $Y^1$-I | $R^{1a}$-II | $R^4$-II |
| X-I | $Y^1$-I | $R^{1a}$-II | $R^4$-III |
| X-I | $Y^1$-I | $R^{1a}$-III | $R^4$-II |
| X-I | $Y^1$-I | $R^{1a}$-III | $R^4$-III |
| X-I | $Y^1$-I | $R^{1a}$-IV | $R^4$-II |
| X-I | $Y^1$-I | $R^{1a}$-IV | $R^4$-III |
| X-I | $Y^1$-I | $R^{1a}$-V | $R^4$-II |
| X-I | $Y^1$-I | $R^{1a}$-V | $R^4$-III |
| X-I | $Y^1$-I | $R^{1a}$-VI | $R^4$-II |
| X-I | $Y^1$-I | $R^{1a}$-VII | $R^4$-II |
| X-I | $Y^1$-I | $R^{1a}$-VIII | $R^4$-II |
| X-I | $Y^1$-II | $R^{1a}$-I | $R^4$-I |
| X-I | $Y^1$-II | $R^{1a}$-I | $R^4$-II |
| X-I | $Y^1$-II | $R^{1a}$-I | $R^4$-III |
| X-I | $Y^1$-II | $R^{1a}$-I | $R^4$-IV |
| X-I | $Y^1$-II | $R^{1a}$-II | $R^4$-I |
| X-I | $Y^1$-II | $R^{1a}$-II | $R^4$-II |
| X-I | $Y^1$-II | $R^{1a}$-II | $R^4$-III |
| X-I | $Y^1$-II | $R^{1a}$-III | $R^4$-I |
| X-I | $Y^1$-II | $R^{1a}$-III | $R^4$-III |
| X-I | $Y^1$-II | $R^{1a}$-IV | $R^4$-I |
| X-I | $Y^1$-II | $R^{1a}$-IV | $R^4$-III |
| X-I | $Y^1$-II | $R^{1a}$-V | $R^4$-I |
| X-I | $Y^1$-II | $R^{1a}$-V | $R^4$-III |
| X-I | $Y^1$-II | $R^{1a}$-VI | $R^4$-I |
| X-I | $Y^1$-II | $R^{1a}$-VII | $R^4$-I |
| X-I | $Y^1$-II | $R^{1a}$-VIII | $R^4$-I |
| X-I | $Y^1$-III | $R^{1a}$-I | $R^4$-I |
| X-I | $Y^1$-III | $R^{1a}$-I | $R^4$-II |
| X-I | $Y^1$-III | $R^{1a}$-I | $R^4$-III |
| X-I | $Y^1$-III | $R^{1a}$-II | $R^4$-I |
| X-I | $Y^1$-III | $R^{1a}$-II | $R^4$-III |
| X-I | $Y^1$-III | $R^{1a}$-III | $R^4$-I |
| X-I | $Y^1$-III | $R^{1a}$-IV | $R^4$-I |
| X-I | $Y^1$-III | $R^{1a}$-V | $R^4$-I |
| X-I | $Y^1$-III | $R^{1a}$-VI | $R^4$-I |
| X-I | $Y^1$-III | $R^{1a}$-VII | $R^4$-I |
| X-I | $Y^1$-III | $R^{1a}$-VIII | $R^4$-I |
| X-I | $Y^1$-IV | $R^{1a}$-I | $R^4$-I |
| X-I | Y-IV | $R^{1a}$-I | $R^4$-III |
| X-I | $Y^1$-IV | $R^{1a}$-II | $R^4$-I |
| X-I | $Y^1$-IV | $R^{1a}$-III | $R^4$-I |
| X-I | $Y^1$-IV | $R^{1a}$-IV | $R^4$-I |
| X-I | $Y^1$-IV | $R^{1a}$-V | $R^4$-I |
| X-I | $Y^1$-V | $R^{1a}$-I | $R^4$-I |
| X-I | $Y^1$-V | $R^{1a}$-II | $R^4$-I |
| X-II | $Y^1$-I | $R^{1a}$-I | $R^4$-I |
| X-II | $Y^1$-I | $R^{1a}$-I | $R^4$-II |
| X-II | $Y^1$-I | $R^{1a}$-I | $R^4$-III |
| X-II | $Y^1$-I | $R^{1a}$-I | $R^4$-IV |
| X-II | $Y^1$-I | $R^{1a}$-II | $R^4$-I |
| X-II | $Y^1$-I | $R^{1a}$-II | $R^4$-II |
| X-II | $Y^1$-I | $R^{1a}$-II | $R^4$-III |
| X-II | $Y^1$-I | $R^{1a}$-III | $R^4$-II |
| X-II | $Y^1$-I | $R^{1a}$-III | $R^4$-III |
| X-II | $Y^1$-I | $R^{1a}$-IV | $R^4$-II |
| X-II | $Y^1$-I | $R^{1a}$-IV | $R^4$-III |
| X-II | $Y^1$-I | $R^{1a}$-V | $R^4$-II |
| X-II | $Y^1$-I | $R^{1a}$-V | $R^4$-III |
| X-II | $Y^1$-I | $R^{1a}$-VI | $R^4$-II |
| X-II | $Y^1$-I | $R^{1a}$-VII | $R^4$-II |
| X-II | $Y^1$-I | $R^{1a}$-VIII | $R^4$-II |
| X-II | $Y^1$-II | $R^{1a}$-I | $R^4$-I |
| X-II | $Y^1$-II | $R^{1a}$-I | $R^4$-II |

TABLE 1-continued

| X | $Y^1$ | $R^{1a}$ | $R^4$ |
|---|---|---|---|
| X-II | $Y^1$-II | $R^{1a}$-I | $R^4$-III |
| X-II | $Y^1$-II | $R^{1a}$-I | $R^4$-IV |
| X-II | $Y^1$-II | $R^{1a}$-II | $R^4$-I |
| X-II | $Y^1$-II | $R^{1a}$-II | $R^4$-II |
| X-II | $Y^1$-II | $R^{1a}$-II | $R^4$-III |
| X-II | $Y^1$-II | $R^{1a}$-III | $R^4$-I |
| X-II | $Y^1$-II | $R^{1a}$-III | $R^4$-III |
| X-II | $Y^1$-II | $R^{1a}$-IV | $R^4$-I |
| X-II | $Y^1$-II | $R^{1a}$-IV | $R^4$-III |
| X-II | $Y^1$-II | $R^{1a}$-V | $R^4$-I |
| X-II | $Y^1$-II | $R^{1a}$-V | $R^4$-III |
| X-II | $Y^1$-II | $R^{1a}$-VI | $R^4$-I |
| X-II | $Y^1$-II | $R^{1a}$-VII | $R^4$-I |
| X-II | $Y^1$-II | $R^{1a}$-VIII | $R^4$-I |
| X-II | $Y^1$-III | $R^{1a}$-I | $R^4$-I |
| X-II | $Y^1$-III | $R^{1a}$-I | $R^4$-II |
| X-II | $Y^1$-III | $R^{1a}$-I | $R^4$-III |
| X-II | $Y^1$-III | $R^{1a}$-II | $R^4$-I |
| X-II | $Y^1$-III | $R^{1a}$-II | $R^4$-III |
| X-II | $Y^1$-III | $R^{1a}$-III | $R^4$-I |
| X-II | $Y^1$-III | $R^{1a}$-IV | $R^4$-I |
| X-II | $Y^1$-III | $R^{1a}$-V | $R^4$-I |
| X-II | $Y^1$-III | $R^{1a}$-VI | $R^4$-I |
| X-II | $Y^1$-III | $R^{1a}$-VII | $R^4$-I |
| X-II | $Y^1$-III | $R^{1a}$-VIII | $R^4$-I |
| X-II | $Y^1$-IV | $R^{1a}$-I | $R^4$-I |
| X-II | $Y^1$-IV | $R^{1a}$-I | $R^4$-III |
| X-II | $Y^1$-IV | $R^{1a}$-II | $R^4$-I |
| X-II | $Y^1$-IV | $R^{1a}$-III | $R^4$-I |
| X-II | $Y^1$-IV | $R^{1a}$-IV | $R^4$-I |
| X-II | $Y^1$-IV | $R^{1a}$-V | $R^4$-I |
| X-II | $Y^1$-V | $R^{1a}$-I | $R^4$-I |
| X-II | $Y^1$-V | $R^{1a}$-II | $R^4$-I |
| X-III | $Y^1$-I | $R^{1a}$-I | $R^4$-I |
| X-III | $Y^1$-I | $R^{1a}$-I | $R^4$-II |
| X-III | $Y^1$-I | $R^{1a}$-I | $R^4$-III |
| X-III | $Y^1$-I | $R^{1a}$-I | $R^4$-IV |
| X-III | $Y^1$-I | $R^{1a}$-II | $R^4$-I |
| X-III | $Y^1$-I | $R^{1a}$-II | $R^4$-II |
| X-III | $Y^1$-I | $R^{1a}$-II | $R^4$-III |
| X-III | $Y^1$-I | $R^{1a}$-III | $R^4$-II |
| X-III | $Y^1$-I | $R^{1a}$-III | $R^4$-III |
| X-III | $Y^1$-I | $R^{1a}$-IV | $R^4$-II |
| X-III | $Y^1$-I | $R^{1a}$-IV | $R^4$-III |
| X-III | $Y^1$-I | $R^{1a}$-V | $R^4$-II |
| X-III | $Y^1$-I | $R^{1a}$-V | $R^4$-III |
| X-III | $Y^1$-I | $R^{1a}$-VI | $R^4$-II |
| X-III | $Y^1$-I | $R^{1a}$-VII | $R^4$-II |
| X-III | $Y^1$-I | $R^{1a}$-VIII | $R^4$-II |
| X-III | $Y^1$-II | $R^{1a}$-I | $R^4$-I |
| X-III | $Y^1$-II | $R^{1a}$-I | $R^4$-II |
| X-III | $Y^1$-II | $R^{1a}$-I | $R^4$-III |
| X-III | $Y^1$-II | $R^{1a}$-I | $R^4$-IV |
| X-III | $Y^1$-II | $R^{1a}$-II | $R^4$-I |
| X-III | $Y^1$-II | $R^{1a}$-II | $R^4$-II |
| X-III | $Y^1$-II | $R^{1a}$-II | $R^4$-III |
| X-III | $Y^1$-II | $R^{1a}$-III | $R^4$-I |
| X-III | $Y^1$-II | $R^{1a}$-III | $R^4$-III |
| X-III | $Y^1$-II | $R^{1a}$-IV | $R^4$-I |
| X-III | $Y^1$-II | $R^{1a}$-IV | $R^4$-III |
| X-III | $Y^1$-II | $R^{1a}$-V | $R^4$-I |
| X-III | $Y^1$-II | $R^{1a}$-V | $R^4$-III |
| X-III | $Y^1$-II | $R^{1a}$-VI | $R^4$-I |
| X-III | $Y^1$-II | $R^{1a}$-VII | $R^4$-I |
| X-III | $Y^1$-II | $R^{1a}$-VIII | $R^4$-I |
| X-III | $Y^1$-III | $R^{1a}$-I | $R^4$-I |
| X-III | $Y^1$-III | $R^{1a}$-I | $R^4$-II |
| X-III | $Y^1$-III | $R^{1a}$-I | $R^4$-III |
| X-III | $Y^1$-III | $R^{1a}$-II | $R^4$-I |
| X-III | $Y^1$-III | $R^{1a}$-II | $R^4$-III |
| X-III | $Y^1$-III | $R^{1a}$-III | $R^4$-I |
| X-III | $Y^1$-III | $R^{1a}$-IV | $R^4$-I |
| X-III | $Y^1$-III | $R^{1a}$-V | $R^4$-I |
| X-III | $Y^1$-III | $R^{1a}$-VI | $R^4$-I |
| X-III | $Y^1$-III | $R^{1a}$-VII | $R^4$-I |
| X-III | $Y^1$-III | $R^{1a}$-VIII | $R^4$-I |
| X-III | $Y^1$-IV | $R^{1a}$-I | $R^4$-I |
| X-III | $Y^1$-IV | $R^{1a}$-I | $R^4$-III |
| X-III | $Y^1$-IV | $R^{1a}$-II | $R^4$-I |
| X-III | $Y^1$-IV | $R^{1a}$-III | $R^4$-I |
| X-III | $Y^1$-IV | $R^{1a}$-IV | $R^4$-I |
| X-III | $Y^1$-IV | $R^{1a}$-V | $R^4$-I |
| X-III | $Y^1$-V | $R^{1a}$-I | $R^4$-I |
| X-III | $Y^1$-V | $R^{1a}$-II | $R^4$-I |
| X-IV | $Y^1$-I | $R^{1a}$-I | $R^4$-I |
| X-IV | $Y^1$-I | $R^{1a}$-I | $R^4$-II |
| X-IV | $Y^1$-I | $R^{1a}$-I | $R^4$-III |
| X-IV | $Y^1$-I | $R^{1a}$-II | $R^4$-II |
| X-IV | $Y^1$-I | $R^{1a}$-II | $R^4$-III |
| X-IV | $Y^1$-I | $R^{1a}$-III | $R^4$-II |
| X-IV | $Y^1$-I | $R^{1a}$-IV | $R^4$-II |
| X-IV | $Y^1$-I | $R^{1a}$-V | $R^4$-II |
| X-IV | $Y^1$-II | $R^{1a}$-I | $R^4$-I |
| X-IV | $Y^1$-II | $R^{1a}$-II | $R^4$-I |
| X-IV | $Y^1$-II | $R^{1a}$-III | $R^4$-I |
| X-IV | $Y^1$-II | $R^{1a}$-IV | $R^4$-I |
| X-IV | $Y^1$-II | $R^{1a}$-V | $R^4$-I |
| X-IV | $Y^1$-III | $R^{1a}$-I | $R^4$-I |
| X-IV | $Y^1$-III | $R^{1a}$-II | $R^4$-I |
| X-IV | $Y^1$-III | $R^{1a}$-III | $R^4$-I |
| X-IV | $Y^1$-III | $R^{1a}$-IV | $R^4$-I |
| X-IV | $Y^1$-IV | $R^{1a}$-I | $R^4$-I |
| X-IV | $Y^1$-IV | $R^{1a}$-II | $R^4$-I |
| X-V | $Y^1$-I | $R^{1a}$-I | $R^4$-I |
| X-V | $Y^1$-I | $R^{1a}$-I | $R^4$-II |
| X-V | $Y^1$-I | $R^{1a}$-I | $R^4$-III |
| X-V | $Y^1$-I | $R^{1a}$-II | $R^4$-II |
| X-V | $Y^1$-I | $R^{1a}$-II | $R^4$-III |
| X-V | $Y^1$-I | $R^{1a}$-III | $R^4$-II |
| X-V | $Y^1$-I | $R^{1a}$-IV | $R^4$-II |
| X-V | $Y^1$-I | $R^{1a}$-V | $R^4$-II |
| X-V | $Y^1$-II | $R^{1a}$-I | $R^4$-I |
| X-V | $Y^1$-II | $R^{1a}$-II | $R^4$-I |
| X-V | $Y^1$-II | $R^{1a}$-III | $R^4$-I |
| X-V | $Y^1$-II | $R^{1a}$-IV | $R^4$-I |
| X-V | $Y^1$-II | $R^{1a}$-V | $R^4$-I |
| X-V | $Y^1$-III | $R^{1a}$-I | $R^4$-I |
| X-V | $Y^1$-III | $R^{1a}$-II | $R^4$-I |
| X-V | $Y^1$-III | $R^{1a}$-III | $R^4$-I |
| X-V | $Y^1$-III | $R^{1a}$-IV | $R^4$-I |
| X-V | $Y^1$-IV | $R^{1a}$-I | $R^4$-I |
| X-V | $Y^1$-IV | $R^{1a}$-II | $R^4$-I |
| X-VI | $Y^1$-I | $R^{1a}$-I | $R^4$-I |
| X-VI | $Y^1$-I | $R^{1a}$-I | $R^4$-II |
| X-VI | $Y^1$-I | $R^{1a}$-I | $R^4$-III |
| X-VI | $Y^1$-I | $R^{1a}$-II | $R^4$-II |
| X-VI | $Y^1$-I | $R^{1a}$-II | $R^4$-III |
| X-VI | $Y^1$-I | $R^{1a}$-III | $R^4$-II |
| X-VI | $Y^1$-I | $R^{1a}$-IV | $R^4$-II |
| X-VI | $Y^1$-I | $R^{1a}$-V | $R^4$-II |
| X-VI | $Y^1$-II | $R^{1a}$-I | $R^4$-I |
| X-VI | $Y^1$-II | $R^{1a}$-II | $R^4$-I |
| X-VI | $Y^1$-II | $R^{1a}$-III | $R^4$-I |
| X-VI | $Y^1$-II | $R^{1a}$-IV | $R^4$-I |
| X-VI | $Y^1$-II | $R^{1a}$-V | $R^4$-I |
| X-VI | $Y^1$-III | $R^{1a}$-I | $R^4$-I |
| X-VI | $Y^1$-III | $R^{1a}$-II | $R^4$-I |
| X-VI | $Y^1$-III | $R^{1a}$-III | $R^4$-I |
| X-VI | $Y^1$-III | $R^{1a}$-IV | $R^4$-I |
| X-VI | $Y^1$-IV | $R^{1a}$-I | $R^4$-I |
| X-VI | $Y^1$-IV | $R^{1a}$-II | $R^4$-I |
| X-VII | $Y^1$-I | $R^{1a}$-I | $R^4$-I |
| X-VII | $Y^1$-I | $R^{1a}$-I | $R^4$-II |
| X-VII | $Y^1$-I | $R^{1a}$-I | $R^4$-III |
| X-VII | $Y^1$-I | $R^{1a}$-II | $R^4$-II |
| X-VII | $Y^1$-I | $R^{1a}$-II | $R^4$-III |
| X-VII | $Y^1$-I | $R^{1a}$-III | $R^4$-II |
| X-VII | $Y^1$-I | $R^{1a}$-IV | $R^4$-II |
| X-VII | $Y^1$-I | $R^{1a}$-V | $R^4$-II |
| X-VII | $Y^1$-II | $R^{1a}$-I | $R^4$-I |
| X-VII | $Y^1$-II | $R^{1a}$-II | $R^4$-I |
| X-VII | $Y^1$-II | $R^{1a}$-III | $R^4$-I |
| X-VII | $Y^1$-II | $R^{1a}$-IV | $R^4$-I |
| X-VII | $Y^1$-II | $R^{1a}$-V | $R^4$-I |
| X-VII | $Y^1$-III | $R^{1a}$-I | $R^4$-I |
| X-VII | $Y^1$-III | $R^{1a}$-II | $R^4$-I |

TABLE 1-continued

| X | Y¹ | R$^{1a}$ | R⁴ |
|---|---|---|---|
| X-VII | Y¹-III | R$^{1a}$-III | R⁴-I |
| X-VII | Y¹-III | R$^{1a}$-IV | R⁴-I |
| X-VII | Y¹-IV | R$^{1a}$-I | R⁴-I |
| X-VII | Y¹-IV | R$^{1a}$-II | R⁴-I |
| X-VIII | Y¹-I | R$^{1a}$-I | R⁴-II |
| X-VIII | Y¹-II | R$^{1a}$-I | R⁴-I |
| X-VIII | Y¹-III | R$^{1a}$-I | R⁴-I |
| X-IX | Y¹-I | R$^{1a}$-I | R⁴-II |
| X-IX | Y¹-II | R$^{1a}$-I | R⁴-I |
| X-IX | Y¹-III | R$^{1a}$-I | R⁴-I |
| X-X | Y¹-I | R$^{1a}$-I | R⁴-II |
| X-X | Y¹-II | R$^{1a}$-I | R⁴-I |
| X-X | Y¹-III | R$^{1a}$-I | R⁴-I |

The compound of the present invention can be produced, for example, by the following methods.

Production Method A

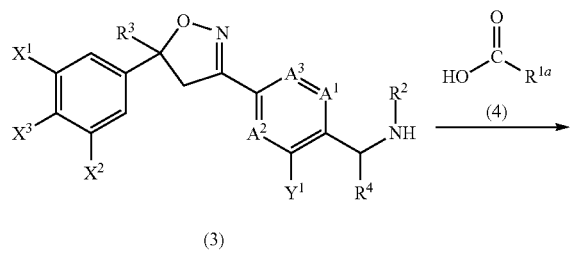

(3)

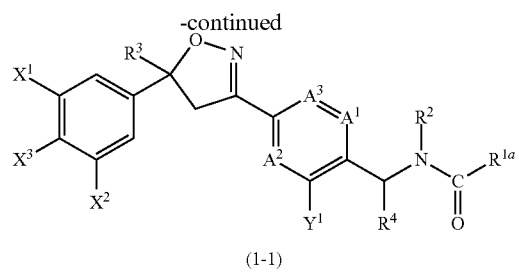

(1-1)

By reacting 1 equivalent of a compound of General Formula (3) (where A¹, A², A³, X¹, X², X³, Y¹, R², R³ and R⁴ are the same as the respective definitions in the above) and 1 to 1.1 equivalent(s) of a carboxylic acid of General Formula (4) (where R$^{1a}$ is —C(R⁹)(R$^{9a}$)—S(O)$_r$—R¹⁰, E-1, E-3, E-5 or E-6), using, for example, dichloromethane, chloroform, diethyl ether, tert-butyl methyl ether, tetrahydrofuran or 1,4-dioxane as a solvent, if necessary in the presence of 1 to 4 equivalent(s) of a base such as sodium carbonate, potassium carbonate, triethylamine, pyridine or 4-(dimethylamino)pyridine, using 1 to 4 equivalent(s) of a condensing agent such as 1-ethyl-3-(3-dimethylaminopropyl)carbodiimide hydrochloride (WSC) or carbonyldiimidazole (CDI), at a temperature ranging from 0° C. to a reflux temperature of the reaction mixture for 10 minutes to 24 hours, a compound of the present invention of General Formula (1-1) (where A¹, A², A³, X¹, X², X³, Y¹, R², R³ and R⁴ are the same as the respective definitions in the above, and R$^{1a}$ is —C(R⁹)(R$^{9a}$)—S(O)$_r$—R¹⁰, E-1, E-3, E-5 or E-6) corresponding to General Formula (1) in which R¹ is —C(O)R$^{1a}$ can be obtained.

Some of the carboxylic acids of General Formula (4) used here are known compounds, and some of them are commercially available. Furthermore, the others can be readily synthesized according to general synthetic methods described in the literatures relating to the known compounds.

Production Method B

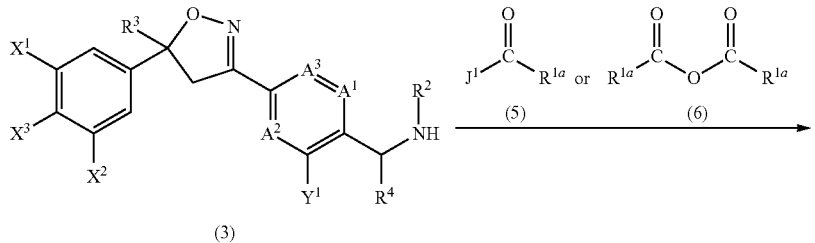

(3)

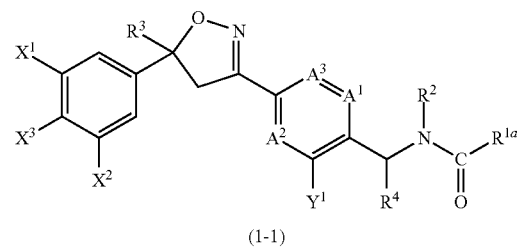

(1-1)

By reacting 1 equivalent of the compound of General Formula (3) (where $A^1, A^2, A^3, X^1, X^2, X^3, Y^1, R^2, R^3$ and $R^4$ are the same as the respective definitions in the above) and 1 to 1.5 equivalent(s) of a carboxylic acid derivative of General Formula (5) (where $R^{1a}$ is $-C(R^9)(R^{9a})-S(O)_r-R^{10}$, E-1, E-3, E-5 or E-6, and $J^1$ is a chlorine atom, a bromine atom, a $C_{1-4}$ alkylcarbonyloxy group (for example, a pivaloyloxy group), a $C_{1-4}$ alkoxycarbonyloxy group (for example, an isobutyloxycarbonyloxy group) or an azolyl group (for example, imidazol-1-yl group)) or a carboxylic acid anhydride of General Formula (6) (where $R^{1a}$ is $-C(R^9)(R^{9a})-S(O)_r-R^{10}$, E-1, E-3, E-5 or E-6), using, for example, dichloromethane, chloroform, diethyl ether, tert-butyl methyl ether, tetrahydrofuran, 1,4-dioxane, ethyl acetate or acetonitrile as a solvent, if necessary in the presence of 1 to 2 equivalent(s) of a base such as sodium carbonate, potassium carbonate, triethylamine, pyridine or 4-(dimethylamino)pyridine, at a temperature ranging from 0° C. to a reflux temperature of the reaction mixture for 10 minutes to 24 hours, the compound of the present invention of General Formula (1-1) (where $A^1, A^2, A^3, X^1, X^2, X^3, Y^1, R^2, R^3$ and $R^4$ are the same as the respective definitions in the above, and $R^{1a}$ is $-C(R^9)(R^{9a})-S(O)_r-R^{10}$, E-1, E-3, E-5 or E-6) corresponding to General Formula (1) in which $R^1$ is $-C(O)R^{1a}$ can be obtained.

Some of the carboxylic acid derivatives of General Formula (5) and the carboxylic acid anhydrides of General Formula (6) used here are known compounds, and some of them are commercially available. Furthermore, the others can be readily synthesized from the carboxylic acids of General Formula (4) according to general synthetic methods described in the literatures on the synthesis of carboxylic halides, mixed carboxylic acid anhydrides or the like.

and $J^2$ are the same as the respective definitions in the above) which is obtained by reacting the compound of General Formula (3) (where $A^1, A^2, A^3, X^1, X^2, X^3, Y^1, R^2, R^3$ and $R^4$ are the same as the respective definitions in the above) and a compound of General Formula (7) (where $R^9, R^{9a}$ and $J^1$ are the same as the respective definitions in the above, and $J^2$ is a chlorine atom, a bromine atom, an iodine atom, a $C_{1-4}$ alkylsulfonyloxy group (for example, a methanesulfonyloxy group), a $C_{1-4}$ haloalkylsulfonyloxy group (for example, a trifluoromethanesulfonyloxy group) or the like) under substantially the same condition as that in Production Method B, and 1 to 3 equivalent(s) of a compound of General Formula (9) (where $R^{10}$ is the same as the definition in the above, and $J^3$ is a hydrogen atom or an alkali metal such as sodium, potassium or cesium), using, for example, dichloromethane, methanol, ethanol, tetrahydrofuran, acetone, N,N-dimethylformamide, acetonitrile, water or a mixture of two or more of them at any ratio as a solvent, if necessary in the presence of 1 to 1.5 equivalent(s) of a base such as potassium hydroxide, potassium ethoxide or triethylamine, at a temperature ranging from 0° C. to a reflux temperature of the reaction mixture for 30 minutes to 24 hours, a compound of the present invention of General Formula (1-2) (where $A^1, A^2, A^3, X^1, X^2, X^3, Y^1, R^2, R^3, R^4, R^9, R^{9a}$ and $R^{10}$ are the same as the respective definitions in the above) corresponding to General Formula (1) in which $R^1$ is $-C(O)R^{1a}$, and $R^{1a}$ is $-C(R^9)(R^{9a})-S-R^{10}$ can be obtained.

Some of the compounds of General Formula (7) and the compounds of General Formula (9) used here are known compounds, and some of them are commercially available. Furthermore, the others can be readily synthesized according to general synthetic methods of the known compounds described in the literatures.

Production Method C

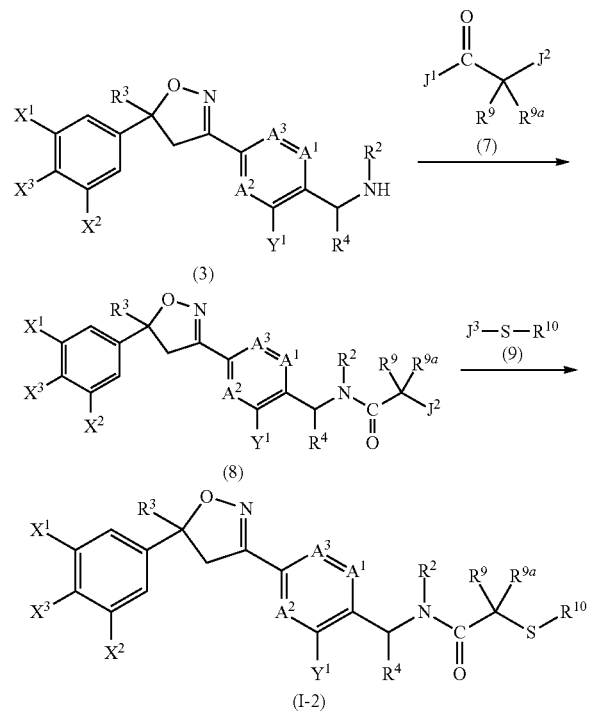

Production Method D

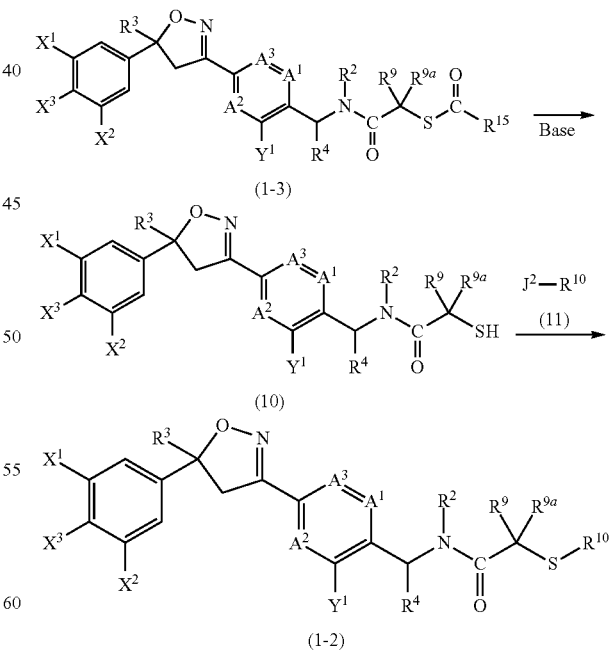

By reacting 1 equivalent of a compound of General Formula (8) (where $A^1, A^2, A^3, X^1, X^2, X^3, Y^1, R^2, R^3, R^4, R^9, R^{9a}$ A compound of the present invention of General Formula (1-3) (where $A^1, A^2, A^3, X^1, X^2, X^3, Y^1, R^2, R^3, R^4, R^9, R^{9a}$ and $R^{15}$ are the same as the respective definitions in the above) corresponding to General Formula (1) in which $R^1$ is $-C(O)$ $R^{1a}$ and $R^{1a}$ is —C($R^9$)($R^{9a}$)—S—C(O)$R^{15}$ is reacted, preferably under an atmosphere of an inert gas such as nitrogen or argon, using, for example, methanol, ethanol, 1,2-dimethoxyethane, tetrahydrofuran, acetone, water or a mixture of two or more of them at any ratio as a solvent, with 1 to 40 equivalent(s) of a base such as lithium hydroxide, sodium hydroxide, potassium carbonate, sodium methoxide, sodium ethoxide, sodium acetate or ammonia with respect to 1 equivalent of the compound of the present invention of General Formula (1-3), at a temperature ranging from 0° C. to a reflux temperature of the reaction mixture for 20 minutes to 16 hours. Subsequently, by neutralizing the resultant reaction mixture with an acid such as an aqueous solution of hydrochloric acid, a compound of General Formula (10) (where $A^1$, $A^2$, $A^3$, $X^1$, $X^2$, $X^3$, $Y^1$, $R^2$, $R^3$, $R^4$, $R^9$ and $R^{9a}$ are the same as the respective definitions in the above) can be obtained.

By reacting 1 equivalent of the compound of General Formula (10) obtained in this manner and 1 to 3 equivalent(s) of a compound of General Formula (11) (where $R^{10}$ and $J^2$ are the same as the respective definitions in the above), preferably under an atmosphere of an inert gas such as nitrogen or argon, using, for example, dichloromethane, methanol, ethanol, diethyl ether, tetrahydrofuran, N,N-dimethylformamide or a mixture of two or more of them at any ratio as a solvent, if necessary in the presence of 1 to 1.5 equivalent(s) of a base such as cesium carbonate, sodium methoxide, potassium tert-butoxide, triethylamine or pyridine, further, if necessary adding 4-(dimethylamino)pyridine or the like as a catalyst, at a temperature ranging from 10° C. to a reflux temperature of the reaction mixture for 30 minutes to 24 hours, the compound of the present invention of General Formula (1-2) (where $A^1$, $A^2$, $A^3$, $X^1$, $X^2$, $X^3$, $R^2$, $R^3$, $R^4$, $R^9$, $R^{9a}$ and $R^{10}$ are the same as the respective definitions in the above) corresponding to General Formula (1) in which $R^1$ is —C(O)$R^{1a}$ and $R^{1a}$ is —C($R^9$)($R^{9a}$)—S—$R^{10}$ can be obtained.

The compounds of General Formula (11) used here are known compounds, and some of them are commercially available. Furthermore, the others can be readily synthesized according to general synthetic methods of the known compounds described in the literatures.

Production Method E

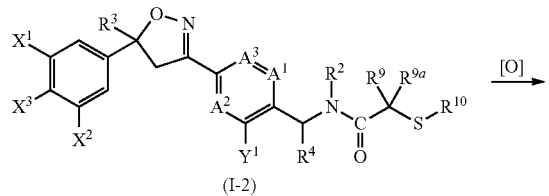

(I-2)

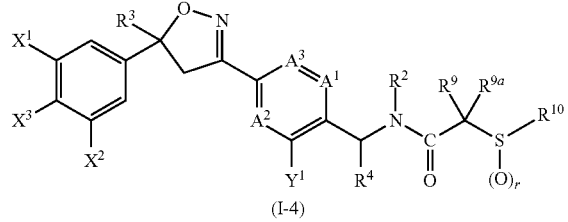

(I-4)

By reacting the compound of the present invention of General Formula (1-2) (where $A^1$, $A^2$, $A^3$, $X^1$, $X^2$, $X^3$, $Y^1$, $R^2$, $R^3$, $R^9$, $R^{9a}$ and $R^{10}$ are the same as the respective definitions in the above) corresponding to General Formula (1) in which $R^1$ is —C(O)$R^{1a}$ and $R^{1a}$ is —C($R^9$)($R^{9a}$)—S—$R^{10}$, using, for example, dichloromethane, methanol, ethanol, hexafluoro-2-propanol, acetic acid, water or a mixture of two or more of them at any ratio as a solvent, with 1 to 4 equivalent(s) of an oxidizing agent such as an aqueous solution of hydrogen peroxide, sodium periodate, potassium periodate or 3-chloroperbenzoic acid with respect to 1 equivalent of the compound of the present invention of General Formula (1-2), at a temperature ranging from −15 to 50° C. for 30 minutes to 24 hours, a sulfoxide which is a compound of the present invention of General Formula (1-4) (where $A^1$, $A^2$, $A^3$, $X^1$, $X^2$, $X^3$, $Y^1$, $R^2$, $R^3$, $R^4$, $R^9$, $R^{9a}$ and $R^{10}$ are the same as the respective definitions in the above, and r is 1) corresponding to General Formula (1) in which $R^1$ is —C(O)$R^{1a}$ and $R^{1a}$ is —C($R^9$)($R^{9a}$)—S(O)$_r$—$R^{10}$, can be obtained. Furthermore, by reacting the compound of the present invention of General Formula (1-2) using 1.1 to 15 equivalents of an oxidizing agent such as an aqueous solution of hydrogen peroxide, sodium periodate, 2KHSO$_5$—KHSO$_4$—K$_2$SO$_4$ (OXONE) or 3-chloroperbenzoic acid with respect to 1 equivalent of the compound of the present invention of General Formula (1-2), if necessary adding 0.005 to 0.05 equivalent of sodium tungstate dihydrate-1.5 equivalents of concentrated hydrochloric acid or the like as a catalyst, at a temperature ranging from 0 to 100° C. for 1 to 18 hour(s), a sulfone which is the compound of the present invention of General Formula (1-4) in which r is 2, can also be obtained.

In a similar manner, sulfoxides and sulfones of the compound of the present invention of General Formula (1-1) in which $R^{1a}$ is E-1, E-3, E-5 and E-6 can be synthesized.

Production Method F

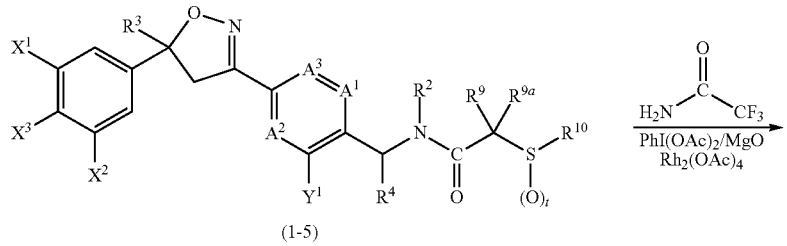

(1-5)

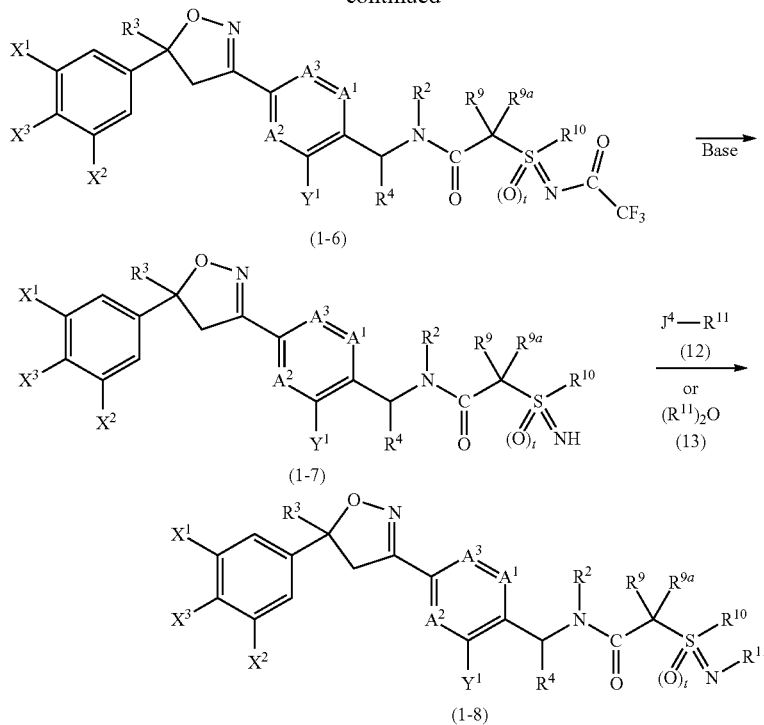

By reacting 1 equivalent of a compound of the present invention of General Formula (1-5)(where $A^1$, $A^2$, $A^3$, $X^1$, $X^2$, $X^3$, $Y^1$, $R^2$, $R^3$, $R^4$, $R^9$, $R^{9a}$, $R^{10}$ and t are the same as the respective definitions in the above) corresponding to General Formula (1) in which $R^1$ is —C(O)$R^{1a}$ and $R^{1a}$ is —C($R^9$)($R^{9a}$)—S(O)$_t$—$R^{10}$ and 2 equivalents of trifluoroacetamide, using, for example, dichloromethane as a solvent, in the presence of 1.5 equivalents of (diacetoxyiodo)benzene, 4 equivalents of magnesium oxide and 0.02 to 0.1 equivalent of tetrakis(acetate)dirhodium (II) with respect to 1 equivalent of the compound of the present invention of General Formula (1-5), at room temperature for 6 to 12 hours, a compound of the present invention of General Formula (1-6) (where $A^1$, $A^2$, $A^3$, $X^1$, $X^2$, $X^3$, $Y^1$, $R^2$, $R^3$, $R^4$, $R^9$, $R^{9a}$, $R^{10}$ and t are the same as the respective definitions in the above) corresponding to General Formula (1) in which $R^1$ is —C(O)$R^{1a}$ and $R^{1a}$ is —C($R^9$)($R^{9a}$)—S(O)$_t$($R^{10}$)=NC(O)CF$_3$ can be obtained.

By reacting 1 equivalent of the compound of the present invention of General Formula (1-6) obtained in this manner and 2 to 10 equivalents of a base such as sodium hydroxide, potassium carbonate, sodium methoxide or ammonia, using, for example, methanol, ethanol, water or a mixture of two or more of them at any ratio as a solvent, at a temperature ranging from 0° C. to room temperature for 2 to 10 hours, a compound of the present invention of General Formula (1-7) (where $A^1$, $A^2$, $A^3$, $X^1$, $X^2$, $X^3$, $Y^1$, $R^2$, $R^3$, $R^4$, $R^9$, $R^{9a}$, $R^{10}$ and t are the same as the respective definitions in the above) corresponding to General Formula (1) in which $R^1$ is —C(O)$R^{1a}$ and $R^{1a}$ is —C($R^9$)($R^{9a}$)—S(O)$_t$($R^{10}$)=NH can be obtained.

Furthermore, by reacting, with respect to 1 equivalent of the compound of the present invention of General Formula (1-7), 1 to 2 equivalent(s) of a compound of General Formula (12) (where $R^{11}$ is the same as the definition in the above, and $J^4$ is a halogen atom, a hydroxy group or the like) or an acid anhydride of General Formula (13) (where $R^{11}$ is a $C_{1-6}$ alkylcarbonyl group, a $C_{1-6}$ haloalkylcarbonyl group, a $C_{1-6}$ alkoxycarbonyl group, a $C_{1-6}$ haloalkoxycarbonyl group, a $C_{1-6}$ alkylsulfonyl group or a $C_{1-6}$ haloalkylsulfonyl group), using, for example, dichloromethane as a solvent, if necessary in the presence of 1 to 5 equivalent(s) of a base such as sodium hydride, triethylamine, pyridine or 4-(dimethylamino)pyridine or 10 to 30 equivalents of acetic anhydride and a catalytic amount of concentrated sulfuric acid, at a temperature ranging from 0° C. to a reflux temperature of the reaction mixture for 15 minutes to 10 hours, a compound of the present invention of General Formula (1-8) (where $A^1$, $A^2$, $A^3$, $X^1$, $X^2$, $X^3$, $R^2$, $R^3$, $R^4$, $R^9$, $R^{9a}$, $R^{10}$, $R^{11}$ and t are the same as the respective definitions in the above) corresponding to General Formula (1) in which $R^1$ is —C(O)$R^{1a}$ and $R^{1a}$ is —C($R^9$)($R^{9a}$)—S(O)$_t$($R^{10}$)=$R^{11}$ can be obtained.

The compounds of General Formula (12) and the compounds of General Formula (13) used here are known compounds, and some of them are commercially available. Furthermore, the others can be readily synthesized according to general synthetic methods of the known compounds described in the literatures.

In a similar manner, the compounds of the present invention of General Formula (1-1) in which $R^{1a}$ is E-2 and E-4 can be synthesized.

Production Method G

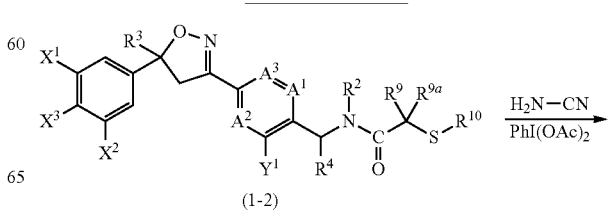

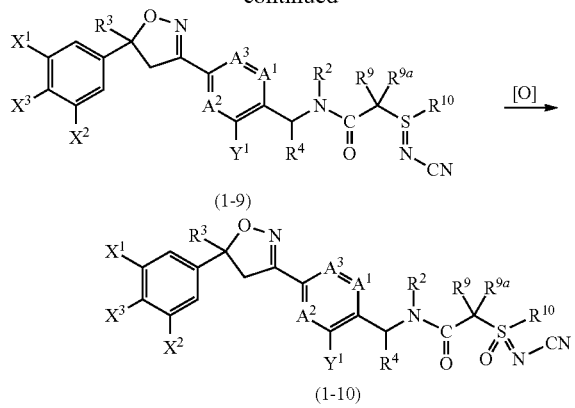

(1-9)

(1-10)

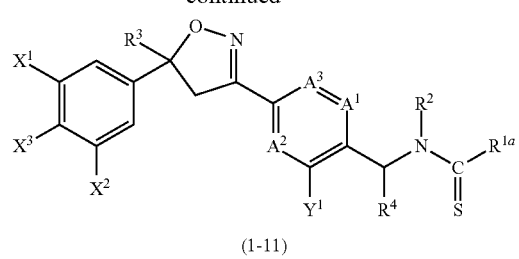

(1-11)

By reacting 1 equivalent of the compound of the present invention of General Formula (1-2) (where $A^1$, $A^2$, $A^3$, $X^1$, $X^2$, $X^3$, $Y^1$, $R^2$, $R^3$, $R^4$, $R^9$, $R^{9a}$ and $R^{10}$ are the same as the respective definitions in the above) corresponding to General Formula (1) in which $R^1$ is —C(O)$R^{1a}$ and $R^{1a}$ is —C($R^9$)($R^{9a}$)—S—$R^{10}$ and 1 to 2 equivalent(s) of cyanamide, using, for example, dichloromethane, tetrahydrofuran or acetonitrile as a solvent, in the presence of 1 to 2 equivalent(s) of (diacetoxyiodo)benzene with respect to 1 equivalent of the compound of the present invention of General Formula (1-2), at a temperature ranging from 0° C. to room temperature for 30 minutes to 18 hours, a compound of the present invention of General Formula (1-9) (where $A^1$, $A^2$, $A^3$, $X^1$, $X^2$, $X^3$, $Y^1$, $R^2$, $R^3$, $R^4$, $R^9$, $R^{9a}$ and $R^{10}$ are the same as the respective definitions in the above) corresponding to General Formula (1) in which $R^1$ is —C(O)$R^{1a}$ and $R^{1a}$ is —C($R^9$)($R^{9a}$)—S—($R^{10}$)=NCN can be obtained.

By reacting the compound of the present invention of General Formula (1-9) obtained in this manner, using, for example, dichloromethane, ethanol, water or a mixture of two or more of them at any ratio as a solvent, with 1 to 2.5 equivalent(s) of an oxidizing agent such as sodium periodate or 3-chloroperbenzoic acid with respect to 1 equivalent of the compound of the present invention of General Formula (1-9), if necessary in the presence of 2 to 5 equivalents of a base such as potassium carbonate, if necessary adding 0.01 to 0.1 equivalent of ruthenium (III) chloride monohydrate or the like as a catalyst, at a temperature ranging from 0° C. to room temperature for 30 minutes to 18 hours, a compound of the present invention of General Formula (1-10) (where $A^1$, $A^2$, $A^3$, $X^1$, $X^3$, $Y^1$, $R^2$, $R^3$, $R^4$, $R^9$, $R^{9a}$ and $R^{10}$ are the same as the respective definitions in the above) corresponding to General Formula (1) in which $R^1$ is —C(O)$R^{1a}$ and $R^{1a}$ is —C($R^9$)($R^{9a}$)—S(O)($R^{10}$)=NCN can be obtained.

In a similar manner, the compounds of the present invention of General Formula (1-1) in which $R^{1a}$ is E-2 and E-4 and $R^{11}$ is cyano can be synthesized.

Production Method H

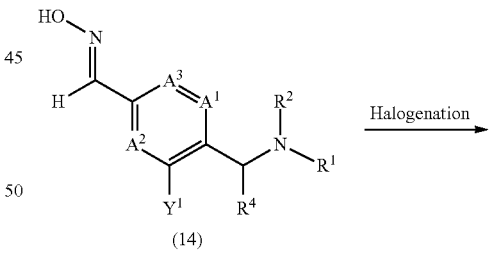

By reacting 1 equivalent of the compound of the present invention of General Formula (1-1) (where $A^1$, $A^2$, $A^3$, $X^1$, $X^2$, $X^3$, $Y^1$, $R^2$, $R^3$, $R^4$ and $R^{1a}$ are the same as the respective definitions in the above) corresponding to General Formula (1) in which $R^1$ is —C(O)$R^{1a}$ and 1 to 10 equivalent(s) of a sulfurizing agent such as diphosphorus pentasulfide, diphosphorus pentasulfide-hexamethyldisiloxane (HMDO) or Lawesson's Reagent (2,4-bis(4-methoxyphenyl)-1,3,2,4-dithiadiphosphetane 2,4-disulfide), if necessary using, for example, benzene, toluene, chlorobenzene, dichloromethane, chloroform, 1,2-dichloroethane, tert-butyl methyl ether, 1,2-dimethoxyethane, tetrahydrofuran, 1,4-dioxane or hexamethylphosphoric triamide (HMPA) as a solvent, if necessary in the presence of 1 to 4 equivalent(s) of a base such as sodium carbonate, potassium carbonate, sodium hydrogen carbonate, triethylamine or pyridine, at a temperature ranging from room temperature to a reflux temperature of the reaction mixture for 10 minutes to 50 hours; or using a base such as pyridine as a solvent, at a temperature ranging from 80° C. to a reflux temperature of the reaction mixture for 1 to 3 hour(s), a compound of the present invention of General Formula (1-11) (where $A^1$, $A^2$, $A^3$, $X^1$, $X^2$, $X^3$, $Y^1$, $R^2$, $R^3$, $R^4$ and $R^{1a}$ are the same as the respective definitions in the above) corresponding to General Formula (1) in which $R^1$ is —C(S)$R^{1a}$ can be obtained.

Production Method I

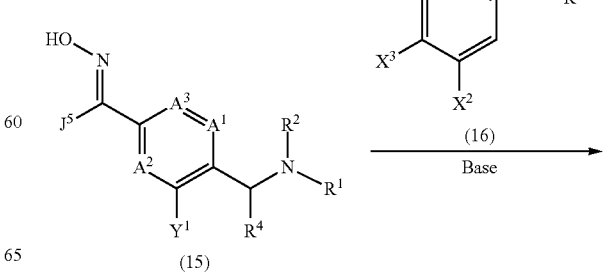

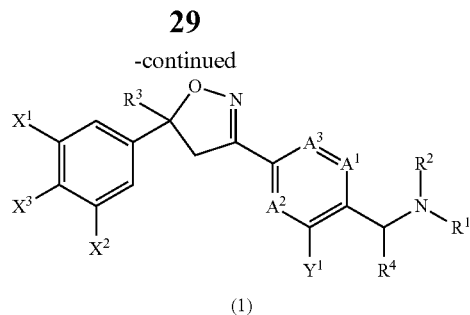

(1)

By reacting 1 equivalent of a compound of General Formula (14) (where $A^1, A^2, A^3, Y^1, R^1, R^2$ and $R^4$ are the same as the respective definitions in the above) and 1 to 2 equivalent(s) of a halogenating agent such as N-chlorosuccinimide, N-bromosuccinimide, an aqueous solution of sodium hypochlorite, hypochlorous acid tert-butyl ester, chlorine gas or bromine, using, for example, dichloromethane, chloroform, 1,2-dichloroethane, 1,2-dimethoxyethane, tetrahydrofuran, 1,4-dioxane, N,N-dimethylformamide or N,N-dimethylacetamide as a solvent, at a temperature ranging from 0° C. to a reflux temperature of the reaction mixture for 10 minutes to 2 hours, a hydroxamic acid chloride of General Formula (15) (where $A^1, A^2, A^3, Y^1, R^1, R^2$ and $R^4$ are the same as the respective definitions in the above, and $J^5$ is a halogen atom such as a chlorine atom or a bromine atom) can be obtained.

By reacting 1 equivalent of the compound of General Formula (15) obtained in this manner and 1 to 2 equivalent(s) of a compound of General Formula (16) (where $X^1, X^2, X^3$ and $R^3$ are the same as the respective definitions in the above), using, for example, dichloromethane, chloroform, 1,2-dichloroethane, 1,2-dimethoxyethane, tetrahydrofuran, 1,4-dioxane, N,N-dimethylformamide or N,N-dimethylacetamide as a solvent, if necessary in the presence of 1 to 2 equivalent(s) of a base such as sodium carbonate, potassium carbonate, sodium hydrogen carbonate, potassium hydrogen carbonate or triethylamine, at a temperature ranging from 0° C. to a reflux temperature of the reaction mixture for 10 minutes to 24 hours, a compound of the present invention of General Formula (1) (where $A^1, A^2, A^3, X^1, X^2, X^3, Y^1, R^1, R^2, R^3$ and $R^4$ are the same as the respective definitions in the above) can be obtained.

The compound of General Formula (16) used here is a known compound described in International Patent Application Publication (WO 2005/085216) and the like.

In Production Method A to Production Method I, the objective compound of the present invention can be obtained by subjecting the reaction mixture after the completion of the reaction to a common aftertreatment: for example, the reaction mixture is directly concentrated; or dissolved in an organic solvent, washed with water, and then concentrated; or charged into ice water, extracted with an organic solvent, and then concentrated. Furthermore, when purification is required, the objective compound can be separated and purified by any purification method such as recrystallization, column chromatography, thin layer chromatography or preparative liquid chromatography.

The compound of General Formula (3) used in Production Method A to Production Method C can be synthesized, for example, according to Reaction Formula 1 to Reaction Formula 6.

Reaction Formula 1

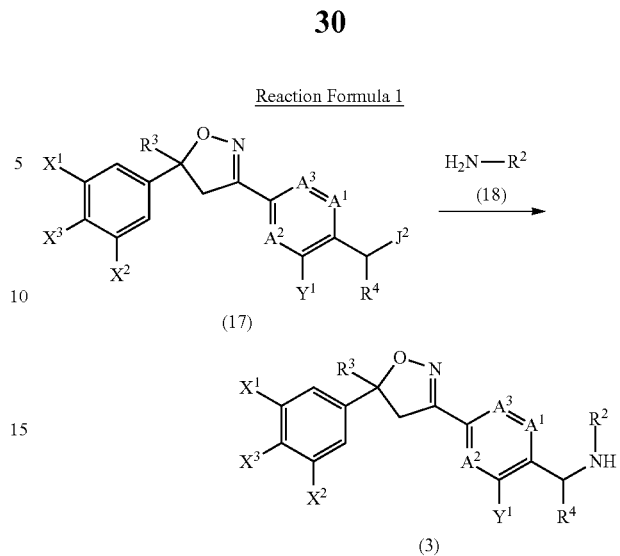

By reacting 1 equivalent of a compound of General Formula (17) (where $A^1, A^2, A^3, X^2, X^3, Y^1, R^3, R^4$ and $J^2$ are the same as the respective definitions in the above) and 1 to 40 equivalent(s) of an amine of General Formula (18) (where $R^2$ is a hydrogen atom, an alkyl group, a substituted alkyl group, an alkenyl group, an alkynyl group or the like) or a salt thereof, if necessary using, for example, benzene, toluene, dichloromethane, chloroform, 1,2-dichloroethane, methanol, ethanol, tert-butyl methyl ether, 1,2-dimethoxyethane, tetrahydrofuran, 1,4-dioxane, N,N-dimethylformamide, N,N'-dimethylpropyleneurea (DMPU), acetonitrile, water or a mixture of two or more of them at any ratio as a solvent, if necessary in the presence of 1 to 10 equivalent(s) of a base such as lithium hydroxide, sodium hydroxide, potassium hydroxide, sodium carbonate, potassium carbonate, triethylamine or ethyldiisopropylamine, if necessary adding 0.1 to 0.5 equivalent of sodium iodide or potassium iodide as a catalyst, at a temperature ranging from 0° C. to a reflux temperature of the reaction mixture for 1 to 48 hour(s), the compound of General Formula (3) (where $A^1, A^2, A^3, X^1, X^2, X^3, Y^1, R^3$ and $R^4$ are the same as the respective definitions in the above and $R^2$ is a hydrogen atom, an alkyl group, a substituted alkyl group, an alkenyl group, an alkynyl group or the like) can be obtained.

The primary amines of General Formula (18) used here are known compounds, and some of them are commercially available. Furthermore, the others can be readily synthesized according to general synthetic methods of the primary amines described in the literatures.

Reaction Formula 2

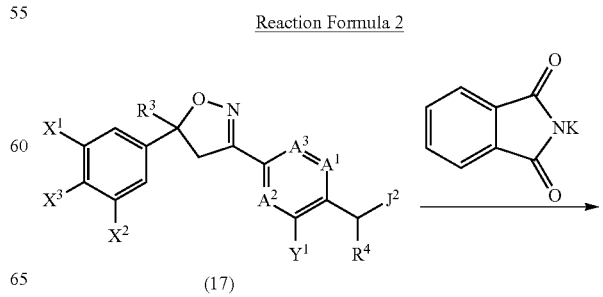

-continued

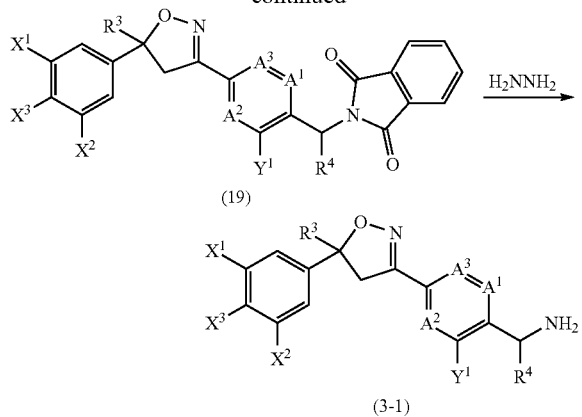

(19)

(3-1)

By reacting 1 equivalent of the compound of General Formula (17) (where $A^1$, $A^2$, $A^3$, $X^1$, $X^2$, $X^3$, $R^3$, $R^4$ and a $J^2$ are the same as the respective definitions in the above) and 1 to 1.5 equivalent(s) of potassium phthalimide, using, for example, toluene, dichloromethane, tetrahydrofuran, 1,4-dioxane, acetone, N,N-dimethylformamide, N,N-dimethylacetamide or dimethylsulfoxide as a solvent, if necessary in the presence of 0.1 to 2 equivalent(s) of a base such as sodium carbonate, potassium carbonate or sodium hydrogen carbonate, if necessary adding 0.1 to 1 equivalent of tetrabutylammonium iodide, tributylhexadecylphosphonium bromide, crown ether (18-Crown-6) or the like as a catalyst, at a temperature ranging from room temperature to a reflux temperature of the reaction mixture for 0.5 to 24 hour(s), a compound of General Formula (19) (where $A^1$, $A^2$, $A^3$, $X^1$, $X^2$, $X^3$, $Y^1$, $R^3$ and $R^4$ are the same as the respective definitions in the above) is obtained. By reacting the compound of General Formula (19) obtained in this manner, using, for example, toluene, dichloromethane, chloroform, methanol, ethanol, tetrahydrofuran, 1,4-dioxane, water or a mixture of two or more of them at any ratio as a solvent, if necessary under an atmosphere of an inert gas such as nitrogen or argon, with 1 to 4 equivalent(s) of hydrazine monohydrate or an aqueous solution of hydrazine with respect to 1 equivalent of the compound of General Formula (19), at a temperature ranging from room temperature to a reflux temperature of the reaction mixture for 1 to 24 hour(s), a compound of General Formula (3-1) (where $A^1$, $A^2$, $A^3$, $X^1$, $X^2$, $X^3$, $Y^1$, $R^3$ and $R^4$ are the same as the respective definitions in the above) corresponding to General Formula (3) in which $R^2$ is a hydrogen atom can be obtained.

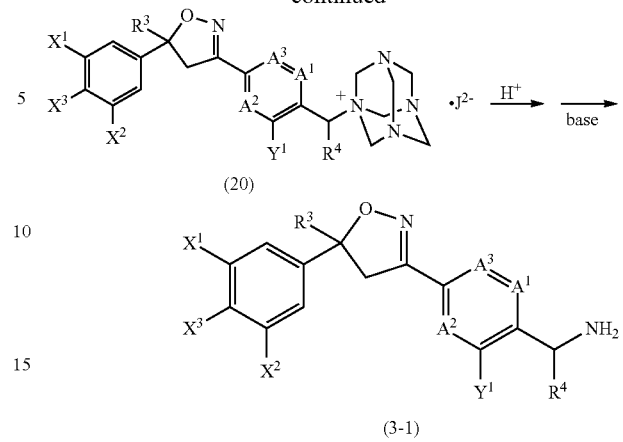

(20)

(3-1)

By reacting 1 equivalent of the compound of General Formula (17) (where $A^1$, $A^2$, $A^3$, $X^1$, $X^2$, $X^3$, $Y^1$, $R^3$, $R^4$ and $J^2$ are the same as the respective definitions in the above) and 1 to 1.3 equivalent(s) of hexamethylenetetramine, using, for example, benzene, toluene, chlorobenzene, dichloromethane, chloroform, 1,2-dichloroethane, methanol or ethanol as a solvent, at a temperature ranging from room temperature to a reflux temperature of the reaction mixture for 0.5 to 24 hour(s), a quaternary ammonium salt of General Formula (20) (where $A^1$, $A^2$, $A^3$, $X^1$, $X^2$, $X^3$, $Y^1$, $R^3$, $R^4$ and $J^2$ are the same as the respective definitions in the above) is obtained. By hydrolyzing the quaternary ammonium salt of General Formula (20) obtained in this manner, using, for example, methanol, ethanol, acetic acid, propionic acid, water or a mixture of two or more of them at any ratio as a solvent, in the presence of 5 to 100 equivalents of an acid catalyst such as hydrochloric acid, hydrobromic acid, propionic acid or phosphoric acid with respect to 1 equivalent of the compound of General Formula (20), at a temperature ranging from room temperature to a reflux temperature of the reaction mixture for 0.5 to 24 hour(s), the compound of General Formula (3-1) (where $A^1$, $A^2$, $A^3$, $X^1$, $X^2$, $X^3$, $R^3$ and $R^4$ are the same as the respective definitions in the above) corresponding to General Formula (3) in which $R^2$ is a hydrogen atom can be obtained.

Reaction Formula 4

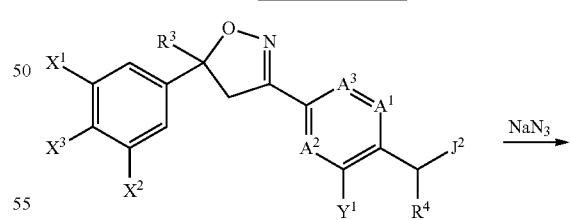

(17)

Reaction Formula 3

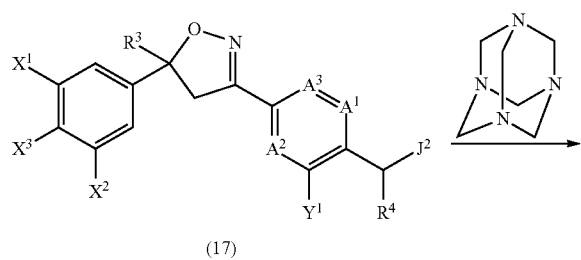

(17)

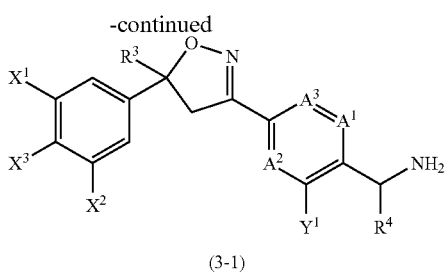

(3-1)

By reacting 1 equivalent of the compound of General Formula (17) (where $A^1, A^2, A^3, X^1, X^2, X^3, Y^1, R^3, R^4$ and $J^2$ are the same as the respective definitions in the above) and 1.1 to 3.0 equivalents of sodium azide or lithium azide, if necessary under an atmosphere of an inert gas such as nitrogen or argon, using, for example, chloroform, ethanol, acetone, N,N-dimethylformamide, N,N'-dimethylpropyleneurea (DMPU), acetonitrile, dimethylsulfoxide, water or a mixture of two or more of them at any ratio as a solvent, if necessary adding 0.005 to 0.3 equivalent of tetrabutylammonium hydrogen sulfate, methyl trioctyl ammonium chloride, lithium iodide, potassium iodide or the like as a catalyst, at a temperature ranging from room temperature to a reflux temperature of the reaction mixture for 0.5 to 48 hour(s), a compound of General Formula (21) (where $A^1, A^2, A^3, X^1, X^2, X^3, Y^1, R^3, R^4$ and $J^2$ are the same as the respective definitions in the above) is obtained. By reacting the compound of General Formula (21) obtained in this manner, using, for example, ethanol, tetrahydrofuran, acetonitrile or a mixture of two or more of them at any ratio as a solvent, with 1 to 1.5 equivalent(s) of triphenylphosphine and 2 to 5 equivalents of water with respect to 1 equivalent of the compound of General Formula (21), at a temperature ranging from room temperature to a reflux temperature of the reaction mixture for 2 to 24 hours, the compound of General Formula (3-1) (where $A^1, A^2, A^3, X^1, X^2, X^3, Y^1, R^3, R^4$ and $J^2$ are the same as the respective definitions in the above) corresponding to General Formula (3) in which $R^2$ is a hydrogen atom can be obtained.

Reaction Formula 5

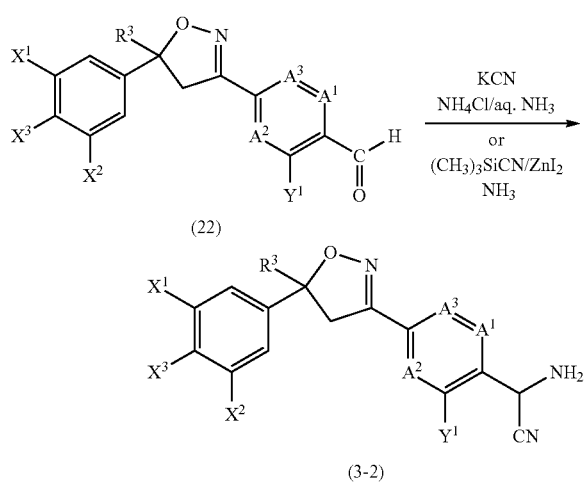

By reacting a compound of General Formula (22) (where $A^1, A^2, A^3, X^1, X^2, X^3, Y^1$ and $R^3$ are the same as the respective definitions in the above), according to, for example, the reaction condition of a common Strecker reaction described in Journal of Medicinal Chemistry (J. Med. Chem.), vol. 28, p. 1280 (1985) or the like or the reaction condition under which the compound is reacted with trimethylsilyl cyanide to obtain a cyanohydrin derivative and then the cyanohydrin derivative is reacted with ammonia, described in Tetrahedron Letters (Tetrahedron Lett.), vol. 25, p. 4583 (1984) or the like, a compound of General Formula (3-2) (where $A^1, A^2, A^3, X^1, X^2, X^3, Y^1$ and $R^3$ are the same as the respective definitions in the above) corresponding to General Formula (3) in which $R^2$ is a hydrogen atom and $R^4$ is cyano can be obtained.

Reaction Formula 6

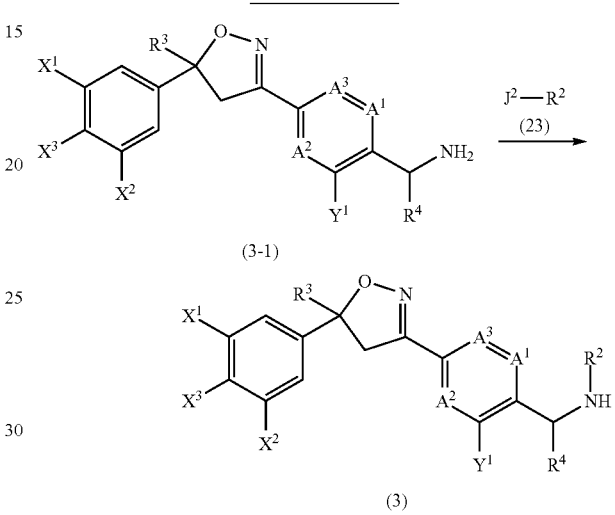

By reacting 1 equivalent of the compound of General Formula (3-1) (where $A^1, A^2, A^3, X^1, X^2, X^3, Y^1, R^3$ and $R^4$ are the same as the respective definitions in the above) corresponding to General Formula (3) in which $R^2$ is a hydrogen atom and equivalent of a compound of General Formula (23) (where $R^2$ is an alkyl group, a substituted alkyl group, an alkenyl group, an alkynyl group or the like, and $J^2$ is the same as the definition in the above) under substantially the same condition as that in Reaction Formula 1, the compound of General Formula (3) (where $A^1, A^1, A^2, A^3, X^1, X^2, X^3, Y^1, R^3$ and $R^4$ are the same as the respective definitions in the above, and $R^2$ is an alkyl group, a substituted alkyl group, an alkenyl group, an alkynyl group or the like) can be obtained.

Some of the compounds of General Formula (23) used here are known compounds, and some of them are commercially available. Furthermore, the others can be readily synthesized according to general synthetic methods of the alkyl halides and the alkyl sulfonate described in the literatures.

The compound of General Formula (14) used in Production Method I can be synthesized, for example, as follows.

Reaction Formula 7

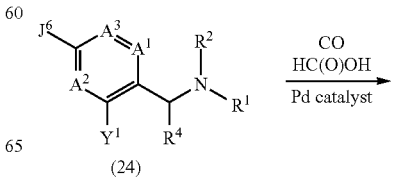

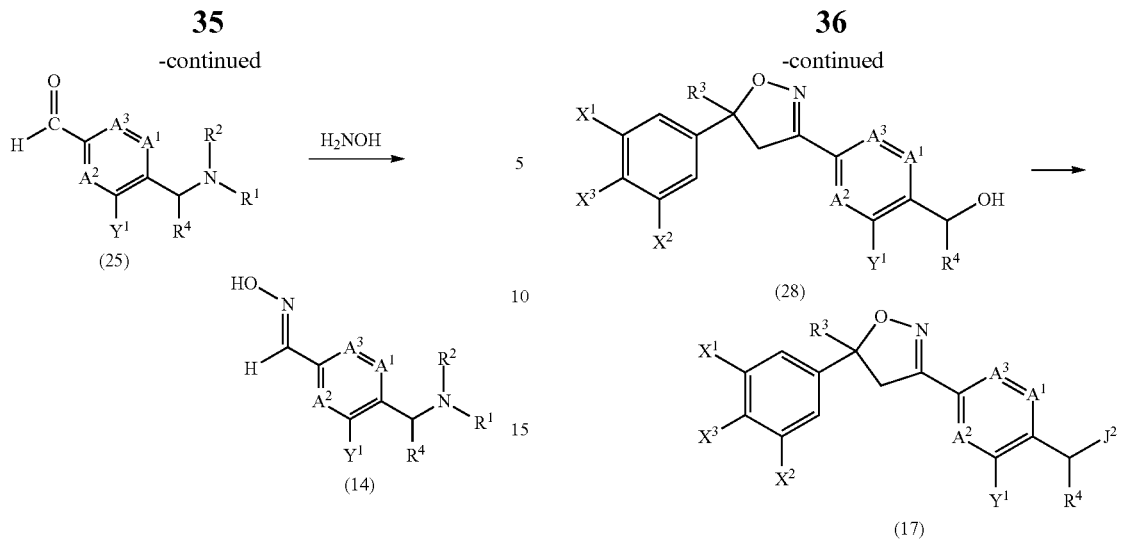

That is, by a CO insertion reaction of a compound of General Formula (24) (where $A^1, A^2, A^3, Y^1, R^1, R^2$ and $R^4$ are the same as the respective definitions in the above, and $J^6$ is a bromine atom, an iodine atom, a $C_{1-4}$ haloalkylsulfonate group (for example, a trifluoromethanesulfonyloxy group) or the like) using a transition metal catalyst such as palladium in the presence of a hydride source such as formic acid according to methods known in the literatures, for example, the method described in Bulletin of the Chemical Society of Japan (Bull. Chem. Sac. Jpn.) vol. 67, p. 2329 (1994) and the like, a compound of General Formula (25) (where $A^1, A^2, A^3, Y^1, R^1, R^2$ and $R^4$ are the same as the respective definitions in the above) can be obtained.

By reacting the compound of General Formula (25) obtained in this manner with hydroxylamine or a salt thereof according to methods known in the literatures, for example, the method described in Journal of Medicinal Chemistry (J. Med. Chem.), vol. 44, p. 2308 (2001), the compound of General Formula (14) (where $A^1, A^2, A^3, Y^1, R^1, R^2$ and $R^4$ are the same as the respective definitions in the above) can be readily synthesized.

The compound of General Formula (17) used in Reaction Formula 1 to Reaction Formula 4 can be synthesized, for example, according to Reaction Formula 8 and Reaction Formula 9.

Reaction Formula 8

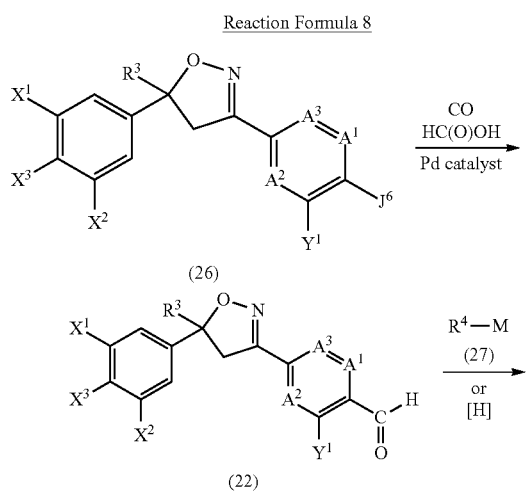

By a CO insertion reaction of a compound of General Formula (26) (where $A^1, A^2, A^3, X^1, X^2, X^3, Y^1, R^3$ and $J^6$ are the same as the respective definitions in the above) under substantially the same condition as that in Reaction Formula 7, the compound of General Formula (22) (where $A^1, A^2, A^3, X^1, X^2, X^3, Y^1$ and $R^3$ are the same as the respective definitions in the above) can be synthesized.

By reacting the compound of General Formula (22) obtained in this manner with a compound of General Formula (27) (where $R^4$ is the same definition in the above except a hydrogen atom, and M is a metal such as lithium and magnesium, a trimethylsilyl or the like) according to methods known in the literatures, for example, the methods described in the Journal of Organic Chemistry (J. Org. Chem.), vol. 64, p. 2873 (1999) and vol. 65, p. 4618 (2000), or by reducing the compound of General Formula (22) according to, for example, the method described in Journal of Medicinal Chemistry (J. Med. Chem.), vol. 50, p. 2424 (2007), a compound of General Formula (28) (where $A^1, A^2, A^3, X^1, X^2, X^3, Y^1, R^3$ and $R^4$ are the same as the respective definitions in the above) is obtained. By halogenating the compound of General Formula (28) obtained in this manner according to, for example, the method described in Journal of the American Chemical Society (J. Am. Chem. Soc.), vol. 108, p. 6819 (1986), or by sulfonyl-esterification of the compound of General Formula (28) according to, for example, the method described in Bioorganic and Medicinal Chemistry (Bioorganic & Med. Chem.), vol. 7, p. 2647 (1999) or the Journal of Organic Chemistry (J. Org. Chem.), vol. 69, p. 1227 (2004), the compound of General Formula (17) (where $A^1, A^2, A^3, X^1, X^2, X^3, Y^1, R^3, R^4$ and $J^2$ are the same as the respective definitions in the above) can be synthesized.

Some of the compounds of General Formula (26) used here are the known compounds described in International Patent Application Publication (WO 2005/085216), and the others can be synthesized in substantially the same manner as that for the known compounds according to the method described in the literature above and according to the method described in International Patent Application Publication (WO 2007/074789). Furthermore, the compounds of General Formula (27) are known compounds, and some of them are commercially available. In addition, the others can be readily synthesized according to a general synthetic method described in the literatures.

Reaction Formula 9

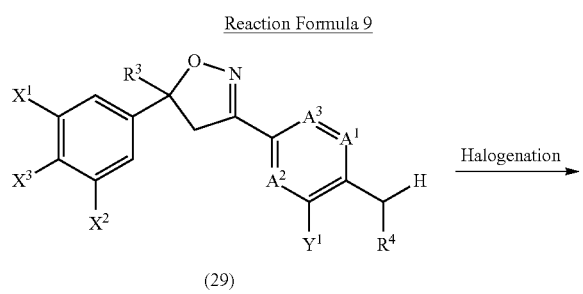

(29)

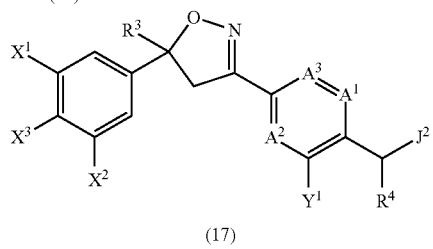

(17)

By halogenating a compound of General Formula (29) (where $A^1, A^2, A^3, X^1, X^2, X^3, Y^1, R^3$ and $R^4$ are the same as the respective definitions in the above) using N-chlorosuccinimide, N-bromosuccinimide or the like according to methods known in the literatures, for example, the method described in Journal of Medicinal Chemistry (J. Med. Chem.), vol. 34, p. 2209 (1991), the compound of General Formula (17) (where $A^1, A^2, A^3, X^1, X^2, X^3, Y^1$, and $R^4$ are the same as the respective definitions in the above, and $J^2$ is a chlorine atom, a bromine atom or the like) can be synthesized.

The compound of General Formula (24) used in Reaction Formula 7 can be synthesized, for example, according to Reaction Formula 10 and Reaction Formula 11.

Reaction Formula 10

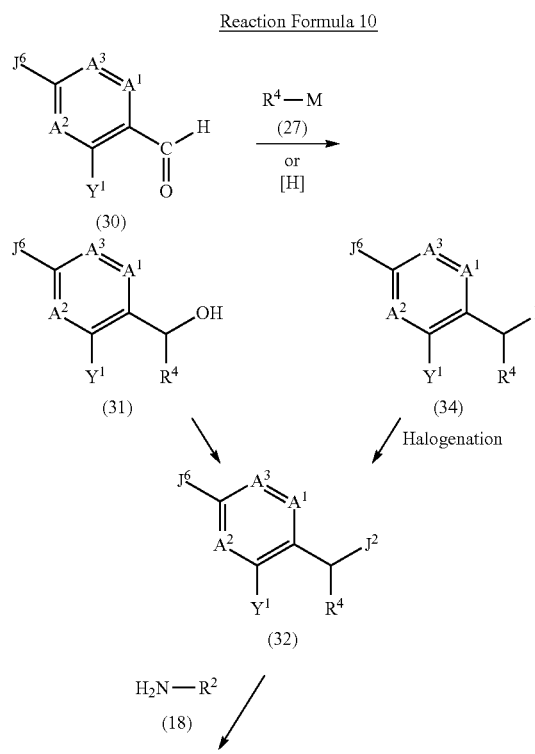

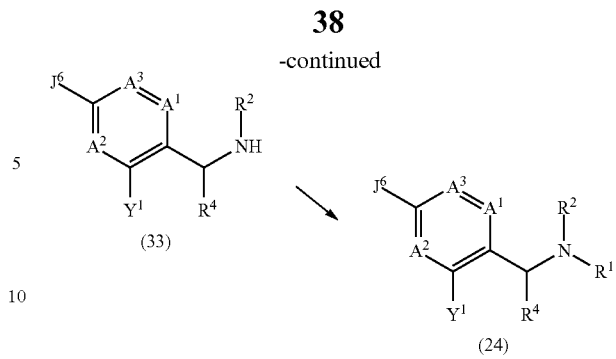

By reacting a compound of General Formula (32) (where $A^1, A^2, A^3, Y^1, R^4, J^2$ and $J^6$ are the same as the respective definitions in the above) which is obtained by reacting a known compound of General Formula (30) (where $A^1, A^2, A^3, Y^1$ and $J^6$ are the same as the respective definitions in the above) in substantially the same manner as that in Reaction Formula 8, and the compound of General Formula (18) (where $R^2$ is the same as the definition in the above) under substantially the same condition as that in Reaction Formula 1, a compound of General Formula (33) (where $A^1, A^2, A^3, Y^1, R^2, R^4$ and $J^6$ are the same as the respective definitions in the above) can be synthesized, By reacting the compound of General Formula (33) obtained in this manner in substantially the same manner as that in Production Method A to Production Method H, the compound of General Formula (24) (where $A^1, A^2, A^3, Y^1, R^1, R^2, R^4$ and $J^6$ are the same as the respective definitions in the above) can be synthesized.

Reaction Formula 11

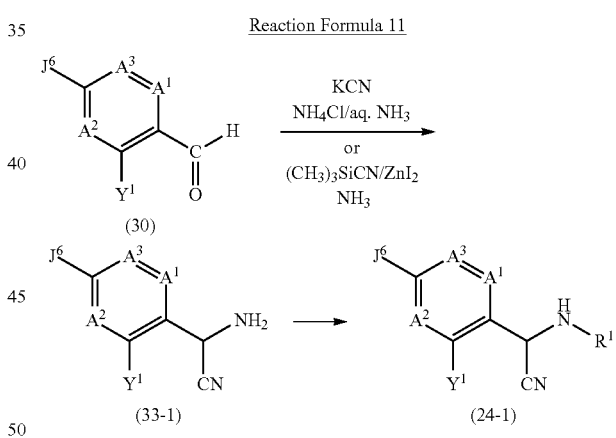

By reacting the known compound of General Formula (30) (where $A^1, A^2, A^3, Y^1$ and $J^6$ are the same as the respective definitions in the above) in substantially the same manner as that in Reaction Formula 5, a compound of General Formula (33-1) (where $A^1, A^2, A^3, Y^1$ and $J^6$ are the same as the respective definitions in the above) corresponding to General Formula (33) in which $R^2$ is a hydrogen atom and $R^4$ is cyano is obtained. By reacting the compound of General Formula (33-1) in substantially the same manner as that in Production Method A to Production Method H, a compound of General Formula (24-1) (where $A^1, A^2, A^3, Y^1, R^1$ and $J^6$ are the same as the respective definitions in the above) corresponding to General Formula (24) in which $R^2$ is a hydrogen atom and $R^4$ is cyano can be synthesized.

The compound of General Formula (29) used in Reaction Formula 9 can be synthesized, for example, as follows.

Reaction Formula 12

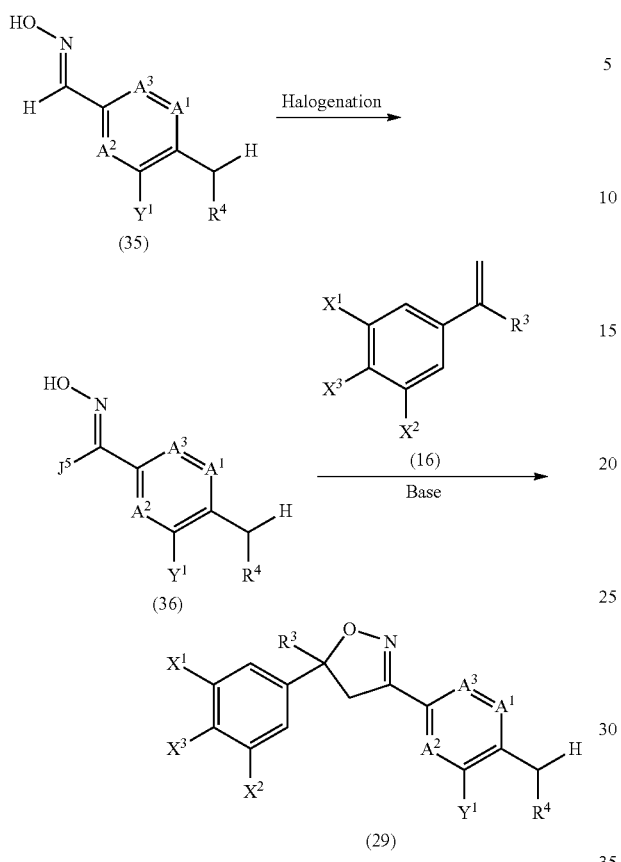

That is, by reacting a compound of General Formula (35) (where $A^1$, $A^2$, $A^3$, $Y^1$ and $R^4$ are the same as the respective definitions in the above) in substantially the same manner as that in Production Method I, the compound of General Formula (29) (where $A^1$, $A^2$, $A^3$, $X^1$, $X^2$, $X^3$, $Y^1$, $R^3$ and $R^4$ are the same as the respective definitions in the above) can be synthesized.

Some of the compounds of General Formula (35) used here are known compounds, and some of them are commercially available. Furthermore, the others can be readily synthesized according to general synthetic methods of the known compounds described in the literatures.

In each of the reactions, each of the production intermediates to be the starting materials of Production Method A to Production Method C and Production Method I can be obtained by common aftertreatment after the completion of the reaction.

Furthermore, each of the production intermediates produced by these methods may be used in a reaction of the next process as they are without isolation and purification.

Specific examples of the active compounds included in the present invention include compounds shown in Table 2. However, the compounds in Table 2 are only for exemplification, and the present invention is not intended to be limited to these compounds.

Here, in Table, the substituent expressed as Et is an ethyl group, n-Pr and Pr-n are a normal propyl group, i-Pr and Pr-i are an isopropyl group, c-Pr and Pr-c are a cyclopropyl group, n-Bu and Bu-n are a normal butyl group, s-Bu and Bu-s are a secondary butyl group, i-Bu and Bu-i are an isobutyl group, t-Bu and Bu-t are a tertiary butyl group, and Ph is a phenyl group, in Table, the substituents expressed as D-7-1a to D-14-1a are individually an aromatic heterocyclic group of Structure Formula:

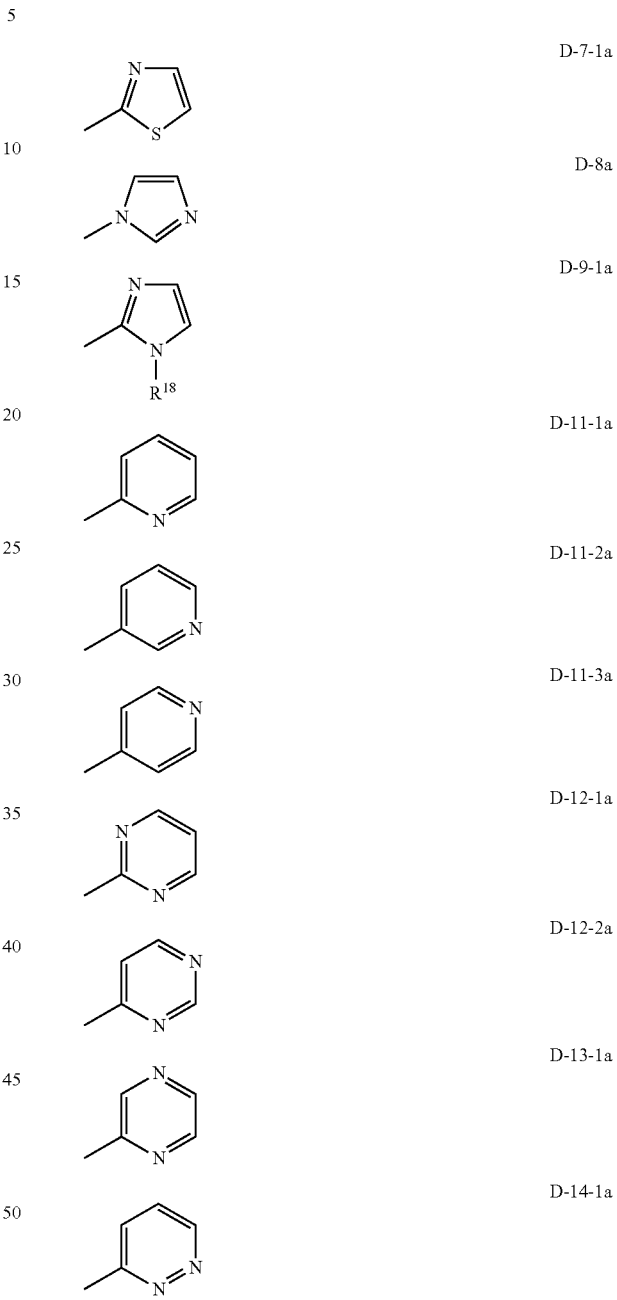

for example, the expression (C(O)CH$_2$S(D-9-1a)CH$_3$) is an (N methylimidazol-2-ylthio)acetyl group, in Table, the substituents expressed as E-1-1a to E-6-1a are individually a saturated heterocyclic group of Structure Formula:

-continued
E-1-1b 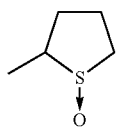
E-1-1c 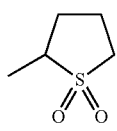
E-2-1a 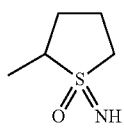
E-1-2a 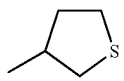
E-1-2b 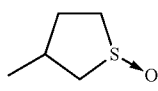
E-1-2c 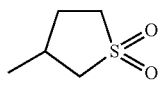
E-2-2a 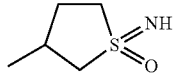
E-5-1a 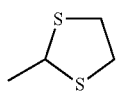
E-3-1a
E-3-1b 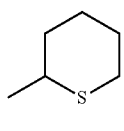
E-3-1c 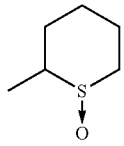
E-4-1a 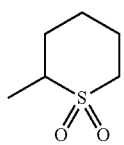
E-3-2a 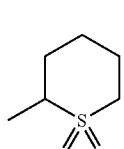
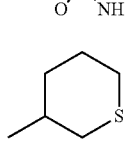
E-3-2b 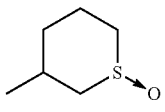
E-3-2c 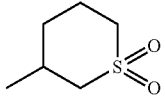
E-4-2a 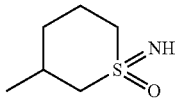
E-3-3a 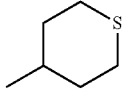
E-3-3b 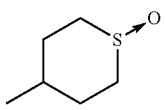
E-3-3c 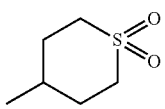
E-4-3a 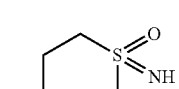
E-6-1a 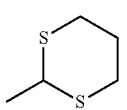
for example, the expression (C(O)(E-1-1a) is a 2-tetrahydrothienylcarbonyl group.
Furthermore, in Table, the substituents expressed as T-1 to T-4 are substituents of Structure Formulae:
T-1: 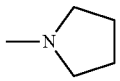
T-2: 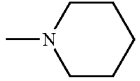
T-3: 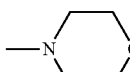
T-4: 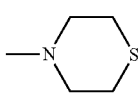
Table 2
In Table, the substituents $X^1$, $X^2$ and $X^3$ in the compound of the present invention of General Formula (1) are $(X)_m$, and each of the numbers representing the substituted sites of $X^1$, $X^2$ and $X^3$ corresponds to the site indicated by the number in Structure Formulae:
[1]-1
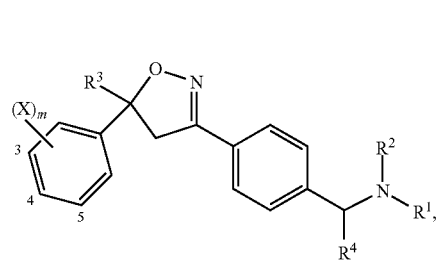
[1]-2
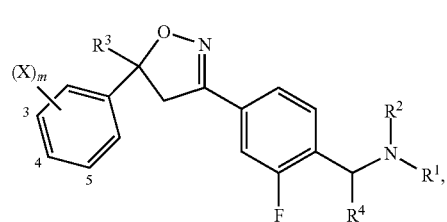
[1]-3
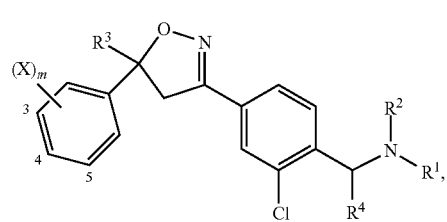
[1]-4
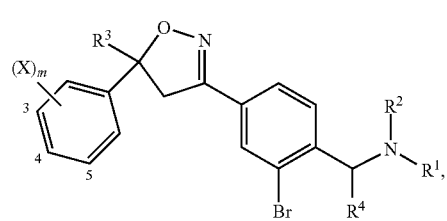
[1]-5
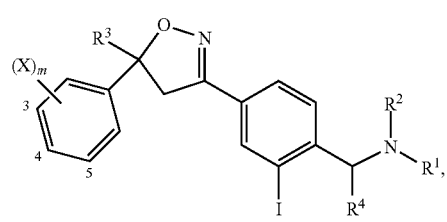
[1]-6
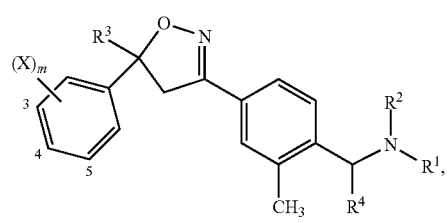
[1]-7
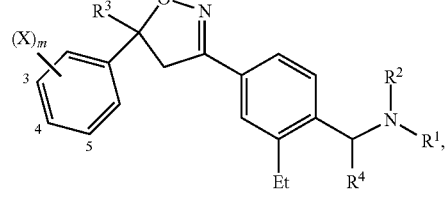
-continued
[1]-8
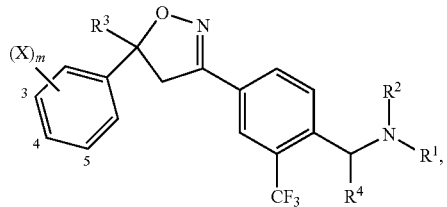
[1]-9
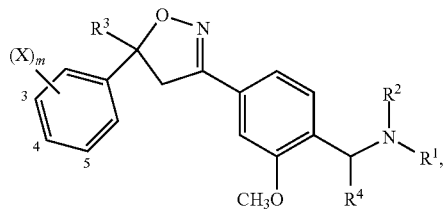
[1]-10
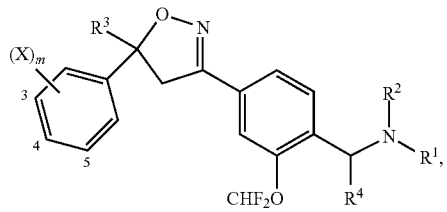
[1]-11
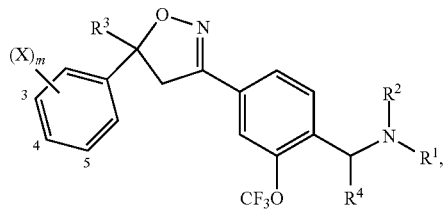
[1]-12
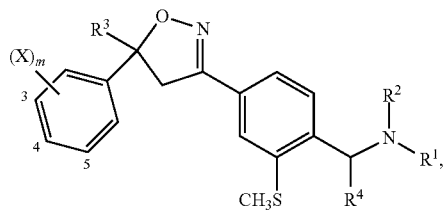
[1]-13
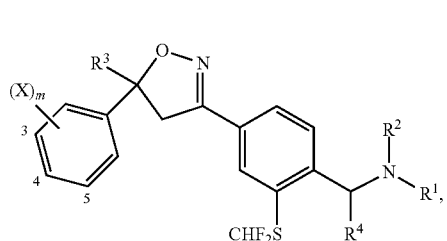
[1]-14
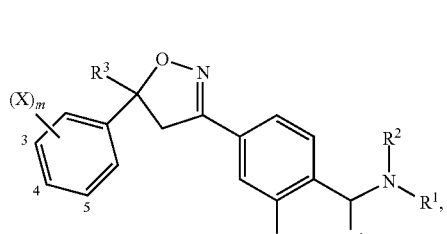

[1]-15
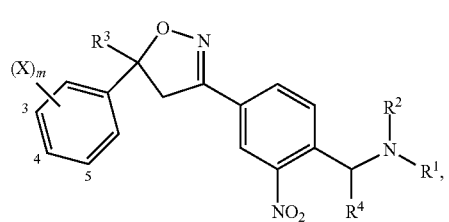
[1]-16
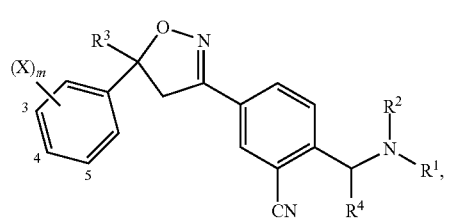
[1]-17
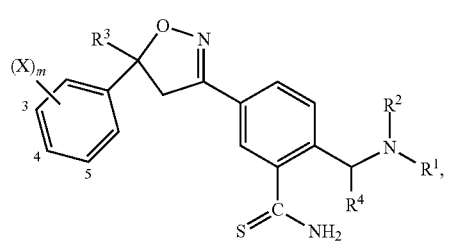
[1]-18
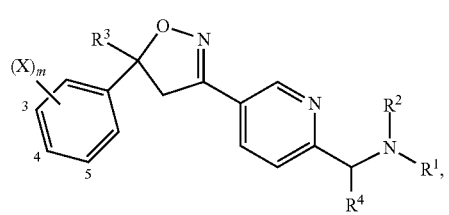
[1]-19
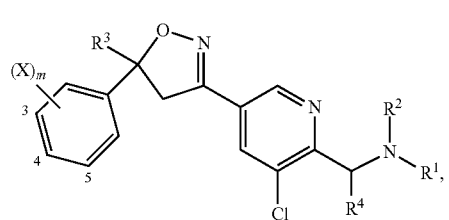
[1]-20
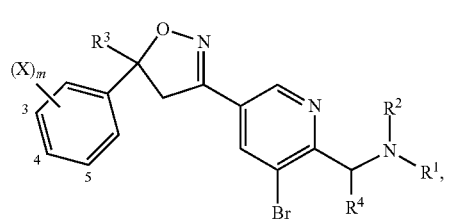
[1]-21
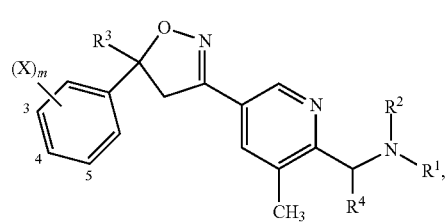
[1]-22
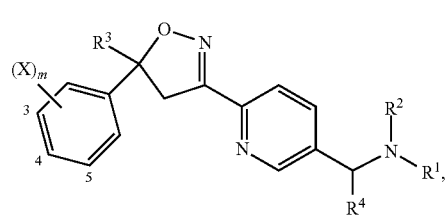
[1]-23
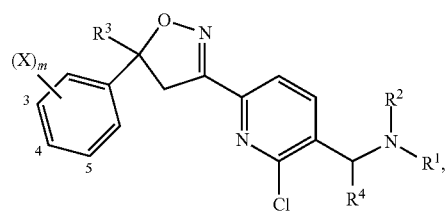
[1]-24
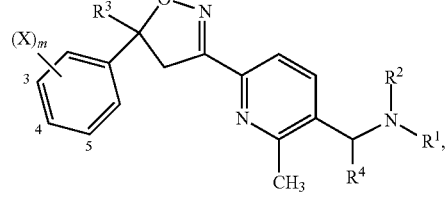
[1]-25
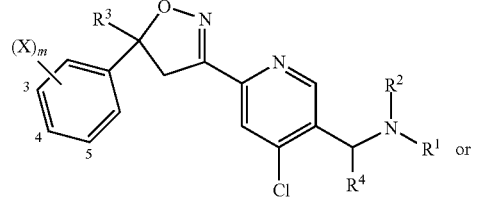
or
[1]-26
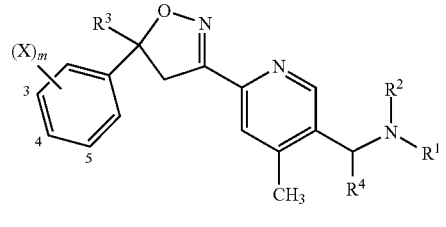
| $(X)_m$ | $R^3$ | $R^4$ | $R^2$ | $R^1$ |
|---|---|---|---|---|
| 3-Cl | $CF_3$ | H | H | $C(O)CH_2SCH_3$ |
| 3-Cl | $CF_3$ | H | H | $C(O)CH_2S(O)CH_3$ |
| 3-Cl | $CF_3$ | H | H | $C(O)CH_2SO_2CH_3$ |
| 3-Cl | $CF_3$ | H | H | $C(O)CH_2SEt$ |
| 3-Cl | $CF_3$ | H | H | $C(O)CH_2S(O)Et$ |
| 3-Cl | $CF_3$ | H | H | $C(O)CH_2SO_2Et$ |
| 3-Br | $CF_3$ | H | H | $C(O)CH_2SCH_3$ |
| 3-Br | $CF_3$ | H | H | $C(O)CH_2S(O)CH_3$ |
| 3-Br | $CF_3$ | H | H | $C(O)CH_2SO_2CH_3$ |

-continued

| (X)$_m$ | R$^3$ | R$^4$ | R$^2$ | R$^1$ |
|---|---|---|---|---|
| 3-Br | CF$_3$ | H | H | C(O)CH$_2$SEt |
| 3-Br | CF$_3$ | H | H | C(O)CH$_2$S(O)Et |
| 3-Br | CF$_3$ | H | H | C(O)CH$_2$SO$_2$Et |
| 3-Br | CF$_3$ | H | H | C(S)CH$_2$SCH$_3$ |
| 3-Br | CF$_3$ | H | H | C(S)CH$_2$SO$_2$CH$_3$ |
| 3-Br | CF$_3$ | H | H | C(S)CH$_2$SEt |
| 3-Br | CF$_3$ | H | H | C(S)CH$_2$SO$_2$Et |
| 3-I | CF$_3$ | H | H | C(O)CH$_2$SCH$_3$ |
| 3-I | CF$_3$ | H | H | C(O)CH$_2$S(O)CH$_3$ |
| 3-I | CF$_3$ | H | H | C(O)CH$_2$SO$_2$CH$_3$ |
| 3-I | CF$_3$ | H | H | C(O)CH$_2$SEt |
| 3-I | CF$_3$ | H | Et | C(O)CH$_2$SEt |
| 3-I | CF$_3$ | H | CH$_2$C≡CH | C(O)CH$_2$SEt |
| 3-I | CF$_3$ | H | H | C(O)CH$_2$S(O)Et |
| 3-I | CF$_3$ | H | H | C(O)CH$_2$SO$_2$Et |
| 3-I | CF$_3$ | H | H | C(O)CH(CH$_3$)SCH$_3$ |
| 3-I | CF$_3$ | H | H | C(O)(E-1-1a) |
| 3-I | CF$_3$ | H | H | C(O)(E-1-1b) |
| 3-I | CF$_3$ | H | H | C(O)(E-1-1c) |
| 3-I | CF$_3$ | H | H | C(O)CH(SCH$_3$)$_2$ |
| 3-I | CF$_3$ | H | H | C(O)CH[S(O)CH$_3$]$_2$ |
| 3-I | CF$_3$ | H | H | C(O)CH(SEt)$_2$ |
| 3-I | CF$_3$ | H | H | C(O)CH(SEt)S(O)Et |
| 3-I | CF$_3$ | H | H | C(S)CH$_2$SCH$_3$ |
| 3-I | CF$_3$ | H | H | C(S)CH$_2$SO$_2$CH$_3$ |
| 3-I | CF$_3$ | H | H | C(S)CH$_2$SEt |
| 3-I | CF$_3$ | H | H | C(S)CH$_2$SO$_2$Et |
| 3-I | CF$_2$Cl | H | H | C(O)CH$_2$SCH$_3$ |
| 3-I | CF$_2$Cl | H | H | C(O)CH$_2$S(O)CH$_3$ |
| 3-I | CF$_2$Cl | H | H | C(O)CH$_2$SO$_2$CH$_3$ |
| 3-I | CF$_2$Cl | H | H | C(O)CH$_2$SEt |
| 3-I | CF$_2$Cl | H | H | C(O)CH$_2$S(O)Et |
| 3-I | CF$_2$Cl | H | H | C(O)CH$_2$SO$_2$Et |
| 3-CF$_3$ | CF$_3$ | H | H | C(O)CH$_2$SCH$_3$ |
| 3-CF$_3$ | CF$_3$ | H | H | C(O)CH$_2$S(O)CH$_3$ |
| 3-CF$_3$ | CF$_3$ | H | H | C(O)CH$_2$SO$_2$CH$_3$ |
| 3-CF$_3$ | CF$_3$ | H | H | C(O)CH$_2$SEt |
| 3-CF$_3$ | CF$_3$ | H | Et | C(O)CH$_2$SEt |
| 3-CF$_3$ | CF$_3$ | H | CH$_2$C≡CH | C(O)CH$_2$SEt |
| 3-CF$_3$ | CF$_3$ | H | H | C(O)CH$_2$S(O)Et |
| 3-CF$_3$ | CF$_3$ | H | H | C(O)CH$_2$SO$_2$Et |
| 3-CF$_3$ | CF$_3$ | H | H | C(O)CH(CH$_3$)SCH$_3$ |
| 3-CF$_3$ | CF$_3$ | H | H | C(O)(E-1-1a) |
| 3-CF$_3$ | CF$_3$ | H | H | C(O)(E-1-1b) |
| 3-CF$_3$ | CF$_3$ | H | H | C(O)(E-1-1c) |
| 3-CF$_3$ | CF$_3$ | H | H | C(O)CH(SCH$_3$)$_2$ |
| 3-CF$_3$ | CF$_3$ | H | H | C(O)CH[S(O)CH$_3$]$_2$ |
| 3-CF$_3$ | CF$_3$ | H | H | C(O)CH(SEt)$_2$ |
| 3-CF$_3$ | CF$_3$ | H | H | C(O)CH(SEt)S(O)Et |
| 3-CF$_3$ | CF$_3$ | H | H | C(S)CH$_2$SCH$_3$ |
| 3-CF$_3$ | CF$_3$ | H | H | C(S)CH$_2$SO$_2$CH$_3$ |
| 3-CF$_3$ | CF$_3$ | H | H | C(S)CH$_2$SEt |
| 3-CF$_3$ | CF$_3$ | H | H | C(S)CH$_2$SO$_2$Et |
| 3-CF$_3$ | CF$_2$Cl | H | H | C(O)CH$_2$SCH$_3$ |
| 3-CF$_3$ | CF$_2$Cl | H | H | C(O)CH$_2$S(O)CH$_3$ |
| 3-CF$_3$ | CF$_2$Cl | H | H | C(O)CH$_2$SO$_2$CH$_3$ |
| 3-CF$_3$ | CF$_2$Cl | H | H | C(O)CH$_2$SEt |
| 3-CF$_3$ | CF$_2$Cl | H | H | C(O)CH$_2$S(O)Et |
| 3-CF$_3$ | CF$_2$Cl | H | H | C(O)CH$_2$SO$_2$Et |
| 3-CF$_2$CF$_3$ | CF$_3$ | H | H | C(O)CH$_2$SCH$_3$ |
| 3-CF$_2$CF$_3$ | CF$_3$ | H | H | C(O)CH$_2$S(O)CH$_3$ |
| 3-CF$_2$CF$_3$ | CF$_3$ | H | H | C(O)CH$_2$SO$_2$CH$_3$ |
| 3-CF$_2$CF$_3$ | CF$_3$ | H | H | C(O)CH$_2$SEt |
| 3-CF$_2$CF$_3$ | CF$_3$ | H | H | C(O)CH$_2$S(O)Et |
| 3-CF$_2$CF$_3$ | CF$_3$ | H | H | C(O)CH$_2$SO$_2$Et |
| 3-CF$_2$CF$_3$ | CF$_3$ | H | H | C(S)CH$_2$SCH$_3$ |
| 3-CF$_2$CF$_3$ | CF$_3$ | H | H | C(S)CH$_2$SO$_2$CH$_3$ |
| 3-CF$_2$CF$_3$ | CF$_3$ | H | H | C(S)CH$_2$SEt |
| 3-CF$_2$CF$_3$ | CF$_3$ | H | H | C(S)CH$_2$SO$_2$Et |
| 3-CF$_2$CF$_2$CF$_3$ | CF$_3$ | H | H | C(O)CH$_2$SCH$_3$ |
| 3-CF$_2$CF$_2$CF$_3$ | CF$_3$ | H | H | C(O)CH$_2$S(O)CH$_3$ |
| 3-CF$_2$CF$_2$CF$_3$ | CF$_3$ | H | H | C(O)CH$_2$SO$_2$CH$_3$ |
| 3-CF$_2$CF$_2$CF$_3$ | CF$_3$ | H | H | C(O)CH$_2$SEt |
| 3-CF$_2$CF$_2$CF$_3$ | CF$_3$ | H | H | C(O)CH$_2$S(O)Et |
| 3-CF$_2$CF$_2$CF$_3$ | CF$_3$ | H | H | C(O)CH$_2$SO$_2$Et |
| 3-CF(CF$_3$)$_2$ | CF$_3$ | H | H | C(O)CH$_2$SCH$_3$ |
| 3-CF(CF$_3$)$_2$ | CF$_3$ | H | H | C(O)CH$_2$S(O)CH$_3$ |
| 3-CF(CF$_3$)$_2$ | CF$_3$ | H | H | C(O)CH$_2$SO$_2$CH$_3$ |

-continued

| (X)$_m$ | R$^3$ | R$^4$ | R$^2$ | R$^1$ |
|---|---|---|---|---|
| 3-CF(CF$_3$)$_2$ | CF$_3$ | H | H | C(O)CH$_2$SEt |
| 3-CF(CF$_3$)$_2$ | CF$_3$ | H | H | C(O)CH$_2$S(O)Et |
| 3-CF(CF$_3$)$_2$ | CF$_3$ | H | H | C(O)CH$_2$SO$_2$Et |
| 3-OCF$_3$ | CF$_3$ | H | H | C(O)CH$_2$SCH$_3$ |
| 3-OCF$_3$ | CF$_3$ | H | H | C(O)CH$_2$S(O)CH$_3$ |
| 3-OCF$_3$ | CF$_3$ | H | H | C(O)CH$_2$SO$_2$CH$_3$ |
| 3-OCF$_3$ | CF$_3$ | H | H | C(O)CH$_2$SEt |
| 3-OCF$_3$ | CF$_3$ | H | H | C(O)CH$_2$S(O)Et |
| 3-OCF$_3$ | CF$_3$ | H | H | C(O)CH$_2$SO$_2$Et |
| 3-OCF$_3$ | CF$_3$ | H | H | C(S)CH$_2$SCH$_3$ |
| 3-OCF$_3$ | CF$_3$ | H | H | C(S)CH$_2$SO$_2$CH$_3$ |
| 3-OCF$_3$ | CF$_3$ | H | H | C(S)CH$_2$SEt |
| 3-OCF$_3$ | CF$_3$ | H | H | C(S)CH$_2$SO$_2$Et |
| 3-OCF$_2$Br | CF$_3$ | H | H | C(O)CH$_2$SCH$_3$ |
| 3-OCF$_2$Br | CF$_3$ | H | H | C(O)CH$_2$S(O)CH$_3$ |
| 3-OCF$_2$Br | CF$_3$ | H | H | C(O)CH$_2$SO$_2$CH$_3$ |
| 3-OCF$_2$Br | CF$_3$ | H | H | C(O)CH$_2$SEt |
| 3-OCF$_2$Br | CF$_3$ | H | H | C(O)CH$_2$S(O)Et |
| 3-OCF$_2$Br | CF$_3$ | H | H | C(O)CH$_2$SO$_2$Et |
| 3-SCF$_3$ | CF$_3$ | H | H | C(O)CH$_2$SCH$_3$ |
| 3-SCF$_3$ | CF$_3$ | H | H | C(O)CH$_2$S(O)CH$_3$ |
| 3-SCF$_3$ | CF$_3$ | H | H | C(O)CH$_2$SO$_2$CH$_3$ |
| 3-SCF$_3$ | CF$_3$ | H | H | C(O)CH$_2$SEt |
| 3-SCF$_3$ | CF$_3$ | H | H | C(O)CH$_2$S(O)Et |
| 3-SCF$_3$ | CF$_3$ | H | H | C(O)CH$_2$SO$_2$Et |
| 3-SCF$_3$ | CF$_3$ | H | H | C(S)CH$_2$SCH$_3$ |
| 3-SCF$_3$ | CF$_3$ | H | H | C(S)CH$_2$SO$_2$CH$_3$ |
| 3-SCF$_3$ | CF$_3$ | H | H | C(S)CH$_2$SEt |
| 3-SCF$_3$ | CF$_3$ | H | H | C(S)CH$_2$SO$_2$Et |
| 3-SCF$_2$Cl | CF$_3$ | H | H | C(O)CH$_2$SCH$_3$ |
| 3-SCF$_2$Cl | CF$_3$ | H | H | C(O)CH$_2$S(O)CH$_3$ |
| 3-SCF$_2$Cl | CF$_3$ | H | H | C(O)CH$_2$SO$_2$CH$_3$ |
| 3-SCF$_2$Cl | CF$_3$ | H | H | C(O)CH$_2$SEt |
| 3-SCF$_2$Cl | CF$_3$ | H | H | C(O)CH$_2$S(O)Et |
| 3-SCF$_2$Cl | CF$_3$ | H | H | C(O)CH$_2$SO$_2$Et |
| 3-SCF$_2$Br | CF$_3$ | H | H | C(O)CH$_2$SCH$_3$ |
| 3-SCF$_2$Br | CF$_3$ | H | H | C(O)CH$_2$S(O)CH$_3$ |
| 3-SCF$_2$Br | CF$_3$ | H | H | C(O)CH$_2$SO$_2$CH$_3$ |
| 3-SCF$_2$Br | CF$_3$ | H | H | C(O)CH$_2$SEt |
| 3-SCF$_2$Br | CF$_3$ | H | H | C(O)CH$_2$S(O)Et |
| 3-SCF$_2$Br | CF$_3$ | H | H | C(O)CH$_2$SO$_2$Et |
| 3-SF$_5$ | CF$_3$ | H | H | C(O)CH$_2$SCH$_3$ |
| 3-SF$_5$ | CF$_3$ | H | H | C(O)CH$_2$S(O)CH$_3$ |
| 3-SF$_5$ | CF$_3$ | H | H | C(O)CH$_2$SO$_2$CH$_3$ |
| 3-SF$_5$ | CF$_3$ | H | H | C(O)CH$_2$SEt |
| 3-SF$_5$ | CF$_3$ | H | H | C(O)CH$_2$S(O)Et |
| 3-SF$_5$ | CF$_3$ | H | H | C(O)CH$_2$SO$_2$Et |
| 3-SF$_5$ | CF$_3$ | H | H | C(S)CH$_2$SCH$_3$ |
| 3-SF$_5$ | CF$_3$ | H | H | C(S)CH$_2$SO$_2$CH$_3$ |
| 3-SF$_5$ | CF$_3$ | H | H | C(S)CH$_2$SEt |
| 3-SF$_5$ | CF$_3$ | H | H | C(S)CH$_2$SO$_2$Et |
| 3-Cl-4-F | CF$_3$ | H | H | C(O)CH$_2$SCH$_3$ |
| 3-Cl-4-F | CF$_3$ | H | H | C(O)CH$_2$S(O)CH$_3$ |
| 3-Cl-4-F | CF$_3$ | H | H | C(O)CH$_2$SO$_2$CH$_3$ |
| 3-Cl-4-F | CF$_3$ | H | H | C(O)CH$_2$SEt |
| 3-Cl-4-F | CF$_3$ | H | Et | C(O)CH$_2$SEt |
| 3-Cl-4-F | CF$_3$ | H | CH$_2$C≡CH | C(O)CH$_2$SEt |
| 3-Cl-4-F | CF$_3$ | H | H | C(O)CH$_2$S(O)Et |
| 3-Cl-4-F | CF$_3$ | H | H | C(O)CH$_2$SO$_2$Et |
| 3-Cl-4-F | CF$_3$ | H | H | C(O)CH(CH$_3$)SCH$_3$ |
| 3-Cl-4-F | CF$_3$ | H | H | C(O)(E-1-1a) |
| 3-Cl-4-F | CF$_3$ | H | H | C(O)(E-1-1b) |
| 3-Cl-4-F | CF$_3$ | H | H | C(O)(E-1-1c) |
| 3-Cl-4-F | CF$_3$ | H | H | C(O)CH(SCH$_3$)$_2$ |
| 3-Cl-4-F | CF$_3$ | H | H | C(O)CH[S(O)CH$_3$]$_2$ |
| 3-Cl-4-F | CF$_3$ | H | H | C(O)CH(SEt)$_2$ |
| 3-Cl-4-F | CF$_3$ | H | H | C(O)CH(SEt)S(O)Et |
| 3-Cl-4-F | CF$_3$ | H | H | C(S)CH$_2$SCH$_3$ |
| 3-Cl-4-F | CF$_3$ | H | H | C(S)CH$_2$SO$_2$CH$_3$ |
| 3-Cl-4-F | CF$_3$ | H | H | C(S)CH$_2$SEt |
| 3-Cl-4-F | CF$_3$ | H | H | C(S)CH$_2$SO$_2$Et |
| 3-Cl-4-F | CF$_2$Cl | H | H | C(O)CH$_2$SCH$_3$ |
| 3-Cl-4-F | CF$_2$Cl | H | H | C(O)CH$_2$S(O)CH$_3$ |
| 3-Cl-4-F | CF$_2$Cl | H | H | C(O)CH$_2$SO$_2$CH$_3$ |
| 3-Cl-4-F | CF$_2$Cl | H | H | C(O)CH$_2$SEt |
| 3-Cl-4-F | CF$_2$Cl | H | H | C(O)CH$_2$S(O)Et |
| 3-Cl-4-F | CF$_2$Cl | H | H | C(O)CH$_2$SO$_2$Et |
| 3-F-5-Cl | CF$_3$ | H | H | C(O)CH$_2$SCH$_3$ |

| (X)$_m$ | R$^3$ | R$^4$ | R$^2$ | R$^1$ |
|---|---|---|---|---|
| 3-F-5-Cl | CF$_3$ | H | H | C(O)CH$_2$S(O)CH$_3$ |
| 3-F-5-Cl | CF$_3$ | H | H | C(O)CH$_2$SO$_2$CH$_3$ |
| 3-F-5-Cl | CF$_3$ | H | H | C(O)CH$_2$SEt |
| 3-F-5-Cl | CF$_3$ | H | Et | C(O)CH$_2$SEt |
| 3-F-5-Cl | CF$_3$ | H | CH$_2$C≡CH | C(O)CH$_2$SEt |
| 3-F-5-Cl | CF$_3$ | H | H | C(O)CH$_2$S(O)Et |
| 3-F-5-Cl | CF$_3$ | H | H | C(O)CH$_2$SO$_2$Et |
| 3-F-5-Cl | CF$_3$ | H | H | C(O)CH(CH$_3$)SCH$_3$ |
| 3-F-5-Cl | CF$_3$ | H | H | C(O)(E-1-1a) |
| 3-F-5-Cl | CF$_3$ | H | H | C(O)(E-1-1b) |
| 3-F-5-Cl | CF$_3$ | H | H | C(O)(E-1-1c) |
| 3-F-5-Cl | CF$_3$ | H | H | C(O)CH(SCH$_3$)$_2$ |
| 3-F-5-Cl | CF$_3$ | H | H | C(O)CH[S(O)CH$_3$]$_2$ |
| 3-F-5-Cl | CF$_3$ | H | H | C(O)CH(SEt)$_2$ |
| 3-F-5-Cl | CF$_3$ | H | H | C(O)CH(SEt)S(O)Et |
| 3-F-5-Cl | CF$_3$ | H | H | C(S)CH$_2$SCH$_3$ |
| 3-F-5-Cl | CF$_3$ | H | H | C(S)CH$_2$SO$_2$CH$_3$ |
| 3-F-5-Cl | CF$_3$ | H | H | C(S)CH$_2$SEt |
| 3-F-5-Cl | CF$_3$ | H | H | C(S)CH$_2$SO$_2$Et |
| 3-F-5-Cl | CF$_2$Cl | H | H | C(O)CH$_2$SCH$_3$ |
| 3-F-5-Cl | CF$_2$Cl | H | H | C(O)CH$_2$S(O)CH$_3$ |
| 3-F-5-Cl | CF$_2$Cl | H | H | C(O)CH$_2$SO$_2$CH$_3$ |
| 3-F-5-Cl | CF$_2$Cl | H | H | C(O)CH$_2$SEt |
| 3-F-5-Cl | CF$_2$Cl | H | H | C(O)CH$_2$S(O)Et |
| 3-F-5-Cl | CF$_2$Cl | H | H | C(O)CH$_2$SO$_2$Et |
| 3,4-Cl$_2$ | CF$_3$ | H | H | C(O)CH$_2$SCH$_3$ |
| 3,4-Cl$_2$ | CF$_3$ | H | H | C(O)CH$_2$S(O)CH$_3$ |
| 3,4-Cl$_2$ | CF$_3$ | H | H | C(O)CH$_2$SO$_2$CH$_3$ |
| 3,4-Cl$_2$ | CF$_3$ | H | H | C(O)CH$_2$SEt |
| 3,4-Cl$_2$ | CF$_3$ | H | Et | C(O)CH$_2$SEt |
| 3,4-Cl$_2$ | CF$_3$ | H | CH$_2$C≡CH | C(O)CH$_2$SEt |
| 3,4-Cl$_2$ | CF$_3$ | H | H | C(O)CH$_2$S(O)Et |
| 3,4-Cl$_2$ | CF$_3$ | H | H | C(O)CH$_2$SO$_2$Et |
| 3,4-Cl$_2$ | CF$_3$ | H | H | C(O)CH(CH$_3$)SCH$_3$ |
| 3,4-Cl$_2$ | CF$_3$ | H | H | C(O)(E-1-1a) |
| 3,4-Cl$_2$ | CF$_3$ | H | H | C(O)(E-1-1b) |
| 3,4-Cl$_2$ | CF$_3$ | H | H | C(O)(E-1-1c) |
| 3,4-Cl$_2$ | CF$_3$ | H | H | C(O)CH(SCH$_3$)$_2$ |
| 3,4-Cl$_2$ | CF$_3$ | H | H | C(O)CH[S(O)CH$_3$]$_2$ |
| 3,4-Cl$_2$ | CF$_3$ | H | H | C(O)CH(SEt)$_2$ |
| 3,4-Cl$_2$ | CF$_3$ | H | H | C(O)CH(SEt)S(O)Et |
| 3,4-Cl$_2$ | CF$_3$ | H | H | C(S)CH$_2$SCH$_3$ |
| 3,4-Cl$_2$ | CF$_3$ | H | H | C(S)CH$_2$SO$_2$CH$_3$ |
| 3,4-Cl$_2$ | CF$_3$ | H | H | C(S)CH$_2$SEt |
| 3,4-Cl$_2$ | CF$_3$ | H | H | C(S)CH$_2$SO$_2$Et |
| 3,4-Cl$_2$ | CF$_2$Cl | H | H | C(O)CH$_2$SCH$_3$ |
| 3,4-Cl$_2$ | CF$_2$Cl | H | H | C(O)CH$_2$S(O)CH$_3$ |
| 3,4-Cl$_2$ | CF$_2$Cl | H | H | C(O)CH$_2$SO$_2$CH$_3$ |
| 3,4-Cl$_2$ | CF$_2$Cl | H | H | C(O)CH$_2$SEt |
| 3,4-Cl$_2$ | CF$_2$Cl | H | H | C(O)CH$_2$S(O)Et |
| 3,4-Cl$_2$ | CF$_2$Cl | H | H | C(O)CH$_2$SO$_2$Et |
| 3-Br-4-F | CF$_3$ | H | H | C(O)CH$_2$SCH$_3$ |
| 3-Br-4-F | CF$_3$ | H | H | C(O)CH$_2$S(O)CH$_3$ |
| 3-Br-4-F | CF$_3$ | H | H | C(O)CH$_2$SO$_2$CH$_3$ |
| 3-Br-4-F | CF$_3$ | H | H | C(O)CH$_2$SEt |
| 3-Br-4-F | CF$_3$ | H | Et | C(O)CH$_2$SEt |
| 3-Br-4-F | CF$_3$ | H | CH$_2$C≡CH | C(O)CH$_2$SEt |
| 3-Br-4-F | CF$_3$ | H | H | C(O)CH$_2$S(O)Et |
| 3-Br-4-F | CF$_3$ | H | H | C(O)CH$_2$SO$_2$Et |
| 3-Br-4-F | CF$_3$ | H | H | C(O)CH(CH$_3$)SCH$_3$ |
| 3-Br-4-F | CF$_3$ | H | H | C(O)(E-1-1a) |
| 3-Br-4-F | CF$_3$ | H | H | C(O)(E-1-1b) |
| 3-Br-4-F | CF$_3$ | H | H | C(O)(E-1-1c) |
| 3-Br-4-F | CF$_3$ | H | H | C(O)CH(SCH$_3$)$_2$ |
| 3-Br-4-F | CF$_3$ | H | H | C(O)CH[S(O)CH$_3$]$_2$ |
| 3-Br-4-F | CF$_3$ | H | H | C(O)CH(SEt)$_2$ |
| 3-Br-4-F | CF$_3$ | H | H | C(O)CH(SEt)S(O)Et |
| 3-Br-4-F | CF$_3$ | H | H | C(S)CH$_2$SCH$_3$ |
| 3-Br-4-F | CF$_3$ | H | H | C(S)CH$_2$SO$_2$CH$_3$ |
| 3-Br-4-F | CF$_3$ | H | H | C(S)CH$_2$SEt |
| 3-Br-4-F | CF$_3$ | H | H | C(S)CH$_2$SO$_2$Et |
| 3-Br-4-F | CF$_2$Cl | H | H | C(O)CH$_2$SCH$_3$ |
| 3-Br-4-F | CF$_2$Cl | H | H | C(O)CH$_2$S(O)CH$_3$ |
| 3-Br-4-F | CF$_2$Cl | H | H | C(O)CH$_2$SO$_2$CH$_3$ |
| 3-Br-4-F | CF$_2$Cl | H | H | C(O)CH$_2$SEt |
| 3-Br-4-F | CF$_2$Cl | H | H | C(O)CH$_2$S(O)Et |
| 3-Br-4-F | CF$_2$Cl | H | H | C(O)CH$_2$SO$_2$Et |
| 3-F-5-Br | CF$_3$ | H | H | C(O)CH$_2$SCH$_3$ |

-continued

| (X)$_m$ | R$^3$ | R$^4$ | R$^2$ | R$^1$ |
|---|---|---|---|---|
| 3-F-5-Br | CF$_3$ | H | H | C(O)CH$_2$S(O)CH$_3$ |
| 3-F-5-Br | CF$_3$ | H | H | C(O)CH$_2$SO$_2$CH$_3$ |
| 3-F-5-Br | CF$_3$ | H | H | C(O)CH$_2$SEt |
| 3-F-5-Br | CF$_3$ | H | Et | C(O)CH$_2$SEt |
| 3-F-5-Br | CF$_3$ | H | CH$_2$C≡CH | C(O)CH$_2$SEt |
| 3-F-5-Br | CF$_3$ | H | H | C(O)CH$_2$S(O)Et |
| 3-F-5-Br | CF$_3$ | H | H | C(O)CH$_2$SO$_2$Et |
| 3-F-5-Br | CF$_3$ | H | H | C(O)CH(CH$_3$)SCH$_3$ |
| 3-F-5-Br | CF$_3$ | H | H | C(O)(E-1-1a) |
| 3-F-5-Br | CF$_3$ | H | H | C(O)(E-1-1b) |
| 3-F-5-Br | CF$_3$ | H | H | C(O)(E-1-1c) |
| 3-F-5-Br | CF$_3$ | H | H | C(O)CH(SCH$_3$)$_2$ |
| 3-F-5-Br | CF$_3$ | H | H | C(O)CH[S(O)CH$_3$]$_2$ |
| 3-F-5-Br | CF$_3$ | H | H | C(O)CH(SEt)$_2$ |
| 3-F-5-Br | CF$_3$ | H | H | C(O)CH(SEt)S(O)Et |
| 3-F-5-Br | CF$_3$ | H | H | C(S)CH$_2$SCH$_3$ |
| 3-F-5-Br | CF$_3$ | H | H | C(S)CH$_2$SO$_2$CH$_3$ |
| 3-F-5-Br | CF$_3$ | H | H | C(S)CH$_2$SEt |
| 3-F-5-Br | CF$_3$ | H | H | C(S)CH$_2$SO$_2$Et |
| 3-F-5-Br | CF$_2$Cl | H | H | C(O)CH$_2$SCH$_3$ |
| 3-F-5-Br | CF$_2$Cl | H | H | C(O)CH$_2$S(O)CH$_3$ |
| 3-F-5-Br | CF$_2$Cl | H | H | C(O)CH$_2$SO$_2$CH$_3$ |
| 3-F-5-Br | CF$_2$Cl | H | H | C(O)CH$_2$SEt |
| 3-F-5-Br | CF$_2$Cl | H | H | C(O)CH$_2$S(O)Et |
| 3-F-5-Br | CF$_2$Cl | H | H | C(O)CH$_2$SO$_2$Et |
| 3-Br-4-Cl | CF$_3$ | H | H | C(O)CH$_2$SCH$_3$ |
| 3-Br-4-Cl | CF$_3$ | H | H | C(O)CH$_2$S(O)CH$_3$ |
| 3-Br-4-Cl | CF$_3$ | H | H | C(O)CH$_2$SO$_2$CH$_3$ |
| 3-Br-4-Cl | CF$_3$ | H | H | C(O)CH$_2$SEt |
| 3-Br-4-Cl | CF$_3$ | H | H | C(O)CH$_2$S(O)Et |
| 3-Br-4-Cl | CF$_3$ | H | H | C(O)CH$_2$SO$_2$Et |
| 3-Br-4-Cl | CF$_3$ | H | H | C(S)CH$_2$SCH$_3$ |
| 3-Br-4-Cl | CF$_3$ | H | H | C(S)CH$_2$SO$_2$CH$_3$ |
| 3-Br-4-Cl | CF$_3$ | H | H | C(S)CH$_2$SEt |
| 3-Br-4-Cl | CF$_3$ | H | H | C(S)CH$_2$SO$_2$Et |
| 3-Cl-4-Br | CHF$_2$ | H | H | C(O)CH$_2$SCH$_3$ |
| 3-Cl-4-Br | CHF$_2$ | H | H | C(O)CH$_2$S(O)CH$_3$ |
| 3-Cl-4-Br | CHF$_2$ | H | H | C(O)CH$_2$SO$_2$CH$_3$ |
| 3-Cl-4-Br | CHF$_2$ | H | H | C(O)CH$_2$SEt |
| 3-Cl-4-Br | CHF$_2$ | H | H | C(O)CH$_2$S(O)Et |
| 3-Cl-4-Br | CHF$_2$ | H | H | C(O)CH$_2$SO$_2$Et |
| 3-Cl-4-Br | CF$_3$ | H | H | C(O)CH$_2$SO$_2$CH$_3$ |
| 3-Cl-4-Br | CF$_3$ | H | H | C(O)CH$_2$S(O)CH$_3$ |
| 3-Cl-4-Br | CF$_3$ | H | H | C(O)CH$_2$SCH$_3$ |
| 3-Cl-4-Br | CF$_3$ | H | H | C(O)CH$_2$SEt |
| 3-Cl-4-Br | CF$_3$ | H | H | C(O)CH$_2$S(O)Et |
| 3-Cl-4-Br | CF$_3$ | H | H | C(O)CH$_2$SO$_2$Et |
| 3-Cl-4-Br | CF$_3$ | H | H | C(S)CH$_2$SCH$_3$ |
| 3-Cl-4-Br | CF$_3$ | H | H | C(S)CH$_2$SO$_2$CH$_3$ |
| 3-Cl-4-Br | CF$_3$ | H | H | C(S)CH$_2$SEt |
| 3-Cl-4-Br | CF$_3$ | H | H | C(S)CH$_2$SO$_2$Et |
| 3-Cl-5-Br | CF$_3$ | H | H | C(O)CH$_2$SCH$_3$ |
| 3-Cl-5-Br | CF$_3$ | CH$_3$ | H | C(O)CH$_2$SCH$_3$ |
| 3-Cl-5-Br | CF$_3$ | H | Et | C(O)CH$_2$SCH$_3$ |
| 3-Cl-5-Br | CF$_3$ | H | CH$_2$C≡CH | C(O)CH$_2$SCH$_3$ |
| 3-Cl-5-Br | CF$_3$ | H | H | C(O)CH$_2$S(O)CH$_3$ |
| 3-Cl-5-Br | CF$_3$ | CH$_3$ | H | C(O)CH$_2$S(O)CH$_3$ |
| 3-Cl-5-Br | CF$_3$ | H | CH$_3$ | C(O)CH$_2$S(O)CH$_3$ |
| 3-Cl-5-Br | CF$_3$ | H | Et | C(O)CH$_2$S(O)CH$_3$ |
| 3-Cl-5-Br | CF$_3$ | H | CH$_2$C≡CH | C(O)CH$_2$S(O)CH$_3$ |
| 3-Cl-5-Br | CF$_3$ | H | H | C(O)CH$_2$SO$_2$CH$_3$ |
| 3-Cl-5-Br | CF$_3$ | CH$_3$ | H | C(O)CH$_2$SO$_2$CH$_3$ |
| 3-Cl-5-Br | CF$_3$ | H | CH$_3$ | C(O)CH$_2$SO$_2$CH$_3$ |
| 3-Cl-5-Br | CF$_3$ | H | Et | C(O)CH$_2$SO$_2$CH$_3$ |
| 3-Cl-5-Br | CF$_3$ | H | CH$_2$C≡CH | C(O)CH$_2$SO$_2$CH$_3$ |
| 3-Cl-5-Br | CF$_3$ | H | H | C(O)CH$_2$SEt |
| 3-Cl-5-Br | CF$_3$ | CH$_3$ | H | C(O)CH$_2$SEt |
| 3-Cl-5-Br | CF$_3$ | H | CH$_3$ | C(O)CH$_2$SEt |
| 3-Cl-5-Br | CF$_3$ | H | Et | C(O)CH$_2$SEt |
| 3-Cl-5-Br | CF$_3$ | H | CH$_2$CH=CH$_2$ | C(O)CH$_2$SEt |
| 3-Cl-5-Br | CF$_3$ | H | CH$_2$C≡CH | C(O)CH$_2$SEt |
| 3-Cl-5-Br | CF$_3$ | H | H | C(O)CH$_2$S(O)Et |
| 3-Cl-5-Br | CF$_3$ | CH$_3$ | H | C(O)CH$_2$S(O)Et |
| 3-Cl-5-Br | CF$_3$ | H | CH$_3$ | C(O)CH$_2$S(O)Et |
| 3-Cl-5-Br | CF$_3$ | H | Et | C(O)CH$_2$S(O)Et |
| 3-Cl-5-Br | CF$_3$ | H | CH$_2$C≡CH | C(O)CH$_2$S(O)Et |
| 3-Cl-5-Br | CF$_3$ | H | H | C(O)CH$_2$SO$_2$Et |
| 3-Cl-5-Br | CF$_3$ | CH$_3$ | H | C(O)CH$_2$SO$_2$Et |

-continued

| (X)$_m$ | R$^3$ | R$^4$ | R$^2$ | R$^1$ |
|---|---|---|---|---|
| 3-Cl-5-Br | CF$_3$ | H | CH$_3$ | C(O)CH$_2$SO$_2$Et |
| 3-Cl-5-Br | CF$_3$ | H | Et | C(O)CH$_2$SO$_2$Et |
| 3-Cl-5-Br | CF$_3$ | H | CH$_2$C≡CH | C(O)CH$_2$SO$_2$Et |
| 3-Cl-5-Br | CF$_3$ | H | H | C(O)CH$_2$SCH$_2$CF$_3$ |
| 3-Cl-5-Br | CF$_3$ | H | H | C(O)CH$_2$S(O)CH$_2$CF$_3$ |
| 3-Cl-5-Br | CF$_3$ | H | H | C(O)CH$_2$SO$_2$CH$_2$CF$_3$ |
| 3-Cl-5-Br | CF$_3$ | H | H | C(O)CH(CH$_3$)SCH$_3$ |
| 3-Cl-5-Br | CF$_3$ | H | H | C(O)CH(CH$_3$)S(O)CH$_3$ |
| 3-Cl-5-Br | CF$_3$ | H | H | C(O)CH(CH$_3$)SO$_2$CH$_3$ |
| 3-Cl-5-Br | CF$_3$ | H | H | C(O)CH(CH$_3$)SEt |
| 3-Cl-5-Br | CF$_3$ | H | H | C(O)(E-1-1a) |
| 3-Cl-5-Br | CF$_3$ | H | H | C(O)(E-1-1b) |
| 3-Cl-5-Br | CF$_3$ | H | H | C(O)(E-1-1c) |
| 3-Cl-5-Br | CF$_3$ | H | H | C(O)(E-1-2a) |
| 3-Cl-5-Br | CF$_3$ | H | H | C(O)(E-1-2b) |
| 3-Cl-5-Br | CF$_3$ | H | H | C(O)(E-1-2c) |
| 3-Cl-5-Br | CF$_3$ | H | H | C(O)CH(SCH$_3$)$_2$ |
| 3-Cl-5-Br | CF$_3$ | H | H | C(O)CH(SCH$_3$)S(O)CH$_3$ |
| 3-Cl-5-Br | CF$_3$ | H | H | C(O)CH[S(O)CH$_3$]$_2$ |
| 3-Cl-5-Br | CF$_3$ | H | H | C(O)CH[S(O)CH$_3$]SO$_2$CH$_3$ |
| 3-Cl-5-Br | CF$_3$ | H | H | C(O)CH(SEt)$_2$ |
| 3-Cl-5-Br | CF$_3$ | H | H | C(O)CH(SEt)S(O)Et |
| 3-Cl-5-Br | CF$_3$ | H | H | C(O)CH[S(O)Et]$_2$ |
| 3-Cl-5-Br | CF$_3$ | H | H | C(O)CH[S(O)Et]SO$_2$Et |
| 3-Cl-5-Br | CF$_3$ | H | H | C(S)CH$_2$SCH$_3$ |
| 3-Cl-5-Br | CF$_3$ | H | H | C(S)CH$_2$SO$_2$CH$_3$ |
| 3-Cl-5-Br | CF$_3$ | H | H | C(S)CH$_2$SEt |
| 3-Cl-5-Br | CF$_3$ | H | H | C(S)CH$_2$SO$_2$Et |
| 3-Cl-5-Br | CF$_2$Cl | H | H | C(O)CH$_2$SCH$_3$ |
| 3-Cl-5-Br | CF$_2$Cl | H | H | C(O)CH$_2$S(O)CH$_3$ |
| 3-Cl-5-Br | CF$_2$Cl | H | H | C(O)CH$_2$SO$_2$CH$_3$ |
| 3-Cl-5-Br | CF$_2$Cl | H | H | C(O)CH$_2$SEt |
| 3-Cl-5-Br | CF$_2$Cl | H | H | C(O)CH$_2$S(O)Et |
| 3-Cl-5-Br | CF$_2$Cl | H | H | C(O)CH$_2$SO$_2$Et |
| 3-Cl-5-Br | CF$_2$Cl | H | H | C(S)CH$_2$SCH$_3$ |
| 3-Cl-5-Br | CF$_2$Cl | H | H | C(S)CH$_2$SO$_2$CH$_3$ |
| 3-Cl-5-Br | CF$_2$Cl | H | H | C(S)CH$_2$SEt |
| 3-Cl-5-Br | CF$_2$Cl | H | H | C(S)CH$_2$SO$_2$Et |
| 3,4-Br$_2$ | CF$_3$ | H | H | C(O)CH$_2$SCH$_3$ |
| 3,4-Br$_2$ | CF$_3$ | H | H | C(O)CH$_2$S(O)CH$_3$ |
| 3,4-Br$_2$ | CF$_3$ | H | H | C(O)CH$_2$SO$_2$CH$_3$ |
| 3,4-Br$_2$ | CF$_3$ | H | H | C(O)CH$_2$SEt |
| 3,4-Br$_2$ | CF$_3$ | H | H | C(O)CH$_2$S(O)Et |
| 3,4-Br$_2$ | CF$_3$ | H | H | C(O)CH$_2$SO$_2$Et |
| 3,4-Br$_2$ | CF$_3$ | H | H | C(S)CH$_2$SCH$_3$ |
| 3,4-Br$_2$ | CF$_3$ | H | H | C(S)CH$_2$SO$_2$CH$_3$ |
| 3,4-Br$_2$ | CF$_3$ | H | H | C(S)CH$_2$SEt |
| 3,4-Br$_2$ | CF$_3$ | H | H | C(S)CH$_2$SO$_2$Et |
| 3,5-Br$_2$ | CHF$_2$ | H | H | C(O)CH$_2$SCH$_3$ |
| 3,5-Br$_2$ | CHF$_2$ | H | H | C(O)CH$_2$S(O)CH$_3$ |
| 3,5-Br$_2$ | CHF$_2$ | H | H | C(O)CH$_2$SO$_2$CH$_3$ |
| 3,5-Br$_2$ | CHF$_2$ | H | H | C(O)CH$_2$SEt |
| 3,5-Br$_2$ | CHF$_2$ | H | H | C(O)CH$_2$S(O)Et |
| 3,5-Br$_2$ | CHF$_2$ | H | H | C(O)CH$_2$SO$_2$Et |
| 3,5-Br$_2$ | CF$_3$ | H | H | C(O)CH$_2$SCH$_3$ |
| 3,5-Br$_2$ | CF$_3$ | CH$_3$ | H | C(O)CH$_2$SCH$_3$ |
| 3,5-Br$_2$ | CF$_3$ | H | Et | C(O)CH$_2$SCH$_3$ |
| 3,5-Br$_2$ | CF$_3$ | H | CH$_2$C≡CH | C(O)CH$_2$SCH$_3$ |
| 3,5-Br$_2$ | CF$_3$ | H | H | C(O)CH$_2$S(O)CH$_3$ |
| 3,5-Br$_2$ | CF$_3$ | CH$_3$ | H | C(O)CH$_2$S(O)CH$_3$ |
| 3,5-Br$_2$ | CF$_3$ | H | CH$_3$ | C(O)CH$_2$S(O)CH$_3$ |
| 3,5-Br$_2$ | CF$_3$ | H | Et | C(O)CH$_2$S(O)CH$_3$ |
| 3,5-Br$_2$ | CF$_3$ | H | CH$_2$C≡CH | C(O)CH$_2$S(O)CH$_3$ |
| 3,5-Br$_2$ | CF$_3$ | H | H | C(O)CH$_2$SO$_2$CH$_3$ |
| 3,5-Br$_2$ | CF$_3$ | CH$_3$ | H | C(O)CH$_2$SO$_2$CH$_3$ |
| 3,5-Br$_2$ | CF$_3$ | H | CH$_3$ | C(O)CH$_2$SO$_2$CH$_3$ |
| 3,5-Br$_2$ | CF$_3$ | H | Et | C(O)CH$_2$SO$_2$CH$_3$ |
| 3,5-Br$_2$ | CF$_3$ | H | CH$_2$C≡CH | C(O)CH$_2$SO$_2$CH$_3$ |
| 3,5-Br$_2$ | CF$_3$ | H | H | C(O)CH$_2$SEt |
| 3,5-Br$_2$ | CF$_3$ | CH$_3$ | H | C(O)CH$_2$SEt |
| 3,5-Br$_2$ | CF$_3$ | H | CH$_3$ | C(O)CH$_2$SEt |
| 3,5-Br$_2$ | CF$_3$ | H | Et | C(O)CH$_2$SEt |
| 3,5-Br$_2$ | CF$_3$ | H | CH$_2$CH═CH$_2$ | C(O)CH$_2$SEt |
| 3,5-Br$_2$ | CF$_3$ | H | CH$_2$C≡CH | C(O)CH$_2$SEt |
| 3,5-Br$_2$ | CF$_3$ | H | H | C(O)CH$_2$S(O)Et |
| 3,5-Br$_2$ | CF$_3$ | CH$_3$ | H | C(O)CH$_2$S(O)Et |
| 3,5-Br$_2$ | CF$_3$ | H | CH$_3$ | C(O)CH$_2$S(O)Et |
| 3,5-Br$_2$ | CF$_3$ | H | Et | C(O)CH$_2$S(O)Et |

-continued

| (X)$_m$ | R$^3$ | R$^4$ | R$^2$ | R$^1$ |
|---|---|---|---|---|
| 3,5-Br$_2$ | CF$_3$ | H | CH$_2$C≡CH | C(O)CH$_2$S(O)Et |
| 3,5-Br$_2$ | CF$_3$ | H | H | C(O)CH$_2$SO$_2$Et |
| 3,5-Br$_2$ | CF$_3$ | CH$_3$ | H | C(O)CH$_2$SO$_2$Et |
| 3,5-Br$_2$ | CF$_3$ | H | CH$_3$ | C(O)CH$_2$SO$_2$Et |
| 3,5-Br$_2$ | CF$_3$ | H | Et | C(O)CH$_2$SO$_2$Et |
| 3,5-Br$_2$ | CF$_3$ | H | CH$_2$C≡CH | C(O)CH$_2$SO$_2$Et |
| 3,5-Br$_2$ | CF$_3$ | H | H | C(O)CH$_2$SCH$_2$CF$_3$ |
| 3,5-Br$_2$ | CF$_3$ | H | H | C(O)CH$_2$S(O)CH$_2$CF$_3$ |
| 3,5-Br$_2$ | CF$_3$ | H | H | C(O)CH$_2$SO$_2$CH$_2$CF$_3$ |
| 3,5-Br$_2$ | CF$_3$ | H | H | C(O)CH(CH$_3$)SCH$_3$ |
| 3,5-Br$_2$ | CF$_3$ | H | H | C(O)CH(CH$_3$)S(O)CH$_3$ |
| 3,5-Br$_2$ | CF$_3$ | H | H | C(O)CH(CH$_3$)SO$_2$CH$_3$ |
| 3,5-Br$_2$ | CF$_3$ | H | H | C(O)CH(CH$_3$)SEt |
| 3,5-Br$_2$ | CF$_3$ | H | H | C(O)(E-1-1a) |
| 3,5-Br$_2$ | CF$_3$ | H | H | C(O)(E-1-1b) |
| 3,5-Br$_2$ | CF$_3$ | H | H | C(O)(E-1-1c) |
| 3,5-Br$_2$ | CF$_3$ | H | H | C(O)(E-1-2a) |
| 3,5-Br$_2$ | CF$_3$ | H | H | C(O)(E-1-2b) |
| 3,5-Br$_2$ | CF$_3$ | H | H | C(O)(E-1-2c) |
| 3,5-Br$_2$ | CF$_3$ | H | H | C(O)CH(SCH$_3$)$_2$ |
| 3,5-Br$_2$ | CF$_3$ | H | H | C(O)CH(SCH$_3$)S(O)CH$_3$ |
| 3,5-Br$_2$ | CF$_3$ | H | H | C(O)CH[S(O)CH$_3$]$_2$ |
| 3,5-Br$_2$ | CF$_3$ | H | H | C(O)CH[S(O)CH$_3$]SO$_2$CH$_3$ |
| 3,5-Br$_2$ | CF$_3$ | H | H | C(O)CH(SEt)$_2$ |
| 3,5-Br$_2$ | CF$_3$ | H | H | C(O)CH(SEt)S(O)Et |
| 3,5-Br$_2$ | CF$_3$ | H | H | C(O)CH[S(O)Et]$_2$ |
| 3,5-Br$_2$ | CF$_3$ | H | H | C(O)CH[S(O)Et]SO$_2$Et |
| 3,5-Br$_2$ | CF$_3$ | H | H | C(S)CH$_2$SCH$_3$ |
| 3,5-Br$_2$ | CF$_3$ | H | H | C(S)CH$_2$SO$_2$CH$_3$ |
| 3,5-Br$_2$ | CF$_3$ | H | H | C(S)CH$_2$SEt |
| 3,5-Br$_2$ | CF$_3$ | H | H | C(S)CH$_2$SO$_2$Et |
| 3,5-Br$_2$ | CF$_2$Cl | H | H | C(O)CH$_2$SCH$_3$ |
| 3,5-Br$_2$ | CF$_2$Cl | H | H | C(O)CH$_2$S(O)CH$_3$ |
| 3,5-Br$_2$ | CF$_2$Cl | H | H | C(O)CH$_2$SO$_2$CH$_3$ |
| 3,5-Br$_2$ | CF$_2$Cl | H | H | C(O)CH$_2$SEt |
| 3,5-Br$_2$ | CF$_2$Cl | H | H | C(O)CH$_2$S(O)Et |
| 3,5-Br$_2$ | CF$_2$Cl | H | H | C(O)CH$_2$SO$_2$Et |
| 3,5-Br$_2$ | CF$_2$Cl | H | H | C(S)CH$_2$SCH$_3$ |
| 3,5-Br$_2$ | CF$_2$Cl | H | H | C(S)CH$_2$SO$_2$CH$_3$ |
| 3,5-Br$_2$ | CF$_2$Cl | H | H | C(S)CH$_2$SEt |
| 3,5-Br$_2$ | CF$_2$Cl | H | H | C(S)CH$_2$SO$_2$Et |
| 3-I-4-F | CF$_3$ | H | H | C(O)CH$_2$SCH$_3$ |
| 3-I-4-F | CF$_3$ | H | H | C(O)CH$_2$S(O)CH$_3$ |
| 3-I-4-F | CF$_3$ | H | H | C(O)CH$_2$SO$_2$CH$_3$ |
| 3-I-4-F | CF$_3$ | H | H | C(O)CH$_2$SEt |
| 3-I-4-F | CF$_3$ | H | H | C(O)CH$_2$S(O)Et |
| 3-I-4-F | CF$_3$ | H | H | C(O)CH$_2$SO$_2$Et |
| 3-I-4-F | CF$_3$ | H | H | C(S)CH$_2$SCH$_3$ |
| 3-I-4-F | CF$_3$ | H | H | C(S)CH$_2$SO$_2$CH$_3$ |
| 3-I-4-F | CF$_3$ | H | H | C(S)CH$_2$SEt |
| 3-I-4-F | CF$_3$ | H | H | C(S)CH$_2$SO$_2$Et |
| 3-F-5-I | CF$_3$ | H | H | C(O)CH$_2$SCH$_3$ |
| 3-F-5-I | CF$_3$ | H | H | C(O)CH$_2$S(O)CH$_3$ |
| 3-F-5-I | CF$_3$ | H | H | C(O)CH$_2$SO$_2$CH$_3$ |
| 3-F-5-I | CF$_3$ | H | H | C(O)CH$_2$SEt |
| 3-F-5-I | CF$_3$ | H | H | C(O)CH$_2$S(O)Et |
| 3-F-5-I | CF$_3$ | H | H | C(O)CH$_2$SO$_2$Et |
| 3-F-5-I | CF$_3$ | H | H | C(S)CH$_2$SCH$_3$ |
| 3-F-5-I | CF$_3$ | H | H | C(S)CH$_2$SO$_2$CH$_3$ |
| 3-F-5-I | CF$_3$ | H | H | C(S)CH$_2$SEt |
| 3-F-5-I | CF$_3$ | H | H | C(S)CH$_2$SO$_2$Et |
| 3-Cl-5-I | CF$_3$ | H | H | C(O)CH$_2$SCH$_3$ |
| 3-Cl-5-I | CF$_3$ | H | H | C(O)CH$_2$S(O)CH$_3$ |
| 3-Cl-5-I | CF$_3$ | H | H | C(O)CH$_2$SO$_2$CH$_3$ |
| 3-Cl-5-I | CF$_3$ | H | H | C(O)CH$_2$SEt |
| 3-Cl-5-I | CF$_3$ | H | Et | C(O)CH$_2$SEt |
| 3-Cl-5-I | CF$_3$ | H | CH$_2$C≡CH | C(O)CH$_2$SEt |
| 3-Cl-5-I | CF$_3$ | H | H | C(O)CH$_2$S(O)Et |
| 3-Cl-5-I | CF$_3$ | H | H | C(O)CH$_2$SO$_2$Et |
| 3-Cl-5-I | CF$_3$ | H | H | C(O)CH(CH$_3$)SCH$_3$ |
| 3-Cl-5-I | CF$_3$ | H | H | C(O)(E-1-1a) |
| 3-Cl-5-I | CF$_3$ | H | H | C(O)(E-1-1b) |
| 3-Cl-5-I | CF$_3$ | H | H | C(O)(E-1-1c) |
| 3-Cl-5-I | CF$_3$ | H | H | C(O)CH(SCH$_3$)$_2$ |
| 3-Cl-5-I | CF$_3$ | H | H | C(O)CH[S(O)CH$_3$]$_2$ |
| 3-Cl-5-I | CF$_3$ | H | H | C(O)CH(SEt)$_2$ |
| 3-Cl-5-I | CF$_3$ | H | H | C(O)CH(SEt)S(O)Et |
| 3-Cl-5-I | CF$_3$ | H | H | C(S)CH$_2$SCH$_3$ |

| (X)$_m$ | R$^3$ | R$^4$ | R$^2$ | R$^1$ |
|---|---|---|---|---|
| 3-Cl-5-I | CF$_3$ | H | H | C(S)CH$_2$SO$_2$CH$_3$ |
| 3-Cl-5-I | CF$_3$ | H | H | C(S)CH$_2$SEt |
| 3-Cl-5-I | CF$_3$ | H | H | C(S)CH$_2$SO$_2$Et |
| 3-Cl-5-I | CF$_2$Cl | H | H | C(O)CH$_2$SCH$_3$ |
| 3-Cl-5-I | CF$_2$Cl | H | H | C(O)CH$_2$S(O)CH$_3$ |
| 3-Cl-5-I | CF$_2$Cl | H | H | C(O)CH$_2$SO$_2$CH$_3$ |
| 3-Cl-5-I | CF$_2$Cl | H | H | C(O)CH$_2$SEt |
| 3-Cl-5-I | CF$_2$Cl | H | H | C(O)CH$_2$S(O)Et |
| 3-Cl-5-I | CF$_2$Cl | H | H | C(O)CH$_2$SO$_2$Et |
| 3-Cl-5-CH$_3$ | CF$_3$ | H | H | C(O)CH$_2$SCH$_3$ |
| 3-Cl-5-CH$_3$ | CF$_3$ | H | H | C(O)CH$_2$S(O)CH$_3$ |
| 3-Cl-5-CH$_3$ | CF$_3$ | H | H | C(O)CH$_2$SO$_2$CH$_3$ |
| 3-Cl-5-CH$_3$ | CF$_3$ | H | H | C(O)CH$_2$SEt |
| 3-Cl-5-CH$_3$ | CF$_3$ | H | H | C(O)CH$_2$S(O)Et |
| 3-Cl-5-CH$_3$ | CF$_3$ | H | H | C(O)CH$_2$SO$_2$Et |
| 3-Br-5-CH$_3$ | CF$_3$ | H | H | C(O)CH$_2$SCH$_3$ |
| 3-Br-5-CH$_3$ | CF$_3$ | H | H | C(O)CH$_2$S(O)CH$_3$ |
| 3-Br-5-CH$_3$ | CF$_3$ | H | H | C(O)CH$_2$SO$_2$CH$_3$ |
| 3-Br-5-CH$_3$ | CF$_3$ | H | H | C(O)CH$_2$SEt |
| 3-Br-5-CH$_3$ | CF$_3$ | H | H | C(O)CH$_2$S(O)Et |
| 3-Br-5-CH$_3$ | CF$_3$ | H | H | C(O)CH$_2$SO$_2$Et |
| 3-CF$_3$-4-F | CF$_3$ | H | H | C(O)CH$_2$SCH$_3$ |
| 3-CF$_3$-4-F | CF$_3$ | H | H | C(O)CH$_2$S(O)CH$_3$ |
| 3-CF$_3$-4-F | CF$_3$ | H | H | C(O)CH$_2$SO$_2$CH$_3$ |
| 3-CF$_3$-4-F | CF$_3$ | H | H | C(O)CH$_2$SEt |
| 3-CF$_3$-4-F | CF$_3$ | H | Et | C(O)CH$_2$SEt |
| 3-CF$_3$-4-F | CF$_3$ | H | CH$_2$C≡CH | C(O)CH$_2$SEt |
| 3-CF$_3$-4-F | CF$_3$ | H | H | C(O)CH$_2$S(O)Et |
| 3-CF$_3$-4-F | CF$_3$ | H | H | C(O)CH$_2$SO$_2$Et |
| 3-CF$_3$-4-F | CF$_3$ | H | H | C(O)CH(CH$_3$)SCH$_3$ |
| 3-CF$_3$-4-F | CF$_3$ | H | H | C(O)(E-1-1a) |
| 3-CF$_3$-4-F | CF$_3$ | H | H | C(O)(E-1-1b) |
| 3-CF$_3$-4-F | CF$_3$ | H | H | C(O)(E-1-1c) |
| 3-CF$_3$-4-F | CF$_3$ | H | H | C(O)CH(SCH$_3$)$_2$ |
| 3-CF$_3$-4-F | CF$_3$ | H | H | C(O)CH[S(O)CH$_3$]$_2$ |
| 3-CF$_3$-4-F | CF$_3$ | H | H | C(O)CH(SEt)$_2$ |
| 3-CF$_3$-4-F | CF$_3$ | H | H | C(O)CH(SEt)S(O)Et |
| 3-CF$_3$-4-F | CF$_3$ | H | H | C(S)CH$_2$SCH$_3$ |
| 3-CF$_3$-4-F | CF$_3$ | H | H | C(S)CH$_2$SO$_2$CH$_3$ |
| 3-CF$_3$-4-F | CF$_3$ | H | H | C(S)CH$_2$SEt |
| 3-CF$_3$-4-F | CF$_3$ | H | H | C(S)CH$_2$SO$_2$Et |
| 3-CF$_3$-4-F | CF$_2$Cl | H | H | C(O)CH$_2$SCH$_3$ |
| 3-CF$_3$-4-F | CF$_2$Cl | H | H | C(O)CH$_2$S(O)CH$_3$ |
| 3-CF$_3$-4-F | CF$_2$Cl | H | H | C(O)CH$_2$SO$_2$CH$_3$ |
| 3-CF$_3$-4-F | CF$_2$Cl | H | H | C(O)CH$_2$SEt |
| 3-CF$_3$-4-F | CF$_2$Cl | H | H | C(O)CH$_2$S(O)Et |
| 3-CF$_3$-4-F | CF$_2$Cl | H | H | C(O)CH$_2$SO$_2$Et |
| 3-F-5-CF$_3$ | CF$_3$ | H | H | C(O)CH$_2$SCH$_3$ |
| 3-F-5-CF$_3$ | CF$_3$ | H | H | C(O)CH$_2$S(O)CH$_3$ |
| 3-F-5-CF$_3$ | CF$_3$ | H | H | C(O)CH$_2$SO$_2$CH$_3$ |
| 3-F-5-CF$_3$ | CF$_3$ | H | H | C(O)CH$_2$SEt |
| 3-F-5-CF$_3$ | CF$_3$ | H | Et | C(O)CH$_2$SEt |
| 3-F-5-CF$_3$ | CF$_3$ | H | CH$_2$C≡CH | C(O)CH$_2$SEt |
| 3-F-5-CF$_3$ | CF$_3$ | H | H | C(O)CH$_2$S(O)Et |
| 3-F-5-CF$_3$ | CF$_3$ | H | H | C(O)CH$_2$SO$_2$Et |
| 3-F-5-CF$_3$ | CF$_3$ | H | H | C(O)CH(CH$_3$)SCH$_3$ |
| 3-F-5-CF$_3$ | CF$_3$ | H | H | C(O)(E-1-1a) |
| 3-F-5-CF$_3$ | CF$_3$ | H | H | C(O)(E-1-1b) |
| 3-F-5-CF$_3$ | CF$_3$ | H | H | C(O)(E-1-1c) |
| 3-F-5-CF$_3$ | CF$_3$ | H | H | C(O)CH(SCH$_3$)$_2$ |
| 3-F-5-CF$_3$ | CF$_3$ | H | H | C(O)CH[S(O)CH$_3$]$_2$ |
| 3-F-5-CF$_3$ | CF$_3$ | H | H | C(O)CH(SEt)$_2$ |
| 3-F-5-CF$_3$ | CF$_3$ | H | H | C(O)CH(SEt)S(O)Et |
| 3-F-5-CF$_3$ | CF$_3$ | H | H | C(S)CH$_2$SCH$_3$ |
| 3-F-5-CF$_3$ | CF$_3$ | H | H | C(S)CH$_2$SO$_2$CH$_3$ |
| 3-F-5-CF$_3$ | CF$_3$ | H | H | C(S)CH$_2$SEt |
| 3-F-5-CF$_3$ | CF$_3$ | H | H | C(S)CH$_2$SO$_2$Et |
| 3-F-5-CF$_3$ | CF$_2$Cl | H | H | C(O)CH$_2$SCH$_3$ |
| 3-F-5-CF$_3$ | CF$_2$Cl | H | H | C(O)CH$_2$S(O)CH$_3$ |
| 3-F-5-CF$_3$ | CF$_2$Cl | H | H | C(O)CH$_2$SO$_2$CH$_3$ |
| 3-F-5-CF$_3$ | CF$_2$Cl | H | H | C(O)CH$_2$SEt |
| 3-F-5-CF$_3$ | CF$_2$Cl | H | H | C(O)CH$_2$S(O)Et |
| 3-F-5-CF$_3$ | CF$_2$Cl | H | H | C(O)CH$_2$SO$_2$Et |
| 3-CF$_3$-4-Cl | CF$_3$ | H | H | C(O)CH$_2$SCH$_3$ |
| 3-CF$_3$-4-Cl | CF$_3$ | H | H | C(O)CH$_2$S(O)CH$_3$ |
| 3-CF$_3$-4-Cl | CF$_3$ | H | H | C(O)CH$_2$SO$_2$CH$_3$ |
| 3-CF$_3$-4-Cl | CF$_3$ | H | H | C(O)CH$_2$SEt |
| 3-CF$_3$-4-Cl | CF$_3$ | H | Et | C(O)CH$_2$SEt |

| (X)$_m$ | R$^3$ | R$^4$ | R$^2$ | R$^1$ |
|---|---|---|---|---|
| 3-CF$_3$-4-Cl | CF$_3$ | H | CH$_2$C≡CH | C(O)CH$_2$SEt |
| 3-CF$_3$-4-Cl | CF$_3$ | H | H | C(O)CH$_2$S(O)Et |
| 3-CF$_3$-4-Cl | CF$_3$ | H | H | C(O)CH$_2$SO$_2$Et |
| 3-CF$_3$-4-Cl | CF$_3$ | H | H | C(O)CH(CH$_3$)SCH$_3$ |
| 3-CF$_3$-4-Cl | CF$_3$ | H | H | C(O)(E-1-1a) |
| 3-CF$_3$-4-Cl | CF$_3$ | H | H | C(O)(E-1-1b) |
| 3-CF$_3$-4-Cl | CF$_3$ | H | H | C(O)(E-1-1c) |
| 3-CF$_3$-4-Cl | CF$_3$ | H | H | C(O)CH(SCH$_3$)$_2$ |
| 3-CF$_3$-4-Cl | CF$_3$ | H | H | C(O)CH[S(O)CH$_3$]$_2$ |
| 3-CF$_3$-4-Cl | CF$_3$ | H | H | C(O)CH(SEt)$_2$ |
| 3-CF$_3$-4-Cl | CF$_3$ | H | H | C(O)CH(SEt)S(O)Et |
| 3-CF$_3$-4-Cl | CF$_3$ | H | H | C(S)CH$_2$SCH$_3$ |
| 3-CF$_3$-4-Cl | CF$_3$ | H | H | C(S)CH$_2$SO$_2$CH$_3$ |
| 3-CF$_3$-4-Cl | CF$_3$ | H | H | C(S)CH$_2$SEt |
| 3-CF$_3$-4-Cl | CF$_3$ | H | H | C(S)CH$_2$SO$_2$Et |
| 3-CF$_3$-4-Cl | CF$_2$Cl | H | H | C(O)CH$_2$SCH$_3$ |
| 3-CF$_3$-4-Cl | CF$_2$Cl | H | H | C(O)CH$_2$S(O)CH$_3$ |
| 3-CF$_3$-4-Cl | CF$_2$Cl | H | H | C(O)CH$_2$SO$_2$CH$_3$ |
| 3-CF$_3$-4-Cl | CF$_2$Cl | H | H | C(O)CH$_2$SEt |
| 3-CF$_3$-4-Cl | CF$_2$Cl | H | H | C(O)CH$_2$S(O)Et |
| 3-CF$_3$-4-Cl | CF$_2$Cl | H | H | C(O)CH$_2$SO$_2$Et |
| 3-Cl-5-CF$_3$ | CHF$_2$ | H | H | C(O)CH$_2$SCH$_3$ |
| 3-Cl-5-CF$_3$ | CHF$_2$ | H | H | C(O)CH$_2$S(O)CH$_3$ |
| 3-Cl-5-CF$_3$ | CHF$_2$ | H | H | C(O)CH$_2$SO$_2$CH$_3$ |
| 3-Cl-5-CF$_3$ | CHF$_2$ | H | H | C(O)CH$_2$SEt |
| 3-Cl-5-CF$_3$ | CHF$_2$ | H | H | C(O)CH$_2$S(O)Et |
| 3-Cl-5-CF$_3$ | CHF$_2$ | H | H | C(O)CH$_2$SO$_2$Et |
| 3-Cl-5-CF$_3$ | CF$_3$ | H | H | C(O)CH$_2$SCH$_3$ |
| 3-Cl-5-CF$_3$ | CF$_3$ | CH$_3$ | H | C(O)CH$_2$SCH$_3$ |
| 3-Cl-5-CF$_3$ | CF$_3$ | H | CH$_3$ | C(O)CH$_2$SCH$_3$ |
| 3-Cl-5-CF$_3$ | CF$_3$ | H | Et | C(O)CH$_2$SCH$_3$ |
| 3-Cl-5-CF$_3$ | CF$_3$ | H | CH$_2$Pr-c | C(O)CH$_2$SCH$_3$ |
| 3-Cl-5-CF$_3$ | CF$_3$ | H | CH$_2$OCH$_3$ | C(O)CH$_2$SCH$_3$ |
| 3-Cl-5-CF$_3$ | CF$_3$ | H | CH$_2$CN | C(O)CH$_2$SCH$_3$ |
| 3-Cl-5-CF$_3$ | CF$_3$ | H | CH$_2$C(O)OCH$_3$ | C(O)CH$_2$SCH$_3$ |
| 3-Cl-5-CF$_3$ | CF$_3$ | H | CH$_2$C(O)NH$_2$ | C(O)CH$_2$SCH$_3$ |
| 3-Cl-5-CF$_3$ | CF$_3$ | H | CH$_2$C(O)NHCH$_3$ | C(O)CH$_2$SCH$_3$ |
| 3-Cl-5-CF$_3$ | CF$_3$ | H | CH$_2$C(O)N(CH$_3$)$_2$ | C(O)CH$_2$SCH$_3$ |
| 3-Cl-5-CF$_3$ | CF$_3$ | H | CH$_2$C(S)NH$_2$ | C(O)CH$_2$SCH$_3$ |
| 3-Cl-5-CF$_3$ | CF$_3$ | H | CH$_2$CH=CH$_2$ | C(O)CH$_2$SCH$_3$ |
| 3-Cl-5-CF$_3$ | CF$_3$ | H | CH$_2$C≡CH | C(O)CH$_2$SCH$_3$ |
| 3-Cl-5-CF$_3$ | CF$_3$ | H | H | C(O)CH$_2$S(O)CH$_3$ |
| 3-Cl-5-CF$_3$ | CF$_3$ | CH$_3$ | H | C(O)CH$_2$S(O)CH$_3$ |
| 3-Cl-5-CF$_3$ | CF$_3$ | H | CH$_3$ | C(O)CH$_2$S(O)CH$_3$ |
| 3-Cl-5-CF$_3$ | CF$_3$ | H | Et | C(O)CH$_2$S(O)CH$_3$ |
| 3-Cl-5-CF$_3$ | CF$_3$ | H | CH$_2$Pr-c | C(O)CH$_2$S(O)CH$_3$ |
| 3-Cl-5-CF$_3$ | CF$_3$ | H | CH$_2$OCH$_3$ | C(O)CH$_2$S(O)CH$_3$ |
| 3-Cl-5-CF$_3$ | CF$_3$ | H | CH$_2$CN | C(O)CH$_2$S(O)CH$_3$ |
| 3-Cl-5-CF$_3$ | CF$_3$ | H | CH$_2$C(O)OCH$_3$ | C(O)CH$_2$S(O)CH$_3$ |
| 3-Cl-5-CF$_3$ | CF$_3$ | H | CH$_2$C(O)NH$_2$ | C(O)CH$_2$S(O)CH$_3$ |
| 3-Cl-5-CF$_3$ | CF$_3$ | H | CH$_2$C(O)NHCH$_3$ | C(O)CH$_2$S(O)CH$_3$ |
| 3-Cl-5-CF$_3$ | CF$_3$ | H | CH$_2$C(O)N(CH$_3$)$_2$ | C(O)CH$_2$S(O)CH$_3$ |
| 3-Cl-5-CF$_3$ | CF$_3$ | H | CH$_2$C(S)NH$_2$ | C(O)CH$_2$S(O)CH$_3$ |
| 3-Cl-5-CF$_3$ | CF$_3$ | H | CH$_2$CH=CH$_2$ | C(O)CH$_2$S(O)CH$_3$ |
| 3-Cl-5-CF$_3$ | CF$_3$ | H | CH$_2$C≡CH | C(O)CH$_2$S(O)CH$_3$ |
| 3-Cl-5-CF$_3$ | CF$_3$ | H | H | C(O)CH$_2$SO$_2$CH$_3$ |
| 3-Cl-5-CF$_3$ | CF$_3$ | CH$_3$ | H | C(O)CH$_2$SO$_2$CH$_3$ |
| 3-Cl-5-CF$_3$ | CF$_3$ | H | CH$_3$ | C(O)CH$_2$SO$_2$CH$_3$ |
| 3-Cl-5-CF$_3$ | CF$_3$ | H | Et | C(O)CH$_2$SO$_2$CH$_3$ |
| 3-Cl-5-CF$_3$ | CF$_3$ | H | CH$_2$Pr-c | C(O)CH$_2$SO$_2$CH$_3$ |
| 3-Cl-5-CF$_3$ | CF$_3$ | H | CH$_2$OCH$_3$ | C(O)CH$_2$SO$_2$CH$_3$ |
| 3-Cl-5-CF$_3$ | CF$_3$ | H | CH$_2$CN | C(O)CH$_2$SO$_2$CH$_3$ |
| 3-Cl-5-CF$_3$ | CF$_3$ | H | CH$_2$C(O)OCH$_3$ | C(O)CH$_2$SO$_2$CH$_3$ |
| 3-Cl-5-CF$_3$ | CF$_3$ | H | CH$_2$C(O)NH$_2$ | C(O)CH$_2$SO$_2$CH$_3$ |
| 3-Cl-5-CF$_3$ | CF$_3$ | H | CH$_2$C(O)NHCH$_3$ | C(O)CH$_2$SO$_2$CH$_3$ |
| 3-Cl-5-CF$_3$ | CF$_3$ | H | CH$_2$C(O)N(CH$_3$)$_2$ | C(O)CH$_2$SO$_2$CH$_3$ |
| 3-Cl-5-CF$_3$ | CF$_3$ | H | CH$_2$C(S)NH$_2$ | C(O)CH$_2$SO$_2$CH$_3$ |
| 3-Cl-5-CF$_3$ | CF$_3$ | H | CH$_2$CH=CH$_2$ | C(O)CH$_2$SO$_2$CH$_3$ |
| 3-Cl-5-CF$_3$ | CF$_3$ | H | CH$_2$C≡CH | C(O)CH$_2$SO$_2$CH$_3$ |
| 3-Cl-5-CF$_3$ | CF$_3$ | H | H | C(O)CH$_2$SEt |
| 3-Cl-5-CF$_3$ | CF$_3$ | CH$_3$ | H | C(O)CH$_2$SEt |
| 3-Cl-5-CF$_3$ | CF$_3$ | H | CH$_3$ | C(O)CH$_2$SEt |
| 3-Cl-5-CF$_3$ | CF$_3$ | H | Et | C(O)CH$_2$SEt |
| 3-Cl-5-CF$_3$ | CF$_3$ | H | CH$_2$Pr-c | C(O)CH$_2$SEt |
| 3-Cl-5-CF$_3$ | CF$_3$ | H | CH$_2$OCH$_3$ | C(O)CH$_2$SEt |
| 3-Cl-5-CF$_3$ | CF$_3$ | H | CH$_2$CN | C(O)CH$_2$SEt |
| 3-Cl-5-CF$_3$ | CF$_3$ | H | CH$_2$C(O)OCH$_3$ | C(O)CH$_2$SEt |
| 3-Cl-5-CF$_3$ | CF$_3$ | H | CH$_2$C(O)NH$_2$ | C(O)CH$_2$SEt |

-continued

| (X)$_m$ | R$^3$ | R$^4$ | R$^2$ | R$^1$ |
|---|---|---|---|---|
| 3-Cl-5-CF$_3$ | CF$_3$ | H | CH$_2$C(O)NHCH$_3$ | C(O)CH$_2$SEt |
| 3-Cl-5-CF$_3$ | CF$_3$ | H | CH$_2$C(O)N(CH$_3$)$_2$ | C(O)CH$_2$SEt |
| 3-Cl-5-CF$_3$ | CF$_3$ | H | CH$_2$C(S)NH$_2$ | C(O)CH$_2$SEt |
| 3-Cl-5-CF$_3$ | CF$_3$ | H | CH$_2$CH=CH$_2$ | C(O)CH$_2$SEt |
| 3-Cl-5-CF$_3$ | CF$_3$ | H | CH$_2$C≡CH | C(O)CH$_2$SEt |
| 3-Cl-5-CF$_3$ | CF$_3$ | H | H | C(O)CH$_2$S(O)Et |
| 3-Cl-5-CF$_3$ | CF$_3$ | CH$_3$ | H | C(O)CH$_2$S(O)Et |
| 3-Cl-5-CF$_3$ | CF$_3$ | H | CH$_3$ | C(O)CH$_2$S(O)Et |
| 3-Cl-5-CF$_3$ | CF$_3$ | H | Et | C(O)CH$_2$S(O)Et |
| 3-Cl-5-CF$_3$ | CF$_3$ | H | CH$_2$Pr-c | C(O)CH$_2$S(O)Et |
| 3-Cl-5-CF$_3$ | CF$_3$ | H | CH$_2$OCH$_3$ | C(O)CH$_2$S(O)Et |
| 3-Cl-5-CF$_3$ | CF$_3$ | H | CH$_2$CN | C(O)CH$_2$S(O)Et |
| 3-Cl-5-CF$_3$ | CF$_3$ | H | CH$_2$C(O)OCH$_3$ | C(O)CH$_2$S(O)Et |
| 3-Cl-5-CF$_3$ | CF$_3$ | H | CH$_2$C(O)NH$_2$ | C(O)CH$_2$S(O)Et |
| 3-Cl-5-CF$_3$ | CF$_3$ | H | CH$_2$C(O)NHCH$_3$ | C(O)CH$_2$S(O)Et |
| 3-Cl-5-CF$_3$ | CF$_3$ | H | CH$_2$C(O)N(CH$_3$)$_2$ | C(O)CH$_2$S(O)Et |
| 3-Cl-5-CF$_3$ | CF$_3$ | H | CH$_2$C(S)NH$_2$ | C(O)CH$_2$S(O)Et |
| 3-Cl-5-CF$_3$ | CF$_3$ | H | CH$_2$CH=CH$_2$ | C(O)CH$_2$S(O)Et |
| 3-Cl-5-CF$_3$ | CF$_3$ | H | CH$_2$C≡CH | C(O)CH$_2$S(O)Et |
| 3-Cl-5-CF$_3$ | CF$_3$ | H | H | C(O)CH$_2$SO$_2$Et |
| 3-Cl-5-CF$_3$ | CF$_3$ | CH$_3$ | H | C(O)CH$_2$SO$_2$Et |
| 3-Cl-5-CF$_3$ | CF$_3$ | H | CH$_3$ | C(O)CH$_2$SO$_2$Et |
| 3-Cl-5-CF$_3$ | CF$_3$ | H | Et | C(O)CH$_2$SO$_2$Et |
| 3-Cl-5-CF$_3$ | CF$_3$ | H | CH$_2$Pr-c | C(O)CH$_2$SO$_2$Et |
| 3-Cl-5-CF$_3$ | CF$_3$ | H | CH$_2$OCH$_3$ | C(O)CH$_2$SO$_2$Et |
| 3-Cl-5-CF$_3$ | CF$_3$ | H | CH$_2$CN | C(O)CH$_2$SO$_2$Et |
| 3-Cl-5-CF$_3$ | CF$_3$ | H | CH$_2$C(O)OCH$_3$ | C(O)CH$_2$SO$_2$Et |
| 3-Cl-5-CF$_3$ | CF$_3$ | H | CH$_2$C(O)NH$_2$ | C(O)CH$_2$SO$_2$Et |
| 3-Cl-5-CF$_3$ | CF$_3$ | H | CH$_2$C(O)NHCH$_3$ | C(O)CH$_2$SO$_2$Et |
| 3-Cl-5-CF$_3$ | CF$_3$ | H | CH$_2$C(O)N(CH$_3$)$_2$ | C(O)CH$_2$SO$_2$Et |
| 3-Cl-5-CF$_3$ | CF$_3$ | H | CH$_2$C(S)NH$_2$ | C(O)CH$_2$SO$_2$Et |
| 3-Cl-5-CF$_3$ | CF$_3$ | H | CH$_2$CH=CH$_2$ | C(O)CH$_2$SO$_2$Et |
| 3-Cl-5-CF$_3$ | CF$_3$ | H | CH$_2$C≡CH | C(O)CH$_2$SO$_2$Et |
| 3-Cl-5-CF$_3$ | CF$_3$ | H | H | C(O)CH$_2$SCH$_2$CF$_3$ |
| 3-Cl-5-CF$_3$ | CF$_3$ | H | H | C(O)CH$_2$S(O)CH$_2$CF$_3$ |
| 3-Cl-5-CF$_3$ | CF$_3$ | H | H | C(O)CH$_2$SO$_2$CH$_2$CF$_3$ |
| 3-Cl-5-CF$_3$ | CF$_3$ | H | H | C(O)CH(CH$_3$)SCH$_3$ |
| 3-Cl-5-CF$_3$ | CF$_3$ | H | H | C(O)CH(CH$_3$)S(O)CH$_3$ |
| 3-Cl-5-CF$_3$ | CF$_3$ | H | H | C(O)CH(CH$_3$)SO$_2$CH$_3$ |
| 3-Cl-5-CF$_3$ | CF$_3$ | H | H | C(O)CH(CH$_3$)SEt |
| 3-Cl-5-CF$_3$ | CF$_3$ | H | H | C(O)(E-1-1a) |
| 3-Cl-5-CF$_3$ | CF$_3$ | H | H | C(O)(E-1-1b) |
| 3-Cl-5-CF$_3$ | CF$_3$ | H | H | C(O)(E-1-1c) |
| 3-Cl-5-CF$_3$ | CF$_3$ | H | H | C(O)(E-1-2a) |
| 3-Cl-5-CF$_3$ | CF$_3$ | H | H | C(O)(E-1-2b) |
| 3-Cl-5-CF$_3$ | CF$_3$ | H | H | C(O)(E-1-2c) |
| 3-Cl-5-CF$_3$ | CF$_3$ | H | H | C(O)CH(SCH$_3$)$_2$ |
| 3-Cl-5-CF$_3$ | CF$_3$ | H | H | C(O)CH(SCH$_3$)S(O)CH$_3$ |
| 3-Cl-5-CF$_3$ | CF$_3$ | H | H | C(O)CH[S(O)CH$_3$]$_2$ |
| 3-Cl-5-CF$_3$ | CF$_3$ | H | H | C(O)CH[S(O)CH$_3$]SO$_2$CH$_3$ |
| 3-Cl-5-CF$_3$ | CF$_3$ | H | H | C(O)CH(SEt)$_2$ |
| 3-Cl-5-CF$_3$ | CF$_3$ | H | H | C(O)CH(SEt)S(O)Et |
| 3-Cl-5-CF$_3$ | CF$_3$ | H | H | C(O)CH[S(O)Et]$_2$ |
| 3-Cl-5-CF$_3$ | CF$_3$ | H | H | C(O)CH[S(O)Et]SO$_2$Et |
| 3-Cl-5-CF$_3$ | CF$_3$ | H | H | C(S)CH$_2$SCH$_3$ |
| 3-Cl-5-CF$_3$ | CF$_3$ | H | H | C(S)CH$_2$SO$_2$CH$_3$ |
| 3-Cl-5-CF$_3$ | CF$_3$ | H | H | C(S)CH$_2$SEt |
| 3-Cl-5-CF$_3$ | CF$_3$ | H | H | C(S)CH$_2$SO$_2$Et |
| 3-Cl-5-CF$_3$ | CF$_2$Cl | H | H | C(O)CH$_2$SCH$_3$ |
| 3-Cl-5-CF$_3$ | CF$_2$Cl | H | H | C(O)CH$_2$S(O)CH$_3$ |
| 3-Cl-5-CF$_3$ | CF$_2$Cl | H | H | C(O)CH$_2$SO$_2$CH$_3$ |
| 3-Cl-5-CF$_3$ | CF$_2$Cl | H | H | C(O)CH$_2$SEt |
| 3-Cl-5-CF$_3$ | CF$_2$Cl | H | H | C(O)CH$_2$S(O)Et |
| 3-Cl-5-CF$_3$ | CF$_2$Cl | H | H | C(O)CH$_2$SO$_2$Et |
| 3-Cl-5-CF$_3$ | CF$_2$Cl | H | H | C(S)CH$_2$SCH$_3$ |
| 3-Cl-5-CF$_3$ | CF$_2$Cl | H | H | C(S)CH$_2$SO$_2$CH$_3$ |
| 3-Cl-5-CF$_3$ | CF$_2$Cl | H | H | C(S)CH$_2$SEt |
| 3-Cl-5-CF$_3$ | CF$_2$Cl | H | H | C(S)CH$_2$SO$_2$Et |
| 3-Br-5-CF$_3$ | CHF$_2$ | H | H | C(O)CH$_2$SCH$_3$ |
| 3-Br-5-CF$_3$ | CHF$_2$ | H | H | C(O)CH$_2$S(O)CH$_3$ |
| 3-Br-5-CF$_3$ | CHF$_2$ | H | H | C(O)CH$_2$SO$_2$CH$_3$ |
| 3-Br-5-CF$_3$ | CHF$_2$ | H | H | C(O)CH$_2$SEt |
| 3-Br-5-CF$_3$ | CHF$_2$ | H | H | C(O)CH$_2$S(O)Et |
| 3-Br-5-CF$_3$ | CHF$_2$ | H | H | C(O)CH$_2$SO$_2$Et |
| 3-Br-5-CF$_3$ | CF$_3$ | H | H | C(O)CH$_2$SCH$_3$ |
| 3-Br-5-CF$_3$ | CF$_3$ | CH$_3$ | H | C(O)CH$_2$SCH$_3$ |
| 3-Br-5-CF$_3$ | CF$_3$ | H | CH$_3$ | C(O)CH$_2$SCH$_3$ |
| 3-Br-5-CF$_3$ | CF$_3$ | H | Et | C(O)CH$_2$SCH$_3$ |

| (X)$_m$ | R$^3$ | R$^4$ | R$^2$ | R$^1$ |
|---|---|---|---|---|
| 3-Br-5-CF$_3$ | CF$_3$ | H | CH$_2$Pr-c | C(O)CH$_2$SCH$_3$ |
| 3-Br-5-CF$_3$ | CF$_3$ | H | CH$_2$OCH$_3$ | C(O)CH$_2$SCH$_3$ |
| 3-Br-5-CF$_3$ | CF$_3$ | H | CH$_2$CN | C(O)CH$_2$SCH$_3$ |
| 3-Br-5-CF$_3$ | CF$_3$ | H | CH$_2$C(O)OCH$_3$ | C(O)CH$_2$SCH$_3$ |
| 3-Br-5-CF$_3$ | CF$_3$ | H | CH$_2$C(O)NH$_2$ | C(O)CH$_2$SCH$_3$ |
| 3-Br-5-CF$_3$ | CF$_3$ | H | CH$_2$C(O)NHCH$_3$ | C(O)CH$_2$SCH$_3$ |
| 3-Br-5-CF$_3$ | CF$_3$ | H | CH$_2$C(O)N(CH$_3$)$_2$ | C(O)CH$_2$SCH$_3$ |
| 3-Br-5-CF$_3$ | CF$_3$ | H | CH$_2$C(S)NH$_2$ | C(O)CH$_2$SCH$_3$ |
| 3-Br-5-CF$_3$ | CF$_3$ | H | CH$_2$CH=CH$_2$ | C(O)CH$_2$SCH$_3$ |
| 3-Br-5-CF$_3$ | CF$_3$ | H | CH$_2$C≡CH | C(O)CH$_2$SCH$_3$ |
| 3-Br-5-CF$_3$ | CF$_3$ | H | H | C(O)CH$_2$S(O)CH$_3$ |
| 3-Br-5-CF$_3$ | CF$_3$ | CH$_3$ | H | C(O)CH$_2$S(O)CH$_3$ |
| 3-Br-5-CF$_3$ | CF$_3$ | H | CH$_3$ | C(O)CH$_2$S(O)CH$_3$ |
| 3-Br-5-CF$_3$ | CF$_3$ | H | Et | C(O)CH$_2$S(O)CH$_3$ |
| 3-Br-5-CF$_3$ | CF$_3$ | H | CH$_2$Pr-c | C(O)CH$_2$S(O)CH$_3$ |
| 3-Br-5-CF$_3$ | CF$_3$ | H | CH$_2$OCH$_3$ | C(O)CH$_2$S(O)CH$_3$ |
| 3-Br-5-CF$_3$ | CF$_3$ | H | CH$_2$CN | C(O)CH$_2$S(O)CH$_3$ |
| 3-Br-5-CF$_3$ | CF$_3$ | H | CH$_2$C(O)OCH$_3$ | C(O)CH$_2$S(O)CH$_3$ |
| 3-Br-5-CF$_3$ | CF$_3$ | H | CH$_2$C(O)NH$_2$ | C(O)CH$_2$S(O)CH$_3$ |
| 3-Br-5-CF$_3$ | CF$_3$ | H | CH$_2$C(O)NHCH$_3$ | C(O)CH$_2$S(O)CH$_3$ |
| 3-Br-5-CF$_3$ | CF$_3$ | H | CH$_2$C(O)N(CH$_3$)$_2$ | C(O)CH$_2$S(O)CH$_3$ |
| 3-Br-5-CF$_3$ | CF$_3$ | H | CH$_2$C(S)NH$_2$ | C(O)CH$_2$S(O)CH$_3$ |
| 3-Br-5-CF$_3$ | CF$_3$ | H | CH$_2$CH=CH$_2$ | C(O)CH$_2$S(O)CH$_3$ |
| 3-Br-5-CF$_3$ | CF$_3$ | H | CH$_2$C≡CH | C(O)CH$_2$S(O)CH$_3$ |
| 3-Br-5-CF$_3$ | CF$_3$ | H | H | C(O)CH$_2$SO$_2$CH$_3$ |
| 3-Br-5-CF$_3$ | CF$_3$ | CH$_3$ | H | C(O)CH$_2$SO$_2$CH$_3$ |
| 3-Br-5-CF$_3$ | CF$_3$ | H | CH$_3$ | C(O)CH$_2$SO$_2$CH$_3$ |
| 3-Br-5-CF$_3$ | CF$_3$ | H | Et | C(O)CH$_2$SO$_2$CH$_3$ |
| 3-Br-5-CF$_3$ | CF$_3$ | H | CH$_2$Pr-c | C(O)CH$_2$SO$_2$CH$_3$ |
| 3-Br-5-CF$_3$ | CF$_3$ | H | CH$_2$OCH$_3$ | C(O)CH$_2$SO$_2$CH$_3$ |
| 3-Br-5-CF$_3$ | CF$_3$ | H | CH$_2$CN | C(O)CH$_2$SO$_2$CH$_3$ |
| 3-Br-5-CF$_3$ | CF$_3$ | H | CH$_2$C(O)OCH$_3$ | C(O)CH$_2$SO$_2$CH$_3$ |
| 3-Br-5-CF$_3$ | CF$_3$ | H | CH$_2$C(O)NH$_2$ | C(O)CH$_2$SO$_2$CH$_3$ |
| 3-Br-5-CF$_3$ | CF$_3$ | H | CH$_2$C(O)NHCH$_3$ | C(O)CH$_2$SO$_2$CH$_3$ |
| 3-Br-5-CF$_3$ | CF$_3$ | H | CH$_2$C(O)N(CH$_3$)$_2$ | C(O)CH$_2$SO$_2$CH$_3$ |
| 3-Br-5-CF$_3$ | CF$_3$ | H | CH$_2$C(S)NH$_2$ | C(O)CH$_2$SO$_2$CH$_3$ |
| 3-Br-5-CF$_3$ | CF$_3$ | H | CH$_2$CH=CH$_2$ | C(O)CH$_2$SO$_2$CH$_3$ |
| 3-Br-5-CF$_3$ | CF$_3$ | H | CH$_2$C≡CH | C(O)CH$_2$SO$_2$CH$_3$ |
| 3-Br-5-CF$_3$ | CF$_3$ | H | H | C(O)CH$_2$SEt |
| 3-Br-5-CF$_3$ | CF$_3$ | CH$_3$ | H | C(O)CH$_2$SEt |
| 3-Br-5-CF$_3$ | CF$_3$ | H | CH$_3$ | C(O)CH$_2$SEt |
| 3-Br-5-CF$_3$ | CF$_3$ | H | Et | C(O)CH$_2$SEt |
| 3-Br-5-CF$_3$ | CF$_3$ | H | CH$_2$Pr-c | C(O)CH$_2$SEt |
| 3-Br-5-CF$_3$ | CF$_3$ | H | CH$_2$OCH$_3$ | C(O)CH$_2$SEt |
| 3-Br-5-CF$_3$ | CF$_3$ | H | CH$_2$CN | C(O)CH$_2$SEt |
| 3-Br-5-CF$_3$ | CF$_3$ | H | CH$_2$C(O)OCH$_3$ | C(O)CH$_2$SEt |
| 3-Br-5-CF$_3$ | CF$_3$ | H | CH$_2$C(O)NH$_2$ | C(O)CH$_2$SEt |
| 3-Br-5-CF$_3$ | CF$_3$ | H | CH$_2$C(O)NHCH$_3$ | C(O)CH$_2$SEt |
| 3-Br-5-CF$_3$ | CF$_3$ | H | CH$_2$C(O)N(CH$_3$)$_2$ | C(O)CH$_2$SEt |
| 3-Br-5-CF$_3$ | CF$_3$ | H | CH$_2$C(S)NH$_2$ | C(O)CH$_2$SEt |
| 3-Br-5-CF$_3$ | CF$_3$ | H | CH$_2$CH=CH$_2$ | C(O)CH$_2$SEt |
| 3-Br-5-CF$_3$ | CF$_3$ | H | CH$_2$C≡CH | C(O)CH$_2$SEt |
| 3-Br-5-CF$_3$ | CF$_3$ | H | H | C(O)CH$_2$S(O)Et |
| 3-Br-5-CF$_3$ | CF$_3$ | CH$_3$ | H | C(O)CH$_2$S(O)Et |
| 3-Br-5-CF$_3$ | CF$_3$ | H | CH$_3$ | C(O)CH$_2$S(O)Et |
| 3-Br-5-CF$_3$ | CF$_3$ | H | Et | C(O)CH$_2$S(O)Et |
| 3-Br-5-CF$_3$ | CF$_3$ | H | CH$_2$Pr-c | C(O)CH$_2$S(O)Et |
| 3-Br-5-CF$_3$ | CF$_3$ | H | CH$_2$OCH$_3$ | C(O)CH$_2$S(O)Et |
| 3-Br-5-CF$_3$ | CF$_3$ | H | CH$_2$CN | C(O)CH$_2$S(O)Et |
| 3-Br-5-CF$_3$ | CF$_3$ | H | CH$_2$C(O)OCH$_3$ | C(O)CH$_2$S(O)Et |
| 3-Br-5-CF$_3$ | CF$_3$ | H | CH$_2$C(O)NH$_2$ | C(O)CH$_2$S(O)Et |
| 3-Br-5-CF$_3$ | CF$_3$ | H | CH$_2$C(O)NHCH$_3$ | C(O)CH$_2$S(O)Et |
| 3-Br-5-CF$_3$ | CF$_3$ | H | CH$_2$C(O)N(CH$_3$)$_2$ | C(O)CH$_2$S(O)Et |
| 3-Br-5-CF$_3$ | CF$_3$ | H | CH$_2$C(S)NH$_2$ | C(O)CH$_2$S(O)Et |
| 3-Br-5-CF$_3$ | CF$_3$ | H | CH$_2$CH=CH$_2$ | C(O)CH$_2$S(O)Et |
| 3-Br-5-CF$_3$ | CF$_3$ | H | CH$_2$C≡CH | C(O)CH$_2$S(O)Et |
| 3-Br-5-CF$_3$ | CF$_3$ | H | H | C(O)CH$_2$SO$_2$Et |
| 3-Br-5-CF$_3$ | CF$_3$ | CH$_3$ | H | C(O)CH$_2$SO$_2$Et |
| 3-Br-5-CF$_3$ | CF$_3$ | H | CH$_3$ | C(O)CH$_2$SO$_2$Et |
| 3-Br-5-CF$_3$ | CF$_3$ | H | Et | C(O)CH$_2$SO$_2$Et |
| 3-Br-5-CF$_3$ | CF$_3$ | H | CH$_2$Pr-c | C(O)CH$_2$SO$_2$Et |
| 3-Br-5-CF$_3$ | CF$_3$ | H | CH$_2$OCH$_3$ | C(O)CH$_2$SO$_2$Et |
| 3-Br-5-CF$_3$ | CF$_3$ | H | CH$_2$CN | C(O)CH$_2$SO$_2$Et |
| 3-Br-5-CF$_3$ | CF$_3$ | H | CH$_2$C(O)OCH$_3$ | C(O)CH$_2$SO$_2$Et |
| 3-Br-5-CF$_3$ | CF$_3$ | H | CH$_2$C(O)NH$_2$ | C(O)CH$_2$SO$_2$Et |
| 3-Br-5-CF$_3$ | CF$_3$ | H | CH$_2$C(O)NHCH$_3$ | C(O)CH$_2$SO$_2$Et |
| 3-Br-5-CF$_3$ | CF$_3$ | H | CH$_2$C(O)N(CH$_3$)$_2$ | C(O)CH$_2$SO$_2$Et |
| 3-Br-5-CF$_3$ | CF$_3$ | H | CH$_2$C(S)NH$_2$ | C(O)CH$_2$SO$_2$Et |

-continued

| (X)$_m$ | R$^3$ | R$^4$ | R$^2$ | R$^1$ |
|---|---|---|---|---|
| 3-Br-5-CF$_3$ | CF$_3$ | H | CH$_2$CH=CH$_2$ | C(O)CH$_2$SO$_2$Et |
| 3-Br-5-CF$_3$ | CF$_3$ | H | CH$_2$C≡CH | C(O)CH$_2$SO$_2$Et |
| 3-Br-5-CF$_3$ | CF$_3$ | H | H | C(O)CH$_2$SCH$_2$CF$_3$ |
| 3-Br-5-CF$_3$ | CF$_3$ | H | H | C(O)CH$_2$S(O)CH$_2$CF$_3$ |
| 3-Br-5-CF$_3$ | CF$_3$ | H | H | C(O)CH$_2$SO$_2$CH$_2$CF$_3$ |
| 3-Br-5-CF$_3$ | CF$_3$ | H | H | C(O)CH(CH$_3$)SCH$_3$ |
| 3-Br-5-CF$_3$ | CF$_3$ | H | H | C(O)CH(CH$_3$)S(O)CH$_3$ |
| 3-Br-5-CF$_3$ | CF$_3$ | H | H | C(O)CH(CH$_3$)SO$_2$CH$_3$ |
| 3-Br-5-CF$_3$ | CF$_3$ | H | H | C(O)CH(CH$_3$)SEt |
| 3-Br-5-CF$_3$ | CF$_3$ | H | H | C(O)(E-1-1a) |
| 3-Br-5-CF$_3$ | CF$_3$ | H | H | C(O)(E-1-1b) |
| 3-Br-5-CF$_3$ | CF$_3$ | H | H | C(O)(E-1-1c) |
| 3-Br-5-CF$_3$ | CF$_3$ | H | H | C(O)(E-1-2a) |
| 3-Br-5-CF$_3$ | CF$_3$ | H | H | C(O)(E-1-2b) |
| 3-Br-5-CF$_3$ | CF$_3$ | H | H | C(O)(E-1-2c) |
| 3-Br-5-CF$_3$ | CF$_3$ | H | H | C(O)CH(SCH$_3$)$_2$ |
| 3-Br-5-CF$_3$ | CF$_3$ | H | H | C(O)CH(SCH$_3$)S(O)CH$_3$ |
| 3-Br-5-CF$_3$ | CF$_3$ | H | H | C(O)CH[S(O)CH$_3$]$_2$ |
| 3-Br-5-CF$_3$ | CF$_3$ | H | H | C(O)CH[S(O)CH$_3$]SO$_2$CH$_3$ |
| 3-Br-5-CF$_3$ | CF$_3$ | H | H | C(O)CH(SEt)$_2$ |
| 3-Br-5-CF$_3$ | CF$_3$ | H | H | C(O)CH(SEt)S(O)Et |
| 3-Br-5-CF$_3$ | CF$_3$ | H | H | C(O)CH[S(O)Et]$_2$ |
| 3-Br-5-CF$_3$ | CF$_3$ | H | H | C(O)CH[S(O)Et]SO$_2$Et |
| 3-Br-5-CF$_3$ | CF$_3$ | H | H | C(S)CH$_2$SCH$_3$ |
| 3-Br-5-CF$_3$ | CF$_3$ | H | H | C(S)CH$_2$SO$_2$CH$_3$ |
| 3-Br-5-CF$_3$ | CF$_3$ | H | H | C(S)CH$_2$SEt |
| 3-Br-5-CF$_3$ | CF$_3$ | H | H | C(S)CH$_2$SO$_2$Et |
| 3-Br-5-CF$_3$ | CF$_2$Cl | H | H | C(O)CH$_2$SCH$_3$ |
| 3-Br-5-CF$_3$ | CF$_2$Cl | H | H | C(O)CH$_2$S(O)CH$_3$ |
| 3-Br-5-CF$_3$ | CF$_2$Cl | H | H | C(O)CH$_2$SO$_2$CH$_3$ |
| 3-Br-5-CF$_3$ | CF$_2$Cl | H | H | C(O)CH$_2$SEt |
| 3-Br-5-CF$_3$ | CF$_2$Cl | H | H | C(O)CH$_2$S(O)Et |
| 3-Br-5-CF$_3$ | CF$_2$Cl | H | H | C(O)CH$_2$SO$_2$Et |
| 3-Br-5-CF$_3$ | CF$_2$Cl | H | H | C(O)CH$_2$SCH$_3$ |
| 3-Br-5-CF$_3$ | CF$_2$Cl | H | H | C(O)CH$_2$SO$_2$CH$_3$ |
| 3-Br-5-CF$_3$ | CF$_2$Cl | H | H | C(S)CH$_2$SEt |
| 3-Br-5-CF$_3$ | CF$_2$Cl | H | H | C(S)CH$_2$SO$_2$Et |
| 3-I-5-CF$_3$ | CF$_3$ | H | H | C(O)CH$_2$SCH$_3$ |
| 3-I-5-CF$_3$ | CF$_3$ | CH$_3$ | H | C(O)CH$_2$SCH$_3$ |
| 3-I-5-CF$_3$ | CF$_3$ | H | CH$_3$ | C(O)CH$_2$SCH$_3$ |
| 3-I-5-CF$_3$ | CF$_3$ | H | Et | C(O)CH$_2$SCH$_3$ |
| 3-I-5-CF$_3$ | CF$_3$ | H | CH$_2$Pr-c | C(O)CH$_2$SCH$_3$ |
| 3-I-5-CF$_3$ | CF$_3$ | H | CH$_2$OCH$_3$ | C(O)CH$_2$SCH$_3$ |
| 3-I-5-CF$_3$ | CF$_3$ | H | CH$_2$CN | C(O)CH$_2$SCH$_3$ |
| 3-I-5-CF$_3$ | CF$_3$ | H | CH$_2$C(O)OCH$_3$ | C(O)CH$_2$SCH$_3$ |
| 3-I-5-CF$_3$ | CF$_3$ | H | CH$_2$C(O)NH$_2$ | C(O)CH$_2$SCH$_3$ |
| 3-I-5-CF$_3$ | CF$_3$ | H | CH$_2$C(O)NHCH$_3$ | C(O)CH$_2$SCH$_3$ |
| 3-I-5-CF$_3$ | CF$_3$ | H | CH$_2$C(O)N(CH$_3$)$_2$ | C(O)CH$_2$SCH$_3$ |
| 3-I-5-CF$_3$ | CF$_3$ | H | CH$_2$C(S)NH$_2$ | C(O)CH$_2$SCH$_3$ |
| 3-I-5-CF$_3$ | CF$_3$ | H | CH$_2$CH=CH$_2$ | C(O)CH$_2$SCH$_3$ |
| 3-I-5-CF$_3$ | CF$_3$ | H | CH$_2$C≡CH | C(O)CH$_2$SCH$_3$ |
| 3-I-5-CF$_3$ | CF$_3$ | H | H | C(O)CH$_2$S(O)CH$_3$ |
| 3-I-5-CF$_3$ | CF$_3$ | CH$_3$ | H | C(O)CH$_2$S(O)CH$_3$ |
| 3-I-5-CF$_3$ | CF$_3$ | H | CH$_3$ | C(O)CH$_2$S(O)CH$_3$ |
| 3-I-5-CF$_3$ | CF$_3$ | H | Et | C(O)CH$_2$S(O)CH$_3$ |
| 3-I-5-CF$_3$ | CF$_3$ | H | CH$_2$Pr-c | C(O)CH$_2$S(O)CH$_3$ |
| 3-I-5-CF$_3$ | CF$_3$ | H | CH$_2$OCH$_3$ | C(O)CH$_2$S(O)CH$_3$ |
| 3-I-5-CF$_3$ | CF$_3$ | H | CH$_2$CN | C(O)CH$_2$S(O)CH$_3$ |
| 3-I-5-CF$_3$ | CF$_3$ | H | CH$_2$C(O)OCH$_3$ | C(O)CH$_2$S(O)CH$_3$ |
| 3-I-5-CF$_3$ | CF$_3$ | H | CH$_2$C(O)NH$_2$ | C(O)CH$_2$S(O)CH$_3$ |
| 3-I-5-CF$_3$ | CF$_3$ | H | CH$_2$C(O)NHCH$_3$ | C(O)CH$_2$S(O)CH$_3$ |
| 3-I-5-CF$_3$ | CF$_3$ | H | CH$_2$C(O)N(CH$_3$)$_2$ | C(O)CH$_2$S(O)CH$_3$ |
| 3-I-5-CF$_3$ | CF$_3$ | H | CH$_2$C(S)NH$_2$ | C(O)CH$_2$S(O)CH$_3$ |
| 3-I-5-CF$_3$ | CF$_3$ | H | CH$_2$CH=CH$_2$ | C(O)CH$_2$S(O)CH$_3$ |
| 3-I-5-CF$_3$ | CF$_3$ | H | CH$_2$C≡CH | C(O)CH$_2$S(O)CH$_3$ |
| 3-I-5-CF$_3$ | CF$_3$ | H | H | C(O)CH$_2$SO$_2$CH$_3$ |
| 3-I-5-CF$_3$ | CF$_3$ | CH$_3$ | H | C(O)CH$_2$SO$_2$CH$_3$ |
| 3-I-5-CF$_3$ | CF$_3$ | H | CH$_3$ | C(O)CH$_2$SO$_2$CH$_3$ |
| 3-I-5-CF$_3$ | CF$_3$ | H | Et | C(O)CH$_2$SO$_2$CH$_3$ |
| 3-I-5-CF$_3$ | CF$_3$ | H | CH$_2$Pr-c | C(O)CH$_2$SO$_2$CH$_3$ |
| 3-I-5-CF$_3$ | CF$_3$ | H | CH$_2$OCH$_3$ | C(O)CH$_2$SO$_2$CH$_3$ |
| 3-I-5-CF$_3$ | CF$_3$ | H | CH$_2$CN | C(O)CH$_2$SO$_2$CH$_3$ |
| 3-I-5-CF$_3$ | CF$_3$ | H | CH$_2$C(O)OCH$_3$ | C(O)CH$_2$SO$_2$CH$_3$ |
| 3-I-5-CF$_3$ | CF$_3$ | H | CH$_2$C(O)NH$_2$ | C(O)CH$_2$SO$_2$CH$_3$ |
| 3-I-5-CF$_3$ | CF$_3$ | H | CH$_2$C(O)NHCH$_3$ | C(O)CH$_2$SO$_2$CH$_3$ |
| 3-I-5-CF$_3$ | CF$_3$ | H | CH$_2$C(O)N(CH$_3$)$_2$ | C(O)CH$_2$SO$_2$CH$_3$ |
| 3-I-5-CF$_3$ | CF$_3$ | H | CH$_2$C(S)NH$_2$ | C(O)CH$_2$SO$_2$CH$_3$ |
| 3-I-5-CF$_3$ | CF$_3$ | H | CH$_2$CH=CH$_2$ | C(O)CH$_2$SO$_2$CH$_3$ |

-continued

| (X)$_m$ | R$^3$ | R$^4$ | R$^2$ | R$^1$ |
|---|---|---|---|---|
| 3-I-5-CF$_3$ | CF$_3$ | H | CH$_2$C≡CH | C(O)CH$_2$SO$_2$CH$_3$ |
| 3-I-5-CF$_3$ | CF$_3$ | H | H | C(O)CH$_2$SEt |
| 3-I-5-CF$_3$ | CF$_3$ | CH$_3$ | H | C(O)CH$_2$SEt |
| 3-I-5-CF$_3$ | CF$_3$ | H | CH$_3$ | C(O)CH$_2$SEt |
| 3-I-5-CF$_3$ | CF$_3$ | H | Et | C(O)CH$_2$SEt |
| 3-I-5-CF$_3$ | CF$_3$ | H | CH$_2$Pr-c | C(O)CH$_2$SEt |
| 3-I-5-CF$_3$ | CF$_3$ | H | CH$_2$OCH$_3$ | C(O)CH$_2$SEt |
| 3-I-5-CF$_3$ | CF$_3$ | H | CH$_2$CN | C(O)CH$_2$SEt |
| 3-I-5-CF$_3$ | CF$_3$ | H | CH$_2$C(O)OCH$_3$ | C(O)CH$_2$SEt |
| 3-I-5-CF$_3$ | CF$_3$ | H | CH$_2$C(O)NH$_2$ | C(O)CH$_2$SEt |
| 3-I-5-CF$_3$ | CF$_3$ | H | CH$_2$C(O)NHCH$_3$ | C(O)CH$_2$SEt |
| 3-I-5-CF$_3$ | CF$_3$ | H | CH$_2$C(O)N(CH$_3$)$_2$ | C(O)CH$_2$SEt |
| 3-I-5-CF$_3$ | CF$_3$ | H | CH$_2$C(S)NH$_2$ | C(O)CH$_2$SEt |
| 3-I-5-CF$_3$ | CF$_3$ | H | CH$_2$CH═CH$_2$ | C(O)CH$_2$SEt |
| 3-I-5-CF$_3$ | CF$_3$ | H | CH$_2$C≡CH | C(O)CH$_2$SEt |
| 3-I-5-CF$_3$ | CF$_3$ | H | H | C(O)CH$_2$S(O)Et |
| 3-I-5-CF$_3$ | CF$_3$ | CH$_3$ | H | C(O)CH$_2$S(O)Et |
| 3-I-5-CF$_3$ | CF$_3$ | H | CH$_3$ | C(O)CH$_2$S(O)Et |
| 3-I-5-CF$_3$ | CF$_3$ | H | Et | C(O)CH$_2$S(O)Et |
| 3-I-5-CF$_3$ | CF$_3$ | H | CH$_2$Pr-c | C(O)CH$_2$S(O)Et |
| 3-I-5-CF$_3$ | CF$_3$ | H | CH$_2$OCH$_3$ | C(O)CH$_2$S(O)Et |
| 3-I-5-CF$_3$ | CF$_3$ | H | CH$_2$CN | C(O)CH$_2$S(O)Et |
| 3-I-5-CF$_3$ | CF$_3$ | H | CH$_2$C(O)OCH$_3$ | C(O)CH$_2$S(O)Et |
| 3-I-5-CF$_3$ | CF$_3$ | H | CH$_2$C(O)NH$_2$ | C(O)CH$_2$S(O)Et |
| 3-I-5-CF$_3$ | CF$_3$ | H | CH$_2$C(O)NHCH$_3$ | C(O)CH$_2$S(O)Et |
| 3-I-5-CF$_3$ | CF$_3$ | H | CH$_2$C(O)N(CH$_3$)$_2$ | C(O)CH$_2$S(O)Et |
| 3-I-5-CF$_3$ | CF$_3$ | H | CH$_2$C(S)NH$_2$ | C(O)CH$_2$S(O)Et |
| 3-I-5-CF$_3$ | CF$_3$ | H | CH$_2$CH═CH$_2$ | C(O)CH$_2$S(O)Et |
| 3-I-5-CF$_3$ | CF$_3$ | H | CH$_2$C≡CH | C(O)CH$_2$S(O)Et |
| 3-I-5-CF$_3$ | CF$_3$ | H | H | C(O)CH$_2$SO$_2$Et |
| 3-I-5-CF$_3$ | CF$_3$ | CH$_3$ | H | C(O)CH$_2$SO$_2$Et |
| 3-I-5-CF$_3$ | CF$_3$ | H | CH$_3$ | C(O)CH$_2$SO$_2$Et |
| 3-I-5-CF$_3$ | CF$_3$ | H | Et | C(O)CH$_2$SO$_2$Et |
| 3-I-5-CF$_3$ | CF$_3$ | H | CH$_2$Pr-c | C(O)CH$_2$SO$_2$Et |
| 3-I-5-CF$_3$ | CF$_3$ | H | CH$_2$OCH$_3$ | C(O)CH$_2$SO$_2$Et |
| 3-I-5-CF$_3$ | CF$_3$ | H | CH$_2$CN | C(O)CH$_2$SO$_2$Et |
| 3-I-5-CF$_3$ | CF$_3$ | H | CH$_2$C(O)OCH$_3$ | C(O)CH$_2$SO$_2$Et |
| 3-I-5-CF$_3$ | CF$_3$ | H | CH$_2$C(O)NH$_2$ | C(O)CH$_2$SO$_2$Et |
| 3-I-5-CF$_3$ | CF$_3$ | H | CH$_2$C(O)NHCH$_3$ | C(O)CH$_2$SO$_2$Et |
| 3-I-5-CF$_3$ | CF$_3$ | H | CH$_2$C(O)N(CH$_3$)$_2$ | C(O)CH$_2$SO$_2$Et |
| 3-I-5-CF$_3$ | CF$_3$ | H | CH$_2$C(S)NH$_2$ | C(O)CH$_2$SO$_2$Et |
| 3-I-5-CF$_3$ | CF$_3$ | H | CH$_2$CH═CH$_2$ | C(O)CH$_2$SO$_2$Et |
| 3-I-5-CF$_3$ | CF$_3$ | H | CH$_2$C≡CH | C(O)CH$_2$SO$_2$Et |
| 3-I-5-CF$_3$ | CF$_3$ | H | H | C(O)CH(CH$_3$)SCH$_3$ |
| 3-I-5-CF$_3$ | CF$_3$ | H | H | C(O)(E-1-1a) |
| 3-I-5-CF$_3$ | CF$_3$ | H | H | C(O)(E-1-1b) |
| 3-I-5-CF$_3$ | CF$_3$ | H | H | C(O)(E-1-1c) |
| 3-I-5-CF$_3$ | CF$_3$ | H | H | C(O)CH(SCH$_3$)$_2$ |
| 3-I-5-CF$_3$ | CF$_3$ | H | H | C(O)CH[S(O)CH$_3$]$_2$ |
| 3-I-5-CF$_3$ | CF$_3$ | H | H | C(O)CH(SEt)$_2$ |
| 3-I-5-CF$_3$ | CF$_3$ | H | H | C(O)CH(SEt)S(O)Et |
| 3-I-5-CF$_3$ | CF$_3$ | H | H | C(S)CH$_2$SCH$_3$ |
| 3-I-5-CF$_3$ | CF$_3$ | H | H | C(S)CH$_2$SO$_2$CH$_3$ |
| 3-I-5-CF$_3$ | CF$_3$ | H | H | C(S)CH$_2$SEt |
| 3-I-5-CF$_3$ | CF$_3$ | H | H | C(S)CH$_2$SO$_2$Et |
| 3-I-5-CF$_3$ | CF$_2$Cl | H | H | C(O)CH$_2$SCH$_3$ |
| 3-I-5-CF$_3$ | CF$_2$Cl | H | H | C(O)CH$_2$S(O)CH$_3$ |
| 3-I-5-CF$_3$ | CF$_2$Cl | H | H | C(O)CH$_2$SO$_2$CH$_3$ |
| 3-I-5-CF$_3$ | CF$_2$Cl | H | H | C(O)CH$_2$SEt |
| 3-I-5-CF$_3$ | CF$_2$Cl | H | H | C(O)CH$_2$S(O)Et |
| 3-I-5-CF$_3$ | CF$_2$Cl | H | H | C(O)CH$_2$SO$_2$Et |
| 3-CH$_3$-5-CF$_3$ | CF$_3$ | H | H | C(O)CH$_2$SCH$_3$ |
| 3-CH$_3$-5-CF$_3$ | CF$_3$ | H | H | C(O)CH$_2$S(O)CH$_3$ |
| 3-CH$_3$-5-CF$_3$ | CF$_3$ | H | H | C(O)CH$_2$SO$_2$CH$_3$ |
| 3-CH$_3$-5-CF$_3$ | CF$_3$ | H | H | C(O)CH$_2$SEt |
| 3-CH$_3$-5-CF$_3$ | CF$_3$ | H | H | C(O)CH$_2$S(O)Et |
| 3-CH$_3$-5-CF$_3$ | CF$_3$ | H | H | C(O)CH$_2$SO$_2$Et |
| 3,5-(CF$_3$)$_2$ | CHF$_2$ | H | H | C(O)CH$_2$SCH$_3$ |
| 3,5-(CF$_3$)$_2$ | CHF$_2$ | H | H | C(O)CH$_2$S(O)CH$_3$ |
| 3,5-(CF$_3$)$_2$ | CHF$_2$ | H | H | C(O)CH$_2$SO$_2$CH$_3$ |
| 3,5-(CF$_3$)$_2$ | CHF$_2$ | H | H | C(O)CH$_2$SEt |
| 3,5-(CF$_3$)$_2$ | CHF$_2$ | H | H | C(O)CH$_2$S(O)Et |
| 3,5-(CF$_3$)$_2$ | CHF$_2$ | H | H | C(O)CH$_2$SO$_2$Et |
| 3,5-(CF$_3$)$_2$ | CHF$_2$ | H | H | C(S)CH$_2$SCH$_3$ |
| 3,5-(CF$_3$)$_2$ | CHF$_2$ | H | H | C(S)CH$_2$SO$_2$CH$_3$ |
| 3,5-(CF$_3$)$_2$ | CHF$_2$ | H | H | C(S)CH$_2$SEt |
| 3,5-(CF$_3$)$_2$ | CHF$_2$ | H | H | C(S)CH$_2$SO$_2$Et |
| 3,5-(CF$_3$)$_2$ | CF$_3$ | H | H | C(O)CH$_2$SCH$_3$ |

-continued

| (X)$_m$ | R$^3$ | R$^4$ | R$^2$ | R$^1$ |
| --- | --- | --- | --- | --- |
| 3,5-(CF$_3$)$_2$ | CF$_3$ | CH$_3$ | H | C(O)CH$_2$SCH$_3$ |
| 3,5-(CF$_3$)$_2$ | CF$_3$ | CH$_3$(R) | H | C(O)CH$_2$SCH$_3$ |
| 3,5-(CF$_3$)$_2$ | CF$_3$ | CH$_3$(S) | H | C(O)CH$_2$SCH$_3$ |
| 3,5-(CF$_3$)$_2$ | CF$_3$ | Et | H | C(O)CH$_2$SCH$_3$ |
| 3,5-(CF$_3$)$_2$ | CF$_3$ | CF$_3$ | H | C(O)CH$_2$SCH$_3$ |
| 3,5-(CF$_3$)$_2$ | CF$_3$ | CF$_3$(R) | H | C(O)CH$_2$SCH$_3$ |
| 3,5-(CF$_3$)$_2$ | CF$_3$ | CF$_3$(S) | H | C(O)CH$_2$SCH$_3$ |
| 3,5-(CF$_3$)$_2$ | CF$_3$ | C≡CH | H | C(O)CH$_2$SCH$_3$ |
| 3,5-(CF$_3$)$_2$ | CF$_3$ | C≡CH(R) | H | C(O)CH$_2$SCH$_3$ |
| 3,5-(CF$_3$)$_2$ | CF$_3$ | C≡CH(S) | H | C(O)CH$_2$SCH$_3$ |
| 3,5-(CF$_3$)$_2$ | CF$_3$ | CN | H | C(O)CH$_2$SCH$_3$ |
| 3,5-(CF$_3$)$_2$ | CF$_3$ | CN(R) | H | C(O)CH$_2$SCH$_3$ |
| 3,5-(CF$_3$)$_2$ | CF$_3$ | CN(S) | H | C(O)CH$_2$SCH$_3$ |
| 3,5-(CF$_3$)$_2$ | CF$_3$ | C(S)NH$_2$ | H | C(O)CH$_2$SCH$_3$ |
| 3,5-(CF$_3$)$_2$ | CF$_3$ | C(S)NH$_2$(R) | H | C(O)CH$_2$SCH$_3$ |
| 3,5-(CF$_3$)$_2$ | CF$_3$ | C(S)NH$_2$(S) | H | C(O)CH$_2$SCH$_3$ |
| 3,5-(CF$_3$)$_2$ | CF$_3$ | Ph | H | C(O)CH$_2$SCH$_3$ |
| 3,5-(CF$_3$)$_2$ | CF$_3$ | D-7-1a | H | C(O)CH$_2$SCH$_3$ |
| 3,5-(CF$_3$)$_2$ | CF$_3$ | D-7-1a(R) | H | C(O)CH$_2$SCH$_3$ |
| 3,5-(CF$_3$)$_2$ | CF$_3$ | D-7-1a(S) | H | C(O)CH$_2$SCH$_3$ |
| 3,5-(CF$_3$)$_2$ | CF$_3$ | H | CH$_3$ | C(O)CH$_2$SCH$_3$ |
| 3,5-(CF$_3$)$_2$ | CF$_3$ | H | Et | C(O)CH$_2$SCH$_3$ |
| 3,5-(CF$_3$)$_2$ | CF$_3$ | H | c-Pr | C(O)CH$_2$SCH$_3$ |
| 3,5-(CF$_3$)$_2$ | CF$_3$ | H | CH$_2$Pr-c | C(O)CH$_2$SCH$_3$ |
| 3,5-(CF$_3$)$_2$ | CF$_3$ | H | CH$_2$CF$_3$ | C(O)CH$_2$SCH$_3$ |
| 3,5-(CF$_3$)$_2$ | CF$_3$ | H | CH$_2$OCH$_3$ | C(O)CH$_2$SCH$_3$ |
| 3,5-(CF$_3$)$_2$ | CF$_3$ | H | CH$_2$OEt | C(O)CH$_2$SCH$_3$ |
| 3,5-(CF$_3$)$_2$ | CF$_3$ | H | CH$_2$OCH$_2$CH$_2$Cl | C(O)CH$_2$SCH$_3$ |
| 3,5-(CF$_3$)$_2$ | CF$_3$ | H | CH$_2$OCH$_2$CHF$_2$ | C(O)CH$_2$SCH$_3$ |
| 3,5-(CF$_3$)$_2$ | CF$_3$ | H | CH$_2$OCH$_2$CF$_3$ | C(O)CH$_2$SCH$_3$ |
| 3,5-(CF$_3$)$_2$ | CF$_3$ | H | CH$_2$OCH$_2$CH$_2$OCH$_3$ | C(O)CH$_2$SCH$_3$ |
| 3,5-(CF$_3$)$_2$ | CF$_3$ | H | CH$_2$OCH$_2$Ph | C(O)CH$_2$SCH$_3$ |
| 3,5-(CF$_3$)$_2$ | CF$_3$ | H | CH$_2$OC(O)CH$_3$ | C(O)CH$_2$SCH$_3$ |
| 3,5-(CF$_3$)$_2$ | CF$_3$ | H | CH$_2$OC(O)Et | C(O)CH$_2$SCH$_3$ |
| 3,5-(CF$_3$)$_2$ | CF$_3$ | H | CH$_2$OC(O)Pr-n | C(O)CH$_2$SCH$_3$ |
| 3,5-(CF$_3$)$_2$ | CF$_3$ | H | CH$_2$OC(O)Pr-i | C(O)CH$_2$SCH$_3$ |
| 3,5-(CF$_3$)$_2$ | CF$_3$ | H | CH$_2$OC(O)Pr-c | C(O)CH$_2$SCH$_3$ |
| 3,5-(CF$_3$)$_2$ | CF$_3$ | H | CH$_2$OC(O)Bu-n | C(O)CH$_2$SCH$_3$ |
| 3,5-(CF$_3$)$_2$ | CF$_3$ | H | CH$_2$OC(O)Bu-i | C(O)CH$_2$SCH$_3$ |
| 3,5-(CF$_3$)$_2$ | CF$_3$ | H | CH$_2$OC(O)Bu-s | C(O)CH$_2$SCH$_3$ |
| 3,5-(CF$_3$)$_2$ | CF$_3$ | H | CH$_2$OC(O)Bu-t | C(O)CH$_2$SCH$_3$ |
| 3,5-(CF$_3$)$_2$ | CF$_3$ | H | CH$_2$OC(O)CH$_2$Ph | C(O)CH$_2$SCH$_3$ |
| 3,5-(CF$_3$)$_2$ | CF$_3$ | H | CH$_2$OC(O)Ph | C(O)CH$_2$SCH$_3$ |
| 3,5-(CF$_3$)$_2$ | CF$_3$ | H | CH$_2$OC(O)OCH$_3$ | C(O)CH$_2$SCH$_3$ |
| 3,5-(CF$_3$)$_2$ | CF$_3$ | H | CH$_2$OC(O)OEt | C(O)CH$_2$SCH$_3$ |
| 3,5-(CF$_3$)$_2$ | CF$_3$ | H | CH$_2$OC(O)OBu-n | C(O)CH$_2$SCH$_3$ |
| 3,5-(CF$_3$)$_2$ | CF$_3$ | H | CH$_2$OC(O)OBu-i | C(O)CH$_2$SCH$_3$ |
| 3,5-(CF$_3$)$_2$ | CF$_3$ | H | CH$_2$OC(O)OCH$_2$Ph | C(O)CH$_2$SCH$_3$ |
| 3,5-(CF$_3$)$_2$ | CF$_3$ | H | CH$_2$OC(O)OPh | C(O)CH$_2$SCH$_3$ |
| 3,5-(CF$_3$)$_2$ | CF$_3$ | H | CH$_2$OC(O)NHPh | C(O)CH$_2$SCH$_3$ |
| 3,5-(CF$_3$)$_2$ | CF$_3$ | H | CH$_2$OPh | C(O)CH$_2$SCH$_3$ |
| 3,5-(CF$_3$)$_2$ | CF$_3$ | H | CH$_2$CH$_2$OCH$_3$ | C(O)CH$_2$SCH$_3$ |
| 3,5-(CF$_3$)$_2$ | CF$_3$ | H | CH$_2$SCH$_3$ | C(O)CH$_2$SCH$_3$ |
| 3,5-(CF$_3$)$_2$ | CF$_3$ | H | CH$_2$SO$_2$CH$_3$ | C(O)CH$_2$SCH$_3$ |
| 3,5-(CF$_3$)$_2$ | CF$_3$ | H | CH$_2$SC(O)CH$_3$ | C(O)CH$_2$SCH$_3$ |
| 3,5-(CF$_3$)$_2$ | CF$_3$ | H | CH$_2$SC(O)Et | C(O)CH$_2$SCH$_3$ |
| 3,5-(CF$_3$)$_2$ | CF$_3$ | H | CH$_2$SC(O)Ph | C(O)CH$_2$SCH$_3$ |
| 3,5-(CF$_3$)$_2$ | CF$_3$ | H | CH$_2$SC(S)OCH$_3$ | C(O)CH$_2$SCH$_3$ |
| 3,5-(CF$_3$)$_2$ | CF$_3$ | H | CH$_2$SC(S)OEt | C(O)CH$_2$SCH$_3$ |
| 3,5-(CF$_3$)$_2$ | CF$_3$ | H | CH$_2$SC(S)OPr-n | C(O)CH$_2$SCH$_3$ |
| 3,5-(CF$_3$)$_2$ | CF$_3$ | H | CH$_2$SC(S)OPr-i | C(O)CH$_2$SCH$_3$ |
| 3,5-(CF$_3$)$_2$ | CF$_3$ | H | CH$_2$SC(S)N(CH$_3$)$_2$ | C(O)CH$_2$SCH$_3$ |
| 3,5-(CF$_3$)$_2$ | CF$_3$ | H | CH$_2$SC(S)(T-1) | C(O)CH$_2$SCH$_3$ |
| 3,5-(CF$_3$)$_2$ | CF$_3$ | H | CH$_2$CH$_2$SCH$_3$ | C(O)CH$_2$SCH$_3$ |
| 3,5-(CF$_3$)$_2$ | CF$_3$ | H | CH$_2$N(CH$_3$)$_2$ | C(O)CH$_2$SCH$_3$ |
| 3,5-(CF$_3$)$_2$ | CF$_3$ | H | CH$_2$NHC(O)CH$_3$ | C(O)CH$_2$SCH$_3$ |
| 3,5-(CF$_3$)$_2$ | CF$_3$ | H | CH$_2$NHC(O)CF$_3$ | C(O)CH$_2$SCH$_3$ |
| 3,5-(CF$_3$)$_2$ | CF$_3$ | H | CH$_2$NHC(O)OCl$_3$ | C(O)CH$_2$SCH$_3$ |
| 3,5-(CF$_3$)$_2$ | CF$_3$ | H | CH$_2$NHC(O)Ph | C(O)CH$_2$SCH$_3$ |
| 3,5-(CF$_3$)$_2$ | CF$_3$ | H | CH$_2$NHC(O)(D-11-1a) | C(O)CH$_2$SCH$_3$ |
| 3,5-(CF$_3$)$_2$ | CF$_3$ | H | CH$_2$NHC(O)(D-11-2a) | C(O)CH$_2$SCH$_3$ |
| 3,5-(CF$_3$)$_2$ | CF$_3$ | H | CH$_2$NHC(O)(D-11-3a) | C(O)CH$_2$SCH$_3$ |
| 3,5-(CF$_3$)$_2$ | CF$_3$ | H | CH$_2$NHC(O)OCH$_3$ | C(O)CH$_2$SCH$_3$ |
| 3,5-(CF$_3$)$_2$ | CF$_3$ | H | CH$_2$NHC(O)OEt | C(O)CH$_2$SCH$_3$ |
| 3,5-(CF$_3$)$_2$ | CF$_3$ | H | CH$_2$CN | C(O)CH$_2$SCH$_3$ |
| 3,5-(CF$_3$)$_2$ | CF$_3$ | H | CH$_2$C(O)OCH$_3$ | C(O)CH$_2$SCH$_3$ |
| 3,5-(CF$_3$)$_2$ | CF$_3$ | H | CH$_2$C(O)NH$_2$ | C(O)CH$_2$SCH$_3$ |
| 3,5-(CF$_3$)$_2$ | CF$_3$ | H | CH$_2$C(O)NHCH$_3$ | C(O)CH$_2$SCH$_3$ |

-continued

| $(X)_m$ | $R^3$ | $R^4$ | $R^2$ | $R^1$ |
|---|---|---|---|---|
| 3,5-$(CF_3)_2$ | $CF_3$ | H | $CH_2C(O)N(CH_3)_2$ | $C(O)CH_2SCH_3$ |
| 3,5-$(CF_3)_2$ | $CF_3$ | H | $CH_2C(O)NHEt$ | $C(O)CH_2SCH_3$ |
| 3,5-$(CF_3)_2$ | $CF_3$ | H | $CH_2C(O)NHPr$-n | $C(O)CH_2SCH_3$ |
| 3,5-$(CF_3)_2$ | $CF_3$ | H | $CH_2C(O)NHPr$-i | $C(O)CH_2SCH_3$ |
| 3,5-$(CF_3)_2$ | $CF_3$ | H | $CH_2C(O)NHPr$-c | $C(O)CH_2SCH_3$ |
| 3,5-$(CF_3)_2$ | $CF_3$ | H | $CH_2C(O)NHCH_2CF_3$ | $C(O)CH_2SCH_3$ |
| 3,5-$(CF_3)_2$ | $CF_3$ | H | $CH_2C(S)NH_2$ | $C(O)CH_2SCH_3$ |
| 3,5-$(CF_3)_2$ | $CF_3$ | H | $CH_2CH=CH_2$ | $C(O)CH_2SCH_3$ |
| 3,5-$(CF_3)_2$ | $CF_3$ | H | $CH_2C\equiv CH$ | $C(O)CH_2SCH_3$ |
| 3,5-$(CF_3)_2$ | $CF_3$ | H | $C(O)CH_3$ | $C(O)CH_2SCH_3$ |
| 3,5-$(CF_3)_2$ | $CF_3$ | H | $C(O)Et$ | $C(O)CH_2SCH_3$ |
| 3,5-$(CF_3)_2$ | $CF_3$ | H | $C(O)Pr$-n | $C(O)CH_2SCH_3$ |
| 3,5-$(CF_3)_2$ | $CF_3$ | H | $C(O)OCH_3$ | $C(O)CH_2SCH_3$ |
| 3,5-$(CF_3)_2$ | $CF_3$ | H | $C(O)OEt$ | $C(O)CH_2SCH_3$ |
| 3,5-$(CF_3)_2$ | $CF_3$ | H | $C(O)OPr$-n | $C(O)CH_2SCH_3$ |
| 3,5-$(CF_3)_2$ | $CF_3$ | H | $C(O)OPr$-i | $C(O)CH_2SCH_3$ |
| 3,5-$(CF_3)_2$ | $CF_3$ | H | $C(O)OPr$-c | $C(O)CH_2SCH_3$ |
| 3,5-$(CF_3)_2$ | $CF_3$ | H | $C(O)OBu$-i | $C(O)CH_2SCH_3$ |
| 3,5-$(CF_3)_2$ | $CF_3$ | H | $C(O)OBu$-t | $C(O)CH_2SCH_3$ |
| 3,5-$(CF_3)_2$ | $CF_3$ | H | $C(O)OCH_2Cl$ | $C(O)CH_2SCH_3$ |
| 3,5-$(CF_3)_2$ | $CF_3$ | H | $C(O)OCH_2CH_2Cl$ | $C(O)CH_2SCH_3$ |
| 3,5-$(CF_3)_2$ | $CF_3$ | H | $C(O)OCH_2CH_2OCH_3$ | $C(O)CH_2SCH_3$ |
| 3,5-$(CF_3)_2$ | $CF_3$ | H | $C(O)OCH_2CH_2SO_2CH_3$ | $C(O)CH_2SCH_3$ |
| 3,5-$(CF_3)_2$ | $CF_3$ | H | $C(O)OCH=CH_2$ | $C(O)CH_2SCH_3$ |
| 3,5-$(CF_3)_2$ | $CF_3$ | H | $C(O)OCH_2CH=CH_2$ | $C(O)CH_2SCH_3$ |
| 3,5-$(CF_3)_2$ | $CF_3$ | H | $C(O)OCH_2C\equiv CH$ | $C(O)CH_2SCH_3$ |
| 3,5-$(CF_3)_2$ | $CF_3$ | H | $C(O)SCH_3$ | $C(O)CH_2SCH_3$ |
| 3,5-$(CF_3)_2$ | $CF_3$ | H | $C(S)OCH_3$ | $C(O)CH_2SCH_3$ |
| 3,5-$(CF_3)_2$ | $CF_3$ | H | $C(S)SCH_3$ | $C(O)CH_2SCH_3$ |
| 3,5-$(CF_3)_2$ | $CF_3$ | H | $OCH_3$ | $C(O)CH_2SCH_3$ |
| 3,5-$(CF_3)_2$ | $CF_3$ | H | $OEt$ | $C(O)CH_2SCH_3$ |
| 3,5-$(CF_3)_2$ | $CF_3$ | H | $SCCl_3$ | $C(O)CH_2SCH_3$ |
| 3,5-$(CF_3)_2$ | $CF_3$ | H | $SN(Bu$-n$)_2$ | $C(O)CH_2SCH_3$ |
| 3,5-$(CF_3)_2$ | $CF_3$ | H | $S(T-3)$ | $C(O)CH_2SCH_3$ |
| 3,5-$(CF_3)_2$ | $CF_3$ | H | $SN(Pr$-i$)CH_2CH_2C(O)OEt$ | $C(O)CH_2S(O)CH_3$ |
| 3,5-$(CF_3)_2$ | $CF_3$ | H | $SN(CH_2Ph)CH_2CH_2C(O)OEt$ | $C(O)CH_2S(O)CH_3$ |
| 3,5-$(CF_3)_2$ | $CF_3$ | H | $SN(CH_3)C(O)OBu$-n | $C(O)CH_2S(O)CH_3$ |
| 3,5-$(CF_3)_2$ | $CF_3$ | H | H | $C(O)CH_2S(O)CH_3$ |
| 3,5-$(CF_3)_2$ | $CF_3$ | $CH_3$ | H | $C(O)CH_2S(O)CH_3$ |
| 3,5-$(CF_3)_2$ | $CF_3$ | $CH_3(R)$ | H | $C(O)CH_2S(O)CH_3$ |
| 3,5-$(CF_3)_2$ | $CF_3$ | $CH_3(S)$ | H | $C(O)CH_2S(O)CH_3$ |
| 3,5-$(CF_3)_2$ | $CF_3$ | $C\equiv CH$ | H | $C(O)CH_2S(O)CH_3$ |
| 3,5-$(CF_3)_2$ | $CF_3$ | $C\equiv CH(R)$ | H | $C(O)CH_2S(O)CH_3$ |
| 3,5-$(CF_3)_2$ | $CF_3$ | $C\equiv CH(S)$ | H | $C(O)CH_2S(O)CH_3$ |
| 3,5-$(CF_3)_2$ | $CF_3$ | $CN$ | H | $C(O)CH_2S(O)CH_3$ |
| 3,5-$(CF_3)_2$ | $CF_3$ | $CN(R)$ | H | $C(O)CH_2S(O)CH_3$ |
| 3,5-$(CF_3)_2$ | $CF_3$ | $CN(S)$ | H | $C(O)CH_2S(O)CH_3$ |
| 3,5-$(CF_3)_2$ | $CF_3$ | $C(S)NH_2$ | H | $C(O)CH_2S(O)CH_3$ |
| 3,5-$(CF_3)_2$ | $CF_3$ | $C(S)NH_2(R)$ | H | $C(O)CH_2S(O)CH_3$ |
| 3,5-$(CF_3)_2$ | $CF_3$ | $C(S)NH_2(S)$ | H | $C(O)CH_2S(O)CH_3$ |
| 3,5-$(CF_3)_2$ | $CF_3$ | D-7-1a | H | $C(O)CH_2S(O)CH_3$ |
| 3,5-$(CF_3)_2$ | $CF_3$ | D-7-1a(R) | H | $C(O)CH_2S(O)CH_3$ |
| 3,5-$(CF_3)_2$ | $CF_3$ | D-7-1a(S) | H | $C(O)CH_2S(O)CH_3$ |
| 3,5-$(CF_3)_2$ | $CF_3$ | H | $CH_3$ | $C(O)CH_2S(O)CH_3$ |
| 3,5-$(CF_3)_2$ | $CF_3$ | H | $Et$ | $C(O)CH_2S(O)CH_3$ |
| 3,5-$(CF_3)_2$ | $CF_3$ | H | $CH_2Pr$-c | $C(O)CH_2S(O)CH_3$ |
| 3,5-$(CF_3)_2$ | $CF_3$ | H | $CH_2OCH_3$ | $C(O)CH_2S(O)CH_3$ |
| 3,5-$(CF_3)_2$ | $CF_3$ | H | $CH_2CN$ | $C(O)CH_2S(O)CH_3$ |
| 3,5-$(CF_3)_2$ | $CF_3$ | H | $CH_2C(O)OCH_3$ | $C(O)CH_2S(O)CH_3$ |
| 3,5-$(CF_3)_2$ | $CF_3$ | H | $CH_2C(O)NH_2$ | $C(O)CH_2S(O)CH_3$ |
| 3,5-$(CF_3)_2$ | $CF_3$ | H | $CH_2C(O)NHCH_3$ | $C(O)CH_2S(O)CH_3$ |
| 3,5-$(CF_3)_2$ | $CF_3$ | H | $CH_2C(O)N(CH_3)_2$ | $C(O)CH_2S(O)CH_3$ |
| 3,5-$(CF_3)_2$ | $CF_3$ | H | $CH_2C(S)NH_2$ | $C(O)CH_2S(O)CH_3$ |
| 3,5-$(CF_3)_2$ | $CF_3$ | H | $CH_2CH=CH_2$ | $C(O)CH_2S(O)CH_3$ |
| 3,5-$(CF_3)_2$ | $CF_3$ | H | $CH_2C\equiv CH$ | $C(O)CH_2S(O)CH_3$ |
| 3,5-$(CF_3)_2$ | $CF_3$ | H | H | $C(O)CH_2S(CH_3)=NCN$ |
| 3,5-$(CF_3)_2$ | $CF_3$ | H | H | $C(O)CH_2S(CH_3)=NC(O)CF_3$ |
| 3,5-$(CF_3)_2$ | $CF_3$ | H | H | $C(O)CH_2SO_2CH_3$ |
| 3,5-$(CF_3)_2$ | $CF_3$ | $CH_3$ | H | $C(O)CH_2SO_2CH_3$ |
| 3,5-$(CF_3)_2$ | $CF_3$ | $CH_3(R)$ | H | $C(O)CH_2SO_2CH_3$ |
| 3,5-$(CF_3)_2$ | $CF_3$ | $CH_3(S)$ | H | $C(O)CH_2SO_2CH_3$ |
| 3,5-$(CF_3)_2$ | $CF_3$ | $C\equiv CH$ | H | $C(O)CH_2SO_2CH_3$ |
| 3,5-$(CF_3)_2$ | $CF_3$ | $C\equiv CH(R)$ | H | $C(O)CH_2SO_2CH_3$ |
| 3,5-$(CF_3)_2$ | $CF_3$ | $C\equiv CH(S)$ | H | $C(O)CH_2SO_2CH_3$ |
| 3,5-$(CF_3)_2$ | $CF_3$ | $CN$ | H | $C(O)CH_2SO_2CH_3$ |
| 3,5-$(CF_3)_2$ | $CF_3$ | $CN(R)$ | H | $C(O)CH_2SO_2CH_3$ |
| 3,5-$(CF_3)_2$ | $CF_3$ | $CN(S)$ | H | $C(O)CH_2SO_2CH_3$ |
| 3,5-$(CF_3)_2$ | $CF_3$ | $C(S)NH_2$ | H | $C(O)CH_2SO_2CH_3$ |

-continued

| $(X)_m$ | $R^3$ | $R^4$ | $R^2$ | $R^1$ |
|---|---|---|---|---|
| 3,5-(CF$_3$)$_2$ | CF$_3$ | C(S)NH$_2$(R) | H | C(O)CH$_2$SO$_2$CH$_3$ |
| 3,5-(CF$_3$)$_2$ | CF$_3$ | C(S)NH$_2$(S) | H | C(O)CH$_2$SO$_2$CH$_3$ |
| 3,5-(CF$_3$)$_2$ | CF$_3$ | D-7-1a | H | C(O)CH$_2$SO$_2$CH$_3$ |
| 3,5-(CF$_3$)$_2$ | CF$_3$ | D-7-1a(R) | H | C(O)CH$_2$SO$_2$CH$_3$ |
| 3,5-(CF$_3$)$_2$ | CF$_3$ | D-7-1a(S) | H | C(O)CH$_2$SO$_2$CH$_3$ |
| 3,5-(CF$_3$)$_2$ | CF$_3$ | H | CH$_3$ | C(O)CH$_2$SO$_2$CH$_3$ |
| 3,5-(CF$_3$)$_2$ | CF$_3$ | H | Et | C(O)CH$_2$SO$_2$CH$_3$ |
| 3,5-(CF$_3$)$_2$ | CF$_3$ | H | CH$_2$Pr-c | C(O)CH$_2$SO$_2$CH$_3$ |
| 3,5-(CF$_3$)$_2$ | CF$_3$ | H | CH$_2$OCH$_3$ | C(O)CH$_2$SO$_2$CH$_3$ |
| 3,5-(CF$_3$)$_2$ | CF$_3$ | H | CH$_2$CN | C(O)CH$_2$SO$_2$CH$_3$ |
| 3,5-(CF$_3$)$_2$ | CF$_3$ | H | CH$_2$C(O)OCH$_3$ | C(O)CH$_2$SO$_2$CH$_3$ |
| 3,5-(CF$_3$)$_2$ | CF$_3$ | H | CH$_2$C(O)NH$_2$ | C(O)CH$_2$SO$_2$CH$_3$ |
| 3,5-(CF$_3$)$_2$ | CF$_3$ | H | CH$_2$C(O)NHCH$_3$ | C(O)CH$_2$SO$_2$CH$_3$ |
| 3,5-(CF$_3$)$_2$ | CF$_3$ | H | CH$_2$C(O)N(CH$_3$)$_2$ | C(O)CH$_2$SO$_2$CH$_3$ |
| 3,5-(CF$_3$)$_2$ | CF$_3$ | H | CH$_2$C(S)NH$_2$ | C(O)CH$_2$SO$_2$CH$_3$ |
| 3,5-(CF$_3$)$_2$ | CF$_3$ | H | CH$_2$CH=CH$_2$ | C(O)CH$_2$SO$_2$CH$_3$ |
| 3,5-(CF$_3$)$_2$ | CF$_3$ | H | CH$_2$C≡CH | C(O)CH$_2$SO$_2$CH$_3$ |
| 3,5-(CF$_3$)$_2$ | CF$_3$ | H | H | C(O)CH$_2$S(O)(CH$_3$)=NH |
| 3,5-(CF$_3$)$_2$ | CF$_3$ | CH$_3$ | H | C(O)CH$_2$S(O)(CH$_3$)=NH |
| 3,5-(CF$_3$)$_2$ | CF$_3$ | H | H | C(O)CH$_2$S(O)(CH$_3$)=NCH$_3$ |
| 3,5-(CF$_3$)$_2$ | CF$_3$ | H | H | C(O)CH$_2$S(O)(CH$_3$)=NCN |
| 3,5-(CF$_3$)$_2$ | CF$_3$ | H | H | C(O)CH$_2$S(O)(CH$_3$)=NC(O)CH$_3$ |
| 3,5-(CF$_3$)$_2$ | CF$_3$ | H | H | C(O)CH$_2$S(O)(CH$_3$)=NC(O)CF$_3$ |
| 3,5-(CF$_3$)$_2$ | CF$_3$ | H | H | C(O)CH$_2$S(O)(CH$_3$)=NC(O)OBu-t |
| 3,5-(CF$_3$)$_2$ | CF$_3$ | H | H | C(O)CH$_2$S(O)(CH$_3$)=NSO$_2$CH$_3$ |
| 3,5-(CF$_3$)$_2$ | CF$_3$ | H | H | C(O)CH$_2$S(O)(CH$_3$)=NNO$_2$ |
| 3,5-(CF$_3$)$_2$ | CF$_3$ | H | H | C(O)CH$_2$SEt |
| 3,5-(CF$_3$)$_2$ | CF$_3$ | CH$_3$ | H | C(O)CH$_2$SEt |
| 3,5-(CF$_3$)$_2$ | CF$_3$ | CH$_3$(R) | H | C(O)CH$_2$SEt |
| 3,5-(CF$_3$)$_2$ | CF$_3$ | CH$_3$(S) | H | C(O)CH$_2$SEt |
| 3,5-(CF$_3$)$_2$ | CF$_3$ | C≡CH | H | C(O)CH$_2$SEt |
| 3,5-(CF$_3$)$_2$ | CF$_3$ | C≡CH(R) | H | C(O)CH$_2$SEt |
| 3,5-(CF$_3$)$_2$ | CF$_3$ | C≡CH(S) | H | C(O)CH$_2$SEt |
| 3,5-(CF$_3$)$_2$ | CF$_3$ | CN | H | C(O)CH$_2$SEt |
| 3,5-(CF$_3$)$_2$ | CF$_3$ | CN(R) | H | C(O)CH$_2$SEt |
| 3,5-(CF$_3$)$_2$ | CF$_3$ | CN(S) | H | C(O)CH$_2$SEt |
| 3,5-(CF$_3$)$_2$ | CF$_3$ | C(S)NH$_2$ | H | C(O)CH$_2$SEt |
| 3,5-(CF$_3$)$_2$ | CF$_3$ | C(S)NH$_2$(R) | H | C(O)CH$_2$SEt |
| 3,5-(CF$_3$)$_2$ | CF$_3$ | C(S)NH$_2$(S) | H | C(O)CH$_2$SEt |
| 3,5-(CF$_3$)$_2$ | CF$_3$ | D-7-1a | H | C(O)CH$_2$SEt |
| 3,5-(CF$_3$)$_2$ | CF$_3$ | D-7-1a(R) | H | C(O)CH$_2$SEt |
| 3,5-(CF$_3$)$_2$ | CF$_3$ | D-7-1a(S) | H | C(O)CH$_2$SEt |
| 3,5-(CF$_3$)$_2$ | CF$_3$ | H | CH$_3$ | C(O)CH$_2$SEt |
| 3,5-(CF$_3$)$_2$ | CF$_3$ | H | Et | C(O)CH$_2$SEt |
| 3,5-(CF$_3$)$_2$ | CF$_3$ | H | n-Pr | C(O)CH$_2$SEt |
| 3,5-(CF$_3$)$_2$ | CF$_3$ | H | i-Bu | C(O)CH$_2$SEt |
| 3,5-(CF$_3$)$_2$ | CF$_3$ | H | CH$_2$Pr-c | C(O)CH$_2$SEt |
| 3,5-(CF$_3$)$_2$ | CF$_3$ | H | CH$_2$OCH$_3$ | C(O)CH$_2$SEt |
| 3,5-(CF$_3$)$_2$ | CF$_3$ | H | CH$_2$CN | C(O)CH$_2$SEt |
| 3,5-(CF$_3$)$_2$ | CF$_3$ | H | CH$_2$C(O)OCH$_3$ | C(O)CH$_2$SEt |
| 3,5-(CF$_3$)$_2$ | CF$_3$ | H | CH$_2$C(O)NH$_2$ | C(O)CH$_2$SEt |
| 3,5-(CF$_3$)$_2$ | CF$_3$ | H | CH$_2$C(O)NHCH$_3$ | C(O)CH$_2$SEt |
| 3,5-(CF$_3$)$_2$ | CF$_3$ | H | CH$_2$C(O)N(CH$_3$)$_2$ | C(O)CH$_2$SEt |
| 3,5-(CF$_3$)$_2$ | CF$_3$ | H | CH$_2$C(S)NH$_2$ | C(O)CH$_2$SEt |
| 3,5-(CF$_3$)$_2$ | CF$_3$ | H | CH$_2$CH=CH$_2$ | C(O)CH$_2$SEt |
| 3,5-(CF$_3$)$_2$ | CF$_3$ | H | CH$_2$C≡CH | C(O)CH$_2$SEt |
| 3,5-(CF$_3$)$_2$ | CF$_3$ | H | CH$_2$Ph | C(O)CH$_2$SEt |
| 3,5-(CF$_3$)$_2$ | CF$_3$ | H | H | C(O)CH$_2$S(O)Et |
| 3,5-(CF$_3$)$_2$ | CF$_3$ | CH$_3$ | H | C(O)CH$_2$S(O)Et |
| 3,5-(CF$_3$)$_2$ | CF$_3$ | CH$_3$(R) | H | C(O)CH$_2$S(O)Et |
| 3,5-(CF$_3$)$_2$ | CF$_3$ | CH$_3$(S) | H | C(O)CH$_2$S(O)Et |
| 3,5-(CF$_3$)$_2$ | CF$_3$ | C≡CH | H | C(O)CH$_2$S(O)Et |
| 3,5-(CF$_3$)$_2$ | CF$_3$ | C≡CH(R) | H | C(O)CH$_2$S(O)Et |
| 3,5-(CF$_3$)$_2$ | CF$_3$ | C≡CH(S) | H | C(O)CH$_2$S(O)Et |
| 3,5-(CF$_3$)$_2$ | CF$_3$ | CN | H | C(O)CH$_2$S(O)Et |
| 3,5-(CF$_3$)$_2$ | CF$_3$ | CN(R) | H | C(O)CH$_2$S(O)Et |
| 3,5-(CF$_3$)$_2$ | CF$_3$ | CN(S) | H | C(O)CH$_2$S(O)Et |
| 3,5-(CF$_3$)$_2$ | CF$_3$ | C(S)NH$_2$ | H | C(O)CH$_2$S(O)Et |
| 3,5-(CF$_3$)$_2$ | CF$_3$ | C(S)NH$_2$(R) | H | C(O)CH$_2$S(O)Et |
| 3,5-(CF$_3$)$_2$ | CF$_3$ | C(S)NH$_2$(S) | H | C(O)CH$_2$S(O)Et |
| 3,5-(CF$_3$)$_2$ | CF$_3$ | D-7-1a | H | C(O)CH$_2$S(O)Et |
| 3,5-(CF$_3$)$_2$ | CF$_3$ | D-7-1a(R) | H | C(O)CH$_2$S(O)Et |
| 3,5-(CF$_3$)$_2$ | CF$_3$ | D-7-1a(S) | H | C(O)CH$_2$S(O)Et |
| 3,5-(CF$_3$)$_2$ | CF$_3$ | H | CH$_3$ | C(O)CH$_2$S(O)Et |
| 3,5-(CF$_3$)$_2$ | CF$_3$ | H | Et | C(O)CH$_2$S(O)Et |
| 3,5-(CF$_3$)$_2$ | CF$_3$ | H | CH$_2$Pr-c | C(O)CH$_2$S(O)Et |
| 3,5-(CF$_3$)$_2$ | CF$_3$ | H | CH$_2$OCH$_3$ | C(O)CH$_2$S(O)Et |
| 3,5-(CF$_3$)$_2$ | CF$_3$ | H | CH$_2$CN | C(O)CH$_2$S(O)Et |

-continued

| (X)$_m$ | R$^3$ | R$^4$ | R$^2$ | R$^1$ |
|---|---|---|---|---|
| 3,5-(CF$_3$)$_2$ | CF$_3$ | H | CH$_2$C(O)OCH$_3$ | C(O)CH$_2$S(O)Et |
| 3,5-(CF$_3$)$_2$ | CF$_3$ | H | CH$_2$C(O)NH$_2$ | C(O)CH$_2$S(O)Et |
| 3,5-(CF$_3$)$_2$ | CF$_3$ | H | CH$_2$C(O)NHCH$_3$ | C(O)CH$_2$S(O)Et |
| 3,5-(CF$_3$)$_2$ | CF$_3$ | H | CH$_2$C(O)N(CH$_3$)$_2$ | C(O)CH$_2$S(O)Et |
| 3,5-(CF$_3$)$_2$ | CF$_3$ | H | CH$_2$C(S)NH$_2$ | C(O)CH$_2$S(O)Et |
| 3,5-(CF$_3$)$_2$ | CF$_3$ | H | CH$_2$CH=CH$_2$ | C(O)CH$_2$S(O)Et |
| 3,5-(CF$_3$)$_2$ | CF$_3$ | H | CH$_2$C≡CH | C(O)CH$_2$S(O)Et |
| 3,5-(CF$_3$)$_2$ | CF$_3$ | H | H | CH$_2$S(Et)=NCN |
| 3,5-(CF$_3$)$_2$ | CF$_3$ | H | H | CH$_2$S(Et)=NC(O)CF$_3$ |
| 3,5-(CF$_3$)$_2$ | CF$_3$ | H | H | C(O)CH$_2$SO$_2$Et |
| 3,5-(CF$_3$)$_2$ | CF$_3$ | CH$_3$ | H | C(O)CH$_2$SO$_2$Et |
| 3,5-(CF$_3$)$_2$ | CF$_3$ | CH$_3$(R) | H | C(O)CH$_2$SO$_2$Et |
| 3,5-(CF$_3$)$_2$ | CF$_3$ | CH$_3$(S) | H | C(O)CH$_2$SO$_2$Et |
| 3,5-(CF$_3$)$_2$ | CF$_3$ | C≡CH | H | C(O)CH$_2$SO$_2$Et |
| 3,5-(CF$_3$)$_2$ | CF$_3$ | C≡CH(R) | H | C(O)CH$_2$SO$_2$Et |
| 3,5-(CF$_3$)$_2$ | CF$_3$ | C≡CH(S) | H | C(O)CH$_2$SO$_2$Et |
| 3,5-(CF$_3$)$_2$ | CF$_3$ | CN | H | C(O)CH$_2$SO$_2$Et |
| 3,5-(CF$_3$)$_2$ | CF$_3$ | CN(R) | H | C(O)CH$_2$SO$_2$Et |
| 3,5-(CF$_3$)$_2$ | CF$_3$ | CN(S) | H | C(O)CH$_2$SO$_2$Et |
| 3,5-(CF$_3$)$_2$ | CF$_3$ | C(S)NH$_2$ | H | C(O)CH$_2$SO$_2$Et |
| 3,5-(CF$_3$)$_2$ | CF$_3$ | C(S)NH$_2$(R) | H | C(O)CH$_2$SO$_2$Et |
| 3,5-(CF$_3$)$_2$ | CF$_3$ | C(S)NH$_2$(S) | H | C(O)CH$_2$SO$_2$Et |
| 3,5-(CF$_3$)$_2$ | CF$_3$ | D-7-1a | H | C(O)CH$_2$SO$_2$Et |
| 3,5-(CF$_3$)$_2$ | CF$_3$ | D-7-1a(R) | H | C(O)CH$_2$SO$_2$Et |
| 3,5-(CF$_3$)$_2$ | CF$_3$ | D-7-1a(S) | H | C(O)CH$_2$SO$_2$Et |
| 3,5-(CF$_3$)$_2$ | CF$_3$ | H | CH$_3$ | C(O)CH$_2$SO$_2$Et |
| 3,5-(CF$_3$)$_2$ | CF$_3$ | H | Et | C(O)CH$_2$SO$_2$Et |
| 3,5-(CF$_3$)$_2$ | CF$_3$ | H | CH$_2$Pr-c | C(O)CH$_2$SO$_2$Et |
| 3,5-(CF$_3$)$_2$ | CF$_3$ | H | CH$_2$OCH$_3$ | C(O)CH$_2$SO$_2$Et |
| 3,5-(CF$_3$)$_2$ | CF$_3$ | H | CH$_2$CN | C(O)CH$_2$SO$_2$Et |
| 3,5-(CF$_3$)$_2$ | CF$_3$ | H | CH$_2$C(O)OCH$_3$ | C(O)CH$_2$SO$_2$Et |
| 3,5-(CF$_3$)$_2$ | CF$_3$ | H | CH$_2$C(O)NH$_2$ | C(O)CH$_2$SO$_2$Et |
| 3,5-(CF$_3$)$_2$ | CF$_3$ | H | CH$_2$C(O)NHCH$_3$ | C(O)CH$_2$SO$_2$Et |
| 3,5-(CF$_3$)$_2$ | CF$_3$ | H | CH$_2$C(O)N(CH$_3$)$_2$ | C(O)CH$_2$SO$_2$Et |
| 3,5-(CF$_3$)$_2$ | CF$_3$ | H | CH$_2$C(S)NH$_2$ | C(O)CH$_2$SO$_2$Et |
| 3,5-(CF$_3$)$_2$ | CF$_3$ | H | CH$_2$CH=CH$_2$ | C(O)CH$_2$SO$_2$Et |
| 3,5-(CF$_3$)$_2$ | CF$_3$ | H | CH$_2$C≡CH | C(O)CH$_2$SO$_2$Et |
| 3,5-(CF$_3$)$_2$ | CF$_3$ | H | H | C(O)CH$_2$S(O)(Et)=NH |
| 3,5-(CF$_3$)$_2$ | CF$_3$ | H | H | C(O)CH$_2$S(O)(Et)=NC(O)CF$_3$ |
| 3,5-(CF$_3$)$_2$ | CF$_3$ | H | H | C(O)CH$_2$SPr-n |
| 3,5-(CF$_3$)$_2$ | CF$_3$ | H | H | C(O)CH$_2$SPr-i |
| 3,5-(CF$_3$)$_2$ | CF$_3$ | H | H | C(O)CH$_2$SCHF$_2$ |
| 3,5-(CF$_3$)$_2$ | CF$_3$ | H | H | C(O)CH$_2$S(O)CHF$_2$ |
| 3,5-(CF$_3$)$_2$ | CF$_3$ | H | H | C(O)CH$_2$SO$_2$CHF$_2$ |
| 3,5-(CF$_3$)$_2$ | CF$_3$ | H | H | C(O)CH$_2$SCF$_3$ |
| 3,5-(CF$_3$)$_2$ | CF$_3$ | H | H | C(O)CH$_2$S(O)CF$_3$ |
| 3,5-(CF$_3$)$_2$ | CF$_3$ | H | H | C(O)CH$_2$SO$_2$CF$_3$ |
| 3,5-(CF$_3$)$_2$ | CF$_3$ | H | H | C(O)CH$_2$SCH$_2$CH$_2$F |
| 3,5-(CF$_3$)$_2$ | CF$_3$ | H | H | C(O)CH$_2$SCH$_2$CF$_3$ |
| 3,5-(CF$_3$)$_2$ | CF$_3$ | H | H | C(O)CH$_2$S(O)CH$_2$CF$_3$ |
| 3,5-(CF$_3$)$_2$ | CF$_3$ | H | H | C(O)CH$_2$SO$_2$CH$_2$CF$_3$ |
| 3,5-(CF$_3$)$_2$ | CF$_3$ | H | H | C(O)CH$_2$SCF$_2$CF$_3$ |
| 3,5-(CF$_3$)$_2$ | CF$_3$ | H | H | C(O)CH$_2$SCF$_2$CF$_2$Cl |
| 3,5-(CF$_3$)$_2$ | CF$_3$ | H | H | C(O)CH$_2$SCF$_2$CF$_2$CF$_3$ |
| 3,5-(CF$_3$)$_2$ | CF$_3$ | H | H | C(O)CH$_2$SCH$_2$CH$_2$OCH$_3$ |
| 3,5-(CF$_3$)$_2$ | CF$_3$ | H | H | C(O)CH$_2$SCH$_2$CH$_2$OCH$_3$CF$_3$ |
| 3,5-(CF$_3$)$_2$ | CF$_3$ | H | H | C(O)CH$_2$SCH$_2$CH$_2$SCH$_3$ |
| 3,5-(CF$_3$)$_2$ | CF$_3$ | H | H | C(O)CH$_2$SCF$_2$CH$_2$OH |
| 3,5-(CF$_3$)$_2$ | CF$_3$ | H | H | C(O)CH$_2$SCF$_2$CH$_2$OCH$_3$ |
| 3,5-(CF$_3$)$_2$ | CF$_3$ | H | H | C(O)CH$_2$SCH$_2$Si(CH$_3$)$_3$ |
| 3,5-(CF$_3$)$_2$ | CF$_3$ | H | H | C(O)CH$_2$SCH$_2$CN |
| 3,5-(CF$_3$)$_2$ | CF$_3$ | H | H | C(O)CH$_2$S(O)CH$_2$CN |
| 3,5-(CF$_3$)$_2$ | CF$_3$ | H | H | C(O)CH$_2$SO$_2$CH$_2$CN |
| 3,5-(CF$_3$)$_2$ | CF$_3$ | H | H | C(O)CH$_2$SCH$_2$C(O)OCH$_3$ |
| 3,5-(CF$_3$)$_2$ | CF$_3$ | H | H | C(O)CH$_2$SCH$_2$C(O)OCH$_2$CF$_3$ |
| 3,5-(CF$_3$)$_2$ | CF$_3$ | H | H | C(O)CH$_2$SCH$_2$C(O)NH$_2$ |
| 3,5-(CF$_3$)$_2$ | CF$_3$ | H | H | C(O)CH$_2$SCH$_2$C(O)N(CH$_3$)$_2$ |
| 3,5-(CF$_3$)$_2$ | CF$_3$ | H | H | C(O)CH$_2$SCHFC(O)NHCH$_3$ |
| 3,5-(CF$_3$)$_2$ | CF$_3$ | H | H | C(O)CH$_2$SCH=CH$_2$ |
| 3,5-(CF$_3$)$_2$ | CF$_3$ | H | H | C(O)CH$_2$SO$_2$CH=CH$_2$ |
| 3,5-(CF$_3$)$_2$ | CF$_3$ | H | H | C(O)CH$_2$SCH$_2$CH=CH$_2$ |
| 3,5-(CF$_3$)$_2$ | CF$_3$ | H | H | C(O)CH$_2$SCH=CHF |
| 3,5-(CF$_3$)$_2$ | CF$_3$ | H | H | C(O)CH$_2$SCH=CHCl |
| 3,5-(CF$_3$)$_2$ | CF$_3$ | H | H | C(O)CH$_2$SCH=CCl$_2$ |
| 3,5-(CF$_3$)$_2$ | CF$_3$ | H | H | C(O)CH$_2$SO$_2$CH=CCl$_2$ |
| 3,5-(CF$_3$)$_2$ | CF$_3$ | H | H | C(O)CH$_2$SCCl=CHCl |
| 3,5-(CF$_3$)$_2$ | CF$_3$ | H | H | C(O)CH$_2$SCH$_2$CH=CCl$_2$ |
| 3,5-(CF$_3$)$_2$ | CF$_3$ | H | H | C(O)CH$_2$SCH$_2$CCl=CCl$_2$ |

-continued

| (X)$_m$ | R$^3$ | R$^4$ | R$^2$ | R$^1$ |
|---|---|---|---|---|
| 3,5-(CF$_3$)$_2$ | CF$_3$ | H | H | C(O)CH$_2$SCH$_2$CH$_2$CF=CF$_2$ |
| 3,5-(CF$_3$)$_2$ | CF$_3$ | H | H | C(O)CH$_2$SC≡CCH$_3$ |
| 3,5-(CF$_3$)$_2$ | CF$_3$ | H | H | C(O)CH$_2$SCH$_2$C≡CH |
| 3,5-(CF$_3$)$_2$ | CF$_3$ | H | H | C(O)CH$_2$SCH$_2$Ph |
| 3,5-(CF$_3$)$_2$ | CF$_3$ | H | H | C(O)CH$_2$S(O)CH$_2$Ph |
| 3,5-(CF$_3$)$_2$ | CF$_3$ | H | H | C(O)CH$_2$SO$_2$CH$_2$Ph |
| 3,5-(CF$_3$)$_2$ | CF$_3$ | H | H | C(O)CH$_2$SC(O)Ph |
| 3,5-(CF$_3$)$_2$ | CF$_3$ | H | H | C(O)CH$_2$SC(O)SCH$_3$ |
| 3,5-(CF$_3$)$_2$ | CF$_3$ | H | H | C(O)CH$_2$SC(O)NHCH$_3$ |
| 3,5-(CF$_3$)$_2$ | CF$_3$ | H | H | C(O)CH$_2$SC(O)N(CH$_3$)$_2$ |
| 3,5-(CF$_3$)$_2$ | CF$_3$ | H | H | C(O)CH$_2$SC(O)NHCH$_2$CF$_3$ |
| 3,5-(CF$_3$)$_2$ | CF$_3$ | H | H | C(O)CH$_2$SC(O)(T-1) |
| 3,5-(CF$_3$)$_2$ | CF$_3$ | H | H | C(O)CH$_2$SC(O)(T-2) |
| 3,5-(CF$_3$)$_2$ | CF$_3$ | H | H | C(O)CH$_2$SC(O)(T-3) |
| 3,5-(CF$_3$)$_2$ | CF$_3$ | H | H | C(O)CH$_2$SC(O)(T-4) |
| 3,5-(CF$_3$)$_2$ | CF$_3$ | H | H | C(O)CH$_2$SC(S)OCH$_3$ |
| 3,5-(CF$_3$)$_2$ | CF$_3$ | H | H | C(O)CH$_2$SC(S)SCH$_3$ |
| 3,5-(CF$_3$)$_2$ | CF$_3$ | H | H | C(O)CH$_2$SC(S)NHCH$_3$ |
| 3,5-(CF$_3$)$_2$ | CF$_3$ | H | H | C(O)CH$_2$SC(S)N(CH$_3$)$_2$ |
| 3,5-(CF$_3$)$_2$ | CF$_3$ | H | H | C(O)CH$_2$SC(S)NHCH$_2$CF$_3$ |
| 3,5-(CF$_3$)$_2$ | CF$_3$ | H | H | C(O)CH$_2$SC(S)(T-1) |
| 3,5-(CF$_3$)$_2$ | CF$_3$ | H | H | C(O)CH$_2$SPh |
| 3,5-(CF$_3$)$_2$ | CF$_3$ | H | H | C(O)CH$_2$S(O)Ph |
| 3,5-(CF$_3$)$_2$ | CF$_3$ | H | H | C(O)CH$_2$SO$_2$Ph |
| 3,5-(CF$_3$)$_2$ | CF$_3$ | H | H | C(O)CH$_2$S(D-7-1a) |
| 3,5-(CF$_3$)$_2$ | CF$_3$ | H | H | C(O)CH$_2$SO$_2$(D-7-1a) |
| 3,5-(CF$_3$)$_2$ | CF$_3$ | H | H | C(O)CH$_2$S(D-9-1a)CH$_3$ |
| 3,5-(CF$_3$)$_2$ | CF$_3$ | H | H | C(O)CH$_2$S(D-11-1a) |
| 3,5-(CF$_3$)$_2$ | CF$_3$ | H | H | C(O)CH$_2$S(O)(D-11-1a) |
| 3,5-(CF$_3$)$_2$ | CF$_3$ | H | H | C(O)CH$_2$SO$_2$(D-11-1a) |
| 3,5-(CF$_3$)$_2$ | CF$_3$ | H | H | C(O)CH$_2$S(O)(D-12-1a) |
| 3,5-(CF$_3$)$_2$ | CF$_3$ | H | H | C(O)CH$_2$SO$_2$(D-12-1a) |
| 3,5-(CF$_3$)$_2$ | CF$_3$ | H | H | C(O)CH$_2$S(D-12-2a) |
| 3,5-(CF$_3$)$_2$ | CF$_3$ | H | H | C(O)CH$_2$S(D-13-1a) |
| 3,5-(CF$_3$)$_2$ | CF$_3$ | H | H | C(O)CH$_2$S(D-14-1a) |
| 3,5-(CF$_3$)$_2$ | CF$_3$ | H | H | C(O)CH$_2$SSCH$_3$ |
| 3,5-(CF$_3$)$_2$ | CF$_3$ | H | H | C(O)CH$_2$SS(Ph-2-NO$_2$) |
| 3,5-(CF$_3$)$_2$ | CF$_3$ | H | H | C(O)CH(CH$_3$)SCH$_3$ |
| 3,5-(CF$_3$)$_2$ | CF$_3$ | H | H | C(O)CH(CH$_3$)SCH$_3$(R) |
| 3,5-(CF$_3$)$_2$ | CF$_3$ | H | H | C(O)CH(CH$_3$)SCH$_3$(S) |
| 3,5-(CF$_3$)$_2$ | CF$_3$ | CH$_3$ | H | C(O)CH(CH$_3$)SCH$_3$ |
| 3,5-(CF$_3$)$_2$ | CF$_3$ | H | CH$_3$ | C(O)CH(CH$_3$)SCH$_3$ |
| 3,5-(CF$_3$)$_2$ | CF$_3$ | H | Et | C(O)CH(CH$_3$)SCH$_3$ |
| 3,5-(CF$_3$)$_2$ | CF$_3$ | H | CH$_2$C≡CH | C(O)CH(CH$_3$)SCH$_3$ |
| 3,5-(CF$_3$)$_2$ | CF$_3$ | H | H | C(O)CH(CH$_3$)S(O)CH$_3$ |
| 3,5-(CF$_3$)$_2$ | CF$_3$ | H | H | C(O)CH(CH$_3$)SO$_2$CH$_3$ |
| 3,5-(CF$_3$)$_2$ | CF$_3$ | H | H | C(O)CH(CH$_3$)SO$_2$CH$_3$(R) |
| 3,5-(CF$_3$)$_2$ | CF$_3$ | H | H | C(O)CH(CH$_3$)SO$_2$CH$_3$(S) |
| 3,5-(CF$_3$)$_2$ | CF$_3$ | H | H | C(O)CH(CH$_3$)S(O)(NH)CH$_3$ |
| 3,5-(CF$_3$)$_2$ | CF$_3$ | H | H | C(O)CH(CH$_3$)SEt |
| 3,5-(CF$_3$)$_2$ | CF$_3$ | H | H | C(O)CH(CH$_3$)SEt(R) |
| 3,5-(CF$_3$)$_2$ | CF$_3$ | H | H | C(O)CH(CH$_3$)SEt(S) |
| 3,5-(CF$_3$)$_2$ | CF$_3$ | H | H | C(O)CH(CH$_3$)S(O)Et |
| 3,5-(CF$_3$)$_2$ | CF$_3$ | H | H | C(O)CH(CH$_3$)SO$_2$Et |
| 3,5-(CF$_3$)$_2$ | CF$_3$ | H | H | C(O)CH(CH$_3$)S(O)(NH)Et |
| 3,5-(CF$_3$)$_2$ | CF$_3$ | H | H | C(O)CH(CH$_3$)SCF$_3$ |
| 3,5-(CF$_3$)$_2$ | CF$_3$ | H | H | C(O)CH(CH$_3$)S(O)CF$_3$ |
| 3,5-(CF$_3$)$_2$ | CF$_3$ | H | H | C(O)CH(CH$_3$)SO$_2$CF$_3$ |
| 3,5-(CF$_3$)$_2$ | CF$_3$ | H | H | C(O)(E-1-1a) |
| 3,5-(CF$_3$)$_2$ | CF$_3$ | CH$_3$ | H | C(O)(E-1-1a) |
| 3,5-(CF$_3$)$_2$ | CF$_3$ | CN | H | C(O)(E-1-1a) |
| 3,5-(CF$_3$)$_2$ | CF$_3$ | H | CH$_3$ | C(O)(E-1-1a) |
| 3,5-(CF$_3$)$_2$ | CF$_3$ | H | Et | C(O)(E-1-1a) |
| 3,5-(CF$_3$)$_2$ | CF$_3$ | H | CH$_2$C≡CH | C(O)(E-1-1a) |
| 3,5-(CF$_3$)$_2$ | CF$_3$ | H | H | C(O)(E-1-1b) |
| 3,5-(CF$_3$)$_2$ | CF$_3$ | CH$_3$ | H | C(O)(E-1-1b) |
| 3,5-(CF$_3$)$_2$ | CF$_3$ | H | CH$_3$ | C(O)(E-1-1b) |
| 3,5-(CF$_3$)$_2$ | CF$_3$ | H | Et | C(O)(E-1-1b) |
| 3,5-(CF$_3$)$_2$ | CF$_3$ | H | CH$_2$C≡CH | C(O)(E-1-1b) |
| 3,5-(CF$_3$)$_2$ | CF$_3$ | H | H | C(O)(E-1-1c) |
| 3,5-(CF$_3$)$_2$ | CF$_3$ | CH$_3$ | H | C(O)(E-1-1c) |
| 3,5-(CF$_3$)$_2$ | CF$_3$ | H | CH$_3$ | C(O)(E-1-1c) |
| 3,5-(CF$_3$)$_2$ | CF$_3$ | H | Et | C(O)(E-1-1c) |
| 3,5-(CF$_3$)$_2$ | CF$_3$ | H | CH$_2$C≡CH | C(O)(E-1-1c) |
| 3,5-(CF$_3$)$_2$ | CF$_3$ | H | H | C(O)(E-2-1a) |
| 3,5-(CF$_3$)$_2$ | CF$_3$ | H | H | C(O)(E-3-1a) |
| 3,5-(CF$_3$)$_2$ | CF$_3$ | H | H | C(O)(E-3-1b) |
| 3,5-(CF$_3$)$_2$ | CF$_3$ | H | H | C(O)(E-3-1c) |

| (X)$_m$ | R$^3$ | R$^4$ | R$^2$ | R$^1$ |
|---|---|---|---|---|
| 3,5-(CF$_3$)$_2$ | CF$_3$ | H | H | C(O)(E-4-1a) |
| 3,5-(CF$_3$)$_2$ | CF$_3$ | H | H | C(O)C(CH$_3$)$_2$SCH$_3$ |
| 3,5-(CF$_3$)$_2$ | CF$_3$ | H | H | C(O)C(CH$_3$)$_2$S(O)CH$_3$ |
| 3,5-(CF$_3$)$_2$ | CF$_3$ | H | H | C(O)C(CH$_3$)$_2$SO$_2$CH$_3$ |
| 3,5-(CF$_3$)$_2$ | CF$_3$ | H | H | C(O)(E-1-2a) |
| 3,5-(CF$_3$)$_2$ | CF$_3$ | H | H | C(O)(E-1-2b) |
| 3,5-(CF$_3$)$_2$ | CF$_3$ | H | H | C(O)(E-1-2c) |
| 3,5-(CF$_3$)$_2$ | CF$_3$ | H | H | C(O)(E-2-2a) |
| 3,5-(CF$_3$)$_2$ | CF$_3$ | H | H | C(O)(E-3-2a) |
| 3,5-(CF$_3$)$_2$ | CF$_3$ | H | H | C(O)(E-3-2b) |
| 3,5-(CF$_3$)$_2$ | CF$_3$ | H | H | C(O)(E-3-2c) |
| 3,5-(CF$_3$)$_2$ | CF$_3$ | H | H | C(O)(E-4-2a) |
| 3,5-(CF$_3$)$_2$ | CF$_3$ | H | H | C(O)(E-3-3a) |
| 3,5-(CF$_3$)$_2$ | CF$_3$ | H | H | C(O)(E-3-3b) |
| 3,5-(CF$_3$)$_2$ | CF$_3$ | H | H | C(O)(E-3-3c) |
| 3,5-(CF$_3$)$_2$ | CF$_3$ | H | H | C(O)(E-4-3a) |
| 3,5-(CF$_3$)$_2$ | CF$_3$ | H | H | C(O)CHFSCH$_3$ |
| 3,5-(CF$_3$)$_2$ | CF$_3$ | H | H | C(O)CHFS(O)CH$_3$ |
| 3,5-(CF$_3$)$_2$ | CF$_3$ | H | H | C(O)CHFSO$_2$CH$_3$ |
| 3,5-(CF$_3$)$_2$ | CF$_3$ | H | H | C(O)CHFSEt |
| 3,5-(CF$_3$)$_2$ | CF$_3$ | H | H | C(O)CHFS(O)Et |
| 3,5-(CF$_3$)$_2$ | CF$_3$ | H | H | C(O)CHFSO$_2$Et |
| 3,5-(CF$_3$)$_2$ | CF$_3$ | H | H | C(O)CHClSCH$_3$ |
| 3,5-(CF$_3$)$_2$ | CF$_3$ | H | H | C(O)CF$_2$SCH$_3$ |
| 3,5-(CF$_3$)$_2$ | CF$_3$ | H | H | C(O)CF$_2$S(O)CH$_3$ |
| 3,5-(CF$_3$)$_2$ | CF$_3$ | H | H | C(O)CF$_2$SO$_2$CH$_3$ |
| 3,5-(CF$_3$)$_2$ | CF$_3$ | H | H | C(O)CF$_2$SEt |
| 3,5-(CF$_3$)$_2$ | CF$_3$ | H | H | C(O)CF$_2$S(O)Et |
| 3,5-(CF$_3$)$_2$ | CF$_3$ | H | H | C(O)CF$_2$SO$_2$Et |
| 3,5-(CF$_3$)$_2$ | CF$_3$ | H | H | C(O)CH(OCH$_3$)SCH$_3$ |
| 3,5-(CF$_3$)$_2$ | CF$_3$ | H | H | C(O)CH(OEt)SCH$_3$ |
| 3,5-(CF$_3$)$_2$ | CF$_3$ | H | H | C(O)CH(SCH$_3$)$_2$ |
| 3,5-(CF$_3$)$_2$ | CF$_3$ | CH$_3$ | H | C(O)CH(SCH$_3$)$_2$ |
| 3,5-(CF$_3$)$_2$ | CF$_3$ | H | CH$_3$ | C(O)CH(SCH$_3$)$_2$ |
| 3,5-(CF$_3$)$_2$ | CF$_3$ | H | Et | C(O)CH(SCH$_3$)$_2$ |
| 3,5-(CF$_3$)$_2$ | CF$_3$ | H | CH$_2$C≡CH | C(O)CH(SCH$_3$)$_2$ |
| 3,5-(CF$_3$)$_2$ | CF$_3$ | H | H | C(O)CH(OCH$_3$)S(O)CH$_3$ |
| 3,5-(CF$_3$)$_2$ | CF$_3$ | H | H | C(O)CH(SCH$_3$)S(O)CH$_3$ |
| 3,5-(CF$_3$)$_2$ | CF$_3$ | H | H | C(O)CH[S(O)CH$_3$]$_2$ |
| 3,5-(CF$_3$)$_2$ | CF$_3$ | CH$_3$ | H | C(O)CH[S(O)CH$_3$]$_2$ |
| 3,5-(CF$_3$)$_2$ | CF$_3$ | H | CH$_3$ | C(O)CH[S(O)CH$_3$]$_2$ |
| 3,5-(CF$_3$)$_2$ | CF$_3$ | H | Et | C(O)CH[S(O)CH$_3$]$_2$ |
| 3,5-(CF$_3$)$_2$ | CF$_3$ | H | CH$_2$C≡CH | C(O)CH[S(O)CH$_3$]$_2$ |
| 3,5-(CF$_3$)$_2$ | CF$_3$ | H | H | C(O)CH(OCH$_3$)SO$_2$CH$_3$ |
| 3,5-(CF$_3$)$_2$ | CF$_3$ | H | H | C(O)CH[S(O)CH$_3$]SO$_2$CH$_3$ |
| 3,5-(CF$_3$)$_2$ | CF$_3$ | H | H | C(O)CH(SO$_2$CH$_3$)$_2$ |
| 3,5-(CF$_3$)$_2$ | CF$_3$ | H | H | C(O)CH(SEt)$_2$ |
| 3,5-(CF$_3$)$_2$ | CF$_3$ | CH$_3$ | H | C(O)CH(SEt)$_2$ |
| 3,5-(CF$_3$)$_2$ | CF$_3$ | H | CH$_3$ | C(O)CH(SEt)$_2$ |
| 3,5-(CF$_3$)$_2$ | CF$_3$ | H | Et | C(O)CH(SEt)$_2$ |
| 3,5-(CF$_3$)$_2$ | CF$_3$ | H | CH$_2$C≡CH | C(O)CH(SEt)$_2$ |
| 3,5-(CF$_3$)$_2$ | CF$_3$ | H | H | C(O)CH(SEt)S(O)Et |
| 3,5-(CF$_3$)$_2$ | CF$_3$ | CH$_3$ | H | C(O)CH(SEt)S(O)Et |
| 3,5-(CF$_3$)$_2$ | CF$_3$ | H | CH$_3$ | C(O)CH(SEt)S(O)Et |
| 3,5-(CF$_3$)$_2$ | CF$_3$ | H | Et | C(O)CH(SEt)S(O)Et |
| 3,5-(CF$_3$)$_2$ | CF$_3$ | H | CH$_2$C≡CH | C(O)CH(SEt)S(O)Et |
| 3,5-(CF$_3$)$_2$ | CF$_3$ | H | H | C(O)CH[S(O)Et]$_2$ |
| 3,5-(CF$_3$)$_2$ | CF$_3$ | H | H | C(O)CH(SEt)SO$_2$Et |
| 3,5-(CF$_3$)$_2$ | CF$_3$ | H | H | C(O)CH[S(O)Et]SO$_2$Et |
| 3,5-(CF$_3$)$_2$ | CF$_3$ | H | H | C(O)CH(SO$_2$Et)$_2$ |
| 3,5-(CF$_3$)$_2$ | CF$_3$ | H | H | C(O)(E-5-1a) |
| 3,5-(CF$_3$)$_2$ | CF$_3$ | H | H | C(O)(E-6-1a) |
| 3,5-(CF$_3$)$_2$ | CF$_3$ | H | H | C(S)CH$_2$SCH$_3$ |
| 3,5-(CF$_3$)$_2$ | CF$_3$ | CH$_3$ | H | C(S)CH$_2$SCH$_3$ |
| 3,6-(CF$_3$)$_2$ | CF$_3$ | H | CH$_3$ | C(S)CH$_2$SCH$_3$ |
| 3,5-(CF$_3$)$_2$ | CF$_3$ | H | Et | C(S)CH$_2$SCH$_3$ |
| 3,5-(CF$_3$)$_2$ | CF$_3$ | H | CH$_2$C≡CH | C(S)CH$_2$SCH$_3$ |
| 3,5-(CF$_3$)$_2$ | CF$_3$ | H | H | C(S)CH$_2$SO$_2$CH$_3$ |
| 3,5-(CF$_3$)$_2$ | CF$_3$ | CH$_3$ | H | C(S)CH$_2$SO$_2$CH$_3$ |
| 3,5-(CF$_3$)$_2$ | CF$_3$ | H | CH$_3$ | C(S)CH$_2$SO$_2$CH$_3$ |
| 3,5-(CF$_3$)$_2$ | CF$_3$ | H | Et | C(S)CH$_2$SO$_2$CH$_3$ |
| 3,5-(CF$_3$)$_2$ | CF$_3$ | H | CH$_2$C≡CH | C(S)CH$_2$SO$_2$CH$_3$ |
| 3,5-(CF$_3$)$_2$ | CF$_3$ | H | H | C(S)CH$_2$SEt |
| 3,5-(CF$_3$)$_2$ | CF$_3$ | CH$_3$ | H | C(S)CH$_2$SEt |
| 3,5-(CF$_3$)$_2$ | CF$_3$ | H | CH$_3$ | C(S)CH$_2$SEt |
| 3,5-(CF$_3$)$_2$ | CF$_3$ | H | Et | C(S)CH$_2$SEt |
| 3,5-(CF$_3$)$_2$ | CF$_3$ | H | CH$_2$C≡CH | C(S)CH$_2$SEt |
| 3,5-(CF$_3$)$_2$ | CF$_3$ | H | H | C(S)CH$_2$SO$_2$Et |

-continued

| (X)$_m$ | R$^3$ | R$^4$ | R$^2$ | R$^1$ |
|---|---|---|---|---|
| 3,5-(CF$_3$)$_2$ | CF$_3$ | CH$_3$ | H | C(S)CH$_2$SO$_2$Et |
| 3,5-(CF$_3$)$_2$ | CF$_3$ | H | CH$_3$ | C(S)CH$_2$SO$_2$Et |
| 3,5-(CF$_3$)$_2$ | CF$_3$ | H | Et | C(S)CH$_2$SO$_2$Et |
| 3,5-(CF$_3$)$_2$ | CF$_3$ | H | CH$_2$C≡CH | C(S)CH$_2$SO$_2$Et |
| 3,5-(CF$_3$)$_2$ | CF$_3$ | H | H | C(S)CH(CH$_3$)SCH$_3$ |
| 3,5-(CF$_3$)$_2$ | CF$_3$ | H | H | C(S)CH(CH$_3$)SO$_2$CH$_3$ |
| 3,5-(CF$_3$)$_2$ | CF$_3$ | H | H | C(S)(E-1-1a) |
| 3,5-(CF$_3$)$_2$ | CF$_3$ | H | H | C(S)(E-1-1c) |
| 3,5-(CF$_3$)$_2$ | CF$_3$ | H | H | C(S)CH(SCH$_3$)$_2$ |
| 3,5-(CF$_3$)$_2$ | CF$_3$ | H | H | C(S)CH(SEt)$_2$ |
| 3,5-(CF$_3$)$_2$ | CF$_2$Cl | H | H | C(O)CH$_2$SCH$_3$ |
| 3,5-(CF$_3$)$_2$ | CF$_2$Cl | H | H | C(O)CH$_2$S(O)CH$_3$ |
| 3,5-(CF$_3$)$_2$ | CF$_2$Cl | H | H | C(O)CH$_2$SO$_2$CH$_3$ |
| 3,5-(CF$_3$)$_2$ | CF$_2$Cl | H | H | C(O)CH$_2$SEt |
| 3,5-(CF$_3$)$_2$ | CF$_2$Cl | H | Et | C(O)CH$_2$SEt |
| 3,5-(CF$_3$)$_2$ | CF$_2$Cl | H | CH$_2$C≡CH | C(O)CH$_2$SEt |
| 3,5-(CF$_3$)$_2$ | CF$_2$Cl | H | H | C(O)CH$_2$S(O)Et |
| 3,5-(CF$_3$)$_2$ | CF$_2$Cl | H | H | C(O)CH$_2$SO$_2$Et |
| 3,5-(CF$_3$)$_2$ | CF$_2$Cl | H | H | C(O)CH(CH$_3$)SCH$_3$ |
| 3,5-(CF$_3$)$_2$ | CF$_2$Cl | H | H | C(O)(E-1-1a) |
| 3,5-(CF$_3$)$_2$ | CF$_2$Cl | H | H | C(O)(E-1-1b) |
| 3,5-(CF$_3$)$_2$ | CF$_2$Cl | H | H | C(O)(E-1-1c) |
| 3,5-(CF$_3$)$_2$ | CF$_2$Cl | H | H | C(O)CH(SCH$_3$)$_2$ |
| 3,5-(CF$_3$)$_2$ | CF$_2$Cl | H | H | C(O)CH[S(O)CH$_3$]$_2$ |
| 3,5-(CF$_3$)$_2$ | CF$_2$Cl | H | H | C(O)CH(SEt)$_2$ |
| 3,5-(CF$_3$)$_2$ | CF$_2$Cl | H | H | C(O)CH(SEt)S(O)Et |
| 3,5-(CF$_3$)$_2$ | CF$_2$Cl | H | H | C(S)CH$_2$SCH$_3$ |
| 3,5-(CF$_3$)$_2$ | CF$_2$Cl | H | H | C(S)CH$_2$SO$_2$CH$_3$ |
| 3,5-(CF$_3$)$_2$ | CF$_2$Cl | H | H | C(S)CH$_2$SEt |
| 3,5-(CF$_3$)$_2$ | CF$_2$Cl | H | H | C(S)CH$_2$SO$_2$Et |
| 3,5-(CF$_3$)$_2$ | CF$_2$Br | H | H | C(O)CH$_2$SCH$_3$ |
| 3,5-(CF$_3$)$_2$ | CF$_2$Br | H | H | C(O)CH$_2$S(O)CH$_3$ |
| 3,5-(CF$_3$)$_2$ | CF$_2$Br | H | H | C(O)CH$_2$SO$_2$CH$_3$ |
| 3,5-(CF$_3$)$_2$ | CF$_2$Br | H | H | C(O)CH$_2$SEt |
| 3,5-(CF$_3$)$_2$ | CF$_2$Br | H | H | C(O)CH$_2$S(O)Et |
| 3,5-(CF$_3$)$_2$ | CF$_2$Br | H | H | C(O)CH$_2$SO$_2$Et |
| 3,5-(CF$_3$)$_2$ | CF$_2$CHF$_2$ | H | H | C(O)CH$_2$SCH$_3$ |
| 3,5-(CF$_3$)$_2$ | CF$_2$CHF$_2$ | H | H | C(O)CH$_2$S(O)CH$_3$ |
| 3,5-(CF$_3$)$_2$ | CF$_2$CHF$_2$ | H | H | C(O)CH$_2$SO$_2$CH$_3$ |
| 3,5-(CF$_3$)$_2$ | CF$_2$CHF$_2$ | H | H | C(O)CH$_2$SEt |
| 3,5-(CF$_3$)$_2$ | CF$_2$CHF$_2$ | H | H | C(O)CH$_2$S(O)Et |
| 3,5-(CF$_3$)$_2$ | CF$_2$CHF$_2$ | H | H | C(O)CH$_2$SO$_2$Et |
| 3,5-(CF$_3$)$_2$ | CF$_2$CF$_3$ | H | H | C(O)CH$_2$SCH$_3$ |
| 3,5-(CF$_3$)$_2$ | CF$_2$CF$_3$ | H | H | C(O)CH$_2$S(O)CH$_3$ |
| 3,5-(CF$_3$)$_2$ | CF$_2$CF$_3$ | H | H | C(O)CH$_2$SO$_2$CH$_3$ |
| 3,5-(CF$_3$)$_2$ | CF$_2$CF$_3$ | H | H | C(O)CH$_2$SEt |
| 3,5-(CF$_3$)$_2$ | CF$_2$CF$_3$ | H | H | C(O)CH$_2$S(O)Et |
| 3,5-(CF$_3$)$_2$ | CF$_2$CF$_3$ | H | H | C(O)CH$_2$SO$_2$Et |
| 3-CF$_3$-5-OCH$_3$ | CF$_3$ | H | H | C(O)CH$_2$SCH$_3$ |
| 3-CF$_3$-5-OCH$_3$ | CF$_3$ | H | H | C(O)CH$_2$S(O)CH$_3$ |
| 3-CF$_3$-5-OCH$_3$ | CF$_3$ | H | H | C(O)CH$_2$SO$_2$CH$_3$ |
| 3-CF$_3$-5-OCH$_3$ | CF$_3$ | H | H | C(O)CH$_2$SEt |
| 3-CF$_3$-5-OCH$_3$ | CF$_3$ | H | H | C(O)CH$_2$S(O)Et |
| 3-CF$_3$-5-OCH$_3$ | CF$_3$ | H | H | C(O)CH$_2$SO$_2$Et |
| 3-Cl-5-OCHF$_2$ | CF$_3$ | H | H | C(O)CH$_2$SCH$_3$ |
| 3-Cl-5-OCHF$_2$ | CF$_3$ | H | H | C(O)CH$_2$S(O)CH$_3$ |
| 3-Cl-5-OCHF$_2$ | CF$_3$ | H | H | C(O)CH$_2$SO$_2$CH$_3$ |
| 3-Cl-5-OCHF$_2$ | CF$_3$ | H | H | C(O)CH$_2$SEt |
| 3-Cl-5-OCHF$_2$ | CF$_3$ | H | Et | C(O)CH$_2$SEt |
| 3-Cl-5-OCHF$_2$ | CF$_3$ | H | CH$_2$C≡CH | C(O)CH$_2$SEt |
| 3-Cl-5-OCHF$_2$ | CF$_3$ | H | H | C(O)CH$_2$S(O)Et |
| 3-Cl-5-OCHF$_2$ | CF$_3$ | H | H | C(O)CH$_2$SO$_2$Et |
| 3-Cl-5-OCHF$_2$ | CF$_3$ | H | H | C(O)CH(CH$_3$)SCH$_3$ |
| 3-Cl-5-OCHF$_2$ | CF$_3$ | H | H | C(O)(E-1-1a) |
| 3-Cl-5-OCHF$_2$ | CF$_3$ | H | H | C(O)(E-1-1b) |
| 3-Cl-5-OCHF$_2$ | CF$_3$ | H | H | C(O)(E-1-1c) |
| 3-Cl-5-OCHF$_2$ | CF$_3$ | H | H | C(O)CH(SCH$_3$)$_2$ |
| 3-Cl-5-OCHF$_2$ | CF$_3$ | H | H | C(O)CH[S(O)CH$_3$]$_2$ |
| 3-Cl-5-OCHF$_2$ | CF$_3$ | H | H | C(O)CH(SEt)$_2$ |
| 3-Cl-5-OCHF$_2$ | CF$_3$ | H | H | C(O)CH(SEt)S(O)Et |
| 3-Cl-5-OCHF$_2$ | CF$_3$ | H | H | C(S)CH$_2$SCH$_3$ |
| 3-Cl-5-OCHF$_2$ | CF$_3$ | H | H | C(S)CH$_2$SO$_2$CH$_3$ |
| 3-Cl-5-OCHF$_2$ | CF$_3$ | H | H | C(S)CH$_2$SEt |
| 3-Cl-5-OCHF$_2$ | CF$_3$ | H | H | C(S)CH$_2$SO$_2$Et |
| 3-Cl-5-OCHF$_2$ | CF$_2$Cl | H | H | C(O)CH$_2$SCH$_3$ |
| 3-Cl-5-OCHF$_2$ | CF$_2$Cl | H | H | C(O)CH$_2$S(O)CH$_3$ |
| 3-Cl-5-OCHF$_2$ | CF$_2$Cl | H | H | C(O)CH$_2$SO$_2$CH$_3$ |
| 3-Cl-5-OCHF$_2$ | CF$_2$Cl | H | H | C(O)CH$_2$SEt |

-continued

| (X)$_m$ | R$^3$ | R$^4$ | R$^2$ | R$^1$ |
|---|---|---|---|---|
| 3-Cl-5-OCHF$_2$ | CF$_2$Cl | H | H | C(O)CH$_2$S(O)Et |
| 3-Cl-5-OCHF$_2$ | CF$_2$Cl | H | H | C(O)CH$_2$SO$_2$Et |
| 3-Br-5-OCHF$_2$ | CF$_3$ | H | H | C(O)CH$_2$SCH$_3$ |
| 3-Br-5-OCHF$_2$ | CF$_3$ | H | H | C(O)CH$_2$S(O)CH$_3$ |
| 3-Br-5-OCHF$_2$ | CF$_3$ | H | H | C(O)CH$_2$SO$_2$CH$_3$ |
| 3-Br-5-OCHF$_2$ | CF$_3$ | H | H | C(O)CH$_2$SEt |
| 3-Br-5-OCHF$_2$ | CF$_3$ | H | H | C(O)CH$_2$S(O)Et |
| 3-Br-5-OCHF$_2$ | CF$_3$ | H | H | C(O)CH$_2$SO$_2$Et |
| 3-Br-5-OCHF$_2$ | CF$_3$ | H | H | C(S)CH$_2$SCH$_3$ |
| 3-Br-5-OCHF$_2$ | CF$_3$ | H | H | C(S)CH$_2$SO$_2$CH$_3$ |
| 3-Br-5-OCHF$_2$ | CF$_3$ | H | H | C(S)CH$_2$SEt |
| 3-Br-5-OCHF$_2$ | CF$_3$ | H | H | C(S)CH$_2$SO$_2$Et |
| 3-CF$_3$-5-OCHF$_2$ | CF$_3$ | H | H | C(O)CH$_2$SCH$_3$ |
| 3-CF$_3$-5-OCHF$_2$ | CF$_3$ | H | H | C(O)CH$_2$S(O)CH$_3$ |
| 3-CF$_3$-5-OCHF$_2$ | CF$_3$ | H | H | C(O)CH$_2$SO$_2$CH$_3$ |
| 3-CF$_3$-5-OCHF$_2$ | CF$_3$ | H | H | C(O)CH$_2$SEt |
| 3-CF$_3$-5-OCHF$_2$ | CF$_3$ | H | H | C(O)CH$_2$S(O)Et |
| 3-CF$_3$-5-OCHF$_2$ | CF$_3$ | H | H | C(O)CH$_2$SO$_2$Et |
| 3-CF$_3$-5-OCHF$_2$ | CF$_3$ | H | H | C(S)CH$_2$SCH$_3$ |
| 3-CF$_3$-5-OCHF$_2$ | CF$_3$ | H | H | C(S)CH$_2$SO$_2$CH$_3$ |
| 3-CF$_3$-5-OCHF$_2$ | CF$_3$ | H | H | C(S)CH$_2$SEt |
| 3-CF$_3$-5-OCHF$_2$ | CF$_3$ | H | H | C(S)CH$_2$SO$_2$Et |
| 3-Cl-5-OCF$_3$ | CF$_3$ | H | H | C(O)CH$_2$SCH$_3$ |
| 3-Cl-5-OCF$_3$ | CF$_3$ | H | H | C(O)CH$_2$S(O)CH$_3$ |
| 3-Cl-5-OCF$_3$ | CF$_3$ | H | H | C(O)CH$_2$SO$_2$CH$_3$ |
| 3-Cl-5-OCF$_3$ | CF$_3$ | H | H | C(O)CH$_2$SEt |
| 3-Cl-5-OCF$_3$ | CF$_3$ | H | Et | C(O)CH$_2$SEt |
| 3-Cl-5-OCF$_3$ | CF$_3$ | H | CH$_2$C≡CH | C(O)CH$_2$SEt |
| 3-Cl-5-OCF$_3$ | CF$_3$ | H | H | C(O)CH$_2$S(O)Et |
| 3-Cl-5-OCF$_3$ | CF$_3$ | H | H | C(O)CH$_2$SO$_2$Et |
| 3-Cl-5-OCF$_3$ | CF$_3$ | H | H | C(O)CH(CH$_3$)SCH$_3$ |
| 3-Cl-5-OCF$_3$ | CF$_3$ | H | H | C(O)(E-1-1a) |
| 3-Cl-5-OCF$_3$ | CF$_3$ | H | H | C(O)(E-1-1b) |
| 3-Cl-5-OCF$_3$ | CF$_3$ | H | H | C(O)(E-1-1c) |
| 3-Cl-5-OCF$_3$ | CF$_3$ | H | H | C(O)CH(SCH$_3$)$_2$ |
| 3-Cl-5-OCF$_3$ | CF$_3$ | H | H | C(O)CH[S(O)CH$_3$]$_2$ |
| 3-Cl-5-OCF$_3$ | CF$_3$ | H | H | C(O)CH(SEt)$_2$ |
| 3-Cl-5-OCF$_3$ | CF$_3$ | H | H | C(O)CH(SEt)S(O)Et |
| 3-Cl-5-OCF$_3$ | CF$_3$ | H | H | C(S)CH$_2$SCH$_3$ |
| 3-Cl-5-OCF$_3$ | CF$_3$ | H | H | C(S)CH$_2$SO$_2$CH$_3$ |
| 3-Cl-5-OCF$_3$ | CF$_3$ | H | H | C(S)CH$_2$SEt |
| 3-Cl-5-OCF$_3$ | CF$_3$ | H | H | C(S)CH$_2$SO$_2$Et |
| 3-Cl-5-OCF$_3$ | CF$_2$Cl | H | H | C(O)CH$_2$SCH$_3$ |
| 3-Cl-5-OCF$_3$ | CF$_2$Cl | H | H | C(O)CH$_2$S(O)CH$_3$ |
| 3-Cl-5-OCF$_3$ | CF$_2$Cl | H | H | C(O)CH$_2$SO$_2$CH$_3$ |
| 3-Cl-5-OCF$_3$ | CF$_2$Cl | H | H | C(O)CH$_2$SEt |
| 3-Cl-5-OCF$_3$ | CF$_2$Cl | H | H | C(O)CH$_2$S(O)Et |
| 3-Cl-5-OCF$_3$ | CF$_2$Cl | H | H | C(O)CH$_2$SO$_2$Et |
| 3-Br-5-OCF$_3$ | CF$_3$ | H | H | C(O)CH$_2$SCH$_3$ |
| 3-Br-5-OCF$_3$ | CF$_3$ | H | H | C(O)CH$_2$S(O)CH$_3$ |
| 3-Br-5-OCF$_3$ | CF$_3$ | H | H | C(O)CH$_2$SO$_2$CH$_3$ |
| 3-Br-5-OCF$_3$ | CF$_3$ | H | H | C(O)CH$_2$SEt |
| 3-Br-5-OCF$_3$ | CF$_3$ | H | H | C(O)CH$_2$S(O)Et |
| 3-Br-5-OCF$_3$ | CF$_3$ | H | H | C(O)CH$_2$SO$_2$Et |
| 3-Br-5-OCF$_3$ | CF$_3$ | H | H | C(S)CH$_2$SCH$_3$ |
| 3-Br-5-OCF$_3$ | CF$_3$ | H | H | C(S)CH$_2$SO$_2$CH$_3$ |
| 3-Br-5-OCF$_3$ | CF$_3$ | H | H | C(S)CH$_2$SEt |
| 3-Br-5-OCF$_3$ | CF$_3$ | H | H | C(S)CH$_2$SO$_2$Et |
| 3-CF$_3$-5-OCF$_3$ | CF$_3$ | H | H | C(O)CH$_2$SCH$_3$ |
| 3-CF$_3$-5-OCF$_3$ | CF$_3$ | H | H | C(O)CH$_2$S(O)CH$_3$ |
| 3-CF$_3$-5-OCF$_3$ | CF$_3$ | H | H | C(O)CH$_2$SO$_2$CH$_3$ |
| 3-CF$_3$-5-OCF$_3$ | CF$_3$ | H | H | C(O)CH$_2$SEt |
| 3-CF$_3$-5-OCF$_3$ | CF$_3$ | H | H | C(O)CH$_2$S(O)Et |
| 3-CF$_3$-5-OCF$_3$ | CF$_3$ | H | H | C(O)CH$_2$SO$_2$Et |
| 3-CF$_3$-5-OCF$_3$ | CF$_3$ | H | H | C(S)CH$_2$SCH$_3$ |
| 3-CF$_3$-5-OCF$_3$ | CF 3 | H | H | C(S)CH$_2$SO$_2$CH$_3$ |
| 3-CF$_3$-5-OCF$_3$ | CF 3 | H | H | C(S)CH$_2$SEt |
| 3-CF$_3$-5-OCF$_3$ | CF$_3$ | H | H | C(S)CH$_2$SO$_2$Et |
| 3-Cl-5-SCF$_3$ | CF$_3$ | H | H | C(O)CH$_2$SCH$_3$ |
| 3-Cl-5-SCF$_3$ | CF$_3$ | H | H | C(O)CH$_2$S(O)CH$_3$ |
| 3-Cl-5-SCF$_3$ | CF$_3$ | H | H | C(O)CH$_2$SO$_2$CH$_3$ |
| 3-Cl-5-SCF$_3$ | CF$_3$ | H | H | C(O)CH$_2$SEt |
| 3-Cl-5-SCF$_3$ | CF$_3$ | H | Et | C(O)CH$_2$SEt |
| 3-Cl-5-SCF$_3$ | CF$_3$ | H | CH$_2$C≡CH | C(O)CH$_2$SEt |
| 3-Cl-5-SCF$_3$ | CF$_3$ | H | H | C(O)CH$_2$S(O)Et |
| 3-Cl-5-SCF$_3$ | CF$_3$ | H | H | C(O)CH$_2$SO$_2$Et |
| 3-Cl-5-SCF$_3$ | CF$_3$ | H | H | C(O)CH(CH$_3$)SCH$_3$ |
| 3-Cl-5-SCF$_3$ | CF$_3$ | H | H | C(O)(E-1-1a) |

-continued

| $(X)_m$ | $R^3$ | $R^4$ | $R^2$ | $R^1$ |
|---|---|---|---|---|
| 3-Cl-5-SCF$_3$ | CF$_3$ | H | H | C(O)(E-1-1b) |
| 3-Cl-5-SCF$_3$ | CF$_3$ | H | H | C(O)(E-1-1c) |
| 3-Cl-5-SCF$_3$ | CF$_3$ | H | H | C(O)CH(SCH$_3$)$_2$ |
| 3-Cl-5-SCF$_3$ | CF$_3$ | H | H | C(O)CH[S(O)CH$_3$]$_2$ |
| 3-Cl-5-SCF$_3$ | CF$_3$ | H | H | C(O)CH(SEt)$_2$ |
| 3-Cl-5-SCF$_3$ | CF$_3$ | H | H | C(O)CH(SEt)S(O)Et |
| 3-Cl-5-SCF$_3$ | CF$_3$ | H | H | C(S)CH$_2$SCH$_3$ |
| 3-Cl-5-SCF$_3$ | CF$_3$ | H | H | C(S)CH$_2$SO$_2$CH$_3$ |
| 3-Cl-5-SCF$_3$ | CF$_3$ | H | H | C(S)CH$_2$SEt |
| 3-Cl-5-SCF$_3$ | CF$_3$ | H | H | C(S)CH$_2$SO$_2$Et |
| 3-Cl-5-SCF$_3$ | CF$_2$Cl | H | H | C(O)CH$_2$SCH$_3$ |
| 3-Cl-5-SCF$_3$ | CF$_2$Cl | H | H | C(O)CH$_2$S(O)CH$_3$ |
| 3-Cl-5-SCF$_3$ | CF$_2$Cl | H | H | C(O)CH$_2$SO$_2$CH$_3$ |
| 3-Cl-5-SCF$_3$ | CF$_2$Cl | H | H | C(O)CH$_2$SEt |
| 3-Cl-5-SCF$_3$ | CF$_2$Cl | H | H | C(O)CH$_2$S(O)Et |
| 3-Cl-5-SCF$_3$ | CF$_2$Cl | H | H | C(O)CH$_2$SO$_2$Et |
| 3-Cl-5-SO$_2$CF$_3$ | CF$_3$ | H | H | C(O)CH$_2$SCH$_3$ |
| 3-Cl-5-SO$_2$CF$_3$ | CF$_3$ | H | H | C(O)CH$_2$S(O)CH$_3$ |
| 3-Cl-5-SO$_2$CF$_3$ | CF$_3$ | H | H | C(O)CH$_2$SO$_2$CH$_3$ |
| 3-Cl-5-SO$_2$CF$_3$ | CF$_3$ | H | H | C(O)CH$_2$SEt |
| 3-Cl-5-SO$_2$CF$_3$ | CF$_3$ | H | H | C(O)CH$_2$S(O)Et |
| 3-Cl-5-SO$_2$CF$_3$ | CF$_3$ | H | H | C(O)CH$_2$SO$_2$Et |
| 3-Br-5-SCF$_3$ | CF$_3$ | H | H | C(O)CH$_2$SCH$_3$ |
| 3-Br-5-SCF$_3$ | CF$_3$ | H | H | C(O)CH$_2$S(O)CH$_3$ |
| 3-Br-5-SCF$_3$ | CF$_3$ | H | H | C(O)CH$_2$SO$_2$CH$_3$ |
| 3-Br-5-SCF$_3$ | CF$_3$ | H | H | C(O)CH$_2$SEt |
| 3-Br-5-SCF$_3$ | CF$_3$ | H | H | C(O)CH$_2$S(O)Et |
| 3-Br-5-SCF$_3$ | CF$_3$ | H | H | C(O)CH$_2$SO$_2$Et |
| 3-Br-5-SCF$_3$ | CF$_3$ | H | H | C(S)CH$_2$SCH$_3$ |
| 3-Br-5-SCF$_3$ | CF$_3$ | H | H | C(S)CH$_2$SO$_2$CH$_3$ |
| 3-Br-5-SCF$_3$ | CF$_3$ | H | H | C(S)CH$_2$SEt |
| 3-Br-5-SCF$_3$ | CF$_3$ | H | H | C(S)CH$_2$SO$_2$Et |
| 3-Br-5-SO$_2$CF$_3$ | CF$_3$ | H | H | C(O)CH$_2$SCH$_3$ |
| 3-Br-5-SO$_2$CF$_3$ | CF$_3$ | H | H | C(O)CH$_2$S(O)CH$_3$ |
| 3-Br-5-SO$_2$CF$_3$ | CF$_3$ | H | H | C(O)CH$_2$SO$_2$CH$_3$ |
| 3-Br-5-SO$_2$CF$_3$ | CF$_3$ | H | H | C(O)CH$_2$SEt |
| 3-Br-5-SO$_2$CF$_3$ | CF$_3$ | H | H | C(O)CH$_2$S(O)Et |
| 3-Br-5-SO$_2$CF$_3$ | CF$_3$ | H | H | C(O)CH$_2$SO$_2$Et |
| 3-CF$_3$-5-NO$_2$ | CF$_3$ | H | H | C(O)CH$_2$SCH$_3$ |
| 3-CF$_3$-5-NO$_2$ | CF$_3$ | H | H | C(O)CH$_2$S(O)CH$_3$ |
| 3-CF$_3$-5-NO$_2$ | CF$_3$ | H | H | C(O)CH$_2$SO$_2$CH$_3$ |
| 3-CF$_3$-5-NO$_2$ | CF$_3$ | H | H | C(O)CH$_2$SEt |
| 3-CF$_3$-5-NO$_2$ | CF$_3$ | H | H | C(O)CH$_2$S(O)Et |
| 3-CF$_3$-5-NO$_2$ | CF$_3$ | H | H | C(O)CH$_2$SO$_2$Et |
| 3-Cl-5-CN | CF$_3$ | H | H | C(O)CH$_2$SCH$_3$ |
| 3-Cl-5-CN | CF$_3$ | H | H | C(O)CH$_2$S(O)CH$_3$ |
| 3-Cl-5-CN | CF$_3$ | H | H | C(O)CH$_2$SO$_2$CH$_3$ |
| 3-Cl-5-CN | CF$_3$ | H | H | C(O)CH$_2$SEt |
| 3-Cl-5-CN | CF$_3$ | H | H | C(O)CH$_2$S(O)Et |
| 3-Cl-5-CN | CF$_3$ | H | H | C(O)CH$_2$SO$_2$Et |
| 3-Br-5-CN | CF$_3$ | H | H | C(O)CH$_2$SCH$_3$ |
| 3-Br-5-CN | CF$_3$ | H | H | C(O)CH$_2$S(O)CH$_3$ |
| 3-Br-5-CN | CF$_3$ | H | H | C(O)CH$_2$SO$_2$CH$_3$ |
| 3-Br-5-CN | CF$_3$ | H | H | C(O)CH$_2$SEt |
| 3-Br-5-CN | CF$_3$ | H | H | C(O)CH$_2$S(O)Et |
| 3-Br-5-CN | CF$_3$ | H | H | C(O)CH$_2$SO$_2$Et |
| 3-CF$_3$-5-CN | CF$_3$ | H | H | C(O)CH$_2$SCH$_3$ |
| 3-CF$_3$-5-CN | CF$_3$ | H | H | C(O)CH$_2$S(O)CH$_3$ |
| 3-CF$_3$-5-CN | CF$_3$ | H | H | C(O)CH$_2$SO$_2$CH$_3$ |
| 3-CF$_3$-5-CN | CF$_3$ | H | H | C(O)CH$_2$SEt |
| 3-CF$_3$-5-CN | CF$_3$ | H | H | C(O)CH$_2$S(O)Et |
| 3-CF$_3$-5-CN | CF$_3$ | H | H | C(O)CH$_2$SO$_2$Et |
| 3-CF$_3$-5-CN | CF$_3$ | H | H | C(S)CH$_2$SCH$_3$ |
| 3-CF$_3$-5-CN | CF$_3$ | H | H | C(S)CH$_2$SO$_2$CH$_3$ |
| 3-CF$_3$-5-CN | CF$_3$ | H | H | C(S)CH$_2$SEt |
| 3-CF$_3$-5-CN | CF$_3$ | H | H | C(S)CH$_2$SO$_2$Et |
| 3,4,5-F$_3$ | CF$_3$ | H | H | C(O)CH$_2$SCH$_3$ |
| 3,4,5-F$_3$ | CF$_3$ | H | H | C(O)CH$_2$S(O)CH$_3$ |
| 3,4,5-F$_3$ | CF$_3$ | H | H | C(O)CH$_2$SO$_2$CH$_3$ |
| 3,4,5-F$_3$ | CF$_3$ | H | H | C(O)CH$_2$SEt |
| 3,4,5-F$_3$ | CF$_3$ | H | H | C(O)CH$_2$S(O)Et |
| 3,4,5-F$_3$ | CF$_3$ | H | H | C(O)CH$_2$SO$_2$Et |
| 3,4,5-F$_3$ | CF$_3$ | H | H | C(S)CH$_2$SCH$_3$ |
| 3,4,5-F$_3$ | CF$_3$ | H | H | C(S)CH$_2$SO$_2$CH$_3$ |
| 3,4,5-F$_3$ | CF$_3$ | H | H | C(S)CH$_2$SEt |
| 3,4,5-F$_3$ | CF$_3$ | H | H | C(S)CH$_2$SO$_2$Et |
| 3,5-Cl$_2$-4-F | CHF$_2$ | H | H | C(O)CH$_2$SCH$_3$ |
| 3,5-Cl$_2$-4-F | CHF$_2$ | H | H | C(O)CH$_2$S(O)CH$_3$ |

-continued

| (X)$_m$ | R$^3$ | R$^4$ | R$^2$ | R$^1$ |
|---|---|---|---|---|
| 3,5-Cl$_2$-4-F | CHF$_2$ | H | H | C(O)CH$_2$SO$_2$CH$_3$ |
| 3,5-Cl$_2$-4-F | CHF$_2$ | H | H | C(O)CH$_2$SEt |
| 3,5-Cl$_2$-4-F | CHF$_2$ | H | H | C(O)CH$_2$S(O)Et |
| 3,5-Cl$_2$-4-F | CHF$_2$ | H | H | C(O)CH$_2$SO$_2$Et |
| 3,5-Cl$_2$-4-F | CF$_3$ | H | H | C(O)CH$_2$SCH$_3$ |
| 3,5-Cl$_2$-4-F | CF$_3$ | CH$_3$ | H | C(O)CH$_2$SCH$_3$ |
| 3,5-Cl$_2$-4-F | CF$_3$ | H | Et | C(O)CH$_2$SCH$_3$ |
| 3,5-Cl$_2$-4-F | CF$_3$ | H | CH$_2$C≡CH | C(O)CH$_2$SCH$_3$ |
| 3,5-Cl$_2$-4-F | CF$_3$ | H | H | C(O)CH$_2$S(O)CH$_3$ |
| 3,5-Cl$_2$-4-F | CF$_3$ | CH$_3$ | H | C(O)CH$_2$S(O)CH$_3$ |
| 3,5-Cl$_2$-4-F | CF$_3$ | H | CH$_3$ | C(O)CH$_2$S(O)CH$_3$ |
| 3,5-Cl$_2$-4-F | CF$_3$ | H | Et | C(O)CH$_2$S(O)CH$_3$ |
| 3,5-Cl$_2$-4-F | CF$_3$ | H | CH$_2$C≡CH | C(O)CH$_2$S(O)CH$_3$ |
| 3,5-Cl$_2$-4-F | CF$_3$ | H | H | C(O)CH$_2$SO$_2$CH$_3$ |
| 3,5-Cl$_2$-4-F | CF$_3$ | CH$_3$ | H | C(O)CH$_2$SO$_2$CH$_3$ |
| 3,5-Cl$_2$-4-F | CF$_3$ | H | CH$_3$ | C(O)CH$_2$SO$_2$CH$_3$ |
| 3,5-Cl$_2$-4-F | CF$_3$ | H | Et | C(O)CH$_2$SO$_2$CH$_3$ |
| 3,5-Cl$_2$-4-F | CF$_3$ | H | CH$_2$C≡CH | C(O)CH$_2$SO$_2$CH$_3$ |
| 3,5-Cl$_2$-4-F | CF$_3$ | H | H | C(O)CH$_2$SEt |
| 3,5-Cl$_2$-4-F | CF$_3$ | CH$_3$ | H | C(O)CH$_2$SEt |
| 3,5-Cl$_2$-4-F | CF$_3$ | H | CH$_3$ | C(O)CH$_2$SEt |
| 3,5-Cl$_2$-4-F | CF$_3$ | H | Et | C(O)CH$_2$SEt |
| 3,5-Cl$_2$-4-F | CF$_3$ | H | CH$_2$CH═CH$_2$ | C(O)CH$_2$SEt |
| 3,5-Cl$_2$-4-F | CF$_3$ | H | CH$_2$C≡CH | C(O)CH$_2$SEt |
| 3,5-Cl$_2$-4-F | CF$_3$ | H | H | C(O)CH$_2$S(O)Et |
| 3,5-Cl$_2$-4-F | CF$_3$ | CH$_3$ | H | C(O)CH$_2$S(O)Et |
| 3,5-Cl$_2$-4-F | CF$_3$ | H | CH$_3$ | C(O)CH$_2$S(O)Et |
| 3,5-Cl$_2$-4-F | CF$_3$ | H | Et | C(O)CH$_2$S(O)Et |
| 3,5-Cl$_2$-4-F | CF$_3$ | H | CH$_2$C≡CH | C(O)CH$_2$S(O)Et |
| 3,5-Cl$_2$-4-F | CF$_3$ | H | H | C(O)CH$_2$SO$_2$Et |
| 3,5-Cl$_2$-4-F | CF$_3$ | CH$_3$ | H | C(O)CH$_2$SO$_2$Et |
| 3,5-Cl$_2$-4-F | CF$_3$ | H | CH$_3$ | C(O)CH$_2$SO$_2$Et |
| 3,5-Cl$_2$-4-F | CF$_3$ | H | Et | C(O)CH$_2$SO$_2$Et |
| 3,5-Cl$_2$-4-F | CF$_3$ | H | CH$_2$C≡CH | C(O)CH$_2$SO$_2$Et |
| 3,5-Cl$_2$-4-F | CF$_3$ | H | H | C(O)CH$_2$SCH$_2$CF$_3$ |
| 3,5-Cl$_2$-4-F | CF$_3$ | H | H | C(O)CH$_2$S(O)CH$_2$CF$_3$ |
| 3,5-Cl$_2$-4-F | CF$_3$ | H | H | C(O)CH$_2$SO$_2$CH$_2$CF$_3$ |
| 3,5-Cl$_2$-4-F | CF$_3$ | H | H | C(O)CH(CH$_3$)SCH$_3$ |
| 3,5-Cl$_2$-4-F | CF$_3$ | H | H | C(O)CH(CH$_3$)S(O)CH$_3$ |
| 3,5-Cl$_2$-4-F | CF$_3$ | H | H | C(O)CH(CH$_3$)SO$_2$CH$_3$ |
| 3,5-Cl$_2$-4-F | CF$_3$ | H | H | C(O)CH(CH$_3$)SEt |
| 3,5-Cl$_2$-4-F | CF$_3$ | H | H | C(O)(E-1-1a) |
| 3,5-Cl$_2$-4-F | CF$_3$ | H | H | C(O)(E-1-1b) |
| 3,5-Cl$_2$-4-F | CF$_3$ | H | H | C(O)(E-1-1c) |
| 3,5-Cl$_2$-4-F | CF$_3$ | H | H | C(O)(E-1-2a) |
| 3,5-Cl$_2$-4-F | CF$_3$ | H | H | C(O)(E-1-2b) |
| 3,5-Cl$_2$-4-F | CF$_3$ | H | H | C(O)(E-1-2c) |
| 3,5-Cl$_2$-4-F | CF$_3$ | H | H | C(O)CH(SCH$_3$)$_2$ |
| 3,5-Cl$_2$-4-F | CF$_3$ | H | H | C(O)CH(SCH$_3$)S(O)CH$_3$ |
| 3,5-Cl$_2$-4-F | CF$_3$ | H | H | C(O)CH[S(O)CH$_3$]$_2$ |
| 3,5-Cl$_2$-4-F | CF$_3$ | H | H | C(O)CH[S(O)CH$_3$]SO$_2$CH$_3$ |
| 3,5-Cl$_2$-4-F | CF$_3$ | H | H | C(O)CH(SEt)$_2$ |
| 3,5-Cl$_2$-4-F | CF$_3$ | H | H | C(O)CH(SEt)S(O)Et |
| 3,5-Cl$_2$-4-F | CF$_3$ | H | H | C(O)CH[S(O)Et]$_2$ |
| 3,5-Cl$_2$-4-F | CF$_3$ | H | H | C(O)CH[S(O)Et]SO$_2$Et |
| 3,5-Cl$_2$-4-F | CF$_3$ | H | H | C(S)CH$_2$SCH$_3$ |
| 3,5-Cl$_2$-4-F | CF$_3$ | H | H | C(S)CH$_2$SO$_2$CH$_3$ |
| 3,5-Cl$_2$-4-F | CF$_3$ | H | H | C(S)CH$_2$SEt |
| 3,5-Cl$_2$-4-F | CF$_3$ | H | H | C(S)CH$_2$SO$_2$Et |
| 3,5-Cl$_2$-4-F | CF$_2$Cl | H | H | C(O)CH$_2$SCH$_3$ |
| 3,5-Cl$_2$-4-F | CF$_2$Cl | H | H | C(O)CH$_2$S(O)CH$_3$ |
| 3,5-Cl$_2$-4-F | CF$_2$Cl | H | H | C(O)CH$_2$SO$_2$CH$_3$ |
| 3,5-Cl$_2$-4-F | CF$_2$Cl | H | H | C(O)CH$_2$SEt |
| 3,5-Cl$_2$-4-F | CF$_2$Cl | H | H | C(O)CH$_2$S(O)Et |
| 3,5-Cl$_2$-4-F | CF$_2$Cl | H | H | C(O)CH$_2$SO$_2$Et |
| 3,5-Cl$_2$-4-F | CF$_2$Cl | H | H | C(S)CH$_2$SCH$_3$ |
| 3,5-Cl$_2$-4-F | CF$_2$Cl | H | H | C(S)CH$_2$SO$_2$CH$_3$ |
| 3,5-Cl$_2$-4-F | CF$_2$Cl | H | H | C(S)CH$_2$SEt |
| 3,5-Cl$_2$-4-F | CF$_2$Cl | H | H | C(S)CH$_2$SO$_2$Et |
| 3,4,5-Cl$_3$ | CHF$_2$ | H | H | C(O)CH$_2$SCH$_3$ |
| 3,4,5-Cl$_3$ | CHF$_2$ | H | H | C(O)CH$_2$S(O)CH$_3$ |
| 3,4,5-Cl$_3$ | CHF$_2$ | H | H | C(O)CH$_2$SO$_2$CH$_3$ |
| 3,4,5-Cl$_3$ | CHF$_2$ | H | H | C(O)CH$_2$SEt |
| 3,4,5-Cl$_3$ | CHF$_2$ | H | H | C(O)CH$_2$S(O)Et |
| 3,4,5-Cl$_3$ | CHF$_2$ | H | H | C(O)CH$_2$SO$_2$Et |
| 3,4,5-Cl$_3$ | CF$_3$ | H | H | C(O)CH$_2$SCH$_3$ |
| 3,4,5-Cl$_3$ | CF$_3$ | CH$_3$ | H | C(O)CH$_2$SCH$_3$ |
| 3,4,5-Cl$_3$ | CF$_3$ | CN | H | C(O)CH$_2$SCH$_3$ |

-continued

| (X)$_m$ | R$^3$ | R$^4$ | R$^2$ | R$^1$ |
|---|---|---|---|---|
| 3,4,5-Cl$_3$ | CF$_3$ | H | Et | C(O)CH$_2$SCH$_3$ |
| 3,4,5-Cl$_3$ | CF$_3$ | H | CH$_2$C≡CH | C(O)CH$_2$SCH$_3$ |
| 3,4,5-Cl$_3$ | CF$_3$ | H | H | C(O)CH$_2$S(O)CH$_3$ |
| 3,4,5-Cl$_3$ | CF$_3$ | CH$_3$ | H | C(O)CH$_2$S(O)CH$_3$ |
| 3,4,5-Cl$_3$ | CF$_3$ | H | CH$_3$ | C(O)CH$_2$S(O)CH$_3$ |
| 3,4,5-Cl$_3$ | CF$_3$ | H | Et | C(O)CH$_2$S(O)CH$_3$ |
| 3,4,5-Cl$_3$ | CF$_3$ | H | CH$_2$C≡CH | C(O)CH$_2$S(O)CH$_3$ |
| 3,4,5-Cl$_3$ | CF$_3$ | H | H | C(O)CH$_2$SO$_2$CH$_3$ |
| 3,4,5-Cl$_3$ | CF$_3$ | CH$_3$ | H | C(O)CH$_2$SO$_2$CH$_3$ |
| 3,4,5-Cl$_3$ | CF$_3$ | H | CH$_3$ | C(O)CH$_2$SO$_2$CH$_3$ |
| 3,4,5-Cl$_3$ | CF$_3$ | H | Et | C(O)CH$_2$SO$_2$CH$_3$ |
| 3,4,5-Cl$_3$ | CF$_3$ | H | CH$_2$C≡CH | C(O)CH$_2$SO$_2$CH$_3$ |
| 3,4,5-Cl$_3$ | CF$_3$ | H | H | C(O)CH$_2$SEt |
| 3,4,5-Cl$_3$ | CF$_3$ | CH$_3$ | H | C(O)CH$_2$SEt |
| 3,4,5-Cl$_3$ | CF$_3$ | CN | H | C(O)CH$_2$SEt |
| 3,4,5-Cl$_3$ | CF$_3$ | H | CH$_3$ | C(O)CH$_2$SEt |
| 3,4,5-Cl$_3$ | CF$_3$ | H | Et | C(O)CH$_2$SEt |
| 3,4,5-Cl$_3$ | CF$_3$ | H | CH$_2$CH=CH$_2$ | C(O)CH$_2$SEt |
| 3,4,5-Cl$_3$ | CF$_3$ | H | CH$_2$C≡CH | C(O)CH$_2$SEt |
| 3,4,5-Cl$_3$ | CF$_3$ | H | H | C(O)CH$_2$S(O)Et |
| 3,4,5-Cl$_3$ | CF$_3$ | CH$_3$ | H | C(O)CH$_2$S(O)Et |
| 3,4,5-Cl$_3$ | CF$_3$ | H | CH$_3$ | C(O)CH$_2$S(O)Et |
| 3,4,5-Cl$_3$ | CF$_3$ | H | Et | C(O)CH$_2$S(O)Et |
| 3,4,5-Cl$_3$ | CF$_3$ | H | CH$_2$C≡CH | C(O)CH$_2$S(O)Et |
| 3,4,5-Cl$_3$ | CF$_3$ | H | H | C(O)CH$_2$SO$_2$Et |
| 3,4,5-Cl$_3$ | CF$_3$ | CH$_3$ | H | C(O)CH$_2$SO$_2$Et |
| 3,4,5-Cl$_3$ | CF$_3$ | H | CH$_3$ | C(O)CH$_2$SO$_2$Et |
| 3,4,5-Cl$_3$ | CF$_3$ | H | Et | C(O)CH$_2$SO$_2$Et |
| 3,4,5-Cl$_3$ | CF$_3$ | H | CH$_2$C≡CH | C(O)CH$_2$SO$_2$Et |
| 3,4,5-Cl$_3$ | CF$_3$ | H | H | C(O)CH$_2$SPen-c |
| 3,4,5-Cl$_3$ | CF$_3$ | H | H | C(O)CH$_2$SCH$_2$CF$_3$ |
| 3,4,5-Cl$_3$ | CF$_3$ | H | H | C(O)CH$_2$S(O)CH$_2$CF$_3$ |
| 3,4,5-Cl$_3$ | CF$_3$ | H | H | C(O)CH$_2$SO$_2$CH$_2$CF$_3$ |
| 3,4,5-Cl$_3$ | CF$_3$ | H | H | C(O)CH$_2$SCH$_2$OCH$_3$ |
| 3,4,5-Cl$_3$ | CF$_3$ | H | H | C(O)CH$_2$SCH$_2$CN |
| 3,4,5-Cl$_3$ | CF$_3$ | H | H | C(O)CH$_2$SCH$_2$C(O)OEt |
| 3,4,5-Cl$_3$ | CF$_3$ | H | H | C(O)CH$_2$SCF$_2$C(O)OEt |
| 3,4,5-Cl$_3$ | CF$_3$ | H | H | C(O)CH$_2$SCH$_2$C(O)NHCH$_3$ |
| 3,4,5-Cl$_3$ | CF$_3$ | H | H | C(O)CH$_2$SCF$_2$C(O)NHCH$_3$ |
| 3,4,5-Cl$_3$ | CF$_3$ | H | H | C(O)CH$_2$SCH$_2$CH=CH$_2$ |
| 3,4,5-Cl$_3$ | CF$_3$ | H | H | C(O)CH$_2$SCH$_2$C≡CH |
| 3,4,5-Cl$_3$ | CF$_3$ | H | H | C(O)CH$_2$SC(O)CH$_3$ |
| 3,4,5-Cl$_3$ | CF$_3$ | H | H | C(O)CH$_2$SC(O)CF$_3$ |
| 3,4,5-Cl$_3$ | CF$_3$ | H | H | C(O)CH$_2$SC(O)(D-8a) |
| 3,4,5-Cl$_3$ | CF$_3$ | H | H | C(O)CH$_2$SC(O)OCH$_3$ |
| 3,4,5-Cl$_3$ | CF$_3$ | H | H | C(O)CH$_2$SC(O)NHEt |
| 3,4,5-Cl$_3$ | CF$_3$ | H | H | C(O)CH$_2$S(D-9-1a)H |
| 3,4,5-Cl$_3$ | CF$_3$ | H | H | C(O)CH$_2$S(D-12-1a) |
| 3,4,5-Cl$_3$ | CF$_3$ | H | H | C(O)CH(CH$_3$)SCH$_3$ |
| 3,4,5-Cl$_3$ | CF$_3$ | H | H | C(O)CH(CH$_3$)S(O)CH$_3$ |
| 3,4,5-Cl$_3$ | CF$_3$ | H | H | C(O)CH(CH$_3$)SO$_2$CH$_3$ |
| 3,4,5-Cl$_3$ | CF$_3$ | H | H | C(O)CH(CH$_3$)SEt |
| 3,4,5-Cl$_3$ | CF$_3$ | H | H | C(O)CH(CH$_3$)S(O)Et |
| 3,4,5-Cl$_3$ | CF$_3$ | H | H | C(O)CH(CH$_3$)SO$_2$Et |
| 3,4,5-Cl$_3$ | CF$_3$ | H | H | C(O)(E-1-1a) |
| 3,4,5-Cl$_3$ | CF$_3$ | H | H | C(O)(E-1-1b) |
| 3,4,5-Cl$_3$ | CF$_3$ | H | H | C(O)(E-1-1c) |
| 3,4,5-Cl$_3$ | CF$_3$ | H | H | C(O)C(CH$_3$)$_2$SCH$_3$ |
| 3,4,5-Cl$_3$ | CF$_3$ | H | H | C(O)C(CH$_3$)$_2$S(O)CH$_3$ |
| 3,4,5-Cl$_3$ | CF$_3$ | H | H | C(O)C(CH$_3$)$_2$SO$_2$CH$_3$ |
| 3,4,5-Cl$_3$ | CF$_3$ | H | H | C(O)(E-1-2a) |
| 3,4,5-Cl$_3$ | CF$_3$ | H | H | C(O)(E-1-2b) |
| 3,4,5-Cl$_3$ | CF$_3$ | H | H | C(O)(E-1-2c) |
| 3,4,5-Cl$_3$ | CF$_3$ | H | H | C(O)CF$_2$SCH$_3$ |
| 3,4,5-Cl$_3$ | CF$_3$ | H | H | C(O)CF$_2$S(O)CH$_3$ |
| 3,4,5-Cl$_3$ | CF$_3$ | H | H | C(O)CF$_2$SO$_2$CH$_3$ |
| 3,4,5-Cl$_3$ | CF$_3$ | H | H | C(O)CH(SCH$_3$)$_2$ |
| 3,4,5-Cl$_3$ | CF$_3$ | H | H | C(O)CH(SCH$_3$)S(O)CH$_3$ |
| 3,4,5-Cl$_3$ | CF$_3$ | H | H | C(O)CH[S(O)CH$_3$]$_2$ |
| 3,4,5-Cl$_3$ | CF$_3$ | H | H | C(O)CH[S(O)CH$_3$]SO$_2$CH$_3$ |
| 3,4,5-Cl$_3$ | CF$_3$ | H | H | C(O)CH(SEt)$_2$ |
| 3,4,5-Cl$_3$ | CF$_3$ | H | H | C(O)CH(SEt)S(O)Et |
| 3,4,5-Cl$_3$ | CF$_3$ | H | H | C(O)CH[S(O)Et]$_2$ |
| 3,4,5-Cl$_3$ | CF$_3$ | H | H | C(O)CH[S(O)Et]SO$_2$Et |
| 3,4,5-Cl$_3$ | CF$_3$ | H | H | C(O)(E-5-1a) |
| 3,4,5-Cl$_3$ | CF$_3$ | H | H | C(S)CH$_2$SCH$_3$ |
| 3,4,5-Cl$_3$ | CF$_3$ | H | H | C(S)CH$_2$SO$_2$CH$_3$ |
| 3,4,5-Cl$_3$ | CF$_3$ | H | H | C(S)CH$_2$SEt |

-continued

| (X)$_m$ | R$^3$ | R$^4$ | R$^2$ | R$^1$ |
|---|---|---|---|---|
| 3,4,5-Cl$_3$ | CF$_3$ | H | H | C(S)CH$_2$SO$_2$Et |
| 3,4,5-Cl$_3$ | CF$_2$Cl | H | H | C(O)CH$_2$SCH$_3$ |
| 3,4,5-Cl$_3$ | CF$_2$Cl | H | H | C(O)CH$_2$S(O)CH$_3$ |
| 3,4,5-Cl$_3$ | CF$_2$Cl | H | H | C(O)CH$_2$SO$_2$CH$_3$ |
| 3,4,5-Cl$_3$ | CF$_2$Cl | H | H | C(O)CH$_2$SEt |
| 3,4,5-Cl$_3$ | CF$_2$Cl | H | H | C(O)CH$_2$S(O)Et |
| 3,4,5-Cl$_3$ | CF$_2$Cl | H | H | C(O)CH$_2$SO$_2$Et |
| 3,4,5-Cl$_3$ | CF$_2$Cl | H | H | C(S)CH$_2$SCH$_3$ |
| 3,4,5-Cl$_3$ | CF$_2$Cl | H | H | C(S)CH$_2$SO$_2$SCH$_3$ |
| 3,4,5-Cl$_3$ | CF$_2$Cl | H | H | C(S)CH$_2$SEt |
| 3,4,5-Cl$_3$ | CF$_2$Cl | H | H | C(S)CH$_2$SO$_2$Et |
| 3,5-Br$_2$-4-F | CHF$_2$ | H | H | C(O)CH$_2$SCH$_3$ |
| 3,5-Br$_2$-4-F | CHF$_2$ | H | H | C(O)CH$_2$S(O)CH$_3$ |
| 3,5-Br$_2$-4-F | CHF$_2$ | H | H | C(O)CH$_2$SO$_2$CH$_3$ |
| 3,5-Br$_2$-4-F | CHF$_2$ | H | H | C(O)CH$_2$SEt |
| 3,5-Br$_2$-4-F | CHF$_2$ | H | H | C(O)CH$_2$S(O)Et |
| 3,5-Br$_2$-4-F | CHF$_2$ | H | H | C(O)CH$_2$SO$_2$Et |
| 3,5-Br$_2$-4-F | CF$_3$ | H | H | C(O)CH$_2$SCH$_3$ |
| 3,5-Br$_2$-4-F | CF$_3$ | CH$_3$ | H | C(O)CH$_2$SCH$_3$ |
| 3,5-Br$_2$-4-F | CF$_3$ | H | CH$_3$ | C(O)CH$_2$SCH$_3$ |
| 3,5-Br$_2$-4-F | CF$_3$ | H | Et | C(O)CH$_2$SCH$_3$ |
| 3,5-Br$_2$-4-F | CF$_3$ | H | CH$_2$Pr-c | C(O)CH$_2$SCH$_3$ |
| 3,5-Br$_2$-4-F | CF$_3$ | H | CH$_2$OCH$_3$ | C(O)CH$_2$SCH$_3$ |
| 3,5-Br$_2$-4-F | CF$_3$ | H | CH$_2$CN | C(O)CH$_2$SCH$_3$ |
| 3,5-Br$_2$-4-F | CF$_3$ | H | CH$_2$C(O)OCH$_3$ | C(O)CH$_2$SCH$_3$ |
| 3,5-Br$_2$-4-F | CF$_3$ | H | CH$_2$C(O)NH$_2$ | C(O)CH$_2$SCH$_3$ |
| 3,5-Br$_2$-4-F | CF$_3$ | H | CH$_2$C(O)NHCH$_3$ | C(O)CH$_2$SCH$_3$ |
| 3,5-Br$_2$-4-F | CF$_3$ | H | CH$_2$C(O)N(CH$_3$)$_2$ | C(O)CH$_2$SCH$_3$ |
| 3,5-Br$_2$-4-F | CF$_3$ | H | CH$_2$C(S)NH$_2$ | C(O)CH$_2$SCH$_3$ |
| 3,5-Br$_2$-4-F | CF$_3$ | H | CH$_2$CH=CH$_2$ | C(O)CH$_2$SCH$_3$ |
| 3,5-Br$_2$-4-F | CF$_3$ | H | CH$_2$C≡CH | C(O)CH$_2$SCH$_3$ |
| 3,5-Br$_2$-4-F | CF$_3$ | H | H | C(O)CH$_2$S(O)CH$_3$ |
| 3,5-Br$_2$-4-F | CF$_3$ | CH$_3$ | H | C(O)CH$_2$S(O)CH$_3$ |
| 3,5-Br$_2$-4-F | CF$_3$ | H | CH$_3$ | C(O)CH$_2$S(O)CH$_3$ |
| 3,5-Br$_2$-4-F | CF$_3$ | H | Et | C(O)CH$_2$S(O)CH$_3$ |
| 3,5-Br$_2$-4-F | CF$_3$ | H | CH$_2$Pr-c | C(O)CH$_2$S(O)CH$_3$ |
| 3,5-Br$_2$-4-F | CF$_3$ | H | CH$_2$OCH$_3$ | C(O)CH$_2$S(O)CH$_3$ |
| 3,5-Br$_2$-4-F | CF$_3$ | H | CH$_2$CN | C(O)CH$_2$S(O)CH$_3$ |
| 3,5-Br$_2$-4-F | CF$_3$ | H | CH$_2$C(O)OCH$_3$ | C(O)CH$_2$S(O)CH$_3$ |
| 3,5-Br$_2$-4-F | CF$_3$ | H | CH$_2$C(O)NH$_2$ | C(O)CH$_2$S(O)CH$_3$ |
| 3,5-Br$_2$-4-F | CF$_3$ | H | CH$_2$C(O)NHCH$_3$ | C(O)CH$_2$S(O)CH$_3$ |
| 3,5-Br$_2$-4-F | CF$_3$ | H | CH$_2$C(O)N(CH$_3$)$_2$ | C(O)CH$_2$(O)SCH$_3$ |
| 3,5-Br$_2$-4-F | CF$_3$ | H | CH$_2$C(S)NH$_2$ | C(O)CH$_2$S(O)CH$_3$ |
| 3,5-Br$_2$-4-F | CF$_3$ | H | CH$_2$CH=CH$_2$ | C(O)CH$_2$S(O)CH$_3$ |
| 3,5-Br$_2$-4-F | CF$_3$ | H | CH$_2$CH≡CH | C(O)CH$_2$S(O)CH$_3$ |
| 3,5-Br$_2$-4-F | CF$_3$ | H | H | C(O)CH$_2$SO$_2$CH$_3$ |
| 3,5-Br$_2$-4-F | CF$_3$ | CH$_3$ | H | C(O)CH$_2$SO$_2$CH$_3$ |
| 3,5-Br$_2$-4-F | CF$_3$ | H | CH$_3$ | C(O)CH$_2$SO$_2$CH$_3$ |
| 3,5-Br$_2$-4-F | CF$_3$ | H | Et | C(O)CH$_2$SO$_2$CH$_3$ |
| 3,5-Br$_2$-4-F | CF$_3$ | H | CH$_2$Pr-c | C(O)CH$_2$SO$_2$CH$_3$ |
| 3,5-Br$_2$-4-F | CF$_3$ | H | CH$_2$OCH$_3$ | C(O)CH$_2$SO$_2$CH$_3$ |
| 3,5-Br$_2$-4-F | CF$_3$ | H | CH$_2$CN | C(O)CH$_2$SO$_2$CH$_3$ |
| 3,5-Br$_2$-4-F | CF$_3$ | H | CH$_2$C(O)OCH$_3$ | C(O)CH$_2$SO$_2$CH$_3$ |
| 3,5-Br$_2$-4-F | CF$_3$ | H | CH$_2$C(O)NH$_2$ | C(O)CH$_2$SO$_2$CH$_3$ |
| 3,5-Br$_2$-4-F | CF$_3$ | H | CH$_2$C(O)NHCH$_3$ | C(O)CH$_2$SO$_2$CH$_3$ |
| 3,5-Br$_2$-4-F | CF$_3$ | H | CH$_2$C(O)N(CH$_3$)$_2$ | C(O)CH$_2$SO$_2$CH$_3$ |
| 3,5-Br$_2$-4-F | CF$_3$ | H | CH$_2$C(S)NH$_2$ | C(O)CH$_2$SO$_2$CH$_3$ |
| 3,5-Br$_2$-4-F | CF$_3$ | H | CH$_2$CH=CH$_2$ | C(O)CH$_2$SO$_2$CH$_3$ |
| 3,5-Br$_2$-4-F | CF$_3$ | H | CH$_2$CH≡CH | C(O)CH$_2$SO$_2$CH$_3$ |
| 3,5-Br$_2$-4-F | CF$_3$ | H | H | C(O)CH$_2$SEt |
| 3,5-Br$_2$-4-F | CF$_3$ | CH$_3$ | H | C(O)CH$_2$SEt |
| 3,5-Br$_2$-4-F | CF$_3$ | H | CH$_3$ | C(O)CH$_2$SEt |
| 3,5-Br$_2$-4-F | CF$_3$ | H | Et | C(O)CH$_2$SEt |
| 3,5-Br$_2$-4-F | CF$_3$ | H | CH$_2$Pr-c | C(O)CH$_2$SEt |
| 3,5-Br$_2$-4-F | CF$_3$ | H | CH$_2$OCH$_3$ | C(O)CH$_2$SEt |
| 3,5-Br$_2$-4-F | CF$_3$ | H | CH$_2$CN | C(O)CH$_2$SEt |
| 3,5-Br$_2$-4-F | CF$_3$ | H | CH$_2$C(O)OCH$_3$ | C(O)CH$_2$SEt |
| 3,5-Br$_2$-4-F | CF$_3$ | H | CH$_2$C(O)NH$_2$ | C(O)CH$_2$SEt |
| 3,5-Br$_2$-4-F | CF$_3$ | H | CH$_2$C(O)NHCH$_3$ | C(O)CH$_2$SEt |
| 3,5-Br$_2$-4-F | CF$_3$ | H | CH$_2$C(O)N(CH$_3$)$_2$ | C(O)CH$_2$SEt |
| 3,5-Br$_2$-4-F | CF$_3$ | H | CH$_2$C(S)NH$_2$ | C(O)CH$_2$SEt |
| 3,5-Br$_2$-4-F | CF$_3$ | H | CH$_2$CH=CH$_2$ | C(O)CH$_2$SEt |
| 3,5-Br$_2$-4-F | CF$_3$ | H | CH$_2$C≡CH | C(O)CH$_2$SEt |
| 3,5-Br$_2$-4-F | CF$_3$ | H | H | C(O)CH$_2$S(O)Et |
| 3,5-Br$_2$-4-F | CF$_3$ | CH$_3$ | H | C(O)CH$_2$S(O)Et |
| 3,5-Br$_2$-4-F | CF$_3$ | H | CH$_3$ | C(O)CH$_2$S(O)Et |
| 3,5-Br$_2$-4-F | CF$_3$ | H | Et | C(O)CH$_2$S(O)Et |
| 3,5-Br$_2$-4-F | CF$_3$ | H | CH$_2$Pr-c | C(O)CH$_2$S(O)Et |

| (X)$_m$ | R$^3$ | R$^4$ | R$^2$ | R$^1$ |
|---|---|---|---|---|
| 3,5-Br$_2$-4-F | CF$_3$ | H | CH$_2$OCH$_3$ | C(O)CH$_2$S(O)Et |
| 3,5-Br$_2$-4-F | CF$_3$ | H | CH$_2$CN | C(O)CH$_2$S(O)Et |
| 3,5-Br$_2$-4-F | CF$_3$ | H | CH$_2$C(O)OCH$_3$ | C(O)CH$_2$S(O)Et |
| 3,5-Br$_2$-4-F | CF$_3$ | H | CH$_2$C(O)NH$_2$ | C(O)CH$_2$S(O)Et |
| 3,5-Br$_2$-4-F | CF$_3$ | H | CH$_2$C(O)NHCH$_3$ | C(O)CH$_2$S(O)Et |
| 3,5-Br$_2$-4-F | CF$_3$ | H | CH$_2$C(O)N(CH$_3$)$_2$ | C(O)CH$_2$S(O)Et |
| 3,5-Br$_2$-4-F | CF$_3$ | H | CH$_2$C(S)NH$_2$ | C(O)CH$_2$S(O)Et |
| 3,5-Br$_2$-4-F | CF$_3$ | H | CH$_2$CH=CH$_2$ | C(O)CH$_2$S(O)Et |
| 3,5-Br$_2$-4-F | CF$_3$ | H | CH$_2$C≡CH | C(O)CH$_2$S(O)Et |
| 3,5-Br$_2$-4-F | CF$_3$ | H | H | C(O)CH$_2$SO$_2$Et |
| 3,5-Br$_2$-4-F | CF$_3$ | CH$_3$ | H | C(O)CH$_2$SO$_2$Et |
| 3,5-Br$_2$-4-F | CF$_3$ | H | CH$_3$ | C(O)CH$_2$SO$_2$Et |
| 3,5-Br$_2$-4-F | CF$_3$ | H | Et | C(O)CH$_2$SO$_2$Et |
| 3,5-Br$_2$-4-F | CF$_3$ | H | CH$_2$Pr-c | C(O)CH$_2$SO$_2$Et |
| 3,5-Br$_2$-4-F | CF$_3$ | H | CH$_2$OCH$_3$ | C(O)CH$_2$SO$_2$Et |
| 3,5-Br$_2$-4-F | CF$_3$ | H | CH$_2$CN | C(O)CH$_2$SO$_2$Et |
| 3,5-Br$_2$-4-F | CF$_3$ | H | CH$_2$C(O)OCH$_3$ | C(O)CH$_2$SO$_2$Et |
| 3,5-Br$_2$-4-F | CF$_3$ | H | CH$_2$C(O)NH$_2$ | C(O)CH$_2$SO$_2$Et |
| 3,5-Br$_2$-4-F | CF$_3$ | H | CH$_2$C(O)NHCH$_3$ | C(O)CH$_2$SO$_2$Et |
| 3,5-Br$_2$-4-F | CF$_3$ | H | CH$_2$C(O)N(CH$_3$)$_2$ | C(O)CH$_2$SO$_2$Et |
| 3,5-Br$_2$-4-F | CF$_3$ | H | CH$_2$C(S)NH$_2$ | C(O)CH$_2$SO$_2$Et |
| 3,5-Br$_2$-4-F | CF$_3$ | H | CH$_2$CH=CH$_2$ | C(O)CH$_2$SO$_2$Et |
| 3,5-Br$_2$-4-F | CF$_3$ | H | CH$_2$C≡CH | C(O)CH$_2$SO$_2$Et |
| 3,5-Br$_2$-4-F | CF$_3$ | H | H | C(O)CH$_2$SCH$_2$CF$_3$ |
| 3,5-Br$_2$-4-F | CF$_3$ | H | H | C(O)CH$_2$S(O)CH$_2$CF$_3$ |
| 3,5-Br$_2$-4-F | CF$_3$ | H | H | C(O)CH$_2$SO$_2$CH$_2$CF$_3$ |
| 3,5-Br$_2$-4-F | CF$_3$ | H | H | C(O)CH(CH$_3$)SCH$_3$ |
| 3,5-Br$_2$-4-F | CF$_3$ | H | H | C(O)CH(CH$_3$)S(O)CH$_3$ |
| 3,5-Br$_2$-4-F | CF$_3$ | H | H | C(O)CH(CH$_3$)SO$_2$CH$_3$ |
| 3,5-Br$_2$-4-F | CF$_3$ | H | H | C(O)CH(CH$_3$)SEt |
| 3,5-Br$_2$-4-F | CF$_3$ | H | H | C(O)(E-1-1a) |
| 3,5-Br$_2$-4-F | CF$_3$ | H | H | C(O)(E-1-1b) |
| 3,5-Br$_2$-4-F | CF$_3$ | H | H | C(O)(E-1-1c) |
| 3,5-Br$_2$-4-F | CF$_3$ | H | H | C(O)(E-1-2a) |
| 3,5-Br$_2$-4-F | CF$_3$ | H | H | C(O)(E-1-2b) |
| 3,5-Br$_2$-4-F | CF$_3$ | H | H | C(O)(E-1-2c) |
| 3,5-Br$_2$-4-F | CF$_3$ | H | H | C(O)CH(SCH$_3$)$_2$ |
| 3,5-Br$_2$-4-F | CF$_3$ | H | H | C(O)CH(SCH$_3$)S(O)CH$_3$ |
| 3,5-Br$_2$-4-F | CF$_3$ | H | H | C(O)CH[S(O)CH$_3$]$_2$ |
| 3,5-Br$_2$-4-F | CF$_3$ | H | H | C(O)CH[S(O)CH$_3$]SO$_2$CH$_3$ |
| 3,5-Br$_2$-4-F | CF$_3$ | H | H | C(O)CH(SEt)$_2$ |
| 3,5-Br$_2$-4-F | CF$_3$ | H | H | C(O)CH(SEt)S(O)Et |
| 3,5-Br$_2$-4-F | CF$_3$ | H | H | C(O)CH[S(O)Et]$_2$ |
| 3,5-Br$_2$-4-F | CF$_3$ | H | H | C(O)CH[S(O)Et]SO$_2$Et |
| 3,5-Br$_2$-4-F | CF$_3$ | H | H | C(S)CH$_2$SCH$_3$ |
| 3,5-Br$_2$-4-F | CF$_3$ | H | H | C(S)CH$_2$SO$_2$CH$_3$ |
| 3,5-Br$_2$-4-F | CF$_3$ | H | H | C(S)CH$_2$SEt |
| 3,5-Br$_2$-4-F | CF$_3$ | H | H | C(S)CH$_2$SO$_2$Et |
| 3,5-Br$_2$-4-F | CF$_2$Cl | H | H | C(O)CH$_2$SCH$_3$ |
| 3,5-Br$_2$-4-F | CF$_2$Cl | H | H | C(O)CH$_2$S(O)CH$_3$ |
| 3,5-Br$_2$-4-F | CF$_2$Cl | H | H | C(O)CH$_2$SO$_2$CH$_3$ |
| 3,5-Br$_2$-4-F | CF$_2$Cl | H | H | C(O)CH$_2$SEt |
| 3,5-Br$_2$-4-F | CF$_2$Cl | H | H | C(O)CH$_2$S(O)Et |
| 3,5-Br$_2$-4-F | CF$_2$Cl | H | H | C(O)CH$_2$SO$_2$Et |
| 3,5-Br$_2$-4-F | CF$_2$Cl | H | H | C(S)CH$_2$SCH$_3$ |
| 3,5-Br$_2$-4-F | CF$_2$Cl | H | H | C(S)CH$_2$SO$_2$CH$_3$ |
| 3,5-Br$_2$-4-F | CF$_2$Cl | H | H | C(S)CH$_2$SEt |
| 3,5-Br$_2$-4-F | CF$_2$Cl | H | H | C(S)CH$_2$SO$_2$Et |
| 3,5-Br$_2$-4-Cl | CF$_3$ | H | H | C(O)CH$_2$SCH$_3$ |
| 3,5-Br$_2$-4-Cl | CF$_3$ | H | H | C(O)CH$_2$S(O)CH$_3$ |
| 3,5-Br$_2$-4-Cl | CF$_3$ | H | H | C(O)CH$_2$SO$_2$CH$_3$ |
| 3,5-Br$_2$-4-Cl | CF$_3$ | H | H | C(O)CH$_2$SEt |
| 3,5-Br$_2$-4-Cl | CF$_3$ | H | H | C(O)CH$_2$S(O)Et |
| 3,5-Br$_2$-4-Cl | CF$_3$ | H | H | C(O)CH$_2$SO$_2$Et |
| 3,5-Br$_2$-4-Cl | CF$_3$ | H | H | C(S)CH$_2$SCH$_3$ |
| 3,5-Br$_2$-4-Cl | CF$_3$ | H | H | C(S)CH$_2$SO$_2$CH$_3$ |
| 3,5-Br$_2$-4-Cl | CF$_3$ | H | H | C(S)CH$_2$SEt |
| 3,5-Br$_2$-4-Cl | CF$_3$ | H | H | C(S)CH$_2$SO$_2$Et |
| 3,4,5-Br$_3$ | CF$_3$ | H | H | C(O)CH$_2$SCH$_3$ |
| 3,4,5-Br$_3$ | CF$_3$ | H | H | C(O)CH$_2$S(O)CH$_3$ |
| 3,4,5-Br$_3$ | CF$_3$ | H | H | C(O)CH$_2$SO$_2$CH$_3$ |
| 3,4,5-Br$_3$ | CF$_3$ | H | H | C(O)CH$_2$SEt |
| 3,4,5-Br$_3$ | CF$_3$ | H | H | C(O)CH$_2$S(O)Et |
| 3,4,5-Br$_3$ | CF$_3$ | H | H | C(O)CH$_2$SO$_2$Et |
| 3,4,5-Br$_3$ | CF$_3$ | H | H | C(S)CH$_2$SCH$_3$ |
| 3,4,5-Br$_3$ | CF$_3$ | H | H | C(S)CH$_2$SO$_2$CH$_3$ |
| 3,4,5-Br$_3$ | CF$_3$ | H | H | C(S)CH$_2$SEt |
| 3,4,5-Br$_3$ | CF$_3$ | H | H | C(S)CH$_2$SO$_2$Et |

| (X)$_m$ | R$^3$ | R$^4$ | R$^2$ | R$^1$ |
|---|---|---|---|---|
| 3,4-Cl$_2$-5-CH$_3$ | CF$_3$ | H | H | C(O)CH$_2$SCH$_3$ |
| 3,4-Cl$_2$-5-CH$_3$ | CF$_3$ | H | H | C(O)CH$_2$S(O)CH$_3$ |
| 3,4-Cl$_2$-5-CH$_3$ | CF$_3$ | H | H | C(O)CH$_2$SO$_2$CH$_3$ |
| 3,4-Cl$_2$-5-CH$_3$ | CF$_3$ | H | H | C(O)CH$_2$SEt |
| 3,4-Cl$_2$-5-CH$_3$ | CF$_3$ | H | H | C(O)CH$_2$S(O)Et |
| 3,4-Cl$_2$-5-CH$_3$ | CF$_3$ | H | H | C(O)CH$_2$SO$_2$Et |
| 3,4-F$_2$-5-CF$_3$ | CHF$_2$ | H | H | C(O)CH$_2$SCH$_3$ |
| 3,4-F$_2$-5-CF$_3$ | CHF$_2$ | H | H | C(O)CH$_2$S(O)CH$_3$ |
| 3,4-F$_2$-5-CF$_3$ | CHF$_2$ | H | H | C(O)CH$_2$SO$_2$CH$_3$ |
| 3,4-F$_2$-5-CF$_3$ | CHF$_2$ | H | H | C(O)CH$_2$SEt |
| 3,4-F$_2$-5-CF$_3$ | CHF$_2$ | H | H | C(O)CH$_2$S(O)Et |
| 3,4-F$_2$-5-CF$_3$ | CHF$_2$ | H | H | C(O)CH$_2$SO$_2$Et |
| 3,4-F$_2$-5-CF$_3$ | CF$_3$ | H | H | C(O)CH$_2$SCH$_3$ |
| 3,4-F$_2$-5-CF$_3$ | CF$_3$ | CH$_3$ | H | C(O)CH$_2$SCH$_3$ |
| 3,4-F$_2$-5-CF$_3$ | CF$_3$ | H | Et | C(O)CH$_2$SCH$_3$ |
| 3,4-F$_2$-5-CF$_3$ | CF$_3$ | H | CH$_2$C≡CH | C(O)CH$_2$SCH$_3$ |
| 3,4-F$_2$-5-CF$_3$ | CF$_3$ | H | H | C(O)CH$_2$S(O)CH$_3$ |
| 3,4-F$_2$-5-CF$_3$ | CF$_3$ | CH$_3$ | H | C(O)CH$_2$S(O)CH$_3$ |
| 3,4-F$_2$-5-CF$_3$ | CF$_3$ | H | CH$_3$ | C(O)CH$_2$S(O)CH$_3$ |
| 3,4-F$_2$-5-CF$_3$ | CF$_3$ | H | Et | C(O)CH$_2$S(O)CH$_3$ |
| 3,4-F$_2$-5-CF$_3$ | CF$_3$ | H | CH$_2$C≡CH | C(O)CH$_2$S(O)CH$_3$ |
| 3,4-F$_2$-5-CF$_3$ | CF$_3$ | H | H | C(O)CH$_2$SO$_2$CH$_3$ |
| 3,4-F$_2$-5-CF$_3$ | CF$_3$ | CH$_3$ | H | C(O)CH$_2$SO$_2$CH$_3$ |
| 3,4-F$_2$-5-CF$_3$ | CF$_3$ | H | CH$_3$ | C(O)CH$_2$SO$_2$CH$_3$ |
| 3,4-F$_2$-5-CF$_3$ | CF$_3$ | H | Et | C(O)CH$_2$SO$_2$CH$_3$ |
| 3,4-F$_2$-5-CF$_3$ | CF$_3$ | H | CH$_2$C≡CH | C(O)CH$_2$SO$_2$CH$_3$ |
| 3,4-F$_2$-5-CF$_3$ | CF$_3$ | H | H | C(O)CH$_2$SEt |
| 3,4-F$_2$-5-CF$_3$ | CF$_3$ | CH$_3$ | H | C(O)CH$_2$SEt |
| 3,4-F$_2$-5-CF$_3$ | CF$_3$ | H | CH$_3$ | C(O)CH$_2$SEt |
| 3,4-F$_2$-5-CF$_3$ | CF$_3$ | H | Et | C(O)CH$_2$SEt |
| 3,4-F$_2$-5-CF$_3$ | CF$_3$ | H | CH$_2$CH=CH$_2$ | C(O)CH$_2$SEt |
| 3,4-F$_2$-5-CF$_3$ | CF$_3$ | H | CH$_2$C≡CH | C(O)CH$_2$SEt |
| 3,4-F$_2$-5-CF$_3$ | CF$_3$ | H | H | C(O)CH$_2$S(O)Et |
| 3,4-F$_2$-5-CF$_3$ | CF$_3$ | CH$_3$ | H | C(O)CH$_2$S(O)Et |
| 3,4-F$_2$-5-CF$_3$ | CF$_3$ | H | CH$_3$ | C(O)CH$_2$S(O)Et |
| 3,4-F$_2$-5-CF$_3$ | CF$_3$ | H | Et | C(O)CH$_2$S(O)Et |
| 3,4-F$_2$-5-CF$_3$ | CF$_3$ | H | CH$_2$C≡CH | C(O)CH$_2$S(O)Et |
| 3,4-F$_2$-5-CF$_3$ | CF$_3$ | H | H | C(O)CH$_2$SO$_2$Et |
| 3,4-F$_2$-5-CF$_3$ | CF$_3$ | CH$_3$ | H | C(O)CH$_2$SO$_2$Et |
| 3,4-F$_2$-5-CF$_3$ | CF$_3$ | H | CH$_3$ | C(O)CH$_2$SO$_2$Et |
| 3,4-F$_2$-5-CF$_3$ | CF$_3$ | H | Et | C(O)CH$_2$SO$_2$Et |
| 3,4-F$_2$-5-CF$_3$ | CF$_3$ | H | CH$_2$C≡CH | C(O)CH$_2$SO$_2$Et |
| 3,4-F$_2$-5-CF$_3$ | CF$_3$ | H | H | C(O)CH$_2$SCH$_2$CF$_3$ |
| 3,4-F$_2$-5-CF$_3$ | CF$_3$ | H | H | C(O)CH$_2$S(O)CH$_2$CF$_3$ |
| 3,4-F$_2$-5-CF$_3$ | CF$_3$ | H | H | C(O)CH$_2$SO$_2$CH$_2$CF$_3$ |
| 3,4-F$_2$-5-CF$_3$ | CF$_3$ | H | H | C(O)CH(CH$_3$)SCH$_3$ |
| 3,4-F$_2$-5-CF$_3$ | CF$_3$ | H | H | C(O)CH(CH$_3$)S(O)CH$_3$ |
| 3,4-F$_2$-5-CF$_3$ | CF$_3$ | H | H | C(O)CH(CH$_3$)SO$_2$CH$_3$ |
| 3,4-F$_2$-5-CF$_3$ | CF$_3$ | H | H | C(O)CH(CH$_3$)SEt |
| 3,4-F$_2$-5-CF$_3$ | CF$_3$ | H | H | C(O)(E-1-1a) |
| 3,4-F$_2$-5-CF$_3$ | CF$_3$ | H | H | C(O)(E-1-1b) |
| 3,4-F$_2$-5-CF$_3$ | CF$_3$ | H | H | C(O)(E-1-1c) |
| 3,4-F$_2$-5-CF$_3$ | CF$_3$ | H | H | C(O)(E-1-2a) |
| 3,4-F$_2$-5-CF$_3$ | CF$_3$ | H | H | C(O)(E-1-2b) |
| 3,4-F$_2$-5-CF$_3$ | CF$_3$ | H | H | C(O)(E-1-2c) |
| 3,4-F$_2$-5-CF$_3$ | CF$_3$ | H | H | C(O)CH(SCH$_3$)$_2$ |
| 3,4-F$_2$-5-CF$_3$ | CF$_3$ | H | H | C(O)CH(SCH$_3$)S(O)CH$_3$ |
| 3,4-F$_2$-5-CF$_3$ | CF$_3$ | H | H | C(O)CH[S(O)CH$_3$]$_2$ |
| 3,4-F$_2$-5-CF$_3$ | CF$_3$ | H | H | C(O)CH[S(O)CH$_3$]SO$_2$CH$_3$ |
| 3,4-F$_2$-5-CF$_3$ | CF$_3$ | H | H | C(O)CH(SEt)$_2$ |
| 3,4-F$_2$-5-CF$_3$ | CF$_3$ | H | H | C(O)CH(SEt)S(O)Et |
| 3,4-F$_2$-5-CF$_3$ | CF$_3$ | H | H | C(O)CH[S(O)Et]$_2$ |
| 3,4-F$_2$-5-CF$_3$ | CF$_3$ | H | H | C(O)CH[S(O)Et]SO$_2$Et |
| 3,4-F$_2$-5-CF$_3$ | CF$_3$ | H | H | C(S)CH$_2$SCH$_3$ |
| 3,4-F$_2$-5-CF$_3$ | CF$_3$ | H | H | C(S)CH$_2$SO$_2$CH$_3$ |
| 3,4-F$_2$-5-CF$_3$ | CF$_3$ | H | H | C(S)CH$_2$SEt |
| 3,4-F$_2$-5-CF$_3$ | CF$_3$ | H | H | C(S)CH$_2$SO$_2$Et |
| 3,4-F$_2$-5-CF$_3$ | CF$_2$Cl | H | H | C(O)CH$_2$SCH$_3$ |
| 3,4-F$_2$-5-CF$_3$ | CF$_2$Cl | H | H | C(O)CH$_2$S(O)CH$_3$ |
| 3,4-F$_2$-5-CF$_3$ | CF$_2$Cl | H | H | C(O)CH$_2$SO$_2$CH$_3$ |
| 3,4-F$_2$-5-CF$_3$ | CF$_2$Cl | H | H | C(O)CH$_2$SEt |
| 3,4-F$_2$-5-CF$_3$ | CF$_2$Cl | H | H | C(O)CH$_2$S(O)Et |
| 3,4-F$_2$-5-CF$_3$ | CF$_2$Cl | H | H | C(O)CH$_2$SO$_2$Et |
| 3,4-F$_2$-5-CF$_3$ | CF$_2$Cl | H | H | C(S)CH$_2$SCH$_3$ |
| 3,4-F$_2$-5-CF$_3$ | CF$_2$Cl | H | H | C(S)CH$_2$SO$_2$CH$_3$ |
| 3,4-F$_2$-5-CF$_3$ | CF$_2$Cl | H | H | C(S)CH$_2$SEt |
| 3,4-F$_2$-5-CF$_3$ | CF$_2$Cl | H | H | C(S)CH$_2$SO$_2$Et |
| 3-Cl-4-F-5-CF$_3$ | CHF$_2$ | H | H | C(O)CH$_2$SCH$_3$ |

-continued

| (X)$_m$ | R$^3$ | R$^4$ | R$^2$ | R$^1$ |
|---|---|---|---|---|
| 3-Cl-4-F-5-CF$_3$ | CHF$_2$ | H | H | C(O)CH$_2$S(O)CH$_3$ |
| 3-Cl-4-F-5-CF$_3$ | CHF$_2$ | H | H | C(O)CH$_2$SO$_2$CH$_3$ |
| 3-Cl-4-F-5-CF$_3$ | CHF$_2$ | H | H | C(O)CH$_2$SEt |
| 3-Cl-4-F-5-CF$_3$ | CHF$_2$ | H | H | C(O)CH$_2$S(O)Et |
| 3-Cl-4-F-5-CF$_3$ | CHF$_2$ | H | H | C(O)CH$_2$SO$_2$Et |
| 3-Cl-4-F-5-CF$_3$ | CF$_3$ | H | H | C(O)CH$_2$SCH$_3$ |
| 3-Cl-4-F-5-CF$_3$ | CF$_3$ | CH$_3$ | H | C(O)CH$_2$SCH$_3$ |
| 3-Cl-4-F-5-CF$_3$ | CF$_3$ | H | Et | C(O)CH$_2$SCH$_3$ |
| 3-Cl-4-F-5-CF$_3$ | CF$_3$ | H | CH$_2$C≡CH | C(O)CH$_2$SCH$_3$ |
| 3-Cl-4-F-5-CF$_3$ | CF$_3$ | H | H | C(O)CH$_2$S(O)CH$_3$ |
| 3-Cl-4-F-5-CF$_3$ | CF$_3$ | CH$_3$ | H | C(O)CH$_2$S(O)CH$_3$ |
| 3-Cl-4-F-5-CF$_3$ | CF$_3$ | H | CH$_3$ | C(O)CH$_2$S(O)CH$_3$ |
| 3-Cl-4-F-5-CF$_3$ | CF$_3$ | H | Et | C(O)CH$_2$S(O)CH$_3$ |
| 3-Cl-4-F-5-CF$_3$ | CF$_3$ | H | CH$_2$C≡CH | C(O)CH$_2$S(O)CH$_3$ |
| 3-Cl-4-F-5-CF$_3$ | CF$_3$ | H | H | C(O)CH$_2$SO$_2$CH$_3$ |
| 3-Cl-4-F-5-CF$_3$ | CF$_3$ | CH$_3$ | H | C(O)CH$_2$SO$_2$CH$_3$ |
| 3-Cl-4-F-5-CF$_3$ | CF$_3$ | H | CH$_3$ | C(O)CH$_2$SO$_2$CH$_3$ |
| 3-Cl-4-F-5-CF$_3$ | CF$_3$ | H | Et | C(O)CH$_2$SO$_2$CH$_3$ |
| 3-Cl-4-F-5-CF$_3$ | CF$_3$ | H | CH$_2$C≡CH | C(O)CH$_2$SO$_2$CH$_3$ |
| 3-Cl-4-F-5-CF$_3$ | CF$_3$ | H | H | C(O)CH$_2$SEt |
| 3-Cl-4-F-5-CF$_3$ | CF$_3$ | CH$_3$ | H | C(O)CH$_2$SEt |
| 3-Cl-4-F-5-CF$_3$ | CF$_3$ | H | CH$_3$ | C(O)CH$_2$SEt |
| 3-Cl-4-F-5-CF$_3$ | CF$_3$ | H | Et | C(O)CH$_2$SEt |
| 3-Cl-4-F-5-CF$_3$ | CF$_3$ | H | CH$_2$CH=CH$_2$ | C(O)CH$_2$SEt |
| 3-Cl-4-F-5-CF$_3$ | CF$_3$ | H | CH$_2$C≡CH | C(O)CH$_2$SEt |
| 3-Cl-4-F-5-CF$_3$ | CF$_3$ | H | H | C(O)CH$_2$S(O)Et |
| 3-Cl-4-F-5-CF$_3$ | CF$_3$ | CH$_3$ | H | C(O)CH$_2$S(O)Et |
| 3-Cl-4-F-5-CF$_3$ | CF$_3$ | H | CH$_3$ | C(O)CH$_2$S(O)Et |
| 3-Cl-4-F-5-CF$_3$ | CF$_3$ | H | Et | C(O)CH$_2$S(O)Et |
| 3-Cl-4-F-5-CF$_3$ | CF$_3$ | H | CH$_2$C≡CH | C(O)CH$_2$S(O)Et |
| 3-Cl-4-F-5-CF$_3$ | CF$_3$ | H | H | C(O)CH$_2$SO$_2$Et |
| 3-Cl-4-F-5-CF$_3$ | CF$_3$ | CH$_3$ | H | C(O)CH$_2$SO$_2$Et |
| 3-Cl-4-F-5-CF$_3$ | CF$_3$ | H | CH$_3$ | C(O)CH$_2$SO$_2$Et |
| 3-Cl-4-F-5-CF$_3$ | CF$_3$ | H | Et | C(O)CH$_2$SO$_2$Et |
| 3-Cl-4-F-5-CF$_3$ | CF$_3$ | H | CH$_2$C≡CH | C(O)CH$_2$SO$_2$Et |
| 3-Cl-4-F-5-CF$_3$ | CF$_3$ | H | H | C(O)CH$_2$SCH$_2$CF$_3$ |
| 3-Cl-4-F-5-CF$_3$ | CF$_3$ | H | H | C(O)CH$_2$S(O)CH$_2$CF$_3$ |
| 3-Cl-4-F-5-CF$_3$ | CF$_3$ | H | H | C(O)CH$_2$SO$_2$CH$_2$CF$_3$ |
| 3-Cl-4-F-5-CF$_3$ | CF$_3$ | H | H | C(O)CH(CH$_3$)SCH$_3$ |
| 3-Cl-4-F-5-CF$_3$ | CF$_3$ | H | H | C(O)CH(CH$_3$)S(O)CH$_3$ |
| 3-Cl-4-F-5-CF$_3$ | CF$_3$ | H | H | C(O)CH(CH$_3$)SO$_2$CH$_3$ |
| 3-Cl-4-F-5-CF$_3$ | CF$_3$ | H | H | C(O)CH(CH$_3$)SEt |
| 3-Cl-4-F-5-CF$_3$ | CF$_3$ | H | H | C(O)(E-1-1a) |
| 3-Cl-4-F-5-CF$_3$ | CF$_3$ | H | H | C(O)(E-1-1b) |
| 3-Cl-4-F-5-CF$_3$ | CF$_3$ | H | H | C(O)(E-1-1c) |
| 3-Cl-4-F-5-CF$_3$ | CF$_3$ | H | H | C(O)(E-1-2a) |
| 3-Cl-4-F-5-CF$_3$ | CF$_3$ | H | H | C(O)(E-1-2b) |
| 3-Cl-4-F-5-CF$_3$ | CF$_3$ | H | H | C(O)(E-1-2c) |
| 3-Cl-4-F-5-CF$_3$ | CF$_3$ | H | H | C(O)CH(SCH$_3$)$_2$ |
| 3-Cl-4-F-5-CF$_3$ | CF$_3$ | H | H | C(O)CH(SCH$_3$)S(O)CH$_3$ |
| 3-Cl-4-F-5-CF$_3$ | CF$_3$ | H | H | C(O)CH[S(O)CH$_3$]$_2$ |
| 3-Cl-4-F-5-CF$_3$ | CF$_3$ | H | H | C(O)CH[S(O)CH$_3$]SO$_2$CH$_3$ |
| 3-Cl-4-F-5-CF$_3$ | CF$_3$ | H | H | C(O)CH(SEt)$_2$ |
| 3-Cl-4-F-5-CF$_3$ | CF$_3$ | H | H | C(O)CH(SEt)S(O)Et |
| 3-Cl-4-F-5-CF$_3$ | CF$_3$ | H | H | C(O)CH[S(O)Et]$_2$ |
| 3-Cl-4-F-5-CF$_3$ | CF$_3$ | H | H | C(O)CH[S(O)Et]SO$_2$Et |
| 3-Cl-4-F-5-CF$_3$ | CF$_3$ | H | H | C(S)CH$_2$SCH$_3$ |
| 3-Cl-4-F-5-CF$_3$ | CF$_3$ | H | H | C(S)CH$_2$SO$_2$CH$_3$ |
| 3-Cl-4-F-5-CF$_3$ | CF$_3$ | H | H | C(S)CH$_2$SEt |
| 3-Cl-4-F-5-CF$_3$ | CF$_3$ | H | H | C(S)CH$_2$SO$_2$Et |
| 3-Cl-4-F-5-CF$_3$ | CF$_2$Cl | H | H | C(O)CH$_2$SCH$_3$ |
| 3-Cl-4-F-5-CF$_3$ | CF$_2$Cl | H | H | C(O)CH$_2$S(O)CH$_3$ |
| 3-Cl-4-F-5-CF$_3$ | CF$_2$Cl | H | H | C(O)CH$_2$SO$_2$CH$_3$ |
| 3-Cl-4-F-5-CF$_3$ | CF$_2$Cl | H | H | C(O)CH$_2$SEt |
| 3-Cl-4-F-5-CF$_3$ | CF$_2$Cl | H | H | C(O)CH$_2$S(O)Et |
| 3-Cl-4-F-5-CF$_3$ | CF$_2$Cl | H | H | C(O)CH$_2$SO$_2$Et |
| 3-Cl-4-F-5-CF$_3$ | CF$_2$Cl | H | H | C(S)CH$_2$SCH$_3$ |
| 3-Cl-4-F-5-CF$_3$ | CF$_2$Cl | H | H | C(S)CH$_2$SO$_2$CH$_3$ |
| 3-Cl-4-F-5-CF$_3$ | CF$_2$Cl | H | H | C(S)CH$_2$SEt |
| 3-Cl-4-F-5-CF$_3$ | CF$_2$Cl | H | H | C(S)CH$_2$SO$_2$Et |
| 3,4-Cl$_2$-5-CF$_3$ | CHF$_2$ | H | H | C(O)CH$_2$SCH$_3$ |
| 3,4-Cl$_2$-5-CF$_3$ | CHF$_2$ | H | H | C(O)CH$_2$S(O)CH$_3$ |
| 3,4-Cl$_2$-5-CF$_3$ | CHF$_2$ | H | H | C(O)CH$_2$SO$_2$CH$_3$ |
| 3,4-Cl$_2$-5-CF$_3$ | CHF$_2$ | H | H | C(O)CH$_2$SEt |
| 3,4-Cl$_2$-5-CF$_3$ | CHF$_2$ | H | H | C(O)CH$_2$S(O)Et |
| 3,4-Cl$_2$-5-CF$_3$ | CHF$_2$ | H | H | C(O)CH$_2$SO$_2$Et |
| 3,4-Cl$_2$-5-CF$_3$ | CF$_3$ | H | H | C(O)CH$_2$SCH$_3$ |
| 3,4-Cl$_2$-5-CF$_3$ | CF$_3$ | CH$_3$ | H | C(O)CH$_2$SCH$_3$ |

-continued

| (X)$_m$ | R$^3$ | R$^4$ | R$^2$ | R$^1$ |
|---|---|---|---|---|
| 3,4-Cl$_2$-5-CF$_3$ | CF$_3$ | CN | H | C(O)CH$_2$SCH$_3$ |
| 3,4-Cl$_2$-5-CF$_3$ | CF$_3$ | H | Et | C(O)CH$_2$SCH$_3$ |
| 3,4-Cl$_2$-5-CF$_3$ | CF$_3$ | H | CH$_2$C≡CH | C(O)CH$_2$SCH$_3$ |
| 3,4-Cl$_2$-5-CF$_3$ | CF$_3$ | H | H | C(O)CH$_2$S(O)CH$_3$ |
| 3,4-Cl$_2$-5-CF$_3$ | CF$_3$ | CH$_3$ | H | C(O)CH$_2$S(O)CH$_3$ |
| 3,4-Cl$_2$-5-CF$_3$ | CF$_3$ | H | CH$_3$ | C(O)CH$_2$S(O)CH$_3$ |
| 3,4-Cl$_2$-5-CF$_3$ | CF$_3$ | H | Et | C(O)CH$_2$S(O)CH$_3$ |
| 3,4-Cl$_2$-5-CF$_3$ | CF$_3$ | H | CH$_2$C≡CH | C(O)CH$_2$S(O)CH$_3$ |
| 3,4-Cl$_2$-5-CF$_3$ | CF$_3$ | H | H | C(O)CH$_2$S(CH$_3$)=NC(O)CF$_3$ |
| 3,4-Cl$_2$-5-CF$_3$ | CF$_3$ | H | H | C(O)CH$_2$S(CH$_3$)=NCN |
| 3,4-Cl$_2$-5-CF$_3$ | CF$_3$ | H | H | C(O)CH$_2$SO$_2$CH$_3$ |
| 3,4-Cl$_2$-5-CF$_3$ | CF$_3$ | CH$_3$ | H | C(O)CH$_2$SO$_2$CH$_3$ |
| 3,4-Cl$_2$-5-CF$_3$ | CF$_3$ | CN | H | C(O)CH$_2$SO$_2$CH$_3$ |
| 3,4-Cl$_2$-5-CF$_3$ | CF$_3$ | H | CH$_3$ | C(O)CH$_2$SO$_2$CH$_3$ |
| 3,4-Cl$_2$-5-CF$_3$ | CF$_3$ | H | Et | C(O)CH$_2$SO$_2$CH$_3$ |
| 3,4-Cl$_2$-5-CF$_3$ | CF$_3$ | H | CH$_2$C≡CH | C(O)CH$_2$SO$_2$CH$_3$ |
| 3,4-Cl$_2$-5-CF$_3$ | CF$_3$ | H | H | C(O)CH$_2$SEt |
| 3,4-Cl$_2$-5-CF$_3$ | CF$_3$ | CH$_3$ | H | C(O)CH$_2$SEt |
| 3,4-Cl$_2$-5-CF$_3$ | CF$_3$ | H | CH$_3$ | C(O)CH$_2$SEt |
| 3,4-Cl$_2$-5-CF$_3$ | CF$_3$ | H | Et | C(O)CH$_2$SEt |
| 3,4-Cl$_2$-5-CF$_3$ | CF$_3$ | H | CH$_2$CH=CH$_2$ | C(O)CH$_2$SEt |
| 3,4-Cl$_2$-5-CF$_3$ | CF$_3$ | H | CH$_2$C≡CH | C(O)CH$_2$SEt |
| 3,4-Cl$_2$-5-CF$_3$ | CF$_3$ | H | H | C(O)CH$_2$S(O)Et |
| 3,4-Cl$_2$-5-CF$_3$ | CF$_3$ | CH$_3$ | H | C(O)CH$_2$S(O)Et |
| 3,4-Cl$_2$-5-CF$_3$ | CF$_3$ | H | CH$_3$ | C(O)CH$_2$S(O)Et |
| 3,4-Cl$_2$-5-CF$_3$ | CF$_3$ | H | Et | C(O)CH$_2$S(O)Et |
| 3,4-Cl$_2$-5-CF$_3$ | CF$_3$ | H | CH$_2$C≡CH | C(O)CH$_2$S(O)Et |
| 3,4-Cl$_2$-5-CF$_3$ | CF$_3$ | H | H | C(O)CH$_2$S(Et)=NC(O)CF$_3$ |
| 3,4-Cl$_2$-5-CF$_3$ | CF$_3$ | H | H | C(O)CH$_2$SO$_2$Et |
| 3,4-Cl$_2$-5-CF$_3$ | CF$_3$ | CH$_3$ | H | C(O)CH$_2$SO$_2$Et |
| 3,4-Cl$_2$-5-CF$_3$ | CF$_3$ | H | CH$_3$ | C(O)CH$_2$SO$_2$Et |
| 3,4-Cl$_2$-5-CF$_3$ | CF$_3$ | H | Et | C(O)CH$_2$SO$_2$Et |
| 3,4-Cl$_2$-5-CF$_3$ | CF$_3$ | H | CH$_2$C≡CH | C(O)CH$_2$SO$_2$Et |
| 3,4-Cl$_2$-5-CF$_3$ | CF$_3$ | H | H | C(O)CH$_2$SCH$_2$CF$_3$ |
| 3,4-Cl$_2$-5-CF$_3$ | CF$_3$ | H | H | C(O)CH$_2$S(O)CH$_2$CF$_3$ |
| 3,4-Cl$_2$-5-CF$_3$ | CF$_3$ | H | H | C(O)CH$_2$SO$_2$CH$_2$CF$_3$ |
| 3,4-Cl$_2$-5-CF$_3$ | CF$_3$ | H | H | C(O)CH(CH$_3$)SCH$_3$ |
| 3,4-Cl$_2$-5-CF$_3$ | CF$_3$ | H | H | C(O)CH(CH$_3$)S(O)CH$_3$ |
| 3,4-Cl$_2$-5-CF$_3$ | CF$_3$ | H | H | C(O)CH(CH$_3$)SO$_2$CH$_3$ |
| 3,4-Cl$_2$-5-CF$_3$ | CF$_3$ | H | H | C(O)CH(CH$_3$)SEt |
| 3,4-Cl$_2$-5-CF$_3$ | CF$_3$ | H | H | C(O)(E-1-1a) |
| 3,4-Cl$_2$-5-CF$_3$ | CF$_3$ | H | H | C(O)(E-1-1b) |
| 3,4-Cl$_2$-5-CF$_3$ | CF$_3$ | H | H | C(O)(E-1-1c) |
| 3,4-Cl$_2$-5-CF$_3$ | CF$_3$ | H | H | C(O)(E-1-2a) |
| 3,4-Cl$_2$-5-CF$_3$ | CF$_3$ | H | H | C(O)(E-1-2b) |
| 3,4-Cl$_2$-5-CF$_3$ | CF$_3$ | H | H | C(O)(E-1-2c) |
| 3,4-Cl$_2$-5-CF$_3$ | CF$_3$ | H | H | C(O)CHFSCH$_3$ |
| 3,4-Cl$_2$-5-CF$_3$ | CF$_3$ | H | H | C(O)CH(SCH$_3$)$_2$ |
| 3,4-Cl$_2$-5-CF$_3$ | CF$_3$ | H | H | C(O)CH(SCH$_3$)S(O)CH$_3$ |
| 3,4-Cl$_2$-5-CF$_3$ | CF$_3$ | H | H | C(O)CH[S(O)CH$_3$]$_2$ |
| 3,4-Cl$_2$-5-CF$_3$ | CF$_3$ | H | H | C(O)CH[S(O)CH$_3$]SO$_2$CH$_3$ |
| 3,4-Cl$_2$-5-CF$_3$ | CF$_3$ | H | H | C(O)CH(SEt)$_2$ |
| 3,4-Cl$_2$-5-CF$_3$ | CF$_3$ | H | H | C(O)CH(SEt)S(O)Et |
| 3,4-Cl$_2$-5-CF$_3$ | CF$_3$ | H | H | C(O)CH[S(O)Et]$_2$ |
| 3,4-Cl$_2$-5-CF$_3$ | CF$_3$ | H | H | C(O)CH[S(O)Et]SO$_2$Et |
| 3,4-Cl$_2$-5-CF$_3$ | CF$_3$ | H | H | C(O)CH(SO$_2$Et)$_2$ |
| 3,4-Cl$_2$-5-CF$_3$ | CF$_3$ | H | H | C(S)CH$_2$SCH$_3$ |
| 3,4-Cl$_2$-5-CF$_3$ | CF$_3$ | H | H | C(S)CH$_2$SO$_2$CH$_3$ |
| 3,4-Cl$_2$-5-CF$_3$ | CF$_3$ | H | H | C(S)CH$_2$SEt |
| 3,4-Cl$_2$-5-CF$_3$ | CF$_3$ | H | H | C(S)CH$_2$SO$_2$Et |
| 3,4-Cl$_2$-5-CF$_3$ | CF$_2$Cl | H | H | C(O)CH$_2$SCH$_3$ |
| 3,4-Cl$_2$-5-CF$_3$ | CF$_2$Cl | H | H | C(O)CH$_2$S(O)CH$_3$ |
| 3,4-Cl$_2$-5-CF$_3$ | CF$_2$Cl | H | H | C(O)CH$_2$SO$_2$CH$_3$ |
| 3,4-Cl$_2$-5-CF$_3$ | CF$_2$Cl | H | H | C(O)CH$_2$SEt |
| 3,4-Cl$_2$-5-CF$_3$ | CF$_2$Cl | H | H | C(O)CH$_2$S(O)Et |
| 3,4-Cl$_2$-5-CF$_3$ | CF$_2$Cl | H | H | C(O)CH$_2$SO$_2$Et |
| 3,4-Cl$_2$-5-CF$_3$ | CF$_2$Cl | H | H | C(S)CH$_2$SCH$_3$ |
| 3,4-Cl$_2$-5-CF$_3$ | CF$_2$Cl | H | H | C(S)CH$_2$SO$_2$CH$_3$ |
| 3,4-Cl$_2$-5-CF$_3$ | CF$_2$Cl | H | H | C(S)CH$_2$SEt |
| 3,4-Cl$_2$-5-CF$_3$ | CF$_2$Cl | H | H | C(S)CH$_2$SO$_2$Et |
| 3,5-(CF$_3$)$_2$-4-Cl | CHF$_2$ | H | H | C(O)CH$_2$SCH$_3$ |
| 3,5-(CF$_3$)$_2$-4-Cl | CHF$_2$ | H | H | C(O)CH$_2$S(O)CH$_3$ |
| 3,5-(CF$_3$)$_2$-4-Cl | CHF$_2$ | H | H | C(O)CH$_2$SO$_2$CH$_3$ |
| 3,5-(CF$_3$)$_2$-4-Cl | CHF$_2$ | H | H | C(O)CH$_2$SEt |
| 3,5-(CF$_3$)$_2$-4-Cl | CHF$_2$ | H | H | C(O)CH$_2$S(O)Et |
| 3,5-(CF$_3$)$_2$-4-Cl | CHF$_2$ | H | H | C(O)CH$_2$SO$_2$Et |
| 3,5-(CF$_3$)$_2$-4-Cl | CF$_3$ | H | H | C(O)CH$_2$SCH$_3$ |
| 3,5-(CF$_3$)$_2$-4-Cl | CF$_3$ | CH$_3$ | H | C(O)CH$_2$SCH$_3$ |

-continued

| (X)$_m$ | R$^3$ | R$^4$ | R$^2$ | R$^1$ |
|---|---|---|---|---|
| 3,5-(CF$_3$)$_2$-4-Cl | CF$_3$ | H | Et | C(O)CH$_2$SCH$_3$ |
| 3,5-(CF$_3$)$_2$-4-Cl | CF$_3$ | H | CH$_2$C≡CH | C(O)CH$_2$SCH$_3$ |
| 3,5-(CF$_3$)$_2$-4-Cl | CF$_3$ | H | H | C(O)CH$_2$S(O)CH$_3$ |
| 3,5-(CF$_3$)$_2$-4-Cl | CF$_3$ | CH$_3$ | H | C(O)CH$_2$S(O)CH$_3$ |
| 3,5-(CF$_3$)$_2$-4-Cl | CF$_3$ | H | CH$_3$ | C(O)CH$_2$S(O)CH$_3$ |
| 3,5-(CF$_3$)$_2$-4-Cl | CF$_3$ | H | Et | C(O)CH$_2$S(O)CH$_3$ |
| 3,5-(CF$_3$)$_2$-4-Cl | CF$_3$ | H | CH$_2$C≡CH | C(O)CH$_2$S(O)CH$_3$ |
| 3,5-(CF$_3$)$_2$-4-Cl | CF$_3$ | H | H | C(O)CH$_2$SO$_2$CH$_3$ |
| 3,5-(CF$_3$)$_2$-4-Cl | CF$_3$ | CH$_3$ | H | C(O)CH$_2$SO$_2$CH$_3$ |
| 3,5-(CF$_3$)$_2$-4-Cl | CF$_3$ | H | CH$_3$ | C(O)CH$_2$SO$_2$CH$_3$ |
| 3,5-(CF$_3$)$_2$-4-Cl | CF$_3$ | H | Et | C(O)CH$_2$SO$_2$CH$_3$ |
| 3,5-(CF$_3$)$_2$-4-Cl | CF$_3$ | H | CH$_2$C≡CH | C(O)CH$_2$SO$_2$CH$_3$ |
| 3,5-(CF$_3$)$_2$-4-Cl | CF$_3$ | H | H | C(O)CH$_2$SEt |
| 3,5-(CF$_3$)$_2$-4-Cl | CF$_3$ | CH$_3$ | H | C(O)CH$_2$SEt |
| 3,5-(CF$_3$)$_2$-4-Cl | CF$_3$ | H | CH$_3$ | C(O)CH$_2$SEt |
| 3,5-(CF$_3$)$_2$-4-Cl | CF$_3$ | H | Et | C(O)CH$_2$SEt |
| 3,5-(CF$_3$)$_2$-4-Cl | CF$_3$ | H | CH$_2$CH═CH$_2$ | C(O)CH$_2$SEt |
| 3,5-(CF$_3$)$_2$-4-Cl | CF$_3$ | H | CH$_2$C≡CH | C(O)CH$_2$SEt |
| 3,5-(CF$_3$)$_2$-4-Cl | CF$_3$ | H | H | C(O)CH$_2$S(O)Et |
| 3,5-(CF$_3$)$_2$-4-Cl | CF$_3$ | CH$_3$ | H | C(O)CH$_2$S(O)Et |
| 3,5-(CF$_3$)$_2$-4-Cl | CF$_3$ | H | CH$_3$ | C(O)CH$_2$S(O)Et |
| 3,5-(CF$_3$)$_2$-4-Cl | CF$_3$ | H | Et | C(O)CH$_2$S(O)Et |
| 3,5-(CF$_3$)$_2$-4-Cl | CF$_3$ | H | CH$_2$C≡CH | C(O)CH$_2$S(O)Et |
| 3,5-(CF$_3$)$_2$-4-Cl | CF$_3$ | H | H | C(O)CH$_2$SO$_2$Et |
| 3,5-(CF$_3$)$_2$-4-Cl | CF$_3$ | CH$_3$ | H | C(O)CH$_2$SO$_2$Et |
| 3,5-(CF$_3$)$_2$-4-Cl | CF$_3$ | H | CH$_3$ | C(O)CH$_2$SO$_2$Et |
| 3,5-(CF$_3$)$_2$-4-Cl | CF$_3$ | H | Et | C(O)CH$_2$SO$_2$Et |
| 3,5-(CF$_3$)$_2$-4-Cl | CF$_3$ | H | CH$_2$C≡CH | C(O)CH$_2$SO$_2$Et |
| 3,5-(CF$_3$)$_2$-4-Cl | CF$_3$ | H | H | C(O)CH$_2$SCH$_2$CF$_3$ |
| 3,5-(CF$_3$)$_2$-4-Cl | CF$_3$ | H | H | C(O)CH$_2$S(O)CH$_2$CF$_3$ |
| 3,5-(CF$_3$)$_2$-4-Cl | CF$_3$ | H | H | C(O)CH$_2$SO$_2$CH$_2$CF$_3$ |
| 3,5-(CF$_3$)$_2$-4-Cl | CF$_3$ | H | H | C(O)CH(CH$_3$)SCH$_3$ |
| 3,5-(CF$_3$)$_2$-4-Cl | CF$_3$ | H | H | C(O)CH(CH$_3$)S(O)CH$_3$ |
| 3,5-(CF$_3$)$_2$-4-Cl | CF$_3$ | H | H | C(O)CH(CH$_3$)SO$_2$CH$_3$ |
| 3,5-(CF$_3$)$_2$-4-Cl | CF$_3$ | H | H | C(O)CH(CH$_3$)SEt |
| 3,5-(CF$_3$)$_2$-4-Cl | CF$_3$ | H | H | C(O)(E-1-1a) |
| 3,5-(CF$_3$)$_2$-4-Cl | CF$_3$ | H | H | C(O)(E-1-1b) |
| 3,5-(CF$_3$)$_2$-4-Cl | CF$_3$ | H | H | C(O)(E-1-1c) |
| 3,5-(CF$_3$)$_2$-4-Cl | CF$_3$ | H | H | C(O)(E-1-2a) |
| 3,5-(CF$_3$)$_2$-4-Cl | CF$_3$ | H | H | C(O)(E-1-2b) |
| 3,5-(CF$_3$)$_2$-4-Cl | CF$_3$ | H | H | C(O)(E-1-2c) |
| 3,5-(CF$_3$)$_2$-4-Cl | CF$_3$ | H | H | C(O)CH(SCH$_3$)$_2$ |
| 3,5-(CF$_3$)$_2$-4-Cl | CF$_3$ | H | H | C(O)CH(SCH$_3$)S(O)CH$_3$ |
| 3,5-(CF$_3$)$_2$-4-Cl | CF$_3$ | H | H | C(O)CH[S(O)CH$_3$]$_2$ |
| 3,5-(CF$_3$)$_2$-4-Cl | CF$_3$ | H | H | C(O)CH[S(O)CH$_3$]SO$_2$CH$_3$ |
| 3,5-(CF$_3$)$_2$-4-Cl | CF$_3$ | H | H | C(O)CH(SEt)$_2$ |
| 3,5-(CF$_3$)$_2$-4-Cl | CF$_3$ | H | H | C(O)CH(SEt)S(O)Et |
| 3,5-(CF$_3$)$_2$-4-Cl | CF$_3$ | H | H | C(O)CH[S(O)Et]$_2$ |
| 3,5-(CF$_3$)$_2$-4-Cl | CF$_3$ | H | H | C(O)CH[S(O)Et]SO$_2$Et |
| 3,5-(CF$_3$)$_2$-4-Cl | CF$_3$ | H | H | C(S)CH$_2$SCH$_3$ |
| 3,5-(CF$_3$)$_2$-4-Cl | CF$_3$ | H | H | C(S)CH$_2$SO$_2$CH$_3$ |
| 3,5-(CF$_3$)$_2$-4-Cl | CF$_3$ | H | H | C(S)CH$_2$SEt |
| 3,5-(CF$_3$)$_2$-4-Cl | CF$_3$ | H | H | C(S)CH$_2$SO$_2$Et |
| 3,5-(CF$_3$)$_2$-4-Cl | CF$_2$Cl | H | H | C(O)CH$_2$SCH$_3$ |
| 3,5-(CF$_3$)$_2$-4-Cl | CF$_2$Cl | H | H | C(O)CH$_2$S(O)CH$_3$ |
| 3,5-(CF$_3$)$_2$-4-Cl | CF$_2$Cl | H | H | C(O)CH$_2$SO$_2$CH$_3$ |
| 3,5-(CF$_3$)$_2$-4-Cl | CF$_2$Cl | H | H | C(O)CH$_2$SEt |
| 3,5-(CF$_3$)$_2$-4-Cl | CF$_2$Cl | H | H | C(O)CH$_2$S(O)Et |
| 3,5-(CF$_3$)$_2$-4-Cl | CF$_2$Cl | H | H | C(O)CH$_2$SO$_2$Et |
| 3,5-(CF$_3$)$_2$-4-Cl | CF$_2$Cl | H | H | C(S)CH$_2$SCH$_3$ |
| 3,5-(CF$_3$)$_2$-4-Cl | CF$_2$Cl | H | H | C(S)CH$_2$SO$_2$CH$_3$ |
| 3,5-(CF$_3$)$_2$-4-Cl | CF$_2$Cl | H | H | C(S)CH$_2$SEt |
| 3,5-(CF$_3$)$_2$-4-Cl | CF$_2$Cl | H | H | C(S)CH$_2$SO$_2$Et |
| 3,5-Cl$_2$-4-OCHF$_2$ | CF$_3$ | H | H | C(O)CH$_2$SCH$_3$ |
| 3,5-Cl$_2$-4-OCHF$_2$ | CF$_3$ | H | H | C(O)CH$_2$S(O)CH$_3$ |
| 3,5-Cl$_2$-4-OCHF$_2$ | CF$_3$ | H | H | C(O)CH$_2$SO$_2$CH$_3$ |
| 3,5-Cl$_2$-4-OCHF$_2$ | CF$_3$ | H | H | C(O)CH$_2$SEt |
| 3,5-Cl$_2$-4-OCHF$_2$ | CF$_3$ | H | H | C(O)CH$_2$S(O)Et |
| 3,5-Cl$_2$-4-OCHF$_2$ | CF$_3$ | H | H | C(O)CH$_2$SO$_2$Et |
| 3,5-Cl$_2$-4-OCHF$_2$ | CF$_3$ | H | H | C(S)CH$_2$SCH$_3$ |
| 3,5-Cl$_2$-4-OCHF$_2$ | CF$_3$ | H | H | C(S)CH$_2$SO$_2$CH$_3$ |
| 3,5-Cl$_2$-4-OCHF$_2$ | CF$_3$ | H | H | C(S)CH$_2$SEt |
| 3,5-Cl$_2$-4-OCHF$_2$ | CF$_3$ | H | H | C(S)CH$_2$SO$_2$Et |
| 3,5-Br$_2$-4-OCHF$_2$ | CF$_3$ | H | H | C(O)CH$_2$SCH$_3$ |
| 3,5-Br$_2$-4-OCHF$_2$ | CF$_3$ | H | H | C(O)CH$_2$S(O)CH$_3$ |
| 3,5-Br$_2$-4-OCHF$_2$ | CF$_3$ | H | H | C(O)CH$_2$SO$_2$CH$_3$ |
| 3,5-Br$_2$-4-OCHF$_2$ | CF$_3$ | H | H | C(O)CH$_2$SEt |
| 3,5-Br$_2$-4-OCHF$_2$ | CF$_3$ | H | H | C(O)CH$_2$S(O)Et |

-continued

| (X)$_m$ | R$^3$ | R$^4$ | R$^2$ | R$^1$ |
|---|---|---|---|---|
| 3,5-Br$_2$-4-OCHF$_2$ | CF$_3$ | H | H | C(O)CH$_2$SO$_2$Et |
| 3,5-Br$_2$-4-OCHF$_2$ | CF$_3$ | H | H | C(S)CH$_2$SCH$_3$ |
| 3,5-Br$_2$-4-OCHF$_2$ | CF$_3$ | H | H | C(S)CH$_2$SO$_2$CH$_3$ |
| 3,5-Br$_2$-4-OCHF$_2$ | CF$_3$ | H | H | C(S)CH$_2$SEt |
| 3,5-Br$_2$-4-OCHF$_2$ | CF$_3$ | H | H | C(S)CH$_2$SO$_2$Et |

The compound of the present invention can effectively control with a low concentration thereof, any pests such as insects including so-called agricultural insect pests damaging agricultural or horticultural crops and trees or the like, so-called domestic animal insect pests being parasitic in domestic animals/fowls, so-called sanitary insects adversely affecting in various manners, the living environment of the human such as houses and so-called stored grain insect pests damaging grains and the like stored in warehouses; and mites, Crustacea, Mollusc and Nematoda which are generated and cause damages in a situation similar to that in the case of the insects.

Specific examples of the insects, the mites, the Crustacea, the Mollusc and the Nematoda capable of being controlled using the compound of the present invention include:

Lepidopteran insects such as *Adoxophyes honmai, Adoxophyes orana faciata, Archips breviplicanus, Archips fuscocupreanus, Grapholita molesta, Homona magnanima, Leguminivora glycinivorella, Matsumuraeses phaseoli, Pandemis heparana, Bucculatrix pyrivorella, Lyonetia clerkella, Lyonetia prunifoliella malinella, Caloptilia theivora, Phyllonorycter ringoniella, Phyllocnistis citrella, Acrolepiopsis sapporensis, Acrolepiopsis suzukiella, Plutella xylostella, Stathmopoda masinissa, Helcystogramma triannulella, Pectinophora gossypiella, Carposina sasakii, Cydla pomonella, Chilo suppressalis, Cnaphalocrocis medinalis, Conogethes punctiferalis, Diaphania indica, Etiella zinckenella, Glyphodes pyloalis, Hellula undalis, Ostrinia furnacalis, Ostrinia scapulalis, Ostrinia nubilalis, Parapediasia teterrella, Parnara guttata, Pieris brassicae, Pieris rapae crucivora, Ascotis selenaria, Pseudoplusia includens, Euproctis pseudoconspersa, Lymantria dispar, Orgyia thyellina, Hyphantria cunea, Lemyra imparilis, Adris tyrannus, Aedia leucomelas, Agrotis ipsilon, Agrotis segetum, Autographa nigrisigna, Ctenoplusia agnata, Helicoverpa armigera, Helicoverpa assulta, Helicoverpa zea, Heliothis virescens, Mamestra brassicae, Mythimna separata, Naranga aenescens, Spodoptera eridania, Spodoptera exigua, Spodoptera frugiperda, Spodoptera littoralis, Spodoptera litura, Spodoptera depravata, Trichoplusia ni, Endopiza viteana, Manduca quinquemaculata* and *Manduca sexta;*

Thysanoptera insects such as *Frankliniella intonsa, Frankliniella occidentalis, Heliothrips haemorrhoidalis, Scirtothrips dorsalis, Thrips palmi, Thrips tabaci* and *Ponticulothrips diospyrosi;*

Hemiptera insects such as *Dolycoris baccarum, Eurydema rugosum, Eysarcoris aeneus, Eysarcoris lewisi, Eysarcoris ventralis, Glaucias subpunctatus, Halyomorpha halys, Nezara antennata, Nezara viridula, Piezodorus hybneri, Plautia crossota, Scotinophora lurida, Cletus punctiger, Leptocorisa chinensis, Riptortus clavatus, Rhopalus msculatus, Cavelerius saccharivorus, Togo hemipterus, Dysdercus cingulatus, Stephanitis pyrioides, Halticus insularis, Lygus lineolaris, Stenodema sibiricum, Stenotus rubrovittatus, Trigonotylus caelestialium, Arboridia apicalis, Balclutha saltuella, Epicanthus stramineus, Empoasca fabae, Empoasca nipponica, Empoasca onukii, Empoasca sakaii, Macrosteles striifrons, Nephotettix cinctinceps, Psuedatomoscelis seriatus, Laodelphax striatella, Nilaparvata lugens, Sogatella furcifera, Diaphorina citri, Psylla pyrisuga, Aleurocanthus spiniferus, Bemisia argentifolii, Bemisia tabaci, Dialeurodes citri, Trialeurodes vaporariorum, Viteus vitifolii, Aphis gossypii, Aphis spiraecola, Myzus persicae, Toxoptera aurantii, Drosicha corpulenta, Icerya purchasi, Phenacoccus solani, Planococcus citri, Planococcus kuraunhiae, Pseudococcus comstocki, Ceroplastes ceriferus, Ceroplastes rubens, Aonidiella aurantii, Comstockaspis perniciosa, Fiorinia theae, Pseudaonidia paeoniae, Pseudaulacaspis pentagona, Pseudaulacaspis prunicola, Unaspis euonymi, Unaspis yanonensis* and *Cimex lectularius;*

Coleoptera insects such as *Anomala cuprea, Anomala rufocuprea, Gametis jucunda, Heptophylla picea, Popillia japonica, Lepinotarsa decemlineata, Melanotus fortnumi, Melanotus tamsuyensis, Lasioderma serricorne, Epuraea domina, Epilachna varivestis, Epilachna vigintioctopunctata, Tenebrio molitor, Tribolium castaneum, Anoplophora malasiaca, Monochamus alternatus, Psacothea hilaris, Xylotrechus pyrrhoderus, Callosobruchus chinensis, Aulacophora femoralis, Chaetocnema concinna, Diabrotica undecimpunctata, Diabrotica virgifera, Diabrotica barberi, Oulema oryzae, Phyllotreta striolata, Psylliodes angusticollis, Rhynchites heros, Cylas formicarius, Anthonomus grandis, Echinocnemus squameus, Euscepes postfasciatus, Hypera postica, Lissohoptrus oryzophilus, Otiorhynchus sulcatus, Sitophilus granarius, Sitophilus zeamais, Sphenophorus venatus vestitus* and *Paederus fuscipes;*

Diptera insects such as *Asphondylia yushimai, Sitodiplosis mosellana, Bactrocera cucurbitae, Bactrocera dorsalis, Ceratitis capitata, Hydrellia griseola, Drosophila suzukii, Agromyza oryzae, Chromatomyia horticola, Liriomyza bryoniae, Liriomyza chinensis, Liriomyza sativae, Liriomyza trifolii, Delia platura, Pegomya cunicularia, Rhagoletis pomonella, Mayetiola destructor, Musca domestica, Stomoxys calcitrans, Melophagus ovinus, Hypoderma bovis, Hypoderma lineatum, Oestrus ovis, Glossina palpalis* (*Glossina morsitans*), *Prosimulium yezoensis, Tabanus trigonus, Telmatoscopus albipunctatus, Leptoconops nipponensis, Culex pipiens pallens, Aedes aegypti, Aedes albopicutus* and *Anopheles hyracanus sinesis;*

Hymenoptera insects such as *Apethymus kuri, Athalia rosae, Arge pagana, Neodiprion sertifer, Dryocosmus kuriphilus, Eciton burchelli* (*Eciton schmitti*), *Camponotus japonicus, Vespa mandarina, Myrmecia* spp., *Solenopsis* spp. and *Monomorium pharaonis;*

Orthoptera insects such as *Teleogryllus emma, Gryllotalpa orientalis, Locusta migratoria, Oxya yezoensis* and *Schistocerca gregaria;*

Collembolan insects such as *Onychiurus folsomi, Onychiurus sibiricus* and *Bourletiella hortensis;*

Dictyoptera insects such as *Periplaneta fuliginosa, Periplaneta japonica* and *Blattella germanica;*

Isoptera insects such as *Coptotermes formosanus, Reticulitermes speratus* and *Odontotermes formosanus;*

Isoptera insects such as *Ctenocephalidae felis, Ctenocephalides canis, Echidnophaga gallinacea, Pulex irritans* and *Xenopsylla cheopis*;

Mallophaga insects such as *Menacanthus stramineus* and *Bovicola bovis*;

Anoplura insects such as *Haematopinus eurystemus, Haematopinus suis, Linognathus vituli* and *Solenopotes capillatus*;

Tarsonemidae such as *Phytonemus pallidus, Polyphagotarsonemus latus* and *Tarsonernus bilobatus*;

Eupodidae such as *Penthaleus erythrocephalus* and *Penthaleus major*;

Tetranychidae such as *Oligonychus shinkajii, Panonychus citri, Panonychus mori, Panonychus ulmi, Tetranychus kanzawai* and *Tetranychus urticae*;

Eriophydae such as *Acaphylla theavagrans, Aceria tulipae, Aculops lycopersici, Aculops pelekassi, Aculus schlechtendali, Eriophyes chibaensis* and *Phyllocoptruta oleivora*;

Acaridae such as *Rhizoglyphus robini, Tyrophagus putrescentiae* and *Tyrophagus similis*;

*Varroa destructor* such as *Varroa jacobsoni*;

Ixodidae such as *Boophilus microplus, Rhipicephalus sanguineus, Haemaphysalis longicornis, Haemophysalis flava, Haemophysalis campanulata, Ixodes ovatus, Ixodes persulcatus, Amblyomma* spp. and *Dermacentor* spp.

Cheyletidae such as *Cheyletiella yasguri* and *Cheyletiella blakei*;

Demodicidae such as *Demodex canis* and *Demodex cati*;

Psoroptidae such as *Psoroptes ovis*;

Sarcoptidae such as *Sarcoptes scabiei, Notoedres cati* and *Knemidocoptes* spp.;

Crustacea such as *Armadillidium vulgare*;

Gastropoda such as *Pomacea canaliculata, Achatina fulica, Meghimatium bilineatum, Limax Valentiana, Acusta despecta sieboldiana* and *Euhadra peliomphala*; and Nematoda such as *Prathylenchus coffeae, Prathylenchus penetrans, Prathylenchus vulnus, Globodera rostochiensis, Heterodera glycines, Meloidogyne hapla, Meloidogyne incognita, Aphelenchoides besseyi* and *Bursaphelenchus xylophilus*, which should not be construed as limiting the scope of the present invention, In addition, specific examples of the internal parasites of domestic animals, fowls, pet animals or the like capable of being controlled using the compound of the present invention include:

Nematoda such as *Haemonchus, Trichostrongylus, Ostertagia, Nematodirus, Cooperia, Ascaris, Bunostomum, Oesophagostomum, Chabertia, Trichuris, Storongylus, Trichonema, Dictyocaulus, Capillaria, Heterakis, Toxocara, Ascaridia, Oxyuris, Ancylostoma, Uncinaria, Toxascaris* and *Parascaris*;

Nematoda, Filariidae such as *Wuchereria, Brugia, Onchoceca, Dirofilaria* and *Loa*;

Nematoda, Dracunculidae such as *Deacunculus*;

Cestoda such as *Dipylidium caninum, Taenia taeniaeformis, Taenia solium, Taenia saginata, Hymenolepis diminuta, Moniezia benedeni, Diphyllobothrium latum, Diphyllobothrium erinacei, Echinococcus granulosus* and *Echinococcus multilocularis*;

Trematoda such as *Fasciola hepatica* and *F. gigantica, Paragonimus westermanii, Fasciolopsis bruski, Eurytrema pancreaticum* and *E. coelomaticum, Clonarchis sinensis, Schistosoma japonicum, Schistosoma haematobium* and *Schistosoma mansoni*;

*Eimeria* spp. such as *Eimeria tenella, Eimeria acervulina, Eimeria brunetti, Eimeria maxima, Eimeria necatrix, Eimeria bovis* and *Eimeria ovinoidalis*;

*Trypanosomsa cruzi; Leishmania* spp.; *Plasmodium* spp.; *Babesis* spp.; *Trichomonadidae* spp.; *Histomanas* spp.; *Giardia* spp.; *Toxoplasma* spp.; *Entamoeba histolytica* and *Theileria* spp, which should not be construed as limiting the scope of the present invention.

Furthermore, the compound of the present invention is effective against pests which have developed the resistance to the related art insecticides such as organic phosphorus-based compounds, carbamate-based compounds or pyrethroid-based compounds.

That is, the compound of the present invention can effectively control pests belonging to insects such as Collembola, Dictyoptera (Blattaria), Orthoptera, Isoptera, Thysanoptera, Hemiptera (Heteroptera and Homoptera), Lepidoptera, Coleoptera, Hymenoptera, Diptera, Isoptera (Siphonaptera) and Phthiraptera; mites; Gastropoda; and Nematoda with a low concentration. On the other hand, the compound of the present invention has an extremely useful characteristic of having substantially no adverse effect on mammals, fish, Crustacea and beneficial insects (useful insects such as Apidae and *Bombus*, and natural enemies such as Aphelimidae, Aphidiidae, Tachimidae, *Orius* and *Amblyseius*).

For using the compound of the present invention, the compound can be put to practical use as a preparation in any dosage form such as a soluble concentrate, an emulsifiable concentrate, a wettable powder, a water soluble powder, a water dispersible granule, a water soluble granule, a suspension concentrate, a concentrated emulsion, a suspoemulsion, a microemulsion, a dustable powder, a granule, a tablet and an emulsifiable gel, typically by mixing the compound with an appropriate solid carrier or liquid carrier, further if desired by adding to the resultant mixture, a surfactant, a penetrant, a spreader, a thickener, an antifreezing agent, a binder, an anti-caking agent, a disintegrant, an antifoamer, an antiseptic or a stabilizer. In addition, from the viewpoint of laborsaving and safety-enhancing, the compound can be put to use by encapsulating the above preparation in any dosage form in a water soluble packaging material such as a water soluble capsule and a bag of a water soluble film.

Examples of the solid carrier include: natural mineral matters such as quartz, calcite, sepiolite, dolomite, chalk, kaolinite, pyrophyllite, sericite, halloysite, methahalloysite, kibushi clay, gairome clay, pottery stone, zeeklite, allophane, Shirasu, mica, talc, bentonite, activated clay, acid clay, pumice, attapulgite, zeolite and diatom earth; burned products of natural mineral matters such as burned clay, perlite, Shirasu balloon, vermiculite, attapulgous clay and burned diatom earth; inorganic salts such as magnesium carbonate, calcium carbonate, sodium carbonate, sodium hydrogen carbonate, ammonium sulfate, sodium sulfate, magnesium sulfate, diammonium hydrogen phosphate, ammonium dihydrogen phosphate and potassium chloride; saccharides such as glucose, fructose, sucrose and lactose; polysaccharides such as starch, powdered cellulose and dextrin; organic substances such as urea, urea derivatives, benzoic acid and salts of benzoic acid; plants such as wood flour, cork flour, corncob, walnut shell and tobacco stem; fly ash; white carbon (such as hydrous synthetic silica, anhydrous synthetic silica and hydrous synthetic silicate); and fertilizers.

Examples of the liquid carrier include: aromatic hydrocarbons such as xylene, alkyl ($C_9$, $C_{10}$, or the like) benzene, phenylxylylethane and alkyl ($C_1$, $C_3$, or the like) naphthalene; aliphatic hydrocarbons such as machine oil, n-paraffin, iso-paraffin and naphthene; a mixture of aromatic hydrocarbons and aliphatic hydrocarbons such as kerosene; alcohols such as ethanol, isopropanol, cyclohexanol, phenoxyethanol and benzyl alcohol; polyalcohols such as ethylene glycol, propylene glycol, diethylene glycol, hexylene glycol, polyethylene glycol and polypropylene glycol; ethers such as propyl cellosolve, butyl cellosolve, phenyl cellosolve, propylene glycol monomethyl ether, propylene glycol monoethyl ether, propylene glycol monopropyl ether, propylene glycol monobutyl ether and propylene glycol monophenyl ether; ketones such as acetophenone, cyclohexanone and γ-butyro lactone; esters such as aliphatic acid methyl esters, succinic acid dialkyl esters, glutamic acid dialkyl esters, dialkyl adipate esters, and dialkyl phthalate esters; acid amides such as N-alkyl ($C_1$, $C_8$, $C_{12}$, or the like) pyrrolidone; oils and fats such as soybean oil, linseed oil, rapeseed oil, coconut oil, cottonseed oil and castor oil; dimethyl sulfoxide; and water.

These solid or liquid carriers may be used individually or in combination of two or more types thereof.

Examples of the surfactant include: nonionic surfactants such as polyoxyethylene alkyl ethers, polyoxyethylene alkyl (mono- or di-)phenyl ethers, polyoxyethylene (mono-, di- or tri-)styryl phenyl ethers, polyoxyethylene-polyoxypropylene block copolymers, polyoxyethylene aliphatic acid (mono- or di-) esters, sorbitan aliphatic acid esters, polyoxyethylene sorbitan aliphatic acid esters, castor oil ethylene-oxide adducts, acetylene glycol, acetylene alcohols, acetylene glycol ethylene-oxide adducts, acetylene alcohol ethylene-oxide adducts and alkylglucosides; anionic surfactants such as alkyl sulfate ester salts, alkylbenzene sulfonates, lignin sulfonates, alkyl sulfosuccinates, naphthalene sulfonates, alkylnaphthalene sulfonates, salts of naphthalene sulfonate formalin condensate, salts of alkylnaphthalene sulfonate formalin condensate, polyoxyethylenealkylether sulfate or phosphate esters, polyoxyethylene (mono- or di-)alkylphenyl ether sulfate or phosphate esters, polyoxyethylene (mono-, di- or tri-) styrylphenyl ether sulfate or phosphate esters, polycarboxylic acid salts (such as polyacrylic acid salts, polymaleic acid salts and maleic acid-olefin copolymer) and polystyrene sulfonates; cationic surfactants such as alkylamine salts and alkyl quaternary ammonium salts; amphoteric surfactants such as amino acid-type surfactants and betaine-type surfactants; silicone-based surfactants; and fluorinated surfactants.

Although the content of these surfactants is not particularly limited, it is desirably in a range of usually 0.05 to 20 parts by weight, relative to 100 parts by weight of the preparation of the present invention. In addition, these surfactants may be used individually or in combination of two or more types thereof.

Although the application dosage of the compound of the present invention varies depending on the application situation, the application period, the application method, the cultivated crop and the like, it is generally appropriate to be around 0.005 to 50 kg per hectare (ha) as an active ingredient amount.

On the other hand, in using the compound of the present invention for controlling external or internal parasites of mammals and birds as domestic animals and pet animals, an effective amount of the compound of the present invention can be administered together with additives for the preparation by: oral administration and parenteral administration such as injections (intramuscular, subcutaneous, intravenous and intraperitoneal injections); a percutaneous administration such as immersing, spraying, bathing, cleaning, pouring-on and spotting-on, and dusting; and transnasal administration. The compound of the present invention can be administered also as a molded product using a strip, a plate, a band, a collar, an ear mark, a limb band and an indicator. For the administration of the compound of the present invention, the compound can be prepared in any dosage form suitable for an administration route.

Examples of the formulation in any form to be prepared include solid preparations such as dustable powders, granules, wettable powders, pellets, tablets, boluses, capsules and molded products containing activated compounds; soluble concentrates for injection, soluble concentrates for oral administration and soluble concentrates used on the skin or in the body cavity; solution preparations such as pour-on drugs, spot-on drugs, flowable drugs and emulsifiable concentrates; and semisolid preparations such as ointments and gels.

The solid preparation can be mainly used for oral administration, percutaneous administration of the preparation diluted with water, or an environmental treatment. The solid preparation can be prepared by mixing an activated compound with an appropriate excipient, if necessary together with an adjuvant, and converting the resultant mixture into a desired form. Examples of the appropriate excipient include: inorganic substances such as carbonate salts, hydrogen carbonate salts, phosphate salts, aluminum oxide, silica and clay; and organic substances such as saccharides, celluloses, ground grains and starch.

The soluble concentrate for injection can be administered intravenously, intramuscularly or subcutaneously. The soluble concentrate for injection can be prepared by dissolving an activated compound in an appropriate solvent, and if necessary by adding to the resultant solution, additives such as solubilizers, acids, bases, buffering salts, antioxidants and protective agents. Examples of the appropriate solvent include water, ethanol, butanol, benzyl alcohol, glycerin, propylene glycol, polyethylene glycol, N-methylpyrrolidone, mixtures thereof, physiologically acceptable vegetable oils and synthetic oils suitable for injection. Examples of the solubilizer include polyvinylpyrrolidone, polyoxyethylated castor oil and polyoxyethylated sorbitan esters. Examples of the protective agents include benzyl alcohol, trichlorobutanol, p-hydroxybenzoic acid esters and n-butanol.

The soluble concentrate for oral administration can be administered directly or as a diluted soluble concentrate and can be prepared in substantially the same manner as that in the case of the soluble concentrate for injection.

The flowable drug, the emulsifiable concentrate and the like can be administered percutaneously directly or as a diluted drug, or through an environmental treatment.

The soluble concentrate used on the skin can be administrated by dropping, spreading, rubbing, spraying, dusting or immersing (immersing, bathing or cleaning) to apply the drug on the skin. These soluble concentrates can be prepared in substantially the same manner as that in the case of the soluble concentrate for injection.

The pour-on drug and the spot-on drug are dropped or sprayed on a limited area of the skin, so that these drugs can immerse activated compounds thereof into the skin to obtain the systemic effect. The pour-on drug and the spot-on drug can be prepared by dissolving, suspending or emulsifying an active ingredient in an appropriate skin-adaptable solvent or solvent mixture. If necessary, in these drugs, an adjuvant such as a surfactant, a colorant, an absorption-accelerating substance, an antioxidant, a light stabilizer and an adhesive can be incorporated.

Examples of the appropriate solvent include water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbons, vegetable or synthetic oils, DMF, liquid paraffin, light liquid paraffin, silicone, dimethylacetamide, N-methylpyrrolidone or 2,2-dimethyl-4-oxy-methylene-1,3-dioxolane. Examples of the absorption accelerating substance include DMSO, isopropyl myristate, dipropylene glycol pelargonate, silicone oil, aliphatic esters, triglycerides and aliphatic alcohols. Examples of the antioxidant include sulfites, metabisulfites, ascorbic acid, butylhydroxytoluene, butylated hydroxyanisole and tocopherol.

The emulsifiable concentrate can be administered by an oral administration, a percutaneous administration or an injection. The emulsifiable concentrate can be prepared by dissolving an active ingredient in a hydrophobic phase or a hydrophilic phase and homogenizing the resultant solution with a solvent of another type of phase using an appropriate emulsifier, if necessary further together with an adjuvant such as a colorant, an absorption accelerating substance, a protective agent, an antioxidant, a sunscreen and a thickener substance.

Examples of the hydrophobic phase (oil) include paraffin oil, silicone oil, sesame oil, almond oil, castor oil, synthetic triglyceride, ethyl stearate, di-n-butyryl adipate, hexyl laurate, dipropylene glycol pelargonate, an ester of a branched aliphatic acid having a short chain length with a saturated aliphatic acid having a chain length of C16 to C18, isopropyl myristate, isopropyl palmitate, caprylate/caprate esters of a saturated aliphatic alcohol having a chain length of C12 to C18, isopropyl stearate, oleyl oleate, decyl oleate, ethyl oleate, ethyl lactate, a wax-like aliphatic acid ester, dibutyl phthalate, diisopropyl adipate, isotridecyl alcohol, 2-octyl dodecanol, cetylstearyl alcohol and oleyl alcohol.

Examples of the hydrophilic phase include water, propylene glycol, glycerin and sorbitol.

Examples of the emulsifier include: nonionic surfactants such as polyoxyethylated castor oil, polyoxyethylated monoolefin acid sorbitan, sorbitan monostearate, glycerin monostearate, polyoxyethyl stearate and alkylphenol polyglycol ether; amphoteric surfactants such as disodium N-lauryl-β-iminodipropionate and lecithin; anionic surfactants such as sodium laurylsulfate, aliphatic alcohol sulfate ether and mono-/di-alkyl polyglycol orthophosphate ester monoethanolamine salt; and cationic surfactants such as cetyltrimethylammonium chloride.

Examples of the other adjuvants include carboxymethyl cellulose, methyl cellulose, polyacrylate, alginate, gelatin, gum Arabic, polyvinylpyrrolidone, polyvinyl alcohol, methyl vinyl ether, copolymers of maleic anhydride, polyethylene glycol, wax and colloidal silica.

The semisolid preparation can be administered by applying or spreading the preparation on the skin or by introducing the preparation into a body cavity. The gel can be prepared by adding to a solution prepared as described above with respect to the soluble concentrate for injection, a thickener in an amount sufficient for generating an ointment-like transparent substance having viscosity.

Next, examples of the formulation of the preparation in the case of using the compound of the present invention are described, with the proviso that the formulation examples of the present invention are not limited to these examples. Here, in the following formulation examples, "part" represents a part by weight.

(Wettable Powder)

| | |
|---|---|
| Compound of the present invention | 0.1 to 80 parts |
| Solid carrier | 5 to 98.9 parts |
| Surfactant | 1 to 10 part(s) |
| Others | 0 to 5 parts |

Examples of the others include an anticaking agent and a stabilizer.

(Emulsifiable Concentrate)

| | |
|---|---|
| Compound of the present invention | 0.1 to 30 parts |
| Organic solvent | 45 to 95 parts |
| Surfactant | 4.9 to 30 parts |
| Water | 0 to 50 parts |
| Others | 0 to 10 parts |

Examples of the others include a spreader and a stabilizer.

(Suspension Concentrate)

| | |
|---|---|
| Compound of the present invention | 0.1 to 70 parts |
| Liquid carrier | 15 to 98.89 parts |
| Surfactant | 1 to 12 part(s) |
| Others | 0.01 to 30 parts |

Examples of the others include an antifreezing agent and a thickener.

(Water Dispersible Granule)

| | |
|---|---|
| Compound of the present invention | 0.1 to 90 parts |
| Solid carrier | 0 to 98.9 parts |
| Surfactant | 1 to 20 part(s) |
| Others | 0 to 10 parts |

Examples of the others include a binder and a stabilizer.

(Soluble Concentrate)

| | |
|---|---|
| Compound of the present invention | 0.01 to 70 parts |
| Liquid carrier | 20 to 99.99 parts |
| Others | 0 to 10 parts |

Examples of the others include an antifreezing agent and a spreader.

(Granule)

| | |
|---|---|
| Compound of the present invention | 0.01 to 80 parts |
| Solid carrier | 10 to 99.99 parts |
| Others | 0 to 10 parts |

Examples of the others include a binder and a stabilizer.

(Dustable Powder)

| | |
|---|---|
| Compound of the present invention | 0.01 to 30 parts |
| Solid carrier | 65 to 99.99 parts |
| Others | 0 to 5 parts |

Examples of the others include an antidrift agent and a stabilizer.

Next, examples of the preparation containing the compound of the present invention as an active ingredient are more specifically described, however the examples should not be construed as limiting the scope of the present invention.

Here, in the following formulation examples, "parts" represents parts by weight.

Formulation Example 1

Wettable Powder prepared by homogeneously mixing and grinding a composition containing:

| | |
|---|---|
| compound of the present invention No. 1-135 | 20 parts; |
| pyrophyllite | 74 parts; |
| SORPOL 5039 | 4 parts |
| (trade name; manufactured by TOHO Chemical Industry Co., LTD.; mixture of nonionic surfactant and anionic surfactant); and | |
| CARPLEX #80D | 2 parts |
| (trade name; manufactured by Shionogi & Co., Ltd.; synthetic hydrous silicic acid). | |

Formulation Example 2

Emulsifiable Concentrate prepared by homogeneously mixing a composition containing:

| | |
|---|---|
| compound of the present invention No. 1-555 | 5 parts; |
| xylene | 75 parts; |
| N-methylpyrrolidone | 15 parts; and |
| SORPOL 2680 | 5 parts |
| (trade name; manufactured by TOHO Chemical Industry Co., LTD.; mixture of nonionic surfactant and anionic surfactant). | |

Formulation Example 3

Emulsifiable Concentrate prepared by homogeneously mixing a composition containing:

| | |
|---|---|
| compound of the present invention No. 1-011 | 4 parts; |
| DBE | 36 parts |
| (trade name; manufactured by Invista; mixture of dimethyl adipate, dimethyl glutarate, and dimethyl succinate); | |
| diisobutyl adipate | 30 parts; |
| N-methylpyrrolidone | 10 parts; |
| SOPROPHOR BSU | 14 parts |
| (trade name; manufactured by Rhodia; nonionic surfactant); and | |
| RHODACAL 70BC | 6 parts |
| (trade name; manufactured by Rhodia; anionic surfactant). | |

Formulation Example 4

Emulsifiable Concentrate prepared by homogeneously mixing a composition containing:

| | |
|---|---|
| compound of the present invention No. 1-149 | 4 parts; |
| DBE | 11 parts |
| (trade name; manufactured by Invista; mixture of dimethyl adipate, dimethyl glutarate, and dimethyl succinate); | |
| diisobutyl adipate | 30 parts; |
| N-methylpyrrolidone | 5 parts; |

-continued

| | |
|---|---|
| SOPROPHOR BSU | 14 parts |
| (trade name; manufactured by Rhodia; nonionic surfactant); | |
| RHODACAL 70BC | 6 parts |
| (trade name; manufactured by Rhodia; anionic surfactant); | |
| propylene glycol | 10 parts; and |
| water | 20 parts. |

Formulation Example 5

Suspension Concentrate prepared by homogeneously mixing a composition containing:

| | |
|---|---|
| compound of the present invention No. 1-113 | 25 parts; |
| AGRISOL S-710 | 10 parts |
| (trade name; manufactured by Kao Corporation; nonionic surfactant); | |
| LUNOX 1000C | 0.5 parts |
| (trade name; manufactured by TOHO Chemical Industry Co., LTD.; anionic surfactant); | |
| xanthan gum | 0.2 parts; and |
| water | 64.3 parts, |
| and then wet-grinding the resultant mixture. | |

Formulation Example 6

Water Dispersible Granule prepared by homogeneously mixing and grinding a composition containing:

| | |
|---|---|
| compound of the present invention No. 1-011 | 75 parts; |
| HITENOL NE-15 | 5 parts; |

-continued (trade name; manufactured by Dai-ichi Kogyo Seiyaku Co., Ltd.; anionic surfactant);
VANILLEX N 10 parts
(trade name; manufactured by Nippon Paper Industries Co., Ltd.; anionic surfactant); and
CARPLEX #80D 10 parts
(trade name; manufactured by Shionogi & Co., Ltd.; synthetic hydrous silicic acid), then adding a small amount of water to the resultant mixture to stir and mix the mixture, granulating the mixture with an extrusion granulator, and drying the resultant granules.

Formulation Example 7

Granule prepared by homogeneously mixing and grinding a composition containing:

| | |
|---|---|
| compound of the present invention No. 1-149 | 5 parts; |
| bentonite | 50 parts; and |
| talc | 45 parts, | then adding a small amount of water to the resultant mixture to stir and mix the mixture, granulating the mixture with an extrusion granulator, and drying the resultant granules.

Formulation Example 8

Dustable Powder prepared by homogeneously mixing and grinding a composition containing:

| | |
|---|---|
| compound of the present invention No. 1-155 | 3 parts; |
| CARPLEX #80D | 0.5 parts |
| (trade name; manufactured by Shionogi & Co., Ltd.; synthetic hydrous silicic acid); | |
| kaolinite | 95 parts; and |
| diisopropyl phosphate | 1.5 parts. |

For using the preparation, the preparation is diluted with water by 1 to 10,000 time(s) to be sprayed or is directly dusted without dilution.

Formulation Example 9

Wettable Powder Preparation

| | |
|---|---|
| compound of the present invention No. 1-152 | 25 parts |
| sodium diisobutylnaphthalenesulfonate | 1 part |
| calcium n-dodecylbenzenesulfonate | 10 parts |
| alkylaryl polyglycol ether | 12 parts |
| sodium salt of naphthalenesulfonic acid formalin condensate | 3 parts |
| emulsion-type silicone | 1 part |
| silicon dioxide | 3 parts |
| kaolin | 45 parts |

Formulation Example 10

Water Soluble Thickener Preparation

| | |
|---|---|
| compound of the present invention No. 1-097 | 20 parts |
| polyoxyethylene lauryl ether | 3 parts |
| sodium dioctylsulfosuccinate | 3.5 parts |
| dimethylsulfoxide | 37 parts |
| 2-propanol | 36.5 parts |

Formulation Example 11

Soluble Concentrate for Spraying

| | |
|---|---|
| compound of the present invention No. 1-084 | 2 parts |
| dimethylsulfoxide | 10 parts |
| 2-propanol | 35 parts |
| acetone | 53 parts |

Formulation Example 12

Soluble Concentrate for Percutaneous Administration

| | |
|---|---|
| compound of the present invention No. 1-137 | 5 parts |
| hexylene glycol | 50 parts |
| isopropanol | 45 parts |

Formulation Example 13

Soluble Concentrate for Percutaneous Administration

| | |
|---|---|
| compound of the present invention No. 1-097 | 5 parts |
| propylene glycol monomethyl ether | 50 parts |
| dipropylene glycol | 45 parts |

Formulation Example 14

Soluble Concentrate for Percutaneous Administration (Dropping)

| | |
|---|---|
| compound of the present invention No. 1-137 | 2 parts |
| light liquid paraffin | 98 parts |

Formulation Example 15

Soluble Concentrate for Percutaneous Administration (Dropping)

| | |
|---|---|
| compound of the present invention No. 1-152 | 2 parts |
| light liquid paraffin | 58 parts |
| olive oil | 30 parts |
| ODO-H | 9 parts |
| Shin-Etsu silicone | 1 part |

In addition, when the compound of the present invention is used as an agricultural chemical, if necessary the compound may be mixed with another type of herbicide, various insecticides, a miticide, a nematicide, a fungicide, a plant growth regulator, a synergist, a fertilizer or a soil conditioner to be applied during the preparation or the dusting.

Particularly, by mixing the compound with other agricultural chemicals or phytohormones to be applied, a cost reduction by reducing the application dose, an enlargement of the insecticidal spectrum by a synergism of a mixed drug and a higher pest control effect can be expected. At this time, a plurality of publicly known agricultural chemicals can be combined simultaneously. Examples of types of agricultural chemicals to be mixed with the compound of the present invention to be used include compounds described in "The Pesticide Manual, vol. 14 (2006)". Specific examples of the general names include the following names, to which the examples are not limited.

Fungicides: acibenzolar-S-methyl, acylaminobenzamide, acypetacs, aldimorph, amisulbrom, amobam, ampropylos, anilazine, azaconazole, azithiram, azoxystrobin, barium polysulfide, benalaxyl, benodanil, benomyl, benquinox, bentaluron, benthiavalicarb, benthiazole, benzamacril, benzamorf, bethoxazine, binapacryl, biphenyl, bitertanol, blasticidin-S, bordeaux mixture, boscalid, bromoconazole, bupirimate, buthiobate, calcium polysulfide, captafol, captan, carpropamid, carbamorph, carbendazim, carboxin, carvone, cheshunt mixture, chinomethionat, chlobenthiazone, chioraniformethane, chloranil, chlorfenazol, chloroneb, chloropicrin, chlorothalonil, chloroquinox, chlozolinate, climbazole, clotrimazole, copper acetate, copper carbonate basic, copper hydroxide, copper naphthenate, copper oleate, copper oxychloride, copper sulfate, copper sulfate basic, copper zinc chromate, cufraneb, cuprobam, cyazofamid, cyclafuramid, cycloheximide, cyflufenamid, cymoxanil, cypendazole, cyproconazol, cyprodinil, cyprofuram, dazomet, debacarb, decafentin, dehydroacetic acid, dichlofluanid, dichlone, dichlorophen, dichlozoline, dichlobutrazol, diclocymet, diclomedine, dicloran, diethofencarb, difenoconazole, diflumetorim, dimethirimol, dimethomorph, dimoxystrobin, diniconazole, diniconazole-M, dinobuton, dinocap, dinocap-4, dinocap-6, dinocton, dinosulfon, dinoterbon, diphenylamine, dipyrithione, ditalimfos, dithianon, dodemorph, dodine, drazoxolon, edifenphos, epoxiconazole, etaconazole, etem, ethirimol, ethoxyquin, etridiazole, famoxadone, fenarimol, febuconazole, fenamidone, fenaminosulf, fenapanil, fendazosulam, fenfuram, fenhexamid, fenitropan, fenoxanil, fenpiclonil, fenpropidin, fenpropimorph, fentin, ferbam, ferimzone, fluazinam, fludioxonil, flumetover, flumorph, fluopicolide, fluoroimide, fluotrimazole, fluoxastrobin, fluquinconazole, flusilazole, flusulfamide, flutolanil, flutriafol, folpet, fosetyl-aluminium, fuberidazole, furalaxyl, furametpyr, furcarbanil, furconazole, furconazole-cis, furmecyclox, furphanate, glyodin, griseofulvin, guazatine, halacrinate, hexachlorobenzene, hexaconazole, hexylthiofos, 8-hydroxyquinoline sulfate, hymexazol, imazalil, imibenconazole, iminoctadine, ipconazole, iprobenfos, iprodione, iprovalicarb, isoprothiolane, isovaledione, kasugamycin, kresoxim-methyl, mancopper, mancozeb, mandipropamid, maneb, mebenil, mecarbinzid, mepanipyrim, mepronil, metalaxyl, metalaxyl-M, metam, metazoxolon, metconazole, methasulfocarb, methfuroxam, methyl isothiocyanate, metiram, metominostrobin, metrafenone, metsulfovax, milneb, myclobutanil, myclozolin, nabam, natamycin, nickel bis (dimethyldithiocarbamate), nitrostyrene, nitrothal-isopropyl, nuarimol, OCH, octhilinone, ofurace, orysastrobin, oxadixyl, oxine copper, oxycarboxin, oxpoconazole fumarate, pefurzoate, penconazole, pencycuron, penthiopyrad, o-phenylphenol, phosdiphen, phthalide, picoxystrobin, piperalin, polycarbamate, polyoxins, polyoxorim, potassium azide, potassium hydrogen carbonate, proquinazid, probenazole, prochloraz, procymidone, propamocarb hydrochloride, propiconazole, propineb, prothiocarb, prothioconazole, pyracarbolid, pyraclostrobin, pyrazophos, pyridinitril, pyrifenox, pyrimethanil, pyroquilon, pyroxychlor, pyroxyfur, quinomethionate, quinoxyfen, quintozene, quinacetol-sulfate, quinazamid, quinconazole, rabenzazole, sodium azide, sodium hydrogen carbonate, sodium hypochlorite, sulfur, spiroxamine, salycylanilide, silthiofam, simeconazole, tebuconazole, tecnazene, tecoram, tetraconazole, thiabendazole, thiadifluor, thicyofen, thifluzamide, thiochlorfenphim, thiophanate, thiophanate-methyl, thioquinox, thiram, tiadinil, tioxymid, tolclofos-methyl, tolylfluanid, triadimefon, toriadimenol, triamiphos, triarimol, triazoxide, triazbutil, tributyltin oxide, trichlamide, tricyclazole, tridemorph, trifloxystrobin, triflumizole, triforine, triticonazole, validamycin, vinclozolin, zarilamide, zinc sulfate, zineb, ziram, zoxamide, siitake mushroom mycelia extract, and the like.

Bactericides: benzalkonium chloride, bithionol, bronopol, cresol, formaldehyde, nitrapyrin, oxolinic acid, oxyterracycline, streptomycin, tecloftalam, and the like, Nematicides: aldoxycarb, cadusafos, DBCP, dichlofenthion, DSP, ethoprophos, fenamiphos, fensulfothion, fosthiazate, fosthietan, imicyafos, isamidofos, isazofos, oxamyl, thionazin, and the like.

Miticides: acequinocyl, acrinathrin, amitraz, BCI-033 (test name), bifenazate, bromopropylate, chinomethionat, chlorobenzilate, clofentezine, cyenopyrafen, cyflumetofen, cyhexatine, dicofol, dienochlor, DNOC, etoxazole, fenazaquin, fenbutatin oxide, fenothiocarb, fenpropathrin, fenpyroximate, fluacrypyrim, halfenprox, hexythiazox, milbemectin, propargite, pyridaben, pyrimidifen, S-1870 (test name), spirodiclofen, spyromesifen, tebufenpyrad, and the like.

Insecticides: abamectin, acephate, acetamipirid, alanycarb, aldicarb, allethrin, azinphos-methyl, bacillus thuringiensis, bendiocarb, benfuracarb, bensultap, bifenthrin, buprofezin, butocarboxim, carbaryl, carbofuran, carbosulfan, cartap, chlorantraniliprole, chlorfenapyr, chlorfenvinphos, chlorfluazuron, chlorpyrifos, chlorpyrifos-methyl, chlromafenozide, clothianidin, cyprothrin, cyflumetofen, cyfluthrin, beta-cyfluthrin, cyhalothrin, lambda-cyhalothrin, cypermethrin, cyromazine, deltamethrin, diacloden, diafenthiuron, diazinon, dichlorvos, diflubenzuron, dimethylvinphos, dinotefuran, diofenolan, disulfoton, dimethoate, emamectin-benzoate, EPN, esfenvalerate, ethiofencarb, ethiprole, etofenprox, etrimfos, fenitrothion, fenobucarb, fenoxycarb, fenpropathrin, fenthion, fenvalerate, fipronil, flonicamid, flubendiamide, flucythrinate, flufenerim, flufenoxuron, flufenprox, fluvalinate, tau-fluvalinate, fonophos, formetanate, formothion, furathiocarb, halofenozide, hexaflumuron, hydramethylnon, imidacloprid, isofenphos, indoxacarb, isoprocarb, isoxathion, lepimectin, lufenuron, malathion, metaldehyde, methamidophos, methidathion, methacrifos, metaflumizone, metalcarb, methomyl, methoprene, methoxychlor, methoxyfenozide, methyl bromide, monocrotophos, muscalure, nitenpyram, novaluron, omethoate, oxamyl, oxydemeton-methyl, oxydeprofos, parathion, parathion-methyl, pentachlorophenol (PCP), permethrin, phenthoate, phoxim, phorate, phosalone, phosmet, phosphamidon, pirimicarb, pirimiphos-methyl, profenofos, prothiofos, propaphos, protrifenbute, pymetrozine, pyraclofos, pyridalyl, pyrifluquinazon, pyriproxyfen, rotenone, SI-0405 (test name), sulprofos, silafluofen, spinetoram, spinosad, spirotetramat, sulfotep, SYJ-159 (test name), tebfenozide, teflubenzuron, tefluthorin, terbufos, tetrachlorvinphos, thiacloprid, thiocyclam, thiodicarb, thiamethoxam, thiofanox, thiometon, tolfenpyrad, tralomethrin, trichlorfon, triazuron, triflumuron, vamidothion, and the like.

EXAMPLES

Hereinafter, the present invention is described more in detail referring specifically to Synthetic Examples and Test Examples of the compound of the present invention as Examples, which should not be construed as limiting the scope of the present invention.

Synthetic Examples

Synthetic Example 1

N-[2-chloro-4-[5-(3,4,5-trichlorophenyl)-5-trifluoromethyl-4,5-dihydroisoxazole-3-yl]phenyl]methyl-2-(methylthio) acetamide (compound of the present invention No. 1-005)

Process 1; Production of 3-chloro-4-methylbenzaldoxime

To a solution of 5.0 g of 3-chloro-4-methylbenzaldehyde in 40 mL of methanol and 30 mL of water, 4.7 g of hydroxylamine hydrochloride was added and the resultant mixture was stirred at room temperature for 2 hours. After the completion of the reaction, the reaction mixture was diluted with 70 mL of ethyl acetate and the diluted reaction mixture was washed with water (30 mL×1) and then dehydrated and dried over saturated saline and anhydrous sodium sulfate in this order, followed by distilling off the solvent under reduced pressure to obtain 5.1 g of the objective substance as a white crystal. This crystal was used in the next process as it was without being further purified.

Melting point: 66.0 to 68.0° C.
$^1$H NMR (CDCl$_3$, Me$_4$Si, 300 MHz) δ 8.12 (bs, 1H), 8.07 (s, 1H), 7.56 (s, 1H), 7.37 (d, J=7.8 Hz, 1H), 7.23 (d, J=7.8 Hz, 1H), 2.39 (s, 3H).

Process 2; Production of 3-(3-chloro-4-methylphenyl)-5-(3,4,5-trichlorophenyl)-5-trifluoromethyl-4,5-dihydroisoxazole To a solution of 10.5 g of 3-chloro-4-methylbenzaldoxime in 50 mL of 1,2-dimethoxyethane, 9.1 g of N-chlorosuccinimide was added and the resultant mixture was stirred at 70° C. for 2 hours. Next, the reaction mixture was left to be cooled down to room temperature and to the reaction mixture, 17.0 g of 3,4,5-trichloro-1-(1-trifluoromethylethenyl)benzene, 9.3 g of potassium hydrogen carbonate and 10 mL of water were added, followed by continuing the stirring of the reaction mixture at room temperature further for 16 hours. After the completion of the reaction, the reaction mixture was diluted with 200 mL of ethyl acetate, and the diluted reaction mixture was washed with water (70 mL×1). Subsequently, the washed reaction mixture was dehydrated and dried over saturated saline and anhydrous sodium sulfate in this order and the solvent was distilled off under reduced pressure. The resultant residue was purified by silica gel column chromatography eluting with ethyl acetate-hexane (1:5) to obtain 26.2 g of the objective substance as a brown resinoid.

$^1$H NMR (CDCl$_3$, Me$_4$Si, 300 MHz) δ 7.64 (s, 2H), 7.62 (d, J=1.5 Hz, 1H), 7.47 (dd, J=8.1, 1.5 Hz, 1H), 7.29 (d, J=8.1 Hz, 1H), 4.06 (d, J=17.4 Hz, 1H), 3.66 (d, J=17.4 Hz, 1H), 2.41 (s, 3H).

Process 3; Production of 3-(4-bromomethyl-3-chlorophenyl)-5-(3,4,5-trichlorophenyl)-5-trifluoromethyl-4,5-dihydroisoxazole To a solution of 26.2 g of 3-(3-chloro-4-methylphenyl)-5-(3,4,5-trichlorophenyl)-5-trifluoromethyl-4,5-dihydroisoxazole in 200 mL of 1,2-dichloroethane, 12.1 g of N-bromosuccinimide and 0.81 g of α,α'-azobisisobutyronitrile were added and the resultant reaction mixture was stirred at 80° C. for 3 hours. After the completion of the reaction, the reaction mixture was left to be cooled down to room temperature and was washed with water (70 mL×2). Subsequently, the washed reaction mixture was dehydrated and dried over saturated saline and anhydrous sodium sulfate in this order and the solvent was distilled off under reduced pressure to obtain 34.1 g of a crude objective substance as a brown oily substance. This substance was used in the next process as it was without being further purified.

Process 4; Production of N-[[2-chloro-4-[5-(3,4,5-trichlorophenyl)-5-trifluoromethyl-4,5-dihydroisoxazole-3-yl]phenyl]methyl]phthalimide To a solution of 34.1 g of 3-(4-bromomethyl-3-chlorophenyl)-5-(3,4,5-trichlorophenyl)-5-trifluoromethyl-4,5-dihydroisoxazole in 200 mL of N,N-dimethylformamide, 12.6 g of potassium phthalimide was added and the resultant mixture was stirred at room temperature for 3 hours. After the completion of the reaction, the reaction mixture was diluted with 350 mL of ethyl acetate and the diluted reaction mixture was washed with water (80 mL×3). Subsequently, the washed reaction mixture was dehydrated and dried over saturated saline and anhydrous sodium sulfate in this order and the solvent was distilled off under reduced pressure. The resultant residue was purified by silica gel column chromatography eluting with ethyl acetate-hexane (1:3) to obtain 24.3 g of the objective substance as a light yellow resinoid.

$^1$H NMR (CDCl$_3$, Me$_4$Si, 300 MHz) δ 7.85-7.95 (m, 2H), 7.75-7.8 (m, 2H), 7.67 (d, J=1.5 Hz, 1H), 7.62 (s, 2H), 7.50 (dd, J=7.8, 1.5 Hz, 1H), 7.28 (d, J=7.8 Hz, 1H), 5.00 (s, 2H), 4.03 (d, J=17.4 Hz, 1H), 3.64 (d, J=17.4 Hz, 1H).

Process 5; Production of 3-(4-aminomethyl-3-chlorophenyl)-5-(3,4,5-trichlorophenyl)-5-trifluoromethyl-4,5-dihydroisoxazole To a solution of 3.0 g of N-[[2-chloro-4-[5-(3,4,5-trichlorophenyl)-5-trifluoromethyl-4,5-dihydroisoxazole-3-yl]phenyl]methyl]phthalimide in 70 mL of ethanol, 1.0 mL of 80% hydrazine monohydrate was added and the resultant mixture was stirred while heating the mixture to reflux for 1 hour.

After the completion of the reaction, the reaction mixture was left to be cooled down to room temperature and 100 mL of chloroform was added to the reaction mixture to filter off an insoluble substance, followed by distilling off the solvent under reduced pressure. To the resultant residue, 50 mL of chloroform was added to dissolve the residue and to filter off the resultant insoluble substance. The filtrate was washed with water (50 mL×1) and then dehydrated and dried over saturated saline and anhydrous magnesium sulfate in this order and the solvent was distilled off under reduced pressure to obtain 2.55 g of the objective substance as a yellow resinoid.

$^1$H NMR (CDCl$_3$, Me$_4$Si, 300 MHz) δ 7.66 (d, J=1.5 Hz, 1H), 7.64 (s, 2H), 7.56 (dd, J=7.8, 1.5 Hz, 1H), 7.50 (d, J=7.8 Hz, 1H), 4.07 (d, J=17.4 Hz, 1H), 3.98 (s, 2H), 3.67 (d, J=17.4 Hz, 1H).

Process 6; Production of N-[2-chloro-4-[5-(3,4,5-trichlorophenyl)-5-trifluoromethyl-4,5-dihydroisoxazole-3-yl]phenyl]methyl-2-(methylthio) acetamide To a solution of 0.11 g of 3-(4-aminomethyl-3-chlorophenyl)-5-(3,4,5-trichlorophenyl)-5-trifluoromethyl-4,5-dihydroisoxazole, 0.051 g of (methylthio) acetic acid and 0.048 g of triethylamine in 2 mL of chloroform, 0.092 g of 1-[3-(dimethylamino)propyl]-3-ethylcarbodiimide hydrochloride was added and the resultant mixture was stirred at room temperature for 15 hours. After the completion of the reaction, 2 mL of a saturated sodium hydrogen carbonate aqueous solution was added to the reaction mixture and the organic phase was separated off, followed by purifying the organic phase as it was by preparative medium pressure liquid chromatography eluting with ethyl acetate-hexane (a gradient from 1:4 to 1:1) using a medium pressure preparative apparatus (trade name: YFLC-Wprep; manufactured by Yamazen Corporation) to obtain 0.12 g of the objective substance as a colorless resinoid.

$^1$H NMR (CDCl$_3$, Me$_4$Si, 300 MHz) δ 7.69 (d, J=1.5 Hz, 1H), 7.63 (s, 2H), 7.51 (dd, J=7.8, 1.5 Hz, 1H), 7.46 (d, J=7.8 Hz, 1H), 7.40 (bs, 1H), 4.58 (d, J=6.6 Hz, 2H), 4.05 (d, J=17.4 Hz, 1H), 3.66 (d, J=17.4 Hz, 1H), 3.23 (s, 2H), 2.10 (s, 3H).

Synthetic Example 2

N-[1-[4-[5-[3,5-bis(trifluoromethyl)phenyl]-5-trifluoromethyl-4,5-dihydroisoxazole-3-yl]phenyl]ethyl]-2-(methylthio)acetamide (compound of the present invention No. 1-001)

Process 1; Production of 5-[3,5-bis(trifluoromethyl)phenyl]-3-(4-ethylphenyl)-5-trifluoromethyl-4,5-dihydroisoxazole To a solution of 1.49 g of 4-ethylbenzaldoxime in 10 mL of N,N-dimethylformamide, 1.60 g of N-chlorosuccinimide was added and the resultant mixture was stirred at room temperature for 2 hours. Next, to the reaction mixture, 3.00 g of 3,5-bis(trifluoromethyl)-1-(1-trifluoromethylethenyl)benzene and 3.00 g of potassium hydrogen carbonate were added and the stirring of the resultant reaction mixture was continued at room temperature further for 14 hours. After the completion of the reaction, 10 mL of water was added to the reaction mixture and the resultant reaction mixture was extracted with ethyl acetate (50 mL×1). The organic phase was washed with 20 mL of water and then dehydrated and dried over saturated saline and anhydrous sodium sulfate in this order, and the solvent was distilled off under reduced pressure. To the resultant residue, hexane was added and a deposited crystal was filtered off to obtain 3.00 g of the objective substance as a white crystal.

$^1$H NMR (CDCl$_3$, Me$_4$Si, 300 MHz) δ 8.09 (s, 2H), 7.96 (s, 1H), 7.60 (d, J=8.4 Hz, 2H), 7.27 (d, J=8.4 Hz, 2H), 4.19 (d, J=17.1 Hz, 1H), 3.74 (d, J=17.1 Hz, 1H), 2.69 (q, J=7.8 Hz, 2H), 1.25 (t, J=7.8 Hz, 3H).

Process 2; Production of 5-[3,5-bis(trifluoromethyl) phenyl]-3-[4-(1-bromoethyl)phenyl]-5-trifluoromethyl-4,5-dihydroisoxazole To a solution of 3.00 g of 5-[3,5-bis(trifluoromethyl)phenyl]-3-(4-ethylphenyl)-5-trifluoromethyl-4,5-dihydroisoxazole in 15 mL of 1,2-dichloroethane, 1.29 g of N-bromosuccinimide and 0.10 g of α,α'-azobisisobutyronitrile were added and the resultant mixture was stirred at 75° C. for 3 hours. After the completion of the reaction, the reaction mixture was left to be cooled down to room temperature and then 10 mL of water was added to the reaction mixture. The resultant mixture was extracted with chloroform (20 mL×1). The organic phase was washed with water (10 mL×1) and then dehydrated and dried over saturated saline and anhydrous sodium sulfate in this order, and the solvent was distilled off under reduced pressure. To the resultant residue, hexane was added and a deposited crystal was filtered off to obtain 3.01 g of the objective substance as a white crystal.

$^1$H NMR (CDCl$_3$, Me$_4$Si, 300 MHz) δ 8.09 (s, 2H), 7.97 (s, 1H), 7.67 (d, J=8.7 Hz, 2H), 7.51 (d, J=8.7 Hz, 2H), 5.19 (q, J=6.9 Hz, 1H), 4.19 (d, J=17.1 Hz, 1H), 3.74 (d, J=17.1 Hz, 1H), 2.04 (d, J=6.9 Hz, 3H).

Process 3; Production of N-[1-[4-[5-[3,5-bis(trifluoromethyl)phenyl]-5-trifluoromethyl-4,5-dihydroisoxazole-3-yl]phenyl]ethyl]phthalimide To a solution of 3.01 g of 5-[3,5-bis(trifluoromethyl)phenyl]-3-[4-(1-bromoethyl)phenyl]-5-trifluoromethyl-4,5-dihydroisoxazole in 10 mL of N,N-dimethylformamide, 1.26 g of potassium phthalimide was added and the resultant mixture was stirred at 80° C. for 3.5 hours. After the completion of the reaction, the reaction mixture was left to be cooled down to room temperature and 20 mL of water was added to the reaction mixture. The resultant mixture was extracted with ethyl acetate (70 mL×1). The organic phase was washed with water (20 mL×1) and then dehydrated and dried over saturated saline and anhydrous magnesium sulfate in this order and the solvent was distilled off under reduced pressure. The resultant residue was purified by silica gel column chromatography eluting with ethyl acetate-hexane (a gradient from 1:10 to 1:5) to obtain 2.80 g of the objective substance as a colorless resinoid.

$^1$H NMR (CDCl$_3$, Me$_4$Si, 300 MHz) δ 8.06 (s, 2H), 7.94 (s, 1H), 7.75-7.85 (m, 2H), 7.65-7.75 (m, 2H), 7.63 (d, J=8.4 Hz, 2H), 7.55 (d, J=8.4, 2H), 5.58 (q, J=7.2 Hz, 1H), 4.16 (d, J=17.3 Hz, 1H), 3.71 (d, J=17.3 Hz, 1H), 1.92 (d, J=7.2 Hz, 3H).

Process 4; Production of 3-[4-(1-aminoethyl)phenyl]-5-[3,5-bis(trifluoromethyl)phenyl]-5-trifluoromethyl-4,5-dihydroisoxazole To a solution of 2.80 g of N-[1-[4-[5-[3,5-bis(trifluoromethyl)phenyl]-5-trifluoromethyl-4,5-dihydroisoxazole-3-yl]phenyl]ethyl]phthalimide in 10 mL of ethanol, 0.22 g of hydrazine monohydrate was added and the resultant reaction mixture was stirred at 80° C. for 2 hours. After the completion of the reaction, the mixture was cooled down to 0° C. and the deposited insoluble substance was filtered off, followed by cleaning the filtered substance with a small amount of chloroform. The filtrate and the resultant chloroform-cleaning liquid were combined and the solvent was distilled off under reduced pressure. The resultant residue was dissolved in 30 mL of ethyl acetate and the resultant solution was washed with water (10 mL×1). Subsequently, the washed solution was dehydrated and dried over saturated saline and anhydrous magnesium sulfate in this order, and the solvent was distilled off under reduced pressure to obtain 1.80 g of the objective substance as a yellow resinoid. This was used in the next process as it was without being further purified.

$^1$H NMR (CDCl$_3$, Me$_4$Si, 300 MHz) δ 8.08 (s, 2H), 7.95 (s, 1H), 7.64 (d, J=8.4 Hz, 2H), 7.43 (d, J=8.4 Hz, 2H), 4.20 (d, J=17.1 Hz, 1H), 4.1-4.25 (m, 1H), 3.74 (d, J=17.1 Hz, 1H), 1.38 (d, J=6.3 Hz, 3H).

Process 5; Production of N-[1-4-[5-[3,5-bis(trifluoromethyl)phenyl]-5-trifluoromethyl-4,5-dihydroisoxazole-3-yl]phenyl]ethyl]-2-(methylthio)acetamide To a solution of 0.10 g of 3-[4-(1-aminoethyl)phenyl)]-5-[3,5-bis(trifluoromethyl)phenyl]-5-trifluoromethyl-4,5-dihydroisoxazole, 0.027 g of (methylthio) acetic acid, 0.064 g of triethylamine and 0.010 g of 4-(dimethylamino) pyridine in 2 mL of dichloromethane, 0.060 g of 1-[3-(dimethylamino)propyl]-3-ethylcarbodiimide hydrochloride was added and the resultant mixture was stirred at room temperature for 14 hours. After the completion of the reaction, 2 mL of water was added to the reaction mixture and the resultant mixture was extracted with ethyl acetate (10 mL×1). The organic phase was washed with water (5 mL×1) and then dehydrated and dried over saturated saline and anhydrous magnesium sulfate in this order, and the solvent was distilled off under reduced pressure. The resultant residue was purified by silica gel column chromatography eluting with ethyl acetate-hexane (1:1) to obtain 0.056 g of the objective substance as a colorless resinoid.

$^1$H NMR (CDCl$_3$, Me$_4$Si, 300 MHz) δ 8.08 (s, 2H), 7.96 (s, 1H), 7.67 (d, J=8.7 Hz, 2H), 7.40 (d, J=8.7 Hz, 2H), 7.14 (d, J=8.1 Hz, 1H), 5.1-5.2 (m, 1H), 4.19 (d, J=17.4 Hz, 1H), 3.73 (d, J=17.4 Hz, 1H), 3.24 (d, J=16.4 Hz, 1H), 3.17 (d, J=16.4 Hz, 1H), 2.13 (s, 3H), 1.53 (d, J=6.9 Hz, 3H).

Synthetic Example 3

N-[4-[5-[3,5-bis(trifluoromethyl)phenyl]-5-trifluoromethyl-4,5-dihydroisoxazole-3-yl]phenyl][cyano]methyl-2-(ethylthio)acetamide (compound of the present invention No. 1-129)

Process 1; Production of 4-[5-[3,5-bis(trifluoromethyl)phenyl]-5-trifluoromethyl-4,5-dihydroisoxazole-3-yl]benzaldehyde To a solution of 1.14 g of 4-[5-[3,5-bis(trifluoromethyl)phenyl]-5-trifluoromethyl-4,5-dihydroisoxazole-3-yl]benzyl alcohol in 20 mL of dichloromethane, 2.00 g of silica gel was added, and 0.80 g of pyridinium chlorochromate (PCC) was added to the resultant mixture while stirring the mixture at room temperature, followed by stirring the resultant mixture at the same temperature for 17 hours. After the completion of the reaction, the reaction mixture was passed through silica gel column chromatography eluting with ethyl acetate to obtain 0.97 g of a crude objective substance as a white solid. This substance was used in the next process as it was without being further purified.

Process 2; Production of 2-amino-2-[4-[5-[3,5-bis(trifluoromethyl)phenyl]-5-trifluoromethyl-4,5-dihydroisoxazole-3-yl]phenyl]acetonitrile To a mixture of 0.83 g of 4-[5-[3,5-bis(trifluoromethyl)phenyl]-5-trifluoromethyl-4,5-dihydroisoxazole-3-yl]benzaldehyde and 0.36 g of trimethylsilylcyanide, 0.01 g of zinc iodide was added while stirring the mixture at 0° C. The resultant mixture was stirred at 60° C. for 10 minutes, and then left to be cooled down to room temperature. 2 mL of a 2M ammonia-methanol solution was added to the resultant reaction mixture, followed by continuing the stirring of the resultant reaction mixture at 50° C. further for 3.5 hours. After the completion of the reaction, the solvent was distilled off under reduced pressure and the resultant residue was purified by silica gel column chromatography eluting with ethyl acetate-hexane (1:2) to obtain 0.60 g of the objective substance as a brown resinoid.

$^1$H NMR (CDCl$_3$, Me$_4$Si, 300 MHz) δ 8.09 (s, 2H), 7.97 (s, 1H), 7.73 (d, J=8.6 Hz, 2H), 7.65 (d, J=8.6 Hz, 2H), 4.95 (s, 1H), 4.22 (d, J=17.4 Hz, 1H), 3.77 (d, J=17.4 Hz, 1H).

Process 3; Production of N-[4-[5-[3,5-bis(trifluoromethyl)phenyl]-5-trifluoromethyl-4,5-dihydroisoxazole-3-yl]phenyl][cyano]methyl-2-(ethylthio)acetamide To a solution of 0.60 g of 2-amino-2-[4-[5-[3,5-bis(trifluoromethyl)phenyl]-5-trifluoromethyl-4,5-dihydroisoxazole-3-yl]phenyl]acetonitrile and 0.15 g of (ethylthio) acetic acid in 13 mL of dichloromethane, 0.24 g of 1-[3-(dimethylamino)propyl]-3-ethylcarbodiimide hydrochloride was added and the resultant mixture was stirred at room temperature for 2 hours. After the completion of the reaction, 10 mL of water was added to the reaction mixture and the resultant reaction mixture was extracted with diethyl ether (20 mL×2). The organic phase was dehydrated and dried over saturated saline and anhydrous magnesium sulfate in this order, and the solvent was distilled off under reduced pressure. The resultant residue was purified by silica gel column chromatography eluting with ethyl acetate-hexane (1:1) to obtain 0.49 g of the objective substance as a colorless resinoid.

$^1$H NMR (CDCl$_3$, Me$_4$Si, 300 MHz) δ 8.09 (s, 2H), 7.98 (s, 1H), 7.77 (d, J=8.4 Hz, 2H), 7.57 (d, J=8.4 Hz, 2H), 7.54 (d, J=9.0 Hz, 1H), 6.20 (d, J=9.0 Hz, 1H), 4.21 (d, J=17.4 Hz, 1H), 3.77 (d, J=17.4 Hz, 1H), 3.36 (d, J=16.8 Hz, 1H), 3.29 (d, J=16.8 Hz, 1H), 2.55 (q, J=7.2 Hz, 2H), 1.25 (t, J=7.2 Hz, 3H).

Synthetic Example 4

N-[2-chloro-4-[5-(3,4,5-trichlorophenyl)-5-trifluoromethyl-4,5-dihydroisoxazole-3-yl]phenyl]methyl-2-ethylthio-N-methylacetamide (compound of the present invention No. 2-002)

Process 1; Production of 3-[3-chloro-4-[N-(methyl)aminomethyl]phenyl]-5-(3,4,5-trichlorophenyl)-5-trifluoromethyl-4,5-dihydroisoxazole To a solution of 1.0 g of 3-(4-bromomethyl-3-chlorophenyl)-5-(3,4,5-trichlorophenyl)-5-trifluoromethyl-4,5-dihydroisoxazole produced in Process 3 of Synthetic Example 1 in 15 mL of dichloromethane, 1.5 g of a 40% methylamine aqueous solution was added and the resultant mixture was stirred at room temperature for 5 days. After the completion of the reaction, 15 mL of water was added to the reaction mixture and the organic phase was separated off, followed by extracting the aqueous phase with chloroform (5 mL×3). The combined organic phases were combined and the combined organic phase was washed with water (5 mL×1), followed by dehydrating and drying the organic phase over saturated saline and anhydrous sodium sulfate in this order and by distilling off the solvent under reduced pressure. The resultant residue was purified by silica gel column chromatography eluting with methanol-chloroform (a gradient from 1:30 to 1:10) to obtain 0.67 g of the objective substance as a colorless resinoid.

$^1$H NMR (CDCl$_3$, Me$_4$Si, 300 MHz) δ 7.6-7.7 (m, 3H), 7.45-7.55 (m, 2H), 4.06 (d, J=17.4 Hz, 1H), 3.87 (s, 2H), 3.67 (d, J=17.4 Hz, 1H), 2.46 (s, 3H).

Process 2; Production of N-[2-chloro-4-[5-(3,4,5-trichlorophenyl)-5-trifluoromethyl-4,5-dihydroisoxazole-3-yl]phenyl]methyl-2-ethylthio-N-methylacetamide To a solution of 0.10 g of 3-[3-chloro-4-[N-(methyl)aminomethyl]phenyl]-5-(3,4,5-trichlorophenyl)-5-trifluoromethyl-4,5-dihydroisoxazole and 0.038 g of (ethylthio)acetic acid in 3 mL of dichloromethane, 0.089 g of 1-[3-(dimethylamino) propyl]-3-ethylcarbodiimide hydrochloride was added and the resultant mixture was stirred at room temperature for 3 hours. After the completion of the reaction, the reaction mixture was washed with water (5 mL×1) and then dehydrated and dried over saturated saline and anhydrous sodium sulfate in this order, and then the solvent was distilled off under reduced pressure. The resultant residue was purified by preparative medium pressure liquid chromatography eluting with ethyl acetate-hexane (a gradient from 1:5 to 1:3) using a medium pressure preparative apparatus (trade name: YFLC-Wprep; manufactured by Yamazen Corporation) to obtain 0.083 g of the objective substance as a colorless resinoid.

$^1$H NMR (CDCl$_3$, Me$_4$Si, 300 MHz) δ 7.6-7.85 (m, 4H), 7.2-7.35 (m, 1H), 4.71 (s, 2H), 4.08 and 4.06 (d, J=17.4 Hz, 1H), 3.67 (d, J=17.4 Hz, 1H), 3.38 and 3.25 (s, 2H), 3.09 and 2.98 (s, 3H), 2.70 and 2.68 (q, J=7.5 Hz, 2H), 1.31 and 1.28 (t, J=7.5 Hz, 3H).

Synthetic Example 5

N-[4-[5-[3-bromo-5-(trifluoromethyl)phenyl]-5-trifluoromethyl-4,5-dihydroisoxazole-3-yl]-2-chlorophenyl]methyl-2-(methylsulfonyl)acetamide (compound of the present invention No. 1-113)

Process 1; Production of 3'-bromo-2,2,2-trifluoro-5'-(trifluoromethyl)acetophenone To a solution of 5.00 g of 2,2,2-trifluoro-5'-(trifluoromethyl)acetophenone in 1 mL of acetic acid and 6 mL of concentrated sulfuric acid, 3.54 g of 1,3-dibromo-5,5-dimethylhydantoin was added and the resultant mixture was stirred at 35° C. for 3.5 hours. After the completion of the reaction, the reaction mixture was charged into 60 mL of ice water and the resultant mixture was extracted with chloroform (30 mL×2). The organic phase was washed with a saturated sodium hydrogen carbonate aqueous solution (50 mL×1) and then dehydrated and dried over saturated saline and anhydrous magnesium sulfate in this order, and the solvent was distilled off under reduced pressure. The resultant residue was dissolved in 20 mL of hexane and an insoluble substance was filtered off, followed by distilling off the solvent under reduced pressure to obtain 6.50 g of the objective substance as a yellow oily substance. This substance was used in the next process as it was without being further purified.

$^1$H NMR (CDCl$_3$, Me$_4$Si, 300 MHz) δ 8.36 (s, 1H), 8.23 (s, 1H), 8.11 (s, 1H).

Process 2; Production of 3-[3-bromo-5-(trifluoromethyl)phenyl]-1-(3-chloro-4-methylphenyl)-4,4,4-trifluoro-3-hydroxybutane-1-one To a solution of 3.91 g of 3'-bromo-2,2,2-trifluoro-5'-(trifluoromethyl)acetophenone and 1.89 g of 3''-chloro-4'-methylacetophenone in 2 mL of heptane, 0.34 g of triethylamine was added and the resultant mixture was stirred at 60° C. for 5 hours. After the completion of the reaction, the reaction mixture was left to be cooled down to room temperature and a deposited crystal was filtered, followed by cleaning the crystal with 3 mL of hexane to obtain 4.28 g of the objective substance as a white crystal.

Melting point: 73.0 to 75.0° C.

$^1$H NMR (CDCl$_3$, Me$_4$Si, 300 MHz) δ 7.94 (s, 1H), 7.88 (d, J=1.8 Hz, 1H), 7.78 (s, 1H), 7.55 (s, 1H), 7.72 (dd, J=7.8, 1.8 Hz, 1H), 7.38 (d, J=7.8 Hz, 1H), 5.81 (s, 1H), 3.81 (d, J=17.4 Hz, 1H), 3.68 (d, J=17.4 Hz, 1H), 2.47 (s, 3H).

Process 3; Production of 3-[3-bromo-5-(trifluoromethyl)phenyl]-1-(3-chloro-4-methylphenyl)-4,4,4-trifluoro-2-butene-1-one To a solution of 4.28 g of 3-[3-bromo-5-(trifluoromethyl)phenyl]-1-(3-chloro-4-methylphenyl)-4,4,4-trifluoro-3-hydroxybutane-1-one in 10 mL of toluene, 2.08 g of thionyl chloride and 1.38 g of pyridine were added while stirring the solution at 80° C. to continue the stirring of the resultant mixture at the same temperature for 2 hours. After the completion of the reaction, 10 mL of water was added to the reaction mixture while ice-cooling the reaction mixture and the stirring of the reaction mixture was continued until the temperature of the reaction mixture returned to room temperature. The organic phase was separated off and charged into a solution of 0.77 g of sodium hydroxide in 5 mL of water. The resultant mixture was stirred at room temperature for 30 minutes. The organic phase was separated off and then was dehydrated and dried over saturated saline and anhydrous magnesium sulfate in this order. The solvent was distilled off under reduced pressure to obtain 4.02 g of a crude objective substance as a yellow oily substance. This substance was used in the next process as it was without being further purified.

$^1$H NMR (CDCl$_3$, Me$_4$Si, 300 MHz) δ 7.7-7.85 (m, 2H), 7.55-7.65 (m, 2H), 7.35-7.45 (m, 2H), 7.30 (d, J=8.1 Hz, 1H), 2.43 (s, 3H).

Process 4; Production of 5-[3-bromo-5-(trifluoromethyl)phenyl]-3-(3-chloro-4-methylphenyl)-5-trifluoromethyl-4,5-dihydroisoxazole Into a solution of 4.02 g of 3-[3-bromo-5-(trifluoromethyl)phenyl]-1-(3-chloro-4-methylphenyl)-4,4,4-trifluoro-2-butene-1-one and 0.82 g of tetrabutylammonium bromide in 23 mL of toluene, a solution of 1.03 g of sodium hydroxide in 2.4 mL of water and a solution of 0.98 g of hydroxylamine sulfate in 3.9 mL of water were dropped while ice-cooling and stirring the solution and after the completion of the dropping, the resultant mixture was stirred at room temperature for 15 hours. After the completion of the reaction, 7.11 g of concentrated hydrochloric acid was added to the reaction mixture while ice-cooling and stirring the reaction mixture. The organic phase was separated off and then was washed with 10 mL of a 3N hydrochloric acid aqueous solution, 10 mL of water and 10 mL of a saturated sodium hydrogen carbonate aqueous solution in this order. Subsequently, the organic phase was dehydrated and dried over saturated saline and anhydrous sodium sulfate in this order and the solvent was distilled off under reduced pressure. The resultant residue was purified by alumina column chromatography eluting with chloroform to obtain 3.56 g of the objective substance as a yellow resinoid.

$^1$H NMR (CDCl$_3$, Me$_4$Si, 300 MHz) δ 7.96 (s, 1H), 7.83 (s, 1H), 7.79 (s, 1H), 7.62 (d, J=1.5 Hz, 1H), 7.48 (dd, J=7.8, 1.5 Hz, 1H), 7.28 (d, J=7.8 Hz, 1H), 4.11 (d, J=17.4 Hz, 1H), 3.69 (d, J=17.4 Hz, 1H), 2.41 (s, 3H).

Process 5; Production of N-[[4-[5-[3-bromo-5-(trifluoromethyl)phenyl]-5-trifluoromethyl-4,5-dihydroisoxazole-3-yl]-2-chlorophenyl]methyl]phthalimide To a solution of 3.56 g of 5-[3-bromo-5-(trifluoromethyl)phenyl]-3-(3-chloro-4-methylphenyl)-5-trifluoromethyl-4,5-dihydroisoxazole in 15 mL of 1,2-dichloroethane, 1.43 g of N-bromosuccinimide and 0.096 g of α,α'-azobisisobutyronitrile were added and the resultant mixture was stirred while heating the reaction mixture to reflux for 3 hours. After the completion of the reaction, the reaction mixture was left to be cooled down to room temperature and 50 mL of 1,2-dichloroethane was added to the reaction mixture. Subsequently, the resultant mixture was washed with water (30 mL×1) and then dehydrated and dried over saturated saline and anhydrous sodium sulfate in this order, and the solvent was distilled off under reduced pressure. The resultant residue was dissolved in 7 mL of an N,N-dimethylformamide solution, and 1.35 g of a phthalimide potassium salt was added to the resultant solution, followed by stirring the resultant mixture at room temperature for 1 hour. After the completion of the reaction, the reaction mixture was charged into 30 mL of water and the resultant reaction mixture was extracted with ethyl acetate (25 mL×2). The organic phase was dehydrated and dried over saturated saline and anhydrous magnesium sulfate in this order, and the solvent was distilled off under reduced pressure to obtain 5.26 g of a crude objective substance as a light yellow resinoid. This substance was used in the next process as it was without being further purified.

$^1$H NMR (CDCl$_3$, Me$_4$Si, 300 MHz) δ 7.7-7.95 (m, 7H), 7.67 (d, J=1.8 Hz, 1H), 7.51 (dd, J=8.1, 1.8 Hz, 1H), 7.27 (d, J=8.4 Hz, 1H), 5.00 (s, 2H), 4.08 (d, J=17.4 Hz, 1H), 3.67 (d, J=17.4 Hz, 1H).

Process 6; Production of 3-(4-aminomethyl-3-chlorophenyl)-5-[3-bromo-5-(trifluoromethyl)phenyl]-5-trifluoromethyl-4,5-dihydroisoxazole To a solution of 5.26 g of N-[[4-[5-[3-bromo-5-(trifluoromethyl)phenyl]-5-trifluoromethyl-4,5-dihydroisoxazole-3-yl]-2-chlorophenyl]methyl]phthalimide in 20 mL of ethanol, 0.73 g of a hydrazine monohydrate aqueous solution was added and the resultant mixture was stirred while heating the mixture to reflux for 1 hour. After the completion of the reaction, the reaction mixture was left to be cooled down to room temperature and from the reaction mixture, an insoluble substance was filtered off and the solvent was distilled off under reduced pressure. To the resultant residue, 20 mL of chloroform was added to dissolve the residue and an insoluble substance was filtered off one more time. The resultant filtrate was washed with water (10 mL×1) and then dehydrated and dried over saturated saline and anhydrous sodium sulfate in this order, and the solvent was distilled off under reduced pressure. The resultant residue was purified by silica gel column chromatography eluting with methanol-ethyl acetate (1:9) to obtain 2.87 g of the objective substance as a yellow resinoid.

$^1$H NMR (CDCl$_3$, Me$_4$Si, 300 MHz) δ 7.96 (s, 1H), 7.83 (s, 1H), 7.79 (s, 1H), 7.66 (d, J=1.8 Hz, 1H), 7.56 (dd, J=7.8, 1.8 Hz, 1H), 7.49 (d, J=7.8 Hz, 1H), 4.12 (d, J=17.4 Hz, 1H), 3.97 (s, 2H), 3.70 (d, J=17.4 Hz, 1H), 1.53 (bs, 2H).

Process 7; Production of N-[4-[5-[3-bromo-5-(trifluoromethyl)phenyl]-5-trifluoromethyl-4,5-dihydroisoxazole-3-yl]-2-chlorophenyl]methyl-2-(methylsulfonyl)acetamide To a solution of 0.15 g of 3-(4-aminomethyl-3-chlorophenyl)-5-[3-bromo-5-(trifluoromethyl)phenyl]-5-trifluoromethyl-4,5-dihydroisoxazole and 0.083 g of (methylsulfonyl)acetic acid in 3 mL of dichloromethane, 0.11 g of 1-[3-(dimethylamino)propyl]-3-ethylcarbodiimide hydrochloride was added and the resultant mixture was stirred at room temperature for 15 hours. After the completion of the reaction, the reaction mixture was diluted with 3 mL of chloroform, and then 3 mL of a saturated sodium hydrogen carbonate aqueous solution was added to the diluted reaction mixture, followed by separating off the organic phase. The separated organic phase was dehydrated and dried over saturated saline and anhydrous magnesium sulfate in this order. From the resultant organic phase, the solvent was distilled off under reduced pressure. The resultant residue was purified by silica gel column chromatography eluting with ethyl acetate to obtain 0.14 g of the objective substance as a white crystal.

Melting point: 125.0 to 128.0° C.

$^1$H NMR (CDCl$_3$, Me$_4$Si, 300 MHz) δ 7.95 (s, 1H), 7.83 (s, 1H), 7.78 (s, 1H), 7.70 (d, J=1.8 Hz, 1H), 7.54 (dd, J=7.8, 1.8 Hz, 1H), 7.48 (d, J=7.8 Hz, 1H), 6.93 (t, J=6.2 Hz, 1H), 4.59 (d, J=6.2 Hz, 2H), 4.10 (d, J=17.4 Hz, 1H), 3.92 (s, 2H), 3.69 (d, J=17.4 Hz, 1H), 3.05 (s, 3H).

Synthetic Example 6

N-[2-chloro-4-[5-(3,4,5-trichlorophenyl)-5-trifluoromethyl-4,5-dihydroisoxazole-3-yl]phenyl]methyl-2-(2,2,2-trifluoroethylthio)acetamide (compound of the present invention No. 1-029)

Process 1; Production of 2-bromo-N-[2-chloro-4-[5-(3,4,5-trichlorophenyl)-5-trifluoromethyl-4,5-dihydroisoxazole-3-yl]phenyl]methyl acetamide To a solution of 1.50 g of 3-(4-aminomethyl-3-chlorophenyl)-5-(3,4,5-trichlorophenyl)-5-trifluoromethyl-4,5-dihydroisoxazole produced in Process 5 of Synthetic Example 1 and 0.364 g of triethylamine in 10 mL of dichloromethane, 0.566 g of bromoacetyl chloride was added while ice-cooling and stirring the solution and the resultant mixture was stirred at room temperature for 10 minutes. After the completion of the reaction, 10 mL of water was added to the reaction mixture and the resultant mixture was extracted with dichloromethane (5 mL×2). The organic phase was dehydrated and dried over saturated saline and anhydrous magnesium sulfate in this order and the solvent was distilled off under reduced pressure. The resultant residue was purified by preparative medium pressure liquid chromatography eluting with ethyl acetate-hexane (a gradient from 1:9 to 1:3) using a medium pressure preparative apparatus (trade name: YFLC-Wprep; manufactured by Yamazen Corporation) to obtain 1.67 g of the objective substance as a colorless resinoid.

$^1$H NMR (CDCl$_3$, Me$_4$Si, 300 MHz) δ 7.6-7.7 (m, 3H), 7.4-7.55 (m, 2H), 7.13 (bs, 1H), 4.59 (d, J=6.0 Hz, 2H), 4.09 (s, 2H), 4.06 (d, J=17.3 Hz, 1H), 3.67 (d, J=17.3 Hz, 1H).

Process 2; Production of N-[2-chloro-4-[5-(3,4,5-trichlorophenyl)-5-trifluoromethyl-4,5-dihydroisoxazole-3-yl]phenyl]methyl-2-(2,2,2-trifluoroethylthio)acetamide To a suspension of 0.0271 g of 55% oily sodium hydride in 2 mL of tetrahydrofuran, a solution of 0.0802 g of 2,2,2-trifluoroethanethiol and 0.20 g of 2-bromo-N-[2-chloro-4-[5-(3,4,5-trichlorophenyl)-5-trifluoromethyl-4,5-dihydroisoxazole-3-yl]phenyl]methylacetamide in 2 mL of tetrahydrofuran was added while stirring the suspension at 0° C., and the resultant mixture was stirred at room temperature for 10 minutes. After the completion of the reaction, 2 mL of a saturated ammonium chloride aqueous solution was added to the reaction mixture and the resultant mixture was extracted with ethyl acetate (3 mL×2). The organic phase was washed with water and then dehydrated and dried over saturated saline and anhydrous sodium sulfate in this order, and the solvent was distilled off under reduced pressure. The resultant residue was purified by preparative medium pressure liquid chromatography eluting with ethyl acetate-hexane (a gradient from 1:9 to 1:3) using a medium pressure preparative apparatus (trade name: YFLC-Wprep; manufactured by Yamazen Corporation) to obtain 0.074 g of the objective substance as a colorless resinoid.

$^1$H NMR (CDCl$_3$, Me$_4$Si, 300 MHz) δ 7.70 (d, J=1.5 Hz, 1H), 7.63 (s, 2H), 7.4-7.55 (m, 2H), 6.93 (t, J=6.0 Hz, 1H), 4.56 (d, J=6.0 Hz, 2H), 4.06 (d, J=17.4 Hz, 1H), 3.66 (d, J=17.4 Hz, 1H), 3.37 (s, 2H), 3.15 (q, J=9.6 Hz, 2H).

Synthetic Example 7

S-[2-[2-chloro-4-[5-(3,4,5-trichlorophenyl)-5-trifluoromethyl-4,5-dihydroisoxazole-3-yl]phenyl]methylamino-2-oxoethyl]thioacetate (compound of the present invention No. 1-036)

To a solution of 0.15 g of 2-bromo-N-[2-chloro-4-[5-(3,4,5-trichlorophenyl)-5-trifluoromethyl-4,5-dihydroisoxazole-3-yl]phenyl]methylamide produced in Process 1 of Synthetic Example 6 in 2 mL of N,N-dimethylformamide, 0.0394 g of thioacetic acid and 0.0644 g of potassium carbonate were added while stirring the solution at room temperature and the resultant mixture was continuously stirred at the same temperature for 3 hours. After the completion of the reaction, 2 mL of a saturated ammonium chloride aqueous solution was added to the reaction mixture and the resultant mixture was extracted with ethyl acetate (3 mL×2). The organic phase was washed with water and then dehydrated and dried over saturated saline and anhydrous sodium sulfate in this order and the solvent was distilled off under reduced pressure. The resultant residue was purified by preparative medium pressure liquid chromatography eluting with ethyl acetate-hexane (a gradient from 1:9 to 1:3) using a medium pressure preparative apparatus (trade name: YFLC-Wprep; manufactured by Yamazen Corporation) to obtain 0.14 g of the objective substance as a colorless resinoid.

$^1$H NMR (CDCl$_3$, Me$_4$Si, 300 MHz) δ 7.6-7.7 (m, 3H), 7.48 (d, J=8.4 Hz, 1H), 7.37 (d, J=8.4 Hz, 1H), 6.84 (bs, 1H), 4.49 (d, J=6.3 Hz, 2H), 4.06 (d, J=17.3 Hz, 1H), 3.68 (d, J=17.3 Hz, 1H), 3.57 (s, 2H), 2.40 (s, 3H).

Synthetic Example 8

N-[2-chloro-4-[5-(3,4,5-trichlorophenyl)-5-trifluoromethyl-4,5-dihydroisoxazole-3-yl]phenyl]methyl-2-(methoxymethylthio)acetamide (compound of the present invention No. 1-030)

Process 1; Production of N-[2-chloro-4-[5-(3,4,5-trichlorophenyl)-5-trifluoromethyl-4,5-dihydroisoxazole-3-yl]phenyl]methyl-2-mercaptoacetamide To a solution of 0.218 g of S-[2-[2-chloro-4-[5-(3,4,5-trichlorophenyl)-5-trifluoromethyl-4,5-dihydroisoxazole-3-yl]phenyl]methylamino-2-oxoethyl]thioacetate produced in Synthetic Example 7 in 5 mL of methanol, 0.169 g of potassium carbonate was added and the resultant mixture was stirred at room temperature for 1 hour. After the completion of the reaction, 5 mL of water was added to the reaction mixture to dilute the reaction mixture and a 3 N hydrochloric acid aqueous solution was added to the diluted reaction mixture to neutralize (pH became substantially 7) the reaction mixture, followed by extracting the reaction mixture with ethyl acetate (5 mL×2). The organic phase was washed with water and then dehydrated and dried over saturated saline and anhydrous sodium sulfate in this order, and the solvent was distilled off under reduced pressure to obtain 0.173 g of a crude objective substance as a light yellow resinoid. This substance was used in the next process as it was without being further purified.

Process 2; Production of N-[2-chloro-4-[5-(3,4,5-trichlorophenyl)-5-trifluoromethyl-4,5-dihydroisoxazole-3-yl]phenyl]methyl-2-(methoxymethylthio)acetamide To a solution of 0.090 g of N-[2-chloro-4-[5-(3,4,5-trichlorophenyl)-5-trifluoromethyl-4,5-dihydroisoxazole-3-yl]phenyl]methyl-2-mercaptoacetamide and 0.0446 g of ethyldiisopropylamine in 2 mL of dichloromethane, 0.0278 g of methoxymethyl chloride was added while stirring the solution at 0° C., and the resultant mixture was stirred at room temperature for 1 hour. After the completion of the reaction, 3 mL of water was added to the reaction mixture and the resultant mixture was extracted with chloroform (3 mL×2). The organic phase was dehydrated and dried over saturated saline and anhydrous sodium sulfate in this order and the solvent was distilled off under reduced pressure. The resultant residue was purified by preparative medium pressure liquid chromatography eluting with ethyl acetate-hexane (a gradient from 1:9 to 1:3) using a medium pressure preparative apparatus (trade name: YFLC-Wprep; manufactured by Yamazen Corporation) to obtain 0.0406 g of the objective substance as a colorless resinoid.

$^1$H NMR (CDCl$_3$, Me$_4$Si, 300 MHz) δ 7.45-7.75 (m, 6H), 5.43 (s, 2H), 4.66 (d, J=6.3 Hz, 2H), 4.06 (d, J=17.4 Hz, 1H), 3.67 (d, J=17.4 Hz, 1H), 3.55 (s, 3H).

Synthetic Example 9

S-[2-[2-chloro-4-[5-(3,4,5-trichlorophenyl)-5-trifluoromethyl-4,5-dihydroisoxazole-3-yl]phenyl]methylamino-2-oxoethyl]O-methyl thiocarbonate (compound of the present invention No. 1-038)

To a solution of 0.10 g of N-[2-chloro-4-[5-(3,4,5-trichlorophenyl)-5-trifluoromethyl-4,5-dihydroisoxazole-3-yl]phenyl]methyl-2-mercaptoacetamide produced in Process 1 of Synthetic Example 8 and 0.0364 g of ethyldiisopropylamine in 2 mL of dichloromethane, 0.0266 g of methyl chloroformate was added while stirring the solution at 0° C. and the resultant mixture was stirred at room temperature for 1 hour. After the completion of the reaction, 3 mL of water was added to the reaction mixture and the resultant mixture was extracted with chloroform (3 mL×2). The organic phase was dehydrated and dried over saturated saline and anhydrous sodium sulfate in this order and the solvent was distilled off under reduced pressure. The resultant residue was purified by preparative medium pressure liquid chromatography eluting with ethyl acetate-hexane (a gradient from 1:9 to 1:3) using a medium pressure preparative apparatus (trade name: YFLC-Wprep; manufactured by Yamazen Corporation) to obtain 0.0701 g of the objective substance as a colorless resinoid.

$^1$H NMR (CDCl$_3$, Me$_4$Si, 300 MHz) δ 7.67 (s, 1H), 7.64 (s, 2H), 7.4-7.55 (m, 2H), 6.95 (t, J=6.0 Hz, 1H), 4.53 (d, J=6.0 Hz, 2H), 4.06 (d, J=17.4 Hz, 1H), 3.86 (s, 3H), 3.69 (d, J=17.4 Hz, 1H), 3.55 (s, 2H).

Synthetic Example 10

N-[4-[5-[3,5-bis(trifluoromethyl)phenyl]-5-trifluoromethyl-4,5-dihydroisoxazole-3-yl]-2-chlorophenyl]methyl-2,2-bis(methylthio)acetamide (compound of the present invention No. 1-206)

Process 1; Production of 2,2-dibromo-N-[4-[5-[3,5-bis(trifluoromethyl)phenyl]-5-trifluoromethyl-4,5-dihydroisoxazole-3-yl]-2-chlorophenyl]methylacetamide To a solution of 0.400 g of 3-(4-aminomethyl-3-chlorophenyl)-5-[3,5-bis(trifluoromethyl)phenyl]-5-trifluoromethyl-4,5-dihydroisoxazole produced in substantially the same manner as in Processes 1 to 5 of Synthetic Example 1 and 0.217 g of dibromoacetic acid in 5 mL of dichloromethane, 0.171 g of 1-[3-(dimethylamino)propyl]-3-ethylcarbodiimide hydrochloride was added and the resultant mixture was stirred at room temperature for 1 hour. After the completion of the reaction, 5 mL of a saturated sodium hydrogen carbonate aqueous solution was added to the reaction mixture and the resultant mixture was extracted with dichloromethane (5 mL×2). The organic phase was dehydrated and dried over saturated saline and anhydrous magnesium sulfate in this order and the solvent was distilled off under reduced pressure. The resultant residue was purified by preparative medium pressure liquid chromatography eluting with ethyl acetate-hexane (a gradient from 1:3 to 1:1) using a medium pressure preparative apparatus (trade name: YFLC-Wprep; manufactured by Yamazen Corporation) to obtain 0.473 g of the objective substance as a white crystal.

Melting point: 107.0 to 109.0° C.

$^1$H NMR (CDCl$_3$, Me$_4$Si, 300 MHz) δ 8.08 (s, 2H), 7.96 (s, 1H), 7.72 (s, 1H), 7.5-7.6 (m, 1H), 7.4-7.5 (m, 1H), 7.13 (bs, 1H), 5.85 (s, 1H), 4.61 (d, J=6.0 Hz, 2H), 4.19 (d, J=17.4 Hz, 1H), 3.75 (d, J=17.4 Hz, 1H).

Process 2; Production of N-[4-[5-[3,5-bis(trifluoromethyl)phenyl]-5-trifluoromethyl-4,5-dihydroisoxazole-3-yl]-2-chlorophenyl]methyl-2,2-bis(methylthio)acetamide To a solution of 0.300 g of 2,2-dibromo-N-[4-[5-[3,5-bis(trifluoromethyl)phenyl]-5-trifluoromethyl-4,5-dihydroisoxazole-3-yl]-2-chlorophenyl]methyl acetamide in 4 mL of tetrahydrofuran, 0.060 g of sodium methanethiolate was added while stirring the solution at 0° C. and the resultant mixture was stirred at room temperature for 2 hours. After the completion of the reaction, 4 mL of water and 5 mL of ethyl acetate were added to the reaction mixture and the organic phase was separated off, followed by extracting the aqueous phase with ethyl acetate (3 mL×2). The organic phases were combined and the combined organic phase was dehydrated and dried over saturated saline and anhydrous sodium sulfate in this order, followed by distilling off the solvent under reduced pressure. The resultant residue was purified by preparative medium pressure liquid chromatography eluting with ethyl acetate-hexane (a gradient from 1:9 to 1:3) using a medium pressure preparative apparatus (trade name: YFLC-Wprep; manufactured by Yamazen Corporation) to obtain 0.262 g of the objective substance as a white crystal.

Melting point: 130.0 to 132.0° C.

$^1$H NMR (CDCl$_3$, Me$_4$Si, 300 MHz) δ 8.07 (s, 2H), 7.97 (s, 1H), 7.72 (s, 1H), 7.45-7.55 (m, 2H), 7.10 (t, J=6.0 Hz, 1H), 4.57 (d, J=6.0 Hz, 2H), 4.28 (s, 1H), 4.17 (d, J=17.4 Hz, 1H), 3.73 (d, J-=17.4 Hz, 1H), 2.16 (s, 6H).

Synthetic Example 11

N-[4-[5-[3,5-bis(trifluoromethyl)phenyl]-5-trifluoromethyl-4,5-dihydroisoxazole-3-yl]phenyl][cyano]methyl-2-(ethylsulfinyl)acetamide (compound of the present invention No, 1-145)

To a solution of 0.25 g of N-[4-[5-[3,5-bis(trifluoromethyl)phenyl]-5-trifluoromethyl-4,5-dihydroisoxazole-3-yl]phenyl][cyano]methyl-2-(methylthio)acetamide produced in Synthetic Example 3 in 5 mL of dichloromethane, 0.12 g of 3-chloroperbenzoic acid was added while stirring the solution at 0° C. and the resultant mixture was stirred at the same temperature for 30 minutes. After the completion of the reaction, 5 mL of a saturated sodium hydrogen carbonate aqueous solution was added to the reaction mixture and the resultant mixture was stirred at room temperature for 10 minutes. The organic phase was separated off, and the resultant organic phase was dehydrated and dried over saturated saline and anhydrous sodium sulfate in this order, and the solvent was distilled off under reduced pressure. The resultant residue was purified by silica gel column chromatography eluting with ethyl acetate-hexane (3:1) to obtain 0.28 g of the objective substance as a colorless resinoid.

$^1$H NMR (CDCl$_3$, Me$_4$Si, 300 MHz) δ 8.1-8.25 (m, 1H), 8.08 (s, 2H), 7.97 (s, 1H), 7.75 (d, J=8.4 Hz, 2H), 7.60 and 7.57 (d, J=8.4 Hz, 2H), 6.14 and 6.11 (d, J=8.1 Hz, 1H), 4.20 (d, J=17.4 Hz, 1H), 3.75 (d, J=17.4 Hz, 1H), 3.73 (d, J=14.4 Hz, 1H), 3.36 and 3.32 (d, J=14.4 Hz, 1H), 2.6-3.0 (m, 2H), 1.37 and 1.27 (t, J=7.5 Hz, 3H).

Synthetic Example 12

N-[2-chloro-4-[5-(3,4,5-trichlorophenyl)-5-trifluoromethyl-4,5-dihydroisoxazole-3-yl]phenyl]methyl-2-ethylsulfonyl-N-methylacetamide (compound of the present invention No. 2-005)

To a solution of 0.073 g of N-[2-chloro-4-[5-(3,4,5-trichlorophenyl)-5-trifluoromethyl-4,5-dihydroisoxazole-3-yl]phenyl]methyl-2-ethylthio-N-methylacetamide produced in Synthetic Example 4 in 2 mL of dichloromethane, 0.066 g of 3-chloroperbenzoic acid was added while stirring the solution at room temperature and the resultant mixture was stirred at the same temperature for 1 hour. After the completion of the reaction, 3 mL of a saturated sodium thiosulfate aqueous solution was added to the reaction mixture and the organic phase was separated off. The resultant organic phase was dehydrated and dried over saturated saline and anhydrous sodium sulfate in this order and the solvent was distilled off under reduced pressure. The resultant residue was purified by preparative medium pressure liquid chromatography eluting with ethyl acetate-hexane (a gradient from 1:3 to 1:1) using a medium pressure preparative apparatus (trade name: YFLC-Wprep; manufactured by Yamazen Corporation) to obtain 0.070 g of the objective substance as a colorless resinoid.

$^1$H NMR (CDCl$_3$, Me$_4$Si, 300 MHz) δ 7.5-7.75 (m, 4H), 7.2-7.4 (m, 1H), 4.80 and 4.77 (s, 2H), 4.17 and 4.15 (s, 2H), 4.06 (d, J=17.4 Hz, 1H), 3.67 (d, J=17.4 Hz, 1H), 3.35 and 3.30 (q, J=7.5 Hz, 2H), 3.21 and 3.02 (s, 3H), 1.46 and 1.45 (t, J=7.5 Hz, 3H).

Synthetic Example 13

N-[4-[5-[3,5-bis(trifluoromethyl)phenyl]-5-trifluoromethyl-4,5-dihydroisoxazole-3-yl]-2-chlorophenyl]methyl-2-ethylsulfinyl-2-(ethylthio)acetamide (compound of the present invention No. 1-220)

To a solution of 0.37 g of N-[4-[5-[3,5-bis(trifluoromethyl)phenyl]-5-trifluoromethyl-4,5-dihydroisoxazole-3-yl]-2-chlorophenyl]methyl-2,2-bis(ethylthio) acetamide (compound of the present invention No. 1-215) in 5 mL of dichloromethane, 0.098 g of 3-chloroperbenzoic acid (75%) was added while stirring the solution at room temperature and the resultant reaction mixture was stirred at the same temperature for 1 hour. After the completion of the reaction, 5 mL of a saturated sodium hydrogen sulfite aqueous solution was added to the reaction mixture and the resultant mixture was extracted with dichloromethane (5 mL×2). The organic phase was washed with water and then dehydrated and dried over saturated saline and anhydrous magnesium sulfate in this order and the solvent was distilled off under reduced pressure. The resultant residue was purified by preparative medium pressure liquid chromatography eluting with ethyl acetate-hexane (a gradient from 1:1 to 1:5) using a medium pressure preparative apparatus (trade name: YFLC-Wprep; manufactured by Yamazen Corporation) to obtain 0.282 g of the objective substance as a colorless resinoid.

$^1$H NMR (CDCl$_3$, Me$_4$Si, 300 MHz) δ 8.07 (s, 2H), 7.97 (s, 1H), 7.35-7.65 (m, 3H), 5.31, 4.72, 4.19 and 4.17 (s, 1H), 4.45-4.7 (m, 2H), 4.17 and 4.18 (d, J=17.4 Hz, 1H), 3.73 (d, J=17.4 Hz, 1H), 2.8-3.2 (m, 4H), 1.35-1.45 (m, 6H).

Synthetic Example 14

N-[4-[5-[3,5-bis(trifluoromethyl)phenyl]-5-trifluoromethyl-4,5-dihydroisoxazole-3-yl]-2-chlorophenyl]methyl-2,2-bis(methylsulfinyl)acetamide (compound of the present invention No. 1-211)

To a solution of 0.15 g of N-[4-[5-[3,5-bis(trifluoromethyl)phenyl]-5-trifluoromethyl-4,5-dihydroisoxazole-3-yl]-2-chlorophenyl]methyl-2,2-bis(methylthio)acetamide produced in Synthetic Example 10 in 2 mL of dichloromethane, 0.11 g of 3-chloroperbenzoic acid (75%) was added while stirring the solution at room temperature and the resultant mixture was stirred at the same temperature for 3 hours. After the completion of the reaction, 2 mL of a saturated sodium hydrogen sulfite aqueous solution was added to the reaction mixture and the resultant mixture was extracted with dichloromethane (3 mL×2). The organic phase was washed with water and then dehydrated and dried over saturated saline and anhydrous magnesium sulfate in this order and the solvent was distilled off under reduced pressure. The resultant residue was purified by thin-layer alumina chromatography (Merck Aluminum oxide 60F) eluting with ethyl acetate-hexane (1:2) to obtain 0.14 g of the objective substance as a colorless resinoid.

$^1$H NMR (CDCl$_3$, Me$_4$Si, 300 MHz) δ 8.04 (s, 2H), 7.98 (s, 1H), 7.71 (s, 1H), 7.5-7.65 (m, 2H), 4.68 and 4.61 (d, J=6.0 Hz, 2H), 4.78 and 4.27 (bs, 1H), 4.18 (d, J=17.4 Hz, 1H), 3.74 (d, J=17.4 Hz, 1H), 2.89, 2.83 and 2.78 (s, 6H).

Synthetic Example 15

N-[4-[5-[3,5-bis(trifluoromethyl)phenyl]-5-trifluoromethyl-4,5-dihydroisoxazole-3-yl]-2-chlorophenyl]methyl-2-ethylsulfonyl-2-(ethylthio)acetamide (compound of the present invention No. 1-225)

To a solution of 0.10 g of N-[4-[5-[3,5-bis(trifluoromethyl)phenyl]-5-trifluoromethyl-4,5-dihydroisoxazole-3-yl]-2-chlorophenyl]methyl-2-ethylsulfinyl-2-(ethylthio)acetamide produced in Synthetic Example 13 in 1 mL of an acetone-water (25:1) solution, 0.0236 g of potassium permanganate was added while stirring the solution at room temperature and the resultant mixture was stirred at the same temperature for 1 hour. After the completion of the reaction, an insoluble substance was filtered off from the reaction mixture by Celite filtration and the resultant filtrate was dehydrated and dried over saturated saline and anhydrous magnesium sulfate in this order, followed by distilling off the solvent under reduced pressure. The resultant residue was purified by preparative medium pressure liquid chromatography eluting with ethyl acetate-hexane (a gradient from 1:9 to 1:3) using a medium pressure preparative apparatus (trade name: YFLC-Wprep; manufactured by Yamazen Corporation) to obtain 0.0627 g of the objective substance as a colorless resinoid.

Melting point: 126.0 to 128.0° C.

$^1$H NMR (CDCl$_3$, Me$_4$Si, 300 MHz) δ 8.07 (s, 2H), 7.97 (s, 1H), 7.66 (dd, J=3.3, 1.8 Hz, 1H), 7.45-7.55 (m, 2H), 7.25-7.35 (m, 1H), 4.63 and 4.63 (s, 1H), 4.58 and 4.57 (d, J=6.0 Hz, 2H), 4.16 (d, J=17.4 Hz, 1H), 3.72 (d, J=17.4 Hz, 1H), 3.35-3.55 (m, 1H), 3.2-3.35 (m, 1H), 2.93 (dt, J=12.4, 7.5 Hz, 1H), 2.86 (dt, J=12.4, 7.5 Hz, 1H), 1.40 (t, J=7.5 Hz, 3H), 1.30 (t, J=7.5 Hz, 3H).

Synthetic Example 16

N-[2-bromo-4-[5-[3,4-dichloro-5-(trifluoromethyl)phenyl]-5-trifluoromethyl-4,5-dihydroisoxazole-3-yl]phenyl]methyl-2-[N-(cyano) methylsulfinimidoyl] acetamide (compound of the present invention No. 1-103)

To a solution of 0.46 g of N-[2-bromo-4-[5-[3,4-dichloro-5-(trifluoromethyl)phenyl]-5-trifluoromethyl-4,5-dihydroisoxazole-3-yl]phenyl]methyl-2-(methylthio) acetamide (compound of the present invention No. 1-084) produced in substantially the same manner as in Synthetic Example 1 and 0.15 g of cyanamide in 7 mL of acetonitrile, 0.77 g of (diacetoxyiodo) benzene was added while stirring the solution at 0° C. and the resultant mixture was stirred for 17 hours while naturally elevating the temperature of the mixture to room temperature. After the completion of the reaction, the solvent was distilled off under reduced pressure and the resultant residue was purified by silica gel column chromatography eluting with ethyl acetate-hexane (5:1) to obtain 0.20 g of the objective substance as a colorless resinoid.

$^1$H NMR (CDCl$_3$, Me$_4$Si, 300 MHz) δ 8.30 (t, J=5.4 Hz, 1H), 7.93 (s, 1H), 7.83 (s, 2H), 7.59 (d, J=7.1 Hz, 1H), 7.44 (d, J=7.1 Hz, 1H), 4.51 (d, J=5.4 Hz, 2H), 3.95-4.2 (m, 3H), 3.69 (d, J=17.4 Hz, 1H), 2.93 (s, 3H).

Synthetic Example 17

N-[2-bromo-4-[5-[3,4-dichloro-5-(trifluoromethyl) phenyl]-5-trifluoromethyl-4,5-dihydroisoxazole-3-yl]phenyl]methyl-2-[N-(trifluoroacetyl)methylsulfinimidoyl]acetamide (compound of the present invention No. 1-102)

To a solution of 0.10 g of N-[2-bromo-4-[5-[3,4-dichloro-5-(trifluoromethyl)phenyl]-5-trifluoromethyl-4,5-dihydroisoxazole-3-yl]phenyl]methyl-2-(methylthio) acetamide (compound of the present invention No. 1-084) produced in substantially the same manner as in Synthetic Example 1 and 0.04 g of trifluoroacetamide in 3 mL of dichloromethane, 0.03 g of magnesium oxide and 0.002 g of tetrakis(acetate) dirhodium (II) were added and the resultant mixture was stirred at room temperature for 5 minutes. Next, to this reaction mixture, 0.08 g of (diacetoxyiodo) benzene was added while stirring the reaction mixture at room temperature and the resultant mixture was continuously stirred at the same temperature further for 17 hours. After the completion of the reaction, an insoluble substance was filtered off from the reaction mixture by Celite filtration and the solvent was distilled off under reduced pressure. The resultant residue was purified by silica gel column chromatography eluting with ethyl acetate-hexane (3:1) to obtain 0.09 g of the objective substance as a colorless resinoid.

$^1$H NMR (CDCl$_3$, Me$_4$Si, 300 MHz) δ 8.04 (bs, 1H), 7.95 (s, 1H), 7.88 (s, 1H), 7.84 (s, 1H), 7.57 (d, J=8.1 Hz, 1H), 7.43 (d, J=8.1 Hz, 1H), 4.45-4.6 (m, 2H), 4.05-4.2 (m, 2H), 3.90 (d, J=14.1 Hz, 1H), 3.72 (d, J=17.4 Hz, 1H), 2.99 (s, 3H).

Synthetic Example 18

N-[4-[5-[3,5-bis(trifluoromethyl)phenyl]-5-trifluoromethyl-4,5-dihydroisoxazole-3-yl]phenyl][cyano] methyl-2-[N-(trifluoroacetyl)ethylsulfonimidoyl] acetamide (compound of the present invention No. 1-174)

To a solution of 0.13 g of N-[4-[5-[3,5-bis(trifluoromethyl) phenyl]-5-trifluoromethyl-4,5-dihydroisoxazole-3-yl]phenyl][cyano]methyl-2-(ethylsulfinyl)acetamide produced in Synthetic Example 11 and 0.05 g of trifluoroacetamide in 2 mL of dichloromethane, 0.04 g of magnesium oxide and 0.002 g of tetrakis(acetate) dirhodium (II) were added and the resultant mixture was stirred at room temperature for 5 minutes. Next, to this reaction mixture, 0.11 g of (diacetoxyiodo) benzene was added while stirring the reaction mixture at room temperature and the resultant mixture was continuously stirred at the same temperature further for 17 hours. After the completion of the reaction, an insoluble substance was filtered off from the reaction mixture by Celite filtration and the solvent was distilled off under reduced pressure. The resultant residue was purified by silica gel column chromatography eluting with ethyl acetate-hexane (1:1) to obtain 0.09 g of the objective substance as a colorless resinoid.

$^1$H NMR (CDCl$_3$, Me$_4$Si, 300 MHz) δ 8.1-8.25 (m, 1H), 8.07 (s, 2H), 7.97 (s, 1H), 7.71 (d, J=8.7 Hz, 2H), 7.45-7.55 (m, 2H), 5.95-6.05 (m, 1H), 4.4-4.7 (m, 2H), 4.19 (d, J=17.4 Hz, 1H), 3.77 (d, J=17.4 Hz, 1H), 3.5-3.65 (m, 2H), 1.51 and 1.50 (t, J=7.8 Hz, 3H).

Synthetic Example 19

N-[2-chloro-4-[5-[3,5-bis(trifluoromethyl)phenyl]-5-trifluoromethyl-4,5-dihydroisoxazole-3-yl]phenyl] methyl-2-(ethylsulfonimidoyl)acetamide (compound of the present invention No. 1-173)

To a solution of 0.20 g of N-[2-chloro-4-[5-[3,5-bis(trifluoromethyl)phenyl]-5-trifluoromethyl-4,5-dihydroisoxazole-3-yl]phenyl]methyl-2-[N-(trifluoroacetyl)ethylsulfonimidoyl]acetamide produced in substantially the same manner as in Synthetic Example 18 in 5 mL of methanol, 0.19 g of potassium carbonate was added and the resultant mixture was stirred at room temperature for 30 minutes. After the completion of the reaction, an insoluble substance was filtered off from the reaction mixture by Celite filtration and the solvent was distilled off under reduced pressure. The resultant residue was purified by a silica gel column chromatography eluting with ethyl acetate-hexane (2:1) to obtain 0.10 g of the objective substance as a white crystal.

Melting point: 173.0 to 175.0° C.

$^1$H NMR (CDCl$_3$, Me$_4$Si, 300 MHz) δ 8.07 (s, 2H), 7.97 (s, 1H), 7.8-7.9 (m, 1H), 7.70 (s, 1H), 7.52 (s, 2H), 6.68 (s, 1H), 4.57 (d, J=6.3 Hz, 2H), 4.16 (d, J=17.4 Hz, 1H), 3.94 (s, 2H), 3.72 (d, J=17.4 Hz, 1H), 3.1-3.25 (m, 2H), 1.41 (t, J=7.5 Hz, 3H).

Reference Example 1

4-chloro-3-trifluoromethyl-1-(1-trifluoromethylethenyl)benzene

In a nitrogen atmosphere, to 53 mL of a 1M tetrahydrofuran solution of 1-trifluoromethylethenyl zinc bromide prepared according to a method described in the literatures, 7.1 g of 2-chloro-5-iodobenzotrifluoride and 0.65 g of dichlorobis (triphenylphosphine) palladium (II) were added and the resultant mixture was stirred while heating the mixture to reflux for 2.5 hours. After the completion of the reaction, the reaction mixture was left to be cooled down to room temperature and 200 mL of hexane was added to the reaction mixture, followed by filtering off the deposited insoluble substance. The resultant filtrate was washed with water (50 mL×1) and then dehydrated and dried over saturated saline and anhydrous sodium sulfate in this order and the solvent was distilled off under reduced pressure. The resultant residue was purified by silica gel column chromatography eluting with hexane to obtain 4.8 g of the objective substance as a colorless oily substance.

$^1$H NMR (CDCl$_3$, Me$_4$Si, 300 MHz) δ 7.75 (s, 1H), 7.57 (d, J=8.8 Hz, 1H), 7.54 (d, J=8.8 Hz, 1H), 6.08 (s, 1H), 5.84 (s, 1H).

Reference Example 2

3,5-bis(trifluoromethyl)-1-(1-trifluoromethylethenyl) benzene

To a solution of 20.0 g of 3,5-bis(trifluoromethyl)phenylboronic acid in 100 mL of tetrahydrofuran and 40 mL of water, 20.2 g of 2-bromo-3,3,3-trifluoropropene, 30.0 g of potassium carbonate and 0.023 g of 1,3-bis(2,6-diisopropylphenyl) imidazole-2-ylidene(1,4-naphthoquinone) palladium (0) dimer were added and the resultant mixture was stirred at 60° C. in a nitrogen atmosphere for 3 hours. After the completion of the reaction, the reaction mixture was left to be cooled down to room temperature and 100 mL of ice water was added to the reaction mixture, followed by extracting the resultant mixture with ethyl acetate (100 mL×2). The organic phase was washed with water and then dehydrated and dried over saturated saline and anhydrous sodium sulfate in this order and the solvent was distilled off under reduced pressure. The resultant residue was purified by silica gel column chromatography eluting with hexane to obtain 21.9 g of the objective substance as an orange oily substance.

$^1$H NMR (CDCl$_3$, Me$_4$Si, 300 MHz) δ 7.92 (s, 1H), 7.89 (s, 2H), 6.18 (s, 1H), 5.93 (d, J=1.5 Hz, 1H).

Reference Example 3

3,4,5-trichloro-1-(1-trifluoromethylethenyl)benzene

Process 1; Production of 3,4,5-trichloro-1-iodobenzene

Into a suspension of 25.0 g of 3,4,5-trichloroaniline in 10 mL of acetonitrile, 25 mL of methanol and 100 mL of water, a solution of 9.7 g of sodium nitrite in 25 mL of water was dropped while stirring and ice-cooling the suspension over 20 minutes and after the completion of the dropping, the resultant mixture was stirred at 5 to 6° C. for 30 minutes. Next, the reaction mixture was dropped into 75 mL of an aqueous solution of 23.2 g of potassium iodide which was heated to 80° C. over 20 minutes and after the completion of the dropping, the resultant mixture was continuously stirred at the same temperature further for 1 hour. After the completion of the reaction, 50 mL of an aqueous solution of 7.64 g of urea was added to the reaction mixture and the resultant mixture was left to be cooled down to room temperature while stirring the mixture, followed by diluting the mixture with 400 mL of ethyl acetate. Subsequently, an insoluble substance was filtered off from the mixture by Celite filtration. The organic phase was washed with 300 mL of a saturated sodium hydrogen sulfite aqueous solution and next with 200 mL of water and then dehydrated and dried over saturated saline and anhydrous sodium sulfate in this order, and the solvent was distilled off under reduced pressure. The resultant residue was purified by silica gel column chromatography eluting with hexane to obtain 29.3 g of the objective substance as a light yellow crystal.

Melting point: 45.0 to 46.0° C.
$^1$H NMR (CDCl$_3$, Me$_4$Si, 300 MHz) δ 7.70 (s, 2H).

Process 2; Production of 3,4,5-triehloro-1-(1-trifluoromethylethenyl)benzene

In a nitrogen atmosphere, to 190 mL of a 1M tetrahydrofuran solution of 1-trifluoromethylethenyl zinc bromide prepared according to a method described in the literatures, 29.2 g of 3,4,5-trichloro-1-iodobenzene and 2.66 g of dichlorobis(triphenylphosphine) palladium (II) were added and the resultant mixture was stirred while heating the mixture to reflux for 3 hours. After the completion of the reaction, the reaction mixture was left to be cooled down to room temperature and 350 mL of hexane was added to the reaction mixture, followed by filtering off the deposited insoluble substance and by distilling off the solvent under reduced pressure. The resultant residue was purified by silica gel column chromatography eluting with hexane to obtain 24.3 g of the objective substance as a brown oily substance.

$^1$H NMR (CDCl$_3$, Me$_4$Si, 300 MHz) δ 7.47 (s, 2H), 6.06 (s, 1H), 5.83 (s, 1H).

Reference Example 4

3,4-dichloro-5-methyl-1-(1-trifluoromethylethenyl)benzene

In a nitrogen atmosphere, to 19 mL of a 1M tetrahydrofuran solution of 1-trifluoromethylethenyl zinc bromide prepared according to a method described in the literatures, a solution of 2.2 g of 5-bromo-2,3-dichlorotoluene in 10 mL of N,N-dimethylformamide was added and tetrahydrofuran was distilled off under reduced pressure. To the remaining N,N-dimethylformamide solution, 0.26 g of dichlorobis(triphenylphosphine) palladium (II) was added and the resultant mixture was stirred at 100° C. for 3.5 hours. After the completion of the reaction, the reaction mixture was left to be cooled down to room temperature and 200 mL of a tetrahydrofuran-hexane (2:5) mixture was added to the reaction mixture, followed by filtering off the deposited insoluble substance. The resultant filtrate was washed with water (100 mL×1) and then dehydrated and dried over saturated saline and anhydrous sodium sulfate in this order, and the solvent was distilled off under reduced pressure. The resultant residue was purified by silica gel column chromatography eluting with hexane to obtain 2.3 g of the objective substance as a brown oily substance.

$^1$H NMR (CDCl$_3$, Me$_4$Si, 300 MHz) δ 7.40 (s, 1H), 7.22 (s, 1H), 5.99 (s, 1H), 5.77 (s, 1H), 2.44 (s, 3H).

Reference Example 5

3,4-dichloro-5-trifluoromethyl-1-(1-trifluoromethylethenyl)benzene

In a nitrogen atmosphere, to a solution of 26.2 g of 5-bromo-2,3-dichlorobenzotrifluoride and 9.1 g of diisopropyl ether in 250 mL of hexane, 57.5 mL of an n-butyl lithium hexane solution (1.55 M) was gradually dropped while stirring the solution at −10° C. After the completion of the dropping, the resultant mixture was stirred at the same temperature for 30 minutes. Next, into the reaction mixture, a solution of 9.26 g of trimethoxyborane in 30 mL of tetrahydrofuran was dropped and the resultant mixture was continuously stirred at room temperature further for 10 minutes. To this reaction mixture, 150 mL of water, 23.4 g of 2-bromo-3,3,3-trifluoropropene, 36.9 g of potassium carbonate and 0.131 g of 1,3-bis(2,6-diisopropylphenyl)imidazole-2-ylidene(1,4-naphthoquinone) palladium (0) dimer were added and the resultant mixture was stirred at 60° C. for 4 hours. After the completion of the reaction, the reaction mixture was left to be cooled down to room temperature, and 50 mL of ice water and 75 mL of ethyl acetate were added to the reaction mixture, followed by separating off the insoluble substance and by cleaning the insoluble substance with 75 mL of ethyl acetate. The organic phase of the filtrate was separated off and the resultant organic phase was washed with water and then dehydrated and dried over saturated saline and anhydrous sodium sulfate in this order. The solvent was distilled off under reduced pressure. The resultant residue was purified by silica gel column chromatography eluting with hexane to obtain 21.8 g of the objective substance as a colorless oily substance.

$^1$H NMR (CDCl$_3$, Me$_4$Si, 300 MHz) δ 7.73 (s, 1H), 7.68 (s, 1H), 6.12 (s, 1H), 5.87 (s, 1H).

Reference Example 6

3,5-dichloro-4-difluoromethoxy-1-(1-trifluoromethylethenyl)benzene

Process 1; Production of 4-bromo-2,6-dichloro(difluoromethoxy)benzene

To a solution of 2.3 g of 4-bromo-2,6-dichlorophenol in 25 mL of acetonitrile, 1.3 g of potassium carbonate and 3.8 g of ethyl bromodifluoroacetate were added and the resultant mixture was stirred while heating the mixture to reflux for 4 hours. After the completion of the reaction, the reaction mixture was left to be cooled down to room temperature and charged into 100 mL of water and the resultant mixture was extracted with ethyl acetate (100 mL×1). The organic phase was washed with water and then dehydrated and dried over saturated saline and anhydrous sodium sulfate in this order and the solvent was distilled off under reduced pressure. The resultant residue was purified by silica gel column chromatography eluting with ethyl acetate-hexane (1:4) to obtain 2.4 g of the objective substance as a yellow oily substance.

$^1$H NMR (CDCl$_3$, Me$_4$Si, 300 MHz) δ 7.54 (s, 2H), 6.56 (d, J=73.6 Hz, 1H).

Process 2; Production of 3,5-dichloro-4-difluoromethoxy-1-(1-trifluoromethylethenyl)benzene To 21 mL of a 1M tetrahydrofuran solution of 1-trifluoromethylethenyl zinc bromide prepared according to a method described in the literatures, a solution of 2.4 g of 4-bromo-2,6-dichloro(difluoromethoxy)benzene in 12 mL of N,N-dimethylformamide was added, and tetrahydrofuran was distilled off under reduced pressure. To the remaining N,N-dimethylformamide solution, 0.23 g of dichlorobis(triphenylphosphine) palladium (II) was added and the resultant mixture was stirred at 100° C. for 3 hours. After the completion of the reaction, the reaction mixture was left to be cooled down to room temperature and charged into 100 mL of water and the resultant mixture was extracted with diethyl ether (100 mL×1). The organic phase was washed with water and then dehydrated and dried over saturated saline and anhydrous sodium sulfate in this order and the solvent was distilled off under reduced pressure. The resultant residue was purified by silica gel column chromatography eluting with hexane to obtain 1.8 g of the objective substance as a brown oily substance.

$^1$H NMR (CDCl$_3$, Me$_4$Si, 300 MHz) δ 7.47 (s, 2H), 6.61 (t, J=73.6 Hz, 1H), 6.08 (s, 1H), 5.83 (s, 1H).

Reference Example 7

3',5'-dibromo-2,2,2,4'-tetrafluoroacetophenone

To a solution of 1.00 g of 2,2,2,4'-tetrafluoroacetophenone in 0.2 mL of acetic acid and 1.0 mL of concentrated sulfuric acid, 1.79 g of 1,3-dibromo-5,5-dimethylhydantoin was added while ice-cooling and stirring the solution and the resultant mixture was stirred at 45° C. for 3 hours. After the completion of the reaction, the reaction mixture was charged into 5 mL of ice water and a 2N sodium hydroxide aqueous solution was added to the resultant mixture to adjust its pH to 7, followed by extracting the resultant mixture with ethyl acetate (3 mL×2). The organic phase was washed with water and then dehydrated and dried over saturated saline and anhydrous sodium sulfate in this order, and the solvent was distilled off under reduced pressure to obtain 0.99 g of the objective substance as a colorless oily substance.

$^1$H NMR (CDCl$_3$, Me$_4$Si, 300 MHz) δ 8.23 (dd, J=6.0, 0.9 Hz, 2H).

Reference Example 8

3',5'-dibromo-4'-chloro-2,2,2-trifluoroacetophenone

To a solution of 2.00 g of 4'-chloro-2,2,2-trifluoroacetophenone in 0.5 mL of acetic acid and 2.8 mL of concentrated sulfuric acid, 3.02 g of 1,3-dibromo-5,5-dimethylhydantoin was added while ice-cooling and stirring the solution and the resultant mixture was stirred at 35° C. After 3 hours, 0.7 mL of acetic acid, 2.0 mL of concentrated sulfuric acid and 0.35 g of 1,3-dibromo-5,5-dimethylhydantoin were additionally added to the reaction mixture, and the resultant mixture was continuously stirred at the same temperature further for 3 hours. After the completion of the reaction, the reaction mixture was charged into 50 mL of ice water and the resultant mixture was extracted with chloroform (50 mL×1). The organic phase was washed with 50 mL of a saturated sodium hydrogen carbonate aqueous solution and then dehydrated and dried over saturated saline and anhydrous magnesium sulfate in this order, and the solvent was distilled off under reduced pressure. The resultant residue was dissolved in 20 mL of hexane and the insoluble substance was filtered off, followed by distilling off the solvent under reduced pressure to obtain 3.89 g of the objective substance as a yellow oily substance.

$^1$H NMR (CDCl$_3$, Me$_4$Si, 300 MHz) δ 8.24 (s, 2H).

Reference Example 9

3'-iodo-5'-trifluoromethyl-2,2,2-trifluoroacetophenone

To 2.42 g of 3'-trifluoromethyl-2,2,2-trifluoroacetophenone, 6 mL of 30% fuming sulfuric acid and 1.90 g of iodine were added and the resultant mixture was stirred at 50° C. for 5 hours. After the completion of the reaction, the reaction mixture was charged onto 10 g of ice and the resultant mixture was extracted with diethyl ether (20 mL×1). The organic phase was washed with 10 mL of a saturated sodium sulfite aqueous solution and then dehydrated and dried over saturated saline and anhydrous sodium sulfate in this order, and the solvent was distilled off under reduced pressure to obtain 2.56 g of the objective substance as a light yellow oily substance.

$^1$H NMR (CDCl$_3$, Me$_4$Si, 300 MHz) δ 8.53 (s, 1H), 8.28 (s, 1H), 8.25 (s, 1H).

The compound of the present invention can be produced according to the above production methods and Examples. Examples of the compound of the present invention produced in substantially the same manner as those in Synthetic Example 1 to Synthetic Example 19 are shown in Table 3 to Table 6, which should not be construed as limiting the scope of the present invention.

Here, in Tables, a substituent expressed as Et is an ethyl group and hereinafter, n-Pr and Pr-n are a normal propyl group; c-Pr and Pr-c are a cyclopropyl group; i-Bu and Bu-i are an isobutyl group; c-Pen and Pen-c are a cyclopentyl group; and Ph is a phenyl group.

In Tables, substituents expressed as D-8a, D-9-1a and D-12-1a individually are aromatic heterocycle groups of the Structural Formulae:

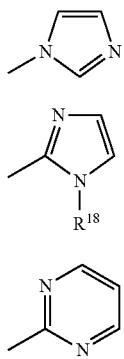

In Tables, substituents expressed as E-1-1a to E-5-1a individually are saturated heterocycle groups of Structural Formulae:

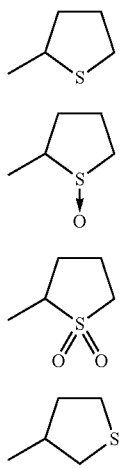

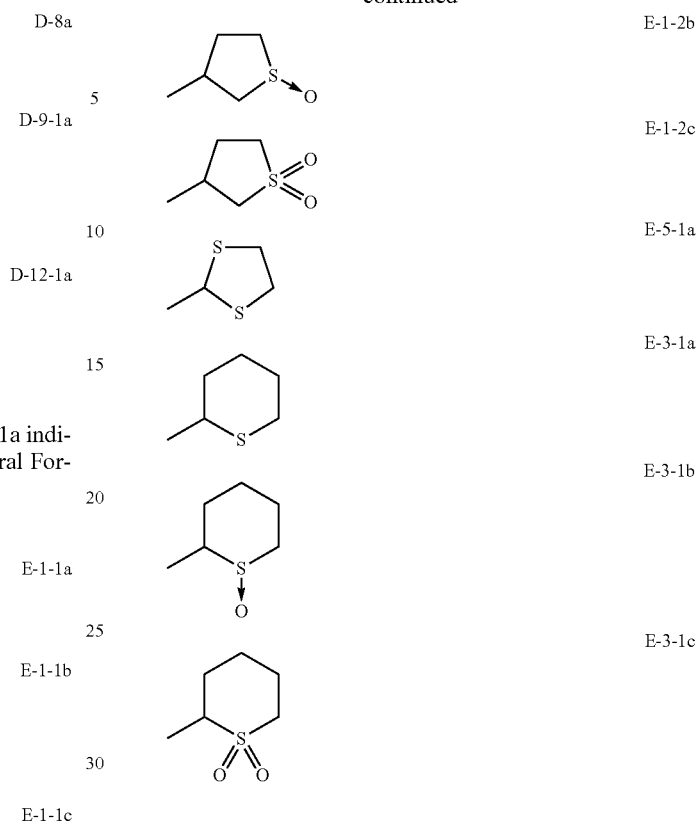

In addition, in Tables, substituents $X^1$, $X^2$ and $X^3$ in the compound of the present invention of General Formula (1) are $(X)_m$, and the numbers for substituted positions of each substituent correspond to the positions of numbers attached to each of the following structural formulae.

Furthermore, in Tables, an expression as "*1" means that the physical property of the compound of the present invention is "resinous".

TABLE 3

| No. | $(X)_m$ | $Y^1$ | $R^4$ | $R^{1a}$ | m.p. (° C.) |
|---|---|---|---|---|---|
| 1-001 | 3,5-$(CF_3)_2$ | H | $CH_3$ | $CH_2SCH_3$ | *1 |
| 1-002 | 3,4,5-$Cl_3$ | H | $CH_3$ | $CH_2SCH_3$ | *1 |
| 1-003 | 3,4,5-$Cl_3$ | H | CN | $CH_2SCH_3$ | *1 |
| 1-004 | 3,5-$(CF_3)_2$ | Cl | H | $CH_2SCH_3$ | 92.0-95.0 |
| 1-004(+) | 99% e. e. | $[\alpha]_D^{26.8}$ + 42.27° | | (EtOH, c = 0.321) | |
| 1-004(-) | 98% e. e. | $[\alpha]_D^{26.4}$ − 39.60° | | (EtOH, c = 0.325) | |
| 1-005 | 3,4 5-$Cl_3$ | Cl | H | $CH_2SCH_3$ | *1 |
| 1-006 | 3,5-$Cl_2$-4-$OCHF_2$ | Cl | H | $CH_2SCH_3$ | *1 |
| 1-007 | 3,5-$(CF_3)_2$ | Br | H | $CH_2SCH_3$ | *1 |
| 1-008 | 3,4,5-$Cl_3$ | Br | H | $CH_2SCH_3$ | *1 |
| 1-009 | 3,4,5-$Cl_3$ | $NO_2$ | H | $CH_2SCH_3$ | 194.0-196.0 |
| 1-010 | 3,4,5-$Cl_3$ | H | $CH_3$ | $CH_2SO_2CH_3$ | *1 |
| 1-011 | 3,5-$(CF_3)_2$ | Cl | H | $CH_2SO_2H_3$ | 160.5-162.5 |
| 1-011(+) | 99% e. e. | $[\alpha]_D^{26.4}$ + 37.42° | | (EtOH, c = 0.511) | |
| 1-011(-) | 98% e. e. | $[\alpha]_D^{26.7}$ − 37.49° | | (EtOH, c = 0.505) | |

TABLE 3-continued

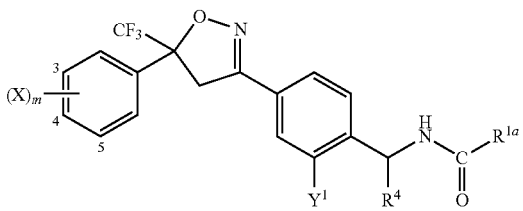

| No. | $(X)_m$ | $Y^1$ | $R^4$ | $R^{1a}$ | m.p. (° C.) |
|---|---|---|---|---|---|
| 1-012 | 3,4,5-Cl$_3$ | Cl | H | CH$_2$SO$_2$CH$_3$ | 211.0-213.0 |
| 1-013 | 3,5-(CF$_3$)$_2$ | Br | H | CH$_2$SO$_2$CH$_3$ | *1 |
| 1-014 | 3,4,5-Cl$_3$ | Br | H | CH$_2$SO$_2$CH$_3$ | 194.5-196.0 |
| 1-015 | 3,4,5-Cl$_3$ | NO$_2$ | H | CH$_2$SO$_2$CH$_3$ | *1 |
| 1-016 | 3,4,5-Cl$_3$ | H | H | CH$_2$SEt | *1 |
| 1-017 | 3,4,5-Cl$_3$ | H | CH$_3$ | CH$_2$SEt | *1 |
| 1-018 | 3,4,5-Cl$_3$ | H | CN | CH$_2$SEt | *1 |
| 1-019 | 3,5-(CF$_3$)$_2$ | Cl | H | CH$_2$SEt | *1 |
| 1-020 | 3,4,5-Cl$_3$ | Cl | H | CH$_2$SEt | *1 |
| 1-021 | 3,5-Cl$_2$-4-OCHF$_2$ | Cl | H | CH$_2$SEt | *1 |
| 1-022 | 3,5-(CF$_3$)$_2$ | Br | H | CH$_2$SEt | *1 |
| 1-023 | 3,4,5-Cl$_3$ | Br | H | CH$_2$SEt | *1 |
| 1-024 | 3,4,5-Cl$_3$ | H | H | CH$_2$S(O)Et | *1 |
| 1-025 | 3,4,5-Cl$_3$ | Cl | H | CH$_2$S(O)Et | *1 |
| 1-026 | 3,4,5-Cl$_3$ | H | H | CH$_2$SO$_2$Et | *1 |
| 1-027 | 3,4,5-Cl$_3$ | Cl | H | CH$_2$SO$_2$Et | 125.0-128.0 |
| 1-028 | 3,4,5-Cl$_3$ | Cl | H | CH$_2$SPen-c | *1 |
| 1-029 | 3,4,5-Cl$_3$ | Cl | H | CH$_2$SCH$_2$CF$_3$ | *1 |
| 1-030 | 3,4,5-Cl$_3$ | Cl | H | CH$_2$SCH$_2$OCH$_3$ | *1 |
| 1-031 | 3,4,5-Cl$_3$ | Cl | H | CH$_2$SCH$_2$CN | *1 |
| 1-032 | 3,4,5-Cl$_3$ | Cl | H | CH$_2$SCH$_2$C(O)OEt | *1 |
| 1-033 | 3,4,5-Cl$_3$ | Cl | H | CH$_2$SCH$_2$C(O)NHCH$_3$ | *1 |
| 1-034 | 3,4,5-Cl$_3$ | Cl | H | CH$_2$SCH$_2$CH=CH$_2$ | *1 |
| 1-035 | 3,4,5-Cl$_3$ | Cl | H | CH$_2$SCH$_2$C≡CH | *1 |
| 1-036 | 3,4,5-Cl$_3$ | Cl | H | CH$_2$SC(O)CH$_3$ | *1 |
| 1-037 | 3,4,5-Cl$_3$ | Cl | H | CH$_2$SC(O)(D-8a) | *1 |
| 1-038 | 3,4,5-Cl$_3$ | Cl | H | CH$_2$SC(O)OCH$_3$ | *1 |
| 1-039 | 3,4,5-Cl$_3$ | Cl | H | CH$_2$SC(O)NHEt | *1 |
| 1-040 | 3,4,5-Cl$_3$ | Cl | H | CH$_2$S(D-9-1a)H | *1 |
| 1-041 | 3,4,5-Cl$_3$ | Cl | H | CH$_2$S(D-12-1a) | *1 |
| 1-042 | 3,5-(CF$_3$)$_2$ | Cl | H | CH(CH$_3$)SCH$_3$ | 119.0-122.0 |
| 1-043 | 3,4,5-Cl$_3$ | Cl | H | CH(CH$_3$)SCH$_3$ | *1 |
| 1-044 | 3,5-(CF$_3$)$_2$ | Cl | H | CH(CH$_3$)S(O)CH$_3$ | *1 |
| 1-045 | 3,4,5-Cl$_3$ | Cl | H | CH(CH$_3$)S(O)CH$_3$ | *1 |
| 1-046 | 3,5-(CF$_3$)$_2$ | Cl | H | CH(CH$_3$)SO$_2$CH$_3$ | 176.0-178.0 |
| 1-047 | 3,4,5-Cl$_3$ | Cl | H | CH(CH$_3$)SO$_2$CH$_3$ | 184.0-189.0 |
| 1-048 | 3,5-(CF$_3$)$_2$ | Cl | H | CH(CH$_3$)SEt | 125.0-128.0 |
| 1-049 | 3,4,5-Cl$_3$ | Cl | H | CH(CH$_3$)SEt | *1 |
| 1-050 | 3,5-(CF$_3$)$_2$ | Cl | H | CH(CH$_3$)S(O)Et | *1 |
| 1-051 | 3,4,5-Cl$_3$ | Cl | H | CH(CH$_3$)S(O)Et | *1 |
| 1-052 | 3,5-(CF$_3$)$_2$ | Cl | H | CH(CH$_3$)SO$_2$Et | *1 |
| 1-053 | 3,4,5-Cl$_3$ | Cl | H | CH(CH$_3$)SO$_2$Et | *1 |
| 1-054 | 3,5-(CF$_3$)$_2$ | Cl | H | E-1-1a | *1 |
| 1-055 | 3,4,5-Cl$_3$ | Cl | H | E-1-1a | *1 |
| 1-056 | 3,5-(CF$_3$)$_2$ | Br | H | E-1-1a | *1 |
| 1-057 | 3,4,5-Cl$_3$ | Cl | H | E-1-1b | *1 |
| 1-058 | 3,4,5-Cl$_3$ | Cl | H | E-1-1c | 178.0-181.0 |
| 1-059 | 3,4,5-Cl$_3$ | Cl | H | E-5-1a | *1 |
| 1-060 | 3,5-(CF$_3$)$_2$ | Cl | H | C(CH$_3$)$_2$SCH$_3$ | *1 |
| 1-061 | 3,4,5-Cl$_3$ | Cl | H | C(CH$_3$)$_2$SCH$_3$ | *1 |
| 1-062 | 3,4,5-Cl$_3$ | Cl | H | E-1-2a | *1 |
| 1-063 | 3,4,5-Cl$_3$ | Cl | H | E-1-2b | *1 |
| 1-064 | 3,4,5-Cl$_3$ | Cl | H | E-1-2c | *1 |
| 1-065 | 3,4,5-Cl$_3$ | Cl | H | CF$_2$SCH$_3$ | *1 |
| 1-066 | 3,4,5-Cl$_3$ | Cl | H | CF$_2$S(O)CH$_3$ | *1 |
| 1-067 | 3,4,5-Cl$_3$ | Cl | H | CF$_2$SO$_2$CH$_3$ | *1 |
| 1-068 | 3-Br-5-CF$_3$ | H | CH$_3$ | CH$_2$SCH$_3$ | *1 |
| 1-069 | 3,4-Cl$_2$-5-CF$_3$ | H | CH$_3$ | CH$_2$SCH$_3$ | *1 |
| 1-070 | 3,4-Cl$_2$-5-CF$_3$ | H | CN | CH$_2$SCH$_3$ | *1 |
| 1-071 | 3,5-(CF$_3$)$_2$ | F | H | CH$_2$SCH$_3$ | 115.0-117.0 |
| 1-072 | 3-CF$_3$ | Cl | H | CH$_2$SCH$_3$ | *1 |
| 1-073 | 3-Br-4-F | Cl | H | CH$_2$SCH$_2$ | *1 |
| 1-074 | 3-CF$_3$-4-Cl | Cl | H | CH$_2$SCH$_3$ | *1 |
| 1-075 | 3-Cl-5-CF$_3$ | Cl | H | CH$_2$SCH$_3$ | 120.0-121.0 |
| 1-076 | 3-Br-5-CF$_3$ | Cl | H | CH$_2$SCH$_3$ | 123.5-125.0 |
| 1-077 | 3-I-5-CF$_3$ | Cl | H | CH$_2$SCH$_3$ | 130.0-133.0 |
| 1-078 | 3,5-Br$_2$-4-F | Cl | H | CH$_2$SCH$_3$ | 151.0-152.0 |

TABLE 3-continued

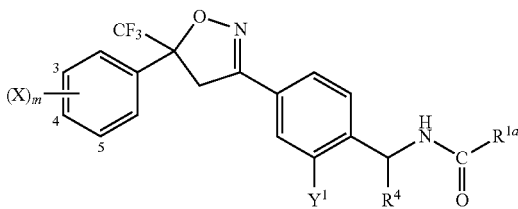

| No. | $(X)_m$ | $Y^1$ | $R^4$ | $R^{1a}$ | m.p. (° C.) |
|---|---|---|---|---|---|
| 1-079 | 3,5-Br$_2$-4-Cl | Cl | H | CH$_2$SCH$_3$ | 129.0-131.0 |
| 1-080 | 3,4-Cl$_2$-5-CF$_3$ | Cl | H | CH$_2$SCH$_3$ | *1 |
| 1-081 | 3-CF$_3$ | Br | H | CH$_2$SCH$_3$ | *1 |
| 1-082 | 3-Cl-5-CF$_3$ | Br | H | CH$_2$SCH$_3$ | 125.0-129.0 |
| 1-083 | 3-Br-5-CF$_3$ | Br | H | CH$_2$SCH$_3$ | *1 |
| 1-084 | 3,4-Cl$_2$-5-CF$_3$ | Br | H | CH$_2$SCH$_3$ | 102.0-104.0 |
| 1-085 | 3,5-(CF$_3$)$_2$ | I | H | CH$_2$SCH$_3$ | *1 |
| 1-086 | 3,5-(CF$_3$)$_2$ | NO$_2$ | H | CH$_2$SCH$_3$ | 145.0-148.0 |
| 1-087 | 3-Br-5-CF$_3$ | H | CH$_3$ | CH$_2$S(O)CH$_3$ | *1 |
| 1-088 | 3,4-Cl$_2$-5-CF$_3$ | H | CH$_3$ | CH$_2$S(O)CH$_3$ | *1 |
| 1-089 | 3,5-(CF$_3$)$_2$ | F | H | CH$_2$S(O)CH$_3$ | *1 |
| 1-090 | 3-CF$_3$-4-Cl | Cl | H | CH$_2$S(O)CH$_3$ | 132.0-135.0 |
| 1-091 | 3-Cl-5-CF$_3$ | Cl | H | CH$_2$S(O)CH$_3$ | *1 |
| 1-092 | 3-Br-5-CF$_3$ | Cl | H | CH$_2$S(O)CH$_3$ | *1 |
| 1-093 | 3-I-5-CF$_3$ | Cl | H | CH$_2$S(O)CH$_3$ | *1 |
| 1-094 | 3,5-(CF$_3$)$_2$ | Cl | H | CH$_2$S(O)CH$_3$ | *1 |
| 1-095 | 3,5-Br$_2$-4-F | Cl | H | CH$_2$S(O)CH$_3$ | *1 |
| 1-096 | 3,5-Br$_2$-4-Cl | Cl | H | CH$_2$S(O)CH$_3$ | *1 |
| 1-097 | 3,4-Cl$_2$-5-CF$_3$ | Cl | H | CH$_2$S(O)CH$_3$ | *1 |
| 1-098 | 3-Cl-5-CF$_3$ | Br | H | CH$_2$S(O)CH$_3$ | *1 |
| 1-099 | 3-Br-5-CF$_3$ | Br | H | CH$_2$S(O)CH$_3$ | *1 |
| 1-100 | 3,5-(CF$_3$)$_2$ | I | H | CH$_2$S(O)CH$_3$ | *1 |
| 1-101 | 3,5-(CF$_3$)$_2$ | NO$_2$ | H | CH$_2$S(O)CH$_3$ | *1 |
| 1-102 | 3,4-Cl$_2$-5-CF$_3$ | Br | H | CH$_2$S(CH$_3$)=NC(O)CF$_3$ | *1 |
| 1-103 | 3,4-Cl$_2$-5-CF$_3$ | Br | H | CH$_2$S(CH$_3$)=NCN | *1 |
| 1-104 | 3-Br-5-CF$_3$ | H | CH$_3$ | CH$_2$SO$_2$CH$_3$ | 185.0-188.0 |
| 1-105 | 3,5-(CF$_3$)$_2$ | H | CH$_3$ | CH$_2$SO$_2$CH$_3$ | *1 |
| 1-106 | 3,4-Cl$_2$-5-CF$_3$ | H | CH$_3$ | CH$_2$SO$_2$CH$_3$ | 210.0-213.0 |
| 1-107 | 3,4-Cl$_2$-5-CF$_3$ | H | CN | CH$_2$SO$_2$CH$_3$ | *1 |
| 1-108 | 3,5-(CF$_3$)$_2$ | F | H | CH$_2$SO$_2$CH$_3$ | 134.0-136.0 |
| 1-109 | 3-CF$_3$ | Cl | H | CH$_2$SO$_2$CH$_3$ | *1 |
| 1-110 | 3-Br-4-F | Cl | H | CH$_2$SO$_2$CH$_3$ | 156.0-157.0 |
| 1-111 | 3-CF$_3$-4-Cl | Cl | H | CH$_2$SO$_2$CH$_3$ | 205.0-208.0 |
| 1-112 | 3-Cl-5-CF$_3$ | Cl | H | CH$_2$SO$_2$CH$_3$ | 174.0-175.0 |
| 1-113 | 3-Br-5-CF$_3$ | Cl | H | CH$_2$SO$_2$CH$_3$ | 125.0-128.0 |
| 1-114 | 3-I-5-CF$_3$ | Cl | H | CH$_2$SO$_2$CH$_3$ | 157.0-160.0 |
| 1-115 | 3,5-Br$_2$-4-F | Cl | H | CH$_2$SO$_2$CH$_3$ | 181.0-182.0 |
| 1-116 | 3,5-Br$_2$-4-Cl | Cl | H | CH$_2$SO$_2$CH$_3$ | 201.0-202.0 |
| 1-117 | 3,4-Cl$_2$-5-CF$_3$ | Cl | H | CH$_2$SO$_2$CH$_3$ | 227.0-229.0 |
| 1-118 | 3-CF$_3$ | Br | H | CH$_2$SO$_2$CH$_3$ | 138.0-141.5 |
| 1-119 | 3-Cl-5-CF$_3$ | Br | H | CH$_2$SO$_2$CH$_3$ | 179.0-182.0 |
| 1-120 | 3-Br-5-CF$_3$ | Br | H | CH$_2$SO$_2$CH$_3$ | 144.0-146.0 |
| 1-121 | 3,4-Cl$_2$-5-CF$_3$ | Br | H | CH$_2$SO$_2$CH$_3$ | 227.0-229.0 |
| 1-122 | 3,5-(CF$_3$)$_2$ | I | H | CH$_2$SO$_2$CH$_3$ | 154.0-156.0 |
| 1-123 | 3,5-(CF$_3$)$_2$ | NO$_2$ | H | CH$_2$SO$_2$CH$_3$ | 223.0-225.0 |
| 1-124 | 3,5-(CF$_3$)$_2$ | H | CH$_3$ | CH$_2$S(O)(CH$_3$)=NH | *1 |
| 1-125 | 3,5-(CF$_3$)$_2$ | Br | H | CH$_2$S(O)(CH$_3$)=NH | *1 |
| 1-126 | 3-Br-5-CF$_3$ | H | CH$_3$ | CH$_2$SEt | *1 |
| 1-127 | 3,5-(CF$_3$)$_2$ | H | CH$_3$ | CH$_2$SEt | *1 |
| 1-128 | 3,4-Cl$_2$-5-CF$_3$ | H | CH$_3$ | CH$_2$SEt | *1 |
| 1-129 | 3,5-(CF$_3$)$_2$ | H | CN | CH$_2$SEt | *1 |
| 1-130 | 3,5-(CF$_3$)$_2$ | F | H | CH$_2$SEt | 89.0-91.0 |
| 1-131 | 3-CF$_3$ | Cl | H | CH$_2$SEt | *1 |
| 1-132 | 3-CF$_3$-4-Cl | Cl | H | CH$_2$SEt | *1 |
| 1-133 | 3-Br-5-CF$_3$ | Cl | H | CH$_2$SEt | 112.0-113.5 |
| 1-134 | 3-I-5-CF$_3$ | Cl | H | CH$_2$SEt | 112.0-115.0 |
| 1-135 | 3,5-Br$_2$-4-F | Cl | H | CH$_2$SEt | *1 |
| 1-136 | 3,5-Br$_2$-4-Cl | Cl | H | CH$_2$SEt | *1 |
| 1-137 | 3,4-Cl$_2$-5-CF$_3$ | Cl | H | CH$_2$SEt | 115.0-118.0 |
| 1-138 | 3-CF$_3$ | Br | H | CH$_2$SEt | *1 |
| 1-139 | 3-Cl-5-CF$_3$ | Br | H | CH$_2$SEt | 121.0-123.0 |
| 1-140 | 3-Br-5-CF$_3$ | Br | H | CH$_2$SEt | *1 |
| 1-141 | 3,4-Cl$_2$-5-CF$_3$ | Br | H | CH$_2$SEt | 110.0-112.0 |
| 1-142 | 3,5-(CF$_3$)$_2$ | I | H | CH$_2$SEt | 156.0-158.0 |
| 1-143 | 3-Br-5-CF$_3$ | H | CH$_3$ | CH$_2$S(O)Et | *1. |
| 1-144 | 3,4-Cl$_2$-5-CF$_3$ | H | CH$_3$ | CH$_2$S(O)Et | *1 |
| 1-145 | 3,5-(CF$_3$)$_2$ | H | CN | CH$_2$S(O)Et | *1 |

TABLE 3-continued

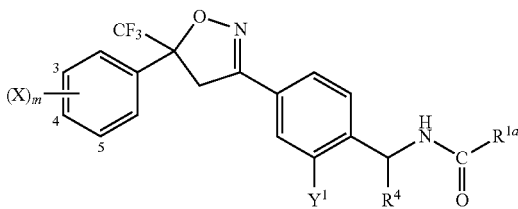

| No. | $(X)_m$ | $Y^1$ | $R^4$ | $R^{1a}$ | m.p. (° C.) |
|---|---|---|---|---|---|
| 1-146 | 3,5-$(CF_3)_2$ | F | H | $CH_2S(O)Et$ | *1 |
| 1-147 | 3-$CF_3$-4-Cl | Cl | H | $CH_2S(O)Et$ | 118.0-120.0 |
| 1-148 | 3-I-5-$CF_3$ | Cl | H | $CH_2S(O)Et$ | *1 |
| 1-149 | 3,5-$(CF_3)_2$ | Cl | H | $CH_2S(O)Et$ | *1 |
| 1-150 | 3,5-$Br_2$-4-F | Cl | H | $CH_2S(O)Et$ | *1 |
| 1-151 | 3,5-$Br_2$-4-Cl | Cl | H | $CH_2S(O)Et$ | *1 |
| 1-152 | 3,4-$Cl_2$-5-$CF_3$ | Cl | H | $CH_2S(O)Et$ | *1 |
| 1-153 | 3-Cl-5-$CF_3$ | Br | H | $CH_2S(O)Et$ | *1 |
| 1-154 | 3-Br-5-$CF_3$ | Br | H | $CH_2S(O)Et$ | *1 |
| 1-155 | 3,5-$(CF_3)_2$ | Br | H | $CH_2S(O)Et$ | 96.0-98.0 |
| 1-156 | 3,5-$(CF_3)_2$ | I | H | $CH_2S(O)Et$ | *1 |
| 1-157 | 3,4-$Cl_2$-5-$CF_3$ | Br | H | $CH_2S(Et)=NC(O)CF_3$ | *1 |
| 1-158 | 3-Br-5-$CF_3$ | H | $CH_3$ | $CH_2SO_2Et$ | *1 |
| 1-159 | 3,5-$(CF_3)_2$ | H | CN | $CH_2SO_2Et$ | *1 |
| 1-160 | 3,5-$(CF_3)_2$ | F | H | $CH_2SO_2Et$ | 128.0-130.0 |
| 1-161 | 3-$CF_3$-4-Cl | Cl | H | $CH_2SO_2Et$ | 130.0-132.0 |
| 1-162 | 3-Br-5-$CF_3$ | Cl | H | $CH_2SO_2Et$ | 141.0-143.0 |
| 1-163 | 3-I-5-$CF_3$ | Cl | H | $CH_2SO_2Et$ | *1 |
| 1-164 | 3,5-$(CF_3)_2$ | Cl | H | $CH_2SO_2Et$ | 155.0-158.0 |
| 1-165 | 3,5-$Br_2$-4-F | Cl | H | $CH_2SO_2Et$ | 112.0-116.0 |
| 1-166 | 3,5-$Br_2$-4-Cl | Cl | H | $CH_2SO_2Et$ | 135.0-136.0 |
| 1-167 | 3,4-$Cl_2$-5-$CF_3$ | Cl | H | $CH_2SO_2Et$ | 193.0-194.0 |
| 1-168 | 3-Cl-5-$CF_3$ | Br | H | $CH_2SO_2Et$ | 152.0-156.0 |
| 1-169 | 3-Br-5-$CF_3$ | Br | H | $CH_2SO_2Et$ | 147.0-149.0 |
| 1-170 | 3,5-$(CF_3)_2$ | Br | H | $CH_2SO_2Et$ | 164.0-167.0 |
| 1-171 | 3,4-$Cl_2$-5-$CF_3$ | Br | H | $CH_2SO_2Et$ | 190.0-192.0 |
| 1-172 | 3,5-$(CF_3)_2$ | I | H | $CH_2SO_2Et$ | 162.0-163.0 |
| 1-173 | 3,5-$(CF_3)_2$ | Cl | H | $CH_2S(O)(Et)=NH$ | 173.0-175.0 |
| 1-174 | 3,5-$(CF_3)_2$ | H | CN | $CH_2S(O)(Et)=NC(O)CF_3$ | *1 |
| 1-175 | 3,5-$(CF_3)_2$ | Cl | H | $CH_2SO_2CF_3$ | 183.0-185.0 |
| 1-176 | 3,5-$(CF_3)_2$ | Cl | H | $CH_2SCH_2CF_3$ | 141.0-142.0 |
| 1-177 | 3,5-$(CF_3)_2$ | Cl | H | $CH_2S(O)CH_2CF_3$ | 146.0-148.0 |
| 1-178 | 3,5-$(CF_3)_2$ | Cl | H | $CH_2SCH_2CN$ | 122.0-124.0 |
| 1-179 | 3,5-$(CF_3)_2$ | Cl | H | $CH_2S(O)CH_2CN$ | *1 |
| 1-180 | 3,5-$(CF_3)_2$ | Cl | H | $CH_2SO_2CH_2CN$ | *1 |
| 1-181 | 3,4,5-$Cl_3$ | Cl | H | $CH_2SCF_2C(O)OEt$ | *1 |
| 1-182 | 3,5-$(CF_3)_2$ | Cl | H | $CH_2SCHFC(O)NHCH_3$ | *1 |
| 1-183 | 3,4,5-$Cl_3$ | Cl | H | $CH_2SCF_2C(O)NHCH_3$ | *1 |
| 1-184 | 3,4,5-$Cl_3$ | Cl | H | $CH_2SC(O)CF_3$ | *1 |
| 1-185 | 3,5-$(CF_3)_2$ | Cl | H | $CH_2SC(O)SCH_3$ | *1 |
| 1-186 | 3,5-$(CF_3)_2$ | Br | H | $CH(CH_3)SCH_3$ | 138.0-140.0 |
| 1-187 | 3,5-$(CF_3)_2$ | Br | H | $CH(CH_3)SO_2CH_3$ | 154.0-156.0 |
| 1-188 | 3,5-$(CF_3)_2$ | Br | H | $CH(CH_3)SEt$ | 131.0-134.0 |
| 1-189 | 3,5-$(CF_3)_2$ | H | $CH_3$ | E-1-1a | *1 |
| 1-190 | 3,5-$(CF_3)_2$ | H | CN | E-1-1a | *1 |
| 1-191 | 3,5-$(CF_3)_2$ | I | H | E-1-1a | *1 |
| 1-192 | 3,5-$(CF_3)_2$ | Cl | H | E-3-1a | 140.0-143.0 |
| 1-193 | 3,5-$(CF_3)_2$ | Cl | H | E-3-1b | *1 |
| 1-194 | 3,5-$(CF_3)_2$ | Cl | H | E-3-1c | *1 |
| 1-195 | 3,5-$(CF_3)_2$ | Br | H | $C(CH_3)_2SCH_3$ | 146.0-150.0 |
| 1-196 | 3,5-$(CF_3)_2$ | Cl | H | $CHFSCH_3$ | *1 |
| 1-197 | 3,4-$Cl_2$-5-$CF_3$ | Cl | H | $CHFSCH_3$ | *1 |
| 1-198 | 3,5-$(CF_3)_2$ | Cl | H | $CHFS(O)CH_3$ | *1 |
| 1-199 | 3,5-$(CF_3)_2$ | Cl | H | $CHFSO_2CH_3$ | *1 |
| 1-200 | 3,5-$(CF_3)_2$ | Cl | H | $CHClSCH_3$ | *1 |
| 1-201 | 3,5-$(CF_3)_2$ | Cl | H | $CH(OCH_3)SCH_3$ | *1 |
| 1-202 | 3,5-$(CF_3)_2$ | Cl | H | $CH(OEt)SCH_3$ | *1 |
| 1-203 | 3,5-$(CF_3)_2$ | Cl | H | $CH(OCH_3)S(O)CH_3$ | *1 |
| 1-204 | 3,5-$(CF_3)_2$ | Cl | H | $CH(OCH_3)SO_2CH_3$ | *1 |
| 1-205 | 3-Br-5-$CF_3$ | Cl | H | $CH(SCH_3)_2$ | 134.0-135.0 |
| 1-206 | 3,5-$(CF_3)_2$ | Cl | H | $CH(SCH_3)_2$ | 130.0-132.0 |
| 1-207 | 3,4,5-$Cl_3$ | Cl | H | $CH(SCH_3)_2$ | *1 |
| 1-208 | 3-Cl-5-$CF_3$ | Br | H | $CH(SCH_3)_2$ | 130.0-133.0 |
| 1-209 | 3,5-$(CF_3)_2$ | Cl | H | $CH(SCH_3)S(O)CH_3$ | *1 |
| 1-210 | 3-Br-5-$CF_3$ | Cl | H | $CH[S(O)CH_3]_2$ | *1 |
| 1-211 | 3,5-$(CF_3)_2$ | Cl | H | $CH[S(O)CH_3]_2$ | *1 |
| 1-212 | 3-Br-5-$CF_3$ | Cl | H | $CH[S(O)CH_3]SO_2CH_3$ | *1 |

TABLE 3-continued

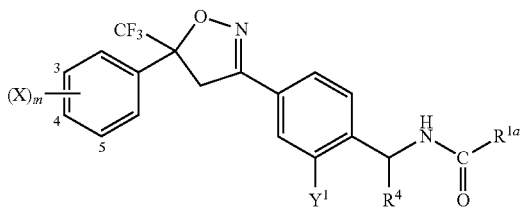

| No. | (X)$_m$ | Y$^1$ | R$^4$ | R$^{1a}$ | m.p. (° C.) |
|---|---|---|---|---|---|
| 1-213 | 3,5-(CF$_3$)$_2$ | Cl | H | CH[S(O)CH$_3$]SO$_2$CH$_3$ | *1 |
| 1-214 | 3,5-(CF$_3$)$_2$ | F | H | CH(SEt)$_2$ | 96.0-97.0 |
| 1-215 | 3,5-(CF$_3$)$_2$ | Cl | H | CH(SEt)$_2$ | 125.0-126.0 |
| 1-216 | 3,5-Br$_2$-4-F | Cl | H | CH(SEt)$_2$ | *1 |
| 1-217 | 3,5-Br$_2$-4-Cl | Cl | H | CH(SEt)$_2$ | *1 |
| 1-218 | 3,4-Cl$_2$-5-CF$_3$ | Cl | H | CH(SEt)$_2$ | *1 |
| 1-219 | 3,5-(CF$_3$)$_2$ | F | H | CH(SEt)S(O)Et | *1 |
| 1-220 | 3,5-(CF$_3$)$_2$ | Cl | H | CH(SEt)S(O)Et | *1 |
| 1-221 | 3,5-Br$_2$-4-F | Cl | H | CH(SEt)S(O)Et | *1 |
| 1-222 | 3,4-Cl$_2$-5-CF$_3$ | Cl | H | CH(SEt)S(O)Et | *1 |
| 1-223 | 3,5-(CF$_3$)$_2$ | Cl | H | CH[S(O)Et]$_2$ | *1 |
| 1-224 | 3,4-Cl$_2$-5-CF$_3$ | Cl | H | CH[S(O)Et]$_2$ | *1 |
| 1-225 | 3,5-(CF$_3$)$_2$ | Cl | H | CH(SEt)SO$_2$Et | 126.0-128.0 |
| 1-226 | 3,5-(CF$_3$)$_2$ | Cl | H | CH[S(O)Et]SO$_2$Et | 122.0-123.0 |
| 1-227 | 3,4-Cl$_2$-5-CF$_3$ | Cl | H | CH[S(O)Et]SO$_2$Et | *1 |
| 1-228 | 3,5-(CF$_3$)$_2$ | Cl | H | CH(SO$_2$Et)$_2$ | 187.0-188.0 |
| 1-229 | 3,4-Cl$_2$-5-CF$_3$ | Cl | H | CH(SO$_2$Et)$_2$ | 193.0-196.0 |
| 1-230 | 3-Cl-5-CF$_3$ | H | CH$_3$ | CH$_2$SCH$_3$ | *1 |
| 1-231 | 3-I-5-CF$_3$ | H | CH$_3$ | CH$_2$SCH$_3$ | *1 |
| 1-232 | 3,5-Br$_2$-4-F | H | CH$_3$ | CH$_2$SCH$_3$ | 149.0-151.0 |
| 1-233 | 3,5-Br$_2$-4-F | H | CH$_3$ | CH$_2$S(O)CH$_3$ | *1 |
| 1-234 | 3-Cl-5-CF$_3$ | H | CH$_3$ | CH$_2$SO$_2$CH$_3$ | 166.0-168.0 |
| 1-235 | 3,5-Br$_2$-4-F | H | CH$_3$ | CH$_2$SO$_2$CH$_3$ | 184.0-188.0 |
| 1-236 | 3-Cl-5-CF$_3$ | H | CH$_3$ | CH$_2$SEt | *1 |
| 1-237 | 3-I-5-CF$_3$ | H | CH$_3$ | CH$_2$SEt | 97.0-98.0 |
| 1-238 | 3,5-Br$_2$-4-F | H | CH$_3$ | CH$_2$SEt | 125.0-129.0 |
| 1-239 | 3-Br-5-CF$_3$ | Cl | H | CH$_2$S(O)Et | *1 |
| 1-240 | 3,5-Br$_2$-4-F | H | CH$_3$ | CH$_2$S(O)Et | *1 |
| 1-241 | 3,5-Br$_2$-4-F | H | CH$_3$ | CH$_2$SO$_2$Et | 152.0-154.0 |
| 1-242 | 3,5-Br$_2$-4-F | H | CH$_3$ | CH(SEt)$_2$ | *1 |

TABLE 4

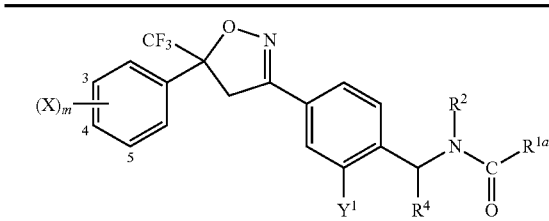

| No. | (X)$_m$ | Y$^1$ | R$^4$ | R$^2$ | R$^1$ | m.p. (° C.) |
|---|---|---|---|---|---|---|
| 2-001 | 3,5-(CF$_3$)$_2$ | Cl | H | CH$_3$ | CH$_2$SEt | *1 |
| 2-002 | 3,4,5-Cl$_3$ | Cl | H | CH$_3$ | CH$_2$SEt | *1 |
| 2-003 | 3,5-(CF$_3$)$_2$ | Cl | H | Et | CH$_2$SEt | *1 |
| 2-004 | 3,5-(CF$_3$)$_2$ | Cl | H | CH$_2$C≡CH | CH$_2$SEt | *1 |
| 2-005 | 3,4,5-Cl$_3$ | Cl | H | CH$_3$ | CH$_2$SO$_2$Et | *1 |
| 2-006 | 3,5-(CF$_3$)$_2$ | Cl | H | CH$_3$ | CH$_2$SCH$_3$ | *1 |
| 2-007 | 3,5-(CF$_3$)$_2$ | Cl | H | Et | CH$_2$SCH$_3$ | *1 |
| 2-008 | 3-Br-5-CF$_3$ | Br | H | Et | CH$_2$SCH$_3$ | *1 |
| 2-009 | 3,5-(CF$_3$)$_2$ | Cl | H | CH$_2$CN | CH$_2$SCH$_3$ | *1 |
| 2-010 | 3,5-(CF$_3$)$_2$ | Cl | H | CH$_2$C≡CH | CH$_2$SCH$_3$ | 148.0-149.0 |
| 2-011 | 3,5-(CF$_3$)$_2$ | Cl | H | CH$_3$ | CH$_2$S(O)CH$_3$ | *1 |
| 2-012 | 3,5-(CF$_3$)$_2$ | Cl | H | Et | CH$_2$S(O)CH$_3$ | *1 |
| 2-013 | 3,5-(CF$_3$)$_2$ | Cl | H | CH$_2$CN | CH$_2$S(O)CH$_3$ | *1 |
| 2-014 | 3,5-(CF$_3$)$_2$ | Cl | H | CH$_2$C≡CH | CH$_2$S(O)CH$_3$ | *1 |
| 2-015 | 3-Br-5-CF$_3$ | Br | H | Et | CH$_2$S(O)CH$_3$ | *1 |
| 2-016 | 3,5-(CF$_3$)$_2$ | Cl | H | CH$_3$ | CH$_2$SO$_2$CH$_3$ | *1 |
| 2-017 | 3,5-(CF$_3$)$_2$ | Cl | H | Et | CH$_2$SO$_2$CH$_3$ | *1 |
| 2-018 | 3,5-(CF$_3$)$_2$ | Cl | H | CH$_2$CN | CH$_2$SO$_2$CH$_3$ | *1 |
| 2-019 | 3,5-(CF$_3$)$_2$ | Cl | H | CH$_2$C≡CH | CH$_2$SO$_2$CH$_3$ | *1 |
| 2-020 | 3-Br-5-CF$_3$ | Br | H | Et | CH$_2$SO$_2$CH$_3$ | 78.0-80.0 |
| 2-021 | 3,5-(CF$_3$)$_2$ | Cl | H | n-Pr | CH$_2$SEt | *1 |
| 2-022 | 3,5-(CF$_3$)$_2$ | Cl | H | i-Bu | CH$_2$SEt | *1 |
| 2-023 | 3,5-(CF$_3$)$_2$ | Cl | H | CH$_2$Pr-c | CH$_2$SEt | *1 |
| 2-024 | 3,5-(CF$_3$)$_2$ | Cl | H | CH$_2$CN | CH$_2$SEt | *1 |
| 2-025 | 3,5-(CF$_3$)$_2$ | Cl | H | CH$_2$CH═CH$_2$ | CH$_2$SEt | *1 |
| 2-026 | 3,5-(CF$_3$)$_2$ | Cl | H | CH$_2$Ph | CH$_2$SEt | *1 |
| 2-027 | 3,5-(CF$_3$)$_2$ | Cl | H | CH$_3$ | CH$_2$S(O)Et | *1 |
| 2-028 | 3,5-(CF$_3$)$_2$ | Cl | H | Et | CH$_2$S(O)Et | *1 |
| 2-029 | 3,5-(CF$_3$)$_2$ | Cl | H | CH$_2$C≡CH | CH$_2$S(O)Et | *1 |
| 2-030 | 3,5-(CF$_3$)$_2$ | Cl | H | CH$_3$ | CH$_2$SO$_2$Et | *1 |
| 2-031 | 3,5-(CF$_3$)$_2$ | Cl | H | Et | CH$_2$SO$_2$Et | *1 |
| 2-032 | 3,5-(CF$_3$)$_2$ | Cl | H | CH$_2$C≡CH | CH$_2$SO$_2$Et | *1 |

TABLE 5

| No. | (X)$_m$ | Y$^1$ | R$^4$ | R$^{1a}$ | m. p. (° C.) |
|---|---|---|---|---|---|
| 3-001 | 3,4-Cl$_2$-5-CF$_3$ | Br | H | CH$_2$SCH$_3$ | *1 |

TABLE 6

| No. | (X)$_m$ | Y$^1$ | A$^1$ | R$^4$ | R$^{1a}$ | m. p. (° C.) |
|---|---|---|---|---|---|---|
| 4-001 | 3,5-(CF$_3$)$_2$ | Cl | C—Cl | H | CH$_2$SO$_2$CH$_3$ | 191.0-195.0 |

Among the compounds of the present invention, $^1$H NMR data of the compounds of which the melting point is not described is shown in Table 7.

TABLE 7

| No. | $^1$H NMR (CDCl$_3$, Me$_4$Si, 300 MHz) |
|---|---|
| 1-002 | δ7.65 (s, 2H), 7.60 (d, J = 8.4 Hz, 2H), 7.40 (d, J = 8.4 Hz, 2H), 7.10 (d, J = 8.1 Hz, 1H), 5.1-5.2 (m, 1H), 4.05 (d, J = 17.4 Hz, 1H), 3.65 (d, J = 17.4 Hz, 1H), 3.15-3.25 (m, 2H), 2.10 (s, 3H), 1.50 (d, J = 6.9 Hz, 3H). |
| 1-003 | δ7.74 (d, J = 8.4 Hz, 2H), 7.63 (s, 2H), 7.56 (d, J = 8.4 Hz, 2H), 7.48 (d, J = 8.4 Hz, 1H), 6.20 (d, J = 8.4 Hz, 1H), 4.08 (d, J = 17.4 Hz, 1H), 3.69 (d, J = 17.4 Hz, 1H), 3.32 (d, J = 16.5 Hz, 1H), 3.26 (d, J = 16.5 Hz, 1H), 2.11 (s, 3H). |
| 1-006 | δ7.70 (d, J = 1.8 Hz, 1H), 7.63 (s, 2H), 7.52 (dd, J = 7.8, 1.8 Hz, 1H), 7.47 (d, J = 7.8 Hz, 1H), 7.40 (bs, 1H), 6.61 (t, J = 73.5 Hz, 1H), 4.58 (d, J = 6.3 Hz, 2H), 4.07 (d, J = 17.4 Hz, 1H), 3.66 (d, J = 17.4 Hz, 1H), 3.24 (s, 2H), 2.10 (s, 3H). |
| 1-007 | δ8.08 (s, 2H), 7.07 (s, 1H), 7.90 (s, 1H), 7.59 (d, J = 8.1 Hz, 1H), 7.47 (d, J = 8.1 Hz, 1H), 7.4-7.5 (m, 1H), 4.56 (d, J = 6.3 Hz, 2H), 4.18 (d, J = 17.4 Hz, 1H), 3.73 (d, J = 17.4 Hz, 1H), 3.23 (s, 2H), 2.11 (s, 3H). |
| 1-008 | δ7.87 (d, J = 1.8 Hz), 7.63 (s, 2H), 7.57 (dd, J = 8.1, 1.8 Hz, 1H), 7.46 (d, J = 8.1 Hz, 1H), 7.44 (bs, 1H), 4.56 (d, J = 6.3 Hz, 2H), 4.05 (d, J = 17.3 Hz, 1H), 3.65 (d, J = 17.3 Hz, 1H), 3.23 (s, 2H), 2.11 (s, 3H). |
| 1-010 | δ7.64 (s, 2H), 7.62 (d, J = 8.1 Hz, 2H), 7.39 (d, J = 8.1 Hz, 2H), 6.96 (d, J = 7.5 Hz, 1H), 5.05-5.15 (m, 1H), 4.06 (d, J = 17.1 Hz, 1H), 3.89 (s, 2H), 3.77 (d, J = 17.1 Hz, 1H), 3.00 (s, 3H), 1.50 (d, J = 6.9 Hz, 3H). |
| 1-013 | δ8.07 (s, 2H), 7.97 (s, 1H), 7.89 (d, J = 1.8 Hz, 1H), 7.62 (dd, J = 8.1, 1.8 Hz, 1H), 7.49 (d, J = 8.1 Hz, 1H), 6.90 (t, J = 6.0 Hz, 1H), 4.59 (d, J = 6.0 Hz, 2H), 4.17 (d, J = 17.1 Hz, 1H), 3.92 (s, 2H), 3.72 (d, J = 17.1 Hz, 1H), 3.06 (s, 3H). |
| 1-015 | δ8.31 (s, 1H), 7.98 (d, J = 8.4 Hz, 1H), 7.77 (d, J = 8.4 Hz, 1H), 7.64 (s, 2H), 7.15 (t, J = 6.6 Hz, 1H), 4.80 (d, J = 6.6 Hz, 2H), 4.11 (d, J = 17.4 Hz, 1H), 3.91 (s, 2H), 3.72 (d, J = 17.4 Hz, 1H), 3.04 (s, 3H). |
| 1-016 | δ7.64 (s, 2H), 7.62 (d, J = 8.4 Hz, 2H), 7.46 (d, J = 8.4 Hz, 2H), 7.26 (bs, 1H), 4.51 (d, J = 6.3 Hz, 2H), 4.08 (d, J = 17.4 Hz, 1H), 3.67 (d, J = 17.4 Hz, 1H), 3.29 (s, 2H), 2.55 (q, J = 7.8 Hz, 2H), 1.25 (t, J = 7.8 Hz, 3H). |
| 1-017 | δ7.65 (s, 2H), 7.60 (d, J = 8.4 Hz, 2H), 7.35 (d, J = 8.4 Hz, 2H), 7.15 (d, J = 8.1 Hz, 1H), 5.05-5.2 (m, 1H), 4.05 (d, J = 17.1 Hz, 1H), 3.65 (d, J = 17.1 Hz, 1H), 3.15-3.3 (m, 2H), 2.50 (q, J = 7.5 Hz, 2H), 1.50 (d, J = 6.9 Hz, 3H), 1.25 (t, J = 7.5 Hz, 3H). |
| 1-018 | δ7.73 (d, J = 8.4 Hz, 2H), 7.64 (s, 2H), 7.55 (d, J = 8.4 Hz, 2H), 7.52 (d, J = 9.0 Hz, 1H), 6.19 (d, J = 9.0 Hz, 1H), 4.08 (d, J = 17.4 Hz, 1H), 3.69 (d, J = 17.4 Hz, 1H), 3.35 (d, J = 16.5 Hz, 1H), 3.29 (d, J = 16.5 Hz, 1H), 2.54 (q, J = 7.5 Hz, 2H), 1.25 (t, J = 7.5 Hz, 3H). |
| 1-019 | δ8.07 (s, 2H), 7.97 (s, 1H), 7.72 (d, J = 1.5 Hz, 1H), 7.54 (dd, J = 7.8, 1.5 Hz, 1H), 7.47 (d, J = 7.8 Hz, 1H), 7.41 (bs, 1H), 4.57 (d, J = 6.3 Hz, 2H), 4.17 (d, J = 17.4 Hz, 1H), 3.72 (d, J = 17.4 Hz, 1H), 3.26 (s, 2H), 2.53 (q, J = 7.5 Hz, 2H), 1.23 (t, J = 7.5 Hz, 3H). |
| 1-020 | δ7.69 (d, J = 1.5 Hz, 1H), 7.63 (s, 2H), 7.51 (dd, J = 7.8, 1.5 Hz, 1H), 7.45 (d, J = 7.8 Hz, 1H), 7.44 (bs, 1H), 4.56 (d, J = 6.3 Hz, 2H), 4.05 (d, J = 17.4 Hz, 1H), 3.66 (d, J = 17.4 Hz, 1H), 3.26 (s, 2H), 2.53 (q, J = 7.5 Hz, 2H), 1.23 (t, J = 7.5 Hz, 3H). |
| 1-021 | δ7.70 (d, J = 1.5 Hz, 1H), 7.63 (s, 2H), 7.52 (dd, J = 8.1, 1.5 Hz, 1H), 7.46 (d, J = 8.1 Hz, 1H), 7.44 (bs, H), 6.61 (t, J = 73.5 Hz, 1H), 4.57 (d, J = 6.3 Hz, 2H), 4.07 (d, J = 17.4 Hz, 1H), 3.67 (d, J = 17.4 Hz, 1H), 3.27 (s, 2H), 2.53 (q, J = 7.5 Hz, 2H), 1.23 (t, J = 7.5 Hz, 3H). |

TABLE 7-continued

| No. | $^1$H NMR (CDCl$_3$, Me$_4$Si, 300 MHz) |
|---|---|
| 1-022 | δ8.07 (s, 2H), 7.93 (s, 1H), 7.89 (d, J = 1.5 Hz, 1H), 7.59 (dd, J = 8.1, 1.5 Hz, 1H), 7.45-7.55 (m, 1H), 7.46 (d, J = 8.1 Hz, 1H), 4.55 (d, J = 6.0 Hz, 2H), 4.17 (d, J = 17.1 Hz, 1H), 3.72 (d, J = 17.1 Hz, 1H), 3.27 (s, 2H), 2.53 (q, J = 7.5 Hz, 2H), 1.24 (t, J = 7.5 Hz, 3H). |
| 1-023 | δ7.86 (d, J = 1.8 Hz, 1H), 7.63 (s, 2H), 7.56 (dd, J = 8.1, 1.8 Hz, 1H), 7.4-7.5 (m, 2H), 4.55 (d, J = 6.0 Hz, 2H), 4.05 (d, J = 17.4 Hz, 1H), 3.65 (d, J = 17.4 Hz, 1H), 3.26 (s, 2H), 2.53 (q, J = 7.4 Hz, 2H), 1.23 (t, J = 7.4 Hz, 3H). |
| 1-024 | δ7.64 (s, 2H), 7.62 (d, J = 8.4 Hz, 2H), 7.39 (bs, 1H), 7.38 (d, J = 8.4 Hz, 2H), 4.53 (d, J = 6.0 Hz, 2H), 4.07 (d, J = 17.4 Hz, 1H), 3.67 (d, J = 17.4 Hz, 1H), 3.67 and 3.31 (d, J = 17.4 Hz, 2H), 2.7-2.95 (m, 2H), 1.33 (t, J = 7.5 Hz, 3H). |
| 1-025 | δ7.45-7.7 (m, 6H), 4.59 (d, J = 6.0 Hz, 2H), 4.04 (d, J = 17.4 Hz, 1H), 3.65-3.75 (m, 1H), 3.65 (d, J = 17.4 Hz, 1H), 3.3-3.4 (m, 1H), 2.85-3.0 (m, 2H), 1.2-1.45 (m, 3H). |
| 1-026 | δ7.64 (s, 2H), 7.62 (d, J = 8.4 Hz, 2H), 7.36 (d, J = 8.4 Hz, 2H), 6.87 (bs, 1H), 4.52 (d, J = 5.7 Hz, 2H), 4.07 (d, J = 17.4 Hz, 1H), 3.89 (s, 2H), 3.67 (d, J = 17.4 Hz, 1H), 3.15 (q, J = 7.5 Hz, 2H), 1.43 (t, J = 7.5 Hz, 3H). |
| 1-028 | δ7.70 (s, 1H), 7.64 (s, 2H), 7.4-7.55 (m, 3H), 4.58 (d, J = 6.3 Hz, 2H), 4.06 (d, J = 17.3 Hz, 1H), 3.66 (d, J = 17.3 Hz, 1H), 3.28 (s, 2H), 3.02 (qui, J = 6.6 Hz, 1H), 1.9-2.0 (m, 2H), 1.4-1.75 (m, 6H). |
| 1-031 | δ7.6-7.7 (m, 3H), 7.4-7.55 (m, 2H), 6.85-7.1 (m, 1H), 4.54 (t, J = 6.0 Hz, 2H), 4.06 (d, J = 17.4 Hz, 1H), 3.68 (d, J = 17.4 Hz, 1H), 3.43 (s, 2H), 3.42 (s, 2H). |
| 1-032 | δ7.68 (d, J = 1.5 Hz, 1H), 7.63 (s, 2H), 7.4-7.55 (m, 3H), 4.56 (d, J = 6.3 Hz, 2H), 4.16 (q, J = 7.2 Hz, 2H), 4.06 (d, J = 17.4 Hz, 1H), 3.68 (d, J = 17.4 Hz, 1H), 3.37 (s, 2H), 3.28 (s, 2H), 1.27 (t, J = 7.2 Hz, 3H). |
| 1-033 | δ7.67 (d, J = 1.2 Hz, 1H), 7.63 (s, 2H), 7.4-7.55 (m, 3H), 6.60 (bs, 1H), 4.55 (d, J = 6.3 Hz, 2H), 4.06 (d, J = 17.4 Hz, 1H), 3.67 (d, J = 17.4 Hz, 1H), 3.29 (s, 2H), 3.20 (s, 2H), 2.81 (d, J = 5.4 Hz, 3H). |
| 1-034 | δ7.3-7.7 (m, 6H), 5.6-5.8 (m, 1H), 5.0-5.15 (m, 2H), 4.55 (d, J = 6.0 Hz, 2H), 4.07 (d, J = 17.3 Hz, 1H), 3.68 (d, J = 17.3 Hz, 1H), 3.20 (s, 2H), 3.12 (d, J = 7.5 Hz, 2H). |
| 1-035 | δ7.68 (s, 1H), 7.63 (s, 2H), 7.4-7.55 (m, 2H), 7.25 (t, J = 6.0 Hz, 1H), 4.56 (d, J = 6.0 Hz, 2H), 4.06 (d, J = 17.4 Hz, 1H), 3.67 (d, J = 17.4 Hz, 1H), 3.42 (s, 2H), 3.29 (d, J = 2.7 Hz, 2H), 2.23 (t, J = 2.7 Hz, 1H). |
| 1-037 | δ8.17 (d, J = 0.6 Hz, 1H), 7.66 (d, J = 1.5 Hz, 1H), 7.62 (s, 2H), 7.4-7.5 (m, 3H), 7.11 (t, J = 0.9 Hz, 1H), 6.87 (bs, 1H), 4.55 (d, J = 6.0 Hz, 2H), 4.05 (d, J = 17.4 Hz, 1H), 3.81 (s, 2H), 3.66 (d, J = 17.4 Hz, 1H). |
| 1-039 | δ7.6-7.7 (m, 3H), 7.3-7.55 (m, 3H), 5.85 (bs, 1H), 4.50 (d, J = 6.0 Hz, 2H), 4.05 (d, J = 17.4 Hz, 1H), 3.67 (d, J = 17.4 Hz, 1H), 3.54 (s, 2H), 3.2-3.4 (m, 2H), 1.17 (t, J = 7.5 Hz, 3H). |
| 1-040 | δ8.89 (bs, 1H), 7.55-7.65 (m, 5H), 7.35-7.45 (m, 1H), 7.01 (bs, 1H), 4.49 (bs, 2H), 4.03 (d, J = 17.3 Hz, 1H), 3.66 (s, 2H), 3.65 (d, J = 17.3 Hz, 1H). |
| 1-041 | δ7.4-7.7 (m, 6H), 7.1-7.2 (m, 2H), 4.53 (d, J = 6.3 Hz, 2H), 4.05 (d, J = 17.4 Hz, 1H), 3.67 (d, J = 17.4 Hz, 1H), 3.44 (s, 2H). |
| 1-043 | δ7.69 (s, 1H), 7.62 (s, 2H), 7.4-7.5 (m, 2H), 7.23 (t, J = 6.0 Hz, 1H), 4.55 (d, J = 6.0 Hz, 2H), 4.05 (d, J = 17.3 Hz, 1H), 3.65 (d, J = 17.3 Hz, 1H), 3.35 (q, J = 7.2 Hz, 1H), 2.03 (s, 3H), 1.47 (d, J = 7.2 Hz, 3H). |
| 1-044 | δ8.07 (s, 2H), 7.97 (s, 1H), 7.69 (d, J = 1.5 Hz, 1H), 7.3-7.6 (m, 3H), 4.5-4.65 (m, 2H), 1.17 (d, J = 17.4 Hz, 1H), 3.72 (d, J = 17.4 Hz, 1H), 3.21 (q, J = 7.5 Hz, 1H), 2.59 and 2.40 (s, 3H), 1.63 and 1.31 (d, J = 7.5 Hz, 3H). |
| 1-045 | δ7.3-7.7 (m, 6H), 4.58 (d, J = 6.3 Hz, 2H), 4.05 (d, J = 17.3 Hz, 1H), 3.66 (d, J = 17.3 Hz, 1H), 3.25 (q, J = 3.9 Hz, 1H), 2.58 (s, 3H), 1.61 (dd, J = 3.9, 1.2 Hz, 3H). |
| 1-049 | δ7.6-7.7 (m, 3H), 7.4-7.5 (m, 2H), 7.30 (t, J = 6.0 Hz, 1H), 4.54 (d, J = 6.0 Hz, 2H), 4.05 (d, J = 17.3 Hz, 1H), 3.67 (d, J = 17.3 Hz, 1H), 3.43 (q, J = 7.5 Hz, 1H), 2.50 (q, J = 7.5 Hz, 2H), 1.47 (d, J = 7.5 Hz, 3H), 1.20 (t, J = 7.5 Hz, 3H). |
| 1-050 | δ8.07 (s, 2H), 7.97 (s, 1H), 7.69 (d, J = 1.5 Hz, 1H), 7.3-7.6 (m, 3H), 4.5-4.7 (m, 2H), 4.17 (d, J = 17.4 Hz, 1H), 3.72 (d, J = 17.4 Hz, 1H), 3.25 (q, J = 7.5 Hz, 1H), 2.65-2.9 and 2.45-2.6 (m, 2H), 1.64 (d, J = 7.5 Hz, 3H), 1.34 and 1.33 (d, J = 7.8 Hz, 3H). |
| 1-051 | δ7.45-7.7 (m, 6H), 4.59 (d, J = 6.0 Hz, 2H), 4.05 (d, J = 17.3 Hz, 1H), 3.66 (d, J = 17.3 Hz, 1H), 3.27 (q, J = 7.5 Hz, 1H), 2.75 (q, J = 7.5 Hz, 2H), 1.63 (d, J = 7.5 Hz, 3H), 1.34 (t, J = 7.5 Hz, 3H). |
| 1-052 | δ8.07 (s, 2H), 7.97 (s, 1H), 7.67 (dd, J = 2.7, 1.5 Hz, 1H), 7.4-7.65 (m, 2H), 7.20 (t, J = 5.7 Hz, 1H), 4.5-4.7 (m, 2H), 4.18 (d, J = 17.4 Hz, 1H), 3.87 (q, J = 7.2 Hz, 1H), 3.74 (d, J = 17.4 Hz, 1H), 3.07 (dq, J = 7.5, 1.8 Hz, 2H), 1.64 (d, J = 7.2 Hz, 3H), 1.36 (t, J = 7.5 Hz, 3H). |

TABLE 7-continued

| No. | $^1$H NMR (CDCl$_3$, Me$_4$Si, 300 MHz) |
|---|---|
| 1-053 | δ7.6-7.7 (m, 3H), 7.45-7.55 (m, 2H), 7.03 (bs, 1H), 4.58 (d, J = 6.0 Hz, 2H), 4.05 (d, J = 17.3 Hz, 1H), 3.82 (q, J = 6.6 Hz, 1H), 3.65 (d, J = 17.3 Hz, 1H), 3.05 (q, J = 7.2 Hz, 2H), 1.65 (d, J = 6.6 Hz, 3H), 1.36 (t, J = 7.2 Hz, 3H). |
| 1-054 | δ8.08 (s, 2H), 7.97 (s, 1H), 7.69 (d, J = 1.5 Hz, 1H), 7.35-7.6 (m, 3H), 4.53 (d, J = 6.0 Hz, 2H), 4.18 (d, J = 17.4 Hz, 1H), 3.96 (dd, J = 7.5, 4.5 Hz, 1H), 3.75 (d, J = 17.4 Hz, 1H), 2.8-3.05 (m, 2H), 1.75-2.4 (m, 4H). |
| 1-055 | δ7.69 (d, J = 1.8 Hz, 1H), 7.63 (s, 2H), 7.5-7.55 (m, 2H), 7.4-7.45 (m, 1H), 4.53 (d, J = 6.0 Hz, 2H), 4.06 (d, J = 17.4 Hz, 1H), 3.96 (dd, J = 7.5, 4.2 Hz, 1H), 3.67 (d, J = 17.4 Hz, 1H), 2.85-3.05 (m, 2H), 2.25-2.35 (m, 1H), 2.0-2.2 (m, 2H), 1.8-1.9 (m, 1H). |
| 1-056 | δ8.07 (s, 2H), 7.97 (s, 1H), 7.89 (s, 1H), 7.59 (d, J = 8.1 Hz, 1H), 7.55 (t, J = 6.0 Hz, 1H), 7.42 (d, J = 8.1 Hz, 1H), 4.52 (d, J = 6.0 Hz, 2H), 4.17 (d, J = 17.4 Hz, 1H), 3.96 (dd, J = 7.5, 4.2 Hz, 1H), 3.71 (d, J = 17.4 Hz, 1H), 2.95-3.05 (m, 1H), 2.85-2.95 (m, 1H), 2.25-2.35 (m, 1H), 2.0-2.25 (m, 2H), 1.75-1.95 (m, 1H). |
| 1-057 | δ8.20 and 7.76 (t, J = 6.0 Hz, 1H), 7.4-7.7 (m, 5H), 4.4-4.7 (m, 2H), 4.0-4.15 (m, 1H), 3.8-3.9 and 3.25-3.35 (m, 1H), 3.6-3.75 (m, 1H), 1.95-3.25 (m, 6H). |
| 1-059 | δ7.6-7.7 (m, 3H), 7.4-7.55 (m, 2H), 4.92 (s, 1H), 4.53 (dd, J = 6.9, 2.4 Hz, 2H), 4.05 (d, J = 17.4 Hz, 1H), 3.67 (d, J = 17.4 Hz, 1H), 3.29 (s, 4H). |
| 1-060 | δ8.07 (s, 2H), 7.96 (s, 1H), 7.71 (d, J = 1.2 Hz, 1H), 7.45-7.6 (m, 3H), 4.52 (d, J = 6.0 Hz, 2H), 4.17 (d, J = 17.4 Hz, 1H), 3.72 (d, J = 17.4 Hz, 1H), 1.97 (s, 3H), 1.50 (s, 6H). |
| 1-061 | δ7.45-7.7 (m, 6H), 4.52 (d, J = 6.3 Hz, 2H), 4.06 (d, J = 17.3 Hz, 1H), 3.67 (d, J = 17.3 Hz, 1H), 2.01 (s, 3H), 1.50 (s, 6H). |
| 1-062 | δ7.67 (s, 1H), 7.62 (s, 2H), 7.4-7.55 (m, 2H), 6.51 (bs, 1H), 4.52 (d, J = 6.3 Hz, 2H), 4.05 (d, J = 17.4 Hz, 1H), 3.69 (d, J = 17.4 Hz, 1H), 2.85-3.1 (m, 5H), 2.1-2.3 (m, 2H). |
| 1-063 | δ8.29 and 6.44 (bs, 1H), 7.35-7.75 (m, 5H), 4.45-4.6 (m, 2H), 4.0-4.1 (m, 1H), 3.6-3.7 (m, 1H), 2.3-3.6 (m, 7H). |
| 1-064 | δ7.69 (d, J = 1.5 Hz, 1H), 7.62 (s, 2H), 7.4-7.55 (m, 2H), 6.53 (t, J = 6.0 Hz, 1H), 4.53 (d, J = 6.0 Hz, 2H), 4.06 (d, J = 17.4 Hz, 1H), 3.68 (d, J = 17.4 Hz, 1H), 3.15-3.35 (m, 4H), 2.95-3.1 (m, 1H), 2.3-2.5 (m, 2H). |
| 1-065 | δ7.70 (d, J = 1.5 Hz, 1H), 7.63 (s, 2H), 7.4-7.55 (m, 2H), 6.91 (bs, 1H), 4.61 (d, J = 6.0 Hz, 2H), 4.07 (d, J = 17.4 Hz, 1H), 3.69 (d, J = 17.4 Hz, 1H), 2.34 (s, 3H). |
| 1-066 | δ7.69 (s, 1H), 7.63 (s, 2H), 7.45-7.6 (m, 2H), 7.26 (bs, 1H), 4.6-4.75 (m, 2H), 4.05 (d, J = 17.4 Hz, 1H), 3.67 (d, J = 17.4 Hz, 1H), 2.75 (s, 3H). |
| 1-067 | δ7.72 (d, J = 1.8 Hz, 1H), 7.62 (s, 2H), 7.4-7.6 (m, 2H), 7.05 (bs, 1H), 4.69 (d, J = 6.0 Hz, 2H), 4.07 (d, J = 17.4 Hz, 1H), 3.66 (d, J = 17.4 Hz, 1H), 3.20 (t, J = 1.5 Hz, 3H). |
| 1-068 | δ7.96 (s, 1H), 7.83 (s, 1H), 7.79 (s, 1H), 7.65 (d, J = 8.7 Hz, 2H), 7.39 (d, J = 8.7 Hz, 2H), 7.05-7.2 (m, 1H), 5.1-5.2 (m, 1H), 4.12 (d, J = 17.1 Hz, 1H), 3.70 (d, J = 17.1 Hz, 1H), 3.23 (d, J = 12.6 Hz, 1H), 3.17 (d, J = 12.6 Hz, 1H), 2.09 (s, 3H), 1.53 (d, J = 7.2 Hz, 3H). |
| 1-069 | δ7.94 (s, 1H), 7.84 (s, 1H), 7.65 (d, J = 8.4 Hz, 2H), 7.40 (d, J = 8.4 Hz, 2H), 7.15 (d, J = 7.8 Hz, 1H), 5.1-5.2 (m, 1H), 4.15 (d, J = 17.4 Hz, 1H), 3.70 (d, J = 17.4 Hz, 1H), 3.24 (d, J = 6.2 Hz, 1H), 3.17 (d, J = 6.2 Hz, 1H), 2.09 (s, 3H), 1.53 (d, J = 6.9 Hz, 3H). |
| 1-070 | δ7.95 (s, 1H), 7.84 (s, 1H), 7.75 (d, J = 8.4 Hz, 2H), 7.55-7.65 (m, 1H), 7.56 (d, J = 8.4 Hz, 2H), 6.19 (d, J = 5.7 Hz, 1H), 4.15 (d, J = 17.1 Hz, 1H), 3.73 (d, J = 17.1 Hz, 1H), 3.28 (s, 2H), 2.11 (s, 3H). |
| 1-072 | δ7.86 (s, 1H), 7.82 (d, J = 7.8 Hz, 1H), 7.45-7.75 (m, 5H), 7.40 (t, J = 6.5 Hz, 1H), 4.58 (d, J = 6.5 Hz, 2H), 4.11 (d, J = 17.5 Hz, 1H), 3.72 (d, J = 17.5 Hz, 1H), 3.23 (s, 2H), 2.10 (s, 3H). |
| 1-073 | δ7.82 (dd, J = 6.3, 2.1 Hz, 1H), 7.70 (t, J = 1.8 Hz, 1H), 7.35-7.6 (m, 4H), 7.20 (t, J = 8.4 Hz, 1H), 4.58 (d, J = 6.0 Hz, 2H), 4.06 (d, J = 17.4 Hz, 1H), 3.68 (d, J = 17.4 Hz, 1H), 3.23 (s, 2H), 2.10 (s, 3H). |
| 1-074 | δ7.91 (s, 1H), 7.74 (d, J = 8.4 Hz, 1H), 7.71 (d, J = 1.5 Hz, 1H), 7.61 (d, J = 8.4 Hz, 1H), 7.53 (dd, J = 8.1, 1.5 Hz, 1H), 7.46 (d, J = 8.1 Hz, 1H), 7.43 (bs, 1H), 4.58 (d, J = 6.0 Hz, 2H), 4.11 (d, J = 17.4 Hz, 1H), 3.69 (d, J = 17.4 Hz, 1H), 3.23 (s, 2H), 2.10 (s, 3H). |
| 1-080 | δ7.93 (d, J = 2.1 Hz, 1H), 7.82 (s, 1H), 7.70 (d, J = 1.5 Hz, 1H), 7.45-7.55 (m, 2H), 7.41 (t, J = 6.0 Hz, 1H), 4.58 (d, J = 6.0 Hz, 2H), 4.10 (d, J = 17.4 Hz, 1H), 3.68 (d, J = 17.4 Hz, 1H), 3.23 (s, 2H), 2.10 (s, 3H). |
| 1-081 | δ7.89 (d, J = 1.7 Hz, 1H), 7.86 (s, 1H), 7.80 (d, J = 7.8 Hz, 1H), 7.69 (d, J = 7.8 Hz, 1H), 7.4-7.65 (m, 4H), 4.56 (d, J = 6.0 Hz, 2H), 4.10 (d, J = 17.1 Hz, 1H), 3.71 (d, J = 17.1 Hz, 1H), 3.23 (s, 2H), 2.10 (s, 3H). |
| 1-083 | δ7.96 (s, 1H), 7.89 (s, 1H), 7.84 (s, 1H), 7.79 (s, 1H), 7.59 (d, J = 8.1 Hz, 1H), 7.47 (d, J = 8.1 Hz, 1H), 7.4-7.5 (m, 1H), |

TABLE 7-continued

| No. | $^1$H NMR (CDCl$_3$, Me$_4$Si, 300 MHz) |
|---|---|
| | 4.58 (d, J = 6.0 Hz, 2H), 4.10 (d, J = 17.4 Hz, 1H), 3.69 (d, J = 17.4 Hz, 1H), 3.24 (s, 2H), 2.10 (s, 3H). |
| 1-085 | δ8.13 (d, J = 1.5 Hz, 1H), 8.07 (s, 2H), 7.96 (s, 1H), 7.63 (dd, J = 8.4, 1.5 Hz, 1H), 7.46 (t, J = 5.7 Hz, 1H), 7.43 (d, J = 8.1 Hz, 1H), 4.51 (d, J = 6.0 Hz, 2H), 4.16 (d, J = 17.1 Hz, 1H), 3.71 (d, J = 17.1 Hz, 1H), 3.24 (s, 2H), 2.12 (s, 3H). |
| 1-087 | δ7.96 (s, 1H), 7.81 (d, J = 8.7 Hz, 2H), 7.64 (d, J = 7.8 Hz, 2H), 7.46 (d, J = 8.1 Hz, 1H), 7.39 (d, J = 8.1 Hz, 2H), 5.1-5.2 (m, 1H), 4.11 (d, J = 17.4 Hz, 1H), 3.6-3.8 (m, 2H), 3.28 and 3.19 (d, J = 14.4 Hz, 1H), 2.72 and 2.52 (s, 3H), 1.45-1.6 (m, 3H). |
| 1-088 | δ7.95 and 7.94 (d, J = 2.1 Hz, 1H), 7.83 and 7.82 (d, J = 2.1 Hz, 1H), 7.64 and 7.63 (d, J = 8.1 Hz, 2H), 7.45 and 7.39 (d, J = 8.1 Hz, 2H), 7.35-7.45 (m, 1H), 5.05-5.2 (m, 1H), 4.13 (d, J = 17.4 Hz, 1H), 3.73 and 3.66 (d, J = 14.4 Hz, 1H), 3.69 (d, J = 17.4 Hz, 1H), 3.27 and 3.18 (d, J = 14.4 Hz, 1H), 2.71 and 2.51 (s, 3H), 1.52 and 1.49 (d, J = 7.2 Hz, 3H). |
| 1-089 | δ8.07 (s, 2H), 7.96 (s, 1H), 7.57 (bs, 1H), 7.35-7.5 (m, 3H), 4.45-4.65 (m, 2H), 4.16 (d, J = 17.4 Hz, 1H), 3.73 (d, J = 17.4 Hz, 1H), 3.72 (d, J = 13.8 Hz, 1H), 3.35 (d, J = 13.8 Hz, 1H), 2.66 (s, 3H). |
| 1-091 | δ7.81 (s, 1H), 7.75 (s, 1H), 7.69 (s, 2H), 7.54 (s, 2H), 7.42 (bs, 1H), 4.62 (d, J = 6.0 Hz, 2H), 4.10 (d, J = 17.4 Hz, 1H), 3.73 (d, J = 14.4 Hz, 1H), 3.69 (d, J = 17.4 Hz, 1H), 3.27 (d, J = 14.4 Hz, 1H), 2.66 (s, 3H). |
| 1-092 | δ7.95 (s, 1H), 7.84 (s, 1H), 7.79 (s, 1H), 7.69 (s, 1H), 7.55 (d, J = 8.2 Hz, 1H), 7.52 (d, J = 8.2 Hz, 1H), 7.42 (t, J = 6.3 Hz, 1H), 4.62 (d, J = 6.3 Hz, 2H), 4.10 (d, J = 17.1 Hz, 1H), 3.73 (d, J = 14.4 Hz, 1H), 3.69 (d, J = 17.1 Hz, 1H), 3.27 (d, J = 14.4 Hz, 1H), 2.65 (s, 3H). |
| 1-093 | δ8.13 (s, 1H), 8.02 (s, 1H), 7.81 (s, 1H), 7.69 (s, 1H), 7.53 (s, 2H), 7.41 (bs, 1H), 4.62 (d, J = 6.0 Hz, 2H), 4.09 (d, J = 17.4 Hz, 1H), 3.72 (d, J = 14.4 Hz, 1H), 3.67 (d, J = 17.4 Hz, 1H), 3.27 (d, J = 14.4 Hz, 1H), 2.65 (s, 3H). |
| 1-094 | δ8.08 (s, 2H), 7.98 (s, 1H), 7.68 (s, 1H), 7.45-7.65 (m, 3H), 4.60 (d, J = 6.0 Hz, 2H), 4.17 (d, J = 17.4 Hz, 1H), 3.74 (d, J = 17.4 Hz, 1H), 3.74 (d, J = 14.4 Hz, 1H), 3.34 (d, J = 14.4 Hz, 1H), 2.67 (s, 3H). |
| 1-095 | δ7.75 (d, J = 5.7 Hz, 2H), 7.67 (s, 1H), 7.35-7.6 (m, 3H), 4.61 (d, J = 6.3 Hz, 2H), 4.05 (d, J = 17.4 Hz, 1H), 3.73 (d, J = 14.4 Hz, 1H), 3.66 (d, J = 17.4 Hz, 1H), 3.28 (d, J = 14.4 Hz, 1H), 2.66 (s, 3H). |
| 1-096 | δ7.82 (s, 2H), 7.65 (s, 1H), 7.45-7.6 (m, 3H), 4.69 (d, J = 6.0 Hz, 2H), 4.04 (d, J = 17.4 Hz, 1H), 3.73 (d, J = 14.4 Hz, 1H), 3.66 (d, J = 17.4 Hz, 1H), 3.32 (d, J = 14.4 Hz, 1H), 2.66 (s, 3H). |
| 1-097 | δ7.45-8.0 (m, 5H), 7.37 (t, J = 7.8 Hz, 1H), 4.55-4.7 (n, 2H), 4.08 (d, J = 17.4 Hz, 1H), 3.83 (d, J = 13.8 Hz, 1H), 3.66 (d, J = 17.4 Hz, 1H), 3.48 (d, J = 13.8 Hz, 1H), 2.73 (s, 3H). |
| 1-098 | δ7.86 (s, 1H), 7.81 (s, 1H), 7.75 (s, 1H), 7.69 (s, 1H), 7.61 (d, J = 7.8 Hz, 1H), 7.52 (d, J = 7.8 Hz, 1H), 7.4-7.5 (m, 1H), 4.61 (d, J = 5.7 Hz, 2H), 4.11 (d, J = 17.4 Hz, 1H), 3.73 (d, J = 14.1 Hz, 1H), 3.69 (d, J = 17.4 Hz, 1H), 3.28 (d, J = 14.1 Hz, 1H), 2.66 (s, 3H). |
| 1-099 | δ7.95 (s, 1H), 7.86 (s, 1H), 7.84 (s, 1H), 7.79 (s, 1H), 7.61 (d, J = 7.8 Hz, 1H), 7.52 (d, J = 7.8 Hz, 1H), 7.35-7.45 (m, 1H), 4.61 (d, J = 5.7 Hz, 2H), 4.10 (d, J = 17.4 Hz, 1H), 3.73 (d, J = 14.4 Hz, 1H), 3.68 (d, J = 17.4 Hz, 1H), 3.26 (d, J = 14.4 Hz, 1H), 2.66 (s, 3H). |
| 1-100 | δ8.12 (s, 1H), 8.07 (s, 2H), 7.97 (s, 1H), 7.66 (d, J = 7.8 Hz, 1H), 7.49 (d, J = 7.8 Hz, 1H), 7.42 (bs, 1H), 4.55 (d, J = 5.8 Hz, 2H), 4.15 (d, J = 17.4 Hz, 1H), 3.73 (d, J = 15.6 Hz, 1H), 3.71 (d, J = 17.4 Hz, 1H), 3.27 (d, J = 15.6 Hz, 1H), 2.67 (s, 3H). |
| 1-101 | δ8.30 (bs, 1H), 8.08 (s, 2H), 8.01 (bs, 1H), 7.98 (s, 1H), 7.80 (d, J = 8.1 Hz, 1H), 7.53 (bs, 1H), 4.84 (d, J = 6.3 Hz, 2H), 4.21 (d, J = 17.4 Hz, 1H), 3.77 (d, J = 17.4 Hz, 1H), 3.72 (d, J = 14.4 Hz, 1H), 3.30 (d, J = 14.4 Hz, 1H), 2.64 (s, 3H). |
| 1-105 | δ8.07 (s, 2H), 7.96 (s, 1H), 7.66 (d, J = 8.1 Hz, 2H), 7.41 (d, J = 8.1 Hz, 2H), 6.69 (bs, 1H), 5.05-5.15 (m, 1H), 4.18 (d, J = 17.1 Hz, 1H), 3.88 (s, 2H), 3.73 (d, J = 17.1 Hz, 1H), 2.99 (s, 3H), 1.53 (d, J = 7.2 Hz, 3H). |
| 1-107 | δ7.93 (s, 1H), 7.83 (s, 1H), 7.72 (d, J = 8.4 Hz, 2H), 7.71 (d, J = 8.7 Hz, 2H), 7.54 (d, J = 8.4 Hz, 2H), 6.07 (d, J = 8.7 Hz, 1H), 4.14 (d, J = 17.4 Hz, 1H), 4.00 (s, 2H), 3.73 (d, J = 17.4 Hz, 1H), 3.07 (s, 3H). |
| 1-109 | δ7.86 (s, 1H), 7.82 (d, J = 7.8 Hz, 1H), 7.65-7.75 (m, 2H), 7.59 (t, J = 7.8 Hz, 1H), 7.45-7.55 (m, 2H), 6.93 (t, J = 5.8 Hz, 1H), 4.60 (d, J = 5.8 Hz, 2H), 4.11 (d, J = 17.5 Hz, 1H), 3.92 (s, 2H), 3.72 (d, J = 17.5 Hz, 1H), 3.05 (s, 3H). |
| 1-124 | δ8.07 (s, 2H), 7.96 (s, 1H), 7.69 (d, J = 7.8 Hz, 1H), 7.64 (d, J = 8.7 Hz, 2H), 7.41 (d, J = 8.7 Hz, 2H), 5.09 (qui, J = 7.2 Hz, 1H), 4.18 (d, J = 17.4 Hz, 1H), 3.97 (s, 2H), 3.74 (d, J = 17.4 Hz, 1H), 3.11 (bs, 1H), 3.07 (s, 3H), 1.50 (d, J = 7.2 Hz, 3H). |
| 1-125 | δ8.06 (s, 2H), 8.00 (s, 1H), 7.87 (s, 1H), 7.61 (d, J = 7.8 Hz, 1H), 7.46 (d, J = 7.8 Hz, 1H), 6.70 (s, 1H), 4.3-4.65 (m, 4H), 4.16 (d, J = 17.4 Hz, 1H), 3.72 (d, J = 17.4 Hz, 1H), 3.24 (s, 3H). |

TABLE 7-continued

| No. | $^1$H NMR (CDCl$_3$, Me$_4$Si, 300 MHz) |
|---|---|
| 1-126 | δ7.96 (s, 1H), 7.83 (s, 1H), 7.80 (s, 1H), 7.64 (d, J = 8.4 Hz, 2H), 7.38 (d, J = 8.4 Hz, 2H), 7.15 (d, J = 7.8 Hz, 1H), 5.1-5.2 (m, 1H), 4.12 (d, J = 17.1 Hz, 1H), 3.70 (d, J = 17.1 Hz, 1H), 3.23 (s, 2H), 2.52 (q, J = 7.65 Hz, 2H), 1.52 (d, J = 7.2 Hz, 3H), 1.24 (t, J = 7.2 Hz, 3H). |
| 1-127 | δ8.08 (s, 2H), 7.96 (s, 1H), 7.65 (d, J = 8.1 Hz, 2H), 7.39 (d, J = 8.1 Hz, 2H), 7.18 (d, J = 7.18 Hz, 1H), 5.05-5.2 (m, 1H), 4.19 (d, J = 17.4 Hz, 1H), 3.74 (d, J = 17.4 Hz, 1H), 3.24 (d, J = 1.8 Hz, 2H), 2.53 (q, J = 7.5 Hz, 2H), 1.52 (d, J = 6.9 Hz, 3H), 1.24 (t, J = 7.5 Hz, 3H). |
| 1-128 | δ7.95 (s, 1H), 7.84 (s, 1H), 7.65 (d, J = 8.4 Hz, 2H), 7.39 (d, J = 8.4 Hz, 2H), 7.15 (d, J = 7.8 Hz, 1H), 5.1-5.2 (m, 1H), 4.13 (d, J = 17.1 Hz, 1H), 3.69 (d, J = 17.1 Hz, 1H), 3.27 (d, J = 16.2 Hz, 1H), 3.21 (d, J = 16.2 Hz, 1H), 2.53 (q, J = 7.2 Hz, 2H), 1.52 (d, J = 6.9 Hz, 3H), 1.24 (t, J = 7.2 Hz, 3H). |
| 1-131 | δ7.86 (s, 1H), 7.82 (d, J = 7.8 Hz, 1H), 7.65-7.75 (m, 2H), 7.59 (t, J = 7.8 Hz, 1H), 7.4-7.55 (m, 3H), 4.57 (d, J = 6.2 Hz, 2H), 4.11 (d, J = 17.1 Hz, 1H), 3.72 (d, J = 17.1 Hz, 1H), 3.27 (s, 2H), 2.53 (q, J = 7.6 Hz, 2H), 1.23 (t, J = 7.6 Hz, 3H). |
| 1-132 | δ7.90 (s, 1H), 7.74 (d, J = 8.4 Hz, 1H), 7.71 (d, J = 1.5 Hz, 1H), 7.61 (d, J = 8.4 Hz, 1H), 7.53 (dd, J = 7.8, 1.5 Hz, 1H), 7.46 (d, J = 7.8 Hz, 1H), 7.44 (bs, 1H), 4.57 (d, J = 6.3 Hz, 2H), 4.10 (d, J = 17.4 Hz, 1H), 3.68 (d, J = 17.4 Hz, 1H), 3.27 (s, 2H), 2.53 (q, J = 7.5 Hz, 2H), 1.23 (t, J = 7.5 Hz, 3H). |
| 1-135 | δ7.75 (d, J = 5.4 Hz, 2H), 7.68 (d, J = 1.5 Hz, 1H), 7.4-7.6 (m, 3H), 4.56 (d, J = 6.3 Hz, 2H), 4.06 (d, J = 17.4 Hz, 1H), 3.68 (d, J = 17.4 Hz, 1H), 3.26 (s, 2H), 2.54 (q, J = 7.5 Hz, 2H), 1.23 (t, J = 7.5 Hz, 3H). |
| 1-136 | δ7.82 (s, 2H), 7.69 (d, J = 1.8 Hz, 1H), 7.4-7.55 (m, 3H), 4.56 (d, J = 6.0 Hz, 2H), 4.05 (d, J = 17.4 Hz, 1H), 3.67 (d J = 17.4 Hz, 1H), 3.26 (s, 2H), 2.53 (q, J = 7.5 Hz, 2H), 1.23 (t, J = 7.5 Hz, 3H). |
| 1-138 | δ7.89 (d, J = 1.8 Hz, 1H), 7.86 (s, 1H), 7.80 (d, J = 7.7 Hz, 1H), 7.70 (d, J = 7.7 Hz, 1H), 7.4-7.65 (m, 4H), 4.55 (d, J = 6.3 Hz, 2H), 4.10 (d, J = 17.4 Hz, 1H), 3.71 (d, J = 17.4 Hz, 1H), 3.26 (s, 2H), 2.53 (q, J = 7.4 Hz, 2H), 1.23 (t, J = 7.4 Hz, 3H). |
| 1-140 | δ7.95 (s, 1H), 7.88 (s, 1H), 7.84 (s, 1H), 7.79 (s, 1H), 7.58 (d, J = 8.1 Hz, 1H), 7.4-7.5 (m, 1H), 7.46 (d, J = 8.1 Hz, 1H), 4.56 (d, J = 6.3 Hz, 2H), 4.10 (d, J = 17.4 Hz, 1H), 3.68 (d, J = 17.4 Hz, 1H), 3.27 (s, 2H), 2.53 (q, J = 7.5 Hz, 2H), 1.23 (t, J = 7.5 Hz, 3H). |
| 1-143 | δ7.96 (s, 1H), 7.81 (d, J = 8.7 Hz, 2H), 7.64 (d, J = 8.1 Hz, 2H), 7.3-7.5 (m, 3H), 5.05-5.2 (m, 1H), 4.12 (d, J = 17.4 Hz, 1H), 3.5-3.75 (m, 2H), 3.27 and 3.19 (d, J = 14.4 Hz, 1H), 2.55-2.95 (m, 2H), 1.51 and 1.49 (d, J = 6.9 Hz, 3H), 1.26 and 1.21 (t, J = 7.5 Hz, 3H). |
| 1-144 | δ7.94 (s, 1H), 7.83 (s, 1H), 7.63 (d, J = 8.1 Hz, 2H), 7.4-7.5 (m, 1H), 7.44 and 7.39 (d, J = 8.1 Hz, 2H), 5.05-5.2 (m, 1H), 4.12 (d, J = 17.1 Hz, 1H), 3.69 (d, J = 17.1 Hz, 1H), 3.66 and 3.60 (d, J = 14.4 Hz, 1H), 3.31 and 3.23 (d, J = 14.4 Hz, 1H), 2.8-2.95 and 2.6-2.75 (m, 2H), 1.51 and 1.49 (d, J = 6.9 Hz, 3H), 1.36 and 1.26 (t, J = 7.5 Hz, 3H). |
| 1-146 | δ8.07 (s, 2H), 7.96 (s, 1H), 7.58 (bs, 1H), 7.3-7.5 (m, 3H), 4.55 (d, J = 6.0 Hz, 2H), 4.15 (d, J = 17.4 Hz, 1H), 3.72 (d, J = 17.4 Hz, 1H), 3.68 (d, J = 14.4 Hz, 1H), 3.38 (d, J = 14.4 Hz, 1H), 2.75-2.95 (m, 2H), 1.33 (t, J = 7.5 Hz, 3H). |
| 1-148 | δ8.13 (s, 1H), 8.02 (s, 1H), 7.82 (s, 1H), 7.68 (s, 1H), 7.4-7.6 (m, 3H), 4.60 (d, J = 6.3 Hz, 2H), 4.09 (d, J = 17.4 Hz, 1H), 3.68 (d, J = 17.4 Hz, 1H), 3.67 (d, J = 14.4 Hz, 1H), 3.31 (d, J = 14.4 Hz, 1H), 2.7-2.95 (m, 2H), 1.34 (t, J = 7.5 Hz, 3H). |
| 1-149 | δ8.07 (s, 2H), 7.97 (s, 1H), 7.67 (s, 1H), 7.45-7.6 (m, 3H), 4.59 (d, J = 6.0 Hz, 2H), 4.17 (d, J = 17.4 Hz, 1H), 3.73 (d, J = 17.4 Hz, 1H), 3.68 (d, J = 14.4 Hz, 1H), 3.34 (d, J = 14.4 Hz, 1H), 2.87 (qd, J = 7.5, 6.0 Hz, 1H), 2.83 (qd, J = 7.5, 6.0 Hz, 1H), 1.33 (t, J = 7.5 Hz, 3H). |
| 1-150 | δ7.75 (d, J = 6.0 Hz, 2H), 7.66 (s, 1H), 7.45-7.6 (m, 3H), 4.59 (d, J = 6.3 Hz, 2H), 4.04 (d, J = 17.4 Hz, 1H), 3.67 (d, J = 14.4 Hz, 1H), 3.66 (d, J = 17.4 Hz, 1H), 3.34 (d, J = 14.4 Hz, 1H), 2.75-2.95 (m, 2H), 1.33 (t, J = 7.5 Hz, 3H). |
| 1-151 | δ7.82 (s, 2H), 7.65 (d, J = 6.0 Hz, 1H), 7.45-7.6 (m, 3H), 4.58 (d, J = 6.0 Hz, 2H), 4.04 (d, J = 17.4 Hz, 1H), 3.68 (d, J = 14.4 Hz, 1H), 3.66 (d, J = 17.4 Hz, 1H), 3.35 (d, J = 14.4 Hz, 1H), 2.84 (tq, J = 13.5, 7.5 Hz, 2H), 1.32 (t, J = 7.5 Hz, 3H). |
| 1-152 | δ7.8-8.0 (m, 3H), 7.6-7.7 (m, 1H), 7.45-7.55 (m, 2H), 4.60 (d, J = 6.0 Hz, 2H), 4.09 (d, J = 17.4 Hz, 1H), 3.72 (d, J = 15.9 Hz, 1H), 3.66 (d, J = 15.9 Hz, 1H), 3.44 (d, J = 17.4 Hz, 1H), 2.8-3.0 (m, 2H), 1.35 (t, J = 6.6 Hz, 3H). |
| 1-153 | δ7.86 (s, 1H), 7.81 (s, 1H), 7.75 (s, 1H), 7.69 (s, 1H), 7.60 (d, J = 9.6 Hz, 1H), 7.50 (d, J = 8.1 Hz, 1H), 7.45-7.55 (m, 1H), 4.59 (d, J = 6.0 Hz, 2H), 4.11 (d, J = 17.4 Hz, 1H), 3.69 (d, J = 17.4 Hz, 1H), 3.68 (d, J = 14.4 Hz, 1H), 3.32 (d, J = 14.1 Hz, 1H), 2.75-3.0 (m, 2H), 1.34 (t, J = 7.5 Hz, 3H). |
| 1-154 | δ7.95 (s, 1H), 7.86 (s, 1H), 7.83 (s, 1H), 7.79 (s, 1H), 7.59 (d, J = 7.8 Hz, 1H), 7.50 (d, J = 7.8 Hz, 1H), 7.4-7.5 (m, 1H), |

TABLE 7-continued

| No. | $^1$H NMR (CDCl$_3$, Me$_4$Si, 300 MHz) |
|---|---|
| | 4.59 (d, J = 6.3 Hz, 2H), 4.10 (d, J = 17.4 Hz, 1H), 3.68 (d, J = 17.4 Hz, 1H), 3.67 (d, J = 14.4 Hz, 1H), 3.30 (d, J = 14.4 Hz, 1H), 2.7-2.95 (m, 2H), 1.34 (t, J = 7.5 Hz, 3H). |
| 1-156 | δ8.10 (d, J = 1.5 Hz, 1H), 8.07 (s, 2H), 7.96 (s, 1H), 7.65 (dd, J = 8.1, 1.5 Hz, 1H), 7.49 (bs, 1H), 7.47 (d, J = 8.1 Hz, 1H), 4.57 (dd, J = 15.6, 6.3 Hz, 1H), 4.50 (dd, J = 15.6, 6.3 Hz, 1H), 4.16 (d, J = 17.8 Hz, 1H), 3.71 (d, J = 17.8 Hz, 1H), 3.68 (d, J = 15.6 Hz, 1H), 3.32 (d, J = 15.6 Hz, 1H), 2.75-2.95 (m, 2H), 1.34 (t, J = 7.5 Hz, 3H). |
| 1-157 | δ8.17 (t, J = 6.0 Hz, 1H), 7.96 (s, 1H), 7.89 (s, 1H), 7.85 (s, 1H), 7.57 (d, J = 8.1 Hz, 1H), 7.43 (d, J = 8.1 Hz, 1H), 4.53 (d, J = 6.0 Hz, 2H), 4.14 (d, J = 17.4 Hz, 1H), 4.05 (d, J = 14.1 Hz, 1H), 3.90 (d, J = 14.1 Hz, 1H), 3.73 (d, J = 17.4 Hz, 1H), 3.25-3.5 (m, 2H), 1.44 (t, J = 7.2 Hz, 3H). |
| 1-158 | δ7.96 (s, 1H), 7.83 (s, 1H), 7.80 (s, 1H), 7.63 (d, J = 8.4 Hz, 2H), 7.39 (d, J = 8.4 Hz, 2H), 7.04 (d, J = 7.5 Hz, 1H), 5.0-5.15 (m, 1H), 4.12 (d, J = 17.4 Hz, 1H), 3.88 (s, 2H), 3.70 (d, J = 17.4 Hz, 1H), 3.11 (q, J = 7.5 Hz, 2H), 1.50 (d, J = 7.5 Hz, 3H), 1.38 (t, J = 7.5 Hz, 3H). |
| 1-159 | δ8.07 (s, 2H), 7.97 (s, 1H), 7.75 (d, J = 6.9 Hz, 1H), 7.73 (d, J = 8.4 Hz, 2H), 7.55 (d, J = 8.4 Hz, 2H), 6.09 (d, J = 6.9 Hz, 1H), 4.20 (d, J = 17.4 Hz, 1H), 3.97 (s, 2H), 3.77 (d, J = 17.4 Hz, 1H), 3.18 (q, J = 7.5 Hz, 2H), 1.39 (t, J = 7.5 Hz, 3H). |
| 1-163 | δ8.13 (s, 1H), 8.03 (s, 1H), 7.82 (s, 1H), 7.71 (s, 1H), 7.55 (d, J = 7.1 Hz, 1H), 7.50 (d, J = 7.1 Hz, 1H), 6.94 (bs, 1H), 4.60 (d, J = 6.0 Hz, 2H), 4.09 (d, J = 17.4 Hz, 1H), 3.88 (s, 2H), 3.68 (d, J = 17.4 Hz, 1H), 3.15 (q, J = 7.5 Hz, 2H), 1.42 (t, J = 7.5 Hz, 3H). |
| 1-179 | δ8.06 (s, 2H), 7.96 (s, 1H), 7.69 (s, 1H), 7.45-7.6 (m, 2H), 7.03 (bs, 1H), 4.56 (d, J = 6.0 Hz, 2H), 4.17 (d, J = 17.4 Hz, 1H), 3.75-4.05 (m, 4H), 3.73 (d, J = 17.4 Hz, 1H). |
| 1-180 | δ8.05 (s, 2H), 7.96 (s, 1H), 7.67 (d, J = 1.5 Hz, 1H), 7.4-7.55 (m, 2H), 6.97 (bs, 1H), 4.55 (d, J = 6.0 Hz, 2H), 4.37 (s, 2H), 4.16 (d, J = 17.4 Hz, 1H), 4.15 (s, 2H), 3.73 (d, J = 17.4 Hz, 1H). |
| 1-181 | δ7.68 (d, J = 1.8 Hz, 1H), 7.63 (s, 2H), 7.4-7.55 (m, 2H), 6.98 (bs, 1H), 4.57 (d, J = 6.0 Hz, 2H), 4.35 (q, J = 4.2 Hz, 2H), 4.06 (d, J = 17.4 Hz, 1H), 3.67 (d, J = 17.4 Hz, 1H), 3.62 (s, 2H), 1.37 (t, J = 7.2 Hz, 3H). |
| 1-182 | δ8.07 (s, 2H), 7.96 (s, 1H), 7.68 (d, J = 1.5 Hz, 1H), 7.35-7.6 (m, 3H), 6.55 (bs, 1H), 5.91 and 6.09 (s, 1H), 4.5-4.65 (m, 2H), 4.17 (d, J = 17.4 Hz, 1H), 3.74 (d, J = 17.4 Hz, 1H), 3.35-3.55 (m, 2H), 2.88 (d, J = 4.8 Hz, 3H). |
| 1-183 | δ7.66 (d, J = 1.5 Hz, 1H), 7.63 (s, 2H), 7.4-7.55 (m, 2H), 7.21 (t, J = 5.1 Hz, 1H), 6.55 (bs, 1H), 4.56 (d, J = 6.0 Hz, 2H), 4.06 (d, J = 17.4 Hz, 1H), 3.68 (d, J = 17.4 Hz, 1H), 3.61 (s, 2H), 2.91 (d, J = 5.1 Hz, 3H). |
| 1-184 | δ7.65-7.7 (m, 1H), 7.63 (s, 2H), 7.45-7.5 (m, 2H), 7.05 (t, J = 6.0 Hz, 1H), 4.56 (d, J = 6.0 Hz, 2H), 4.06 and 4.06 (d, J = 17.4 Hz, 1H), 3.67 (d, J = 17.4 Hz, 1H), 3.44 (s, 2H). |
| 1-185 | δ8.07 (s, 2H), 7.96 (s, 1H), 7.69 (d, J = 1.5 Hz, 1H), 7.52 (dd, J = 7.1, 1.8 Hz, 1H), 7.39 (dd, J = 7.1, 1.8 Hz, 1H), 6.85 (bs, 1H), 4.52 (d, J = 6.0 Hz, 2H), 4.17 (d, J = 17.4 Hz, 1H), 3.73 (d, J = 17.4 Hz, 1H), 3.66 (s, 2H), 2.46 (s, 3H). |
| 1-189 | δ8.07 (s, 2H), 7.95 (s, 1H), 7.6-7.65 (m, 2H), 7.35-7.4 (m, 2H), 5.07 (bs, 1H), 4.18 (d, J = 17.1 Hz, 1H), 3.8-3.9 (m, 1H), 3.72 (d, J = 17.1 Hz, 1H), 2.8-3.1 (m, 2H), 1.7-2.4 (m, 4H), 1.49 (d, J = 7.2 Hz, 3H). |
| 1-190 | δ8.08 (s, 2H), 7.98 (s, 1H), 7.65-7.8 (m, 2H), 7.5-7.6 (m, 2H), 6.15 (d, J = 8.7 Hz, 1H), 4.20 (d, J = 17.4 Hz, 1H), 3.95-4.05 (m, 1H), 3.76 (d, J = 17.4 Hz, 1H), 2.85-3.1 (m, 2H), 1.7-2.4 (m, 4H). |
| 1-191 | δ8.12 (s, 1H), 8.07 (s, 2H), 7.96 (s, 1H), 7.63 (d, J = 8.1 Hz, 1H), 7.56 (t, J = 6.0 Hz, 1H), 7.38 (d, J = 8.1 Hz, 1H), 4.45 (d, J = 6.0 Hz, 2H), 4.16 (d, J = 17.1 Hz, 1H), 3.95 (dd, J = 7.8, 4.5 Hz, 1H), 3.71 (d, J = 17.1 Hz, 1H), 2.9-3.05 (m, 2H), 2.25-2.4 (m, 1H), 2.0-2.25 (m, 2H), 1.8-1.95 (m, 1H). |
| 1-193 | δ8.07 (s, 2H), 7.96 (s, 1H), 7.68 (t, J = 1.5 Hz, 1H), 7.45-7.55 (m, 2H), 7.46 (bs, 1H), 4.59 (d, J = 6.0 Hz, 2H), 4.16 (d, J = 17.4 Hz, 1H), 3.72 (d, J = 17.4 Hz, 1H), 3.50 (d, J = 12.3 Hz, 1H), 3.26 (dd, J = 12.3, 2.4 Hz, 1H), 2.69 (td, J = 12.9, 3.3 Hz, 1H), 2.35-2.45 (m, 1H), 2.1-2.2 (m, 1H), 1.8-1.95 (m, 1H), 1.6-1.8 (m, 2H), 1.3-1.5 (m, 1H). |
| 1-194 | δ8.07 (s, 2H), 7.96 (s, 1H), 7.68 (t, J = 1.5 Hz, 1H), 7.45-7.55 (m, 2H), 7.25 (t, J = 6.0 Hz, 1H), 4.5-4.7 (m, 2H), 4.16 (d, J = 17.4 Hz, 1H), 3.73 (dd, J = 10.8, 6.9 Hz, 1H), 3.72 (d, J = 17.4 Hz, 1H), 3.15-3.25 (m, 1H), 2.95-3.05 (m, 1H), 2.35-2.45 (m, 1H), 1.95-2.3 (m, 4H), 1.45-1.6 (m, 1H). |
| 1-196 | δ8.07 (s, 2H), 7.96 (s, 1H), 7.71 (t, J = 1.2 Hz, 1H), 7.45-7.6 (m, 2H), 7.06 (t, J = 6.3 Hz, 1H), 4.76 (s, 1H), 4.63 (dd, J = 15.3, 6.0 Hz, 1H), 4.55 (dd, J = 15.3, 6.0 Hz, 1H), 4.18 (d, J = 17.4 Hz, 1H), 3.75 (d, J = 17.4 Hz, 1H), 2.00 (s, 3H). |

TABLE 7-continued

| No. | $^1$H NMR (CDCl$_3$, Me$_4$Si, 300 MHz) |
|---|---|
| 1-197 | δ7.92 (d, J = 1.5 Hz, 1H), 7.82 (s, 1H), 7.70 (t, J = 1.5 Hz, 1H), 7.45-7.55 (m, 2H), 7.03 (t, J = 6.3 Hz, 1H), 4.76 (s, 1H), 4.64 (dd, J = 15.3, 6.3 Hz, 1H), 4.55 (dd, J = 15.3, 6.3 Hz, 1H), 4.10 (d, J = 17.4 Hz, 1H), 3.68 (d, J = 17.4 Hz, 1H), 3.83 (s, 3H). |
| 1-198 | δ8.07 (s, 2H), 7.97 (s, 1H), 7.71 (s, 1H), 7.45-7.6 (m, 2H), 7.31 and 7.13 (t, J = 6.3 Hz, 1H), 4.81 and 4.59 (s, 1H), 4.66 (dd, J = 15.3, 6.3 Hz, 1H), 4.52 (dd, J = 15.3, 6.3 Hz, 1H), 4.17 (d, J = 17.4 Hz, 1H), 3.73 (d, J = 17.4 Hz, 1H), 2.67 and 2.55 (s, 3H). |
| 1-199 | δ8.07 (s, 2H), 7.97 (s, 1H), 7.71 (s, 1H), 7.45-7.55 (m, 2H), 7.26 (s, 1H), 4.68 (s, 1H), 4.66 (dd, J = 15.9, 6.6 Hz, 1H), 4.54 (dd, J = 15.9, 6.6 Hz, 1H), 4.17 (d, J = 17.4 Hz, 1H), 3.73 (d, J = 17.4 Hz, 1H), 3.04 (s, 3H). |
| 1-200 | δ8.07 (s, 2H), 7.97 (s, 1H), 7.71 (s, 1H), 7.55-7.6 (m, 1H), 7.4-7.45 (m, 1H), 5.87 (s, 1H), 4.90 (d, J = 15.6 Hz, 1H), 4.86 (d, J = 15.6 Hz, 1H), 4.17 (d, J = 17.4 Hz, 1H), 3.73 (d, J = 17.4 Hz, 1H), 2.17 (s, 3H). |
| 1-201 | δ8.09 (s, 2H), 7.98 (s, 1H), 7.72 (dd, J = 3.0, 1.5 Hz, 1H), 7.45-7.6 (m, 2H), 7.10 (t, J = 6.0 Hz, 1H), 4.79 (s, 1H), 4.65 (dd, J = 15.3, 6.0 Hz, 1H), 4.56 (dd, J = 15.3, 6.0 Hz, 1H), 4.20 (d, J = 17.4 Hz, 1H), 3.77 (d, J = 17.4 Hz, 1H), 3.49 (s, 3H), 1.96 (s, 3H). |
| 1-202 | δ8.07 (s, 2H), 7.96 (s, 1H), 7.72 (t, J = 1.5 Hz, 1H), 7.45-7.6 (m, 2H), 7.11 (t, J = 6.3 Hz, 1H), 4.86 (s, 1H), 4.65 (dd, J = 15.3, 6.3 Hz, 1H), 4.55 (dd, J = 15.3, 6.3 Hz, 1H), 4.17 (d, J = 17.4 Hz, 1H), 3.85-4.0 (m, 1H), 3.72 (d, J = 17.4 Hz, 1H), 3.45-3.6 (m, 1H), 1.97 (s, 3H), 1.26 (t, J = 7.2 Hz, 3H). |
| 1-203 | δ8.07 (s, 2H), 7.96 (s, 1H), 7.72 (d, J = 2.4 Hz, 1H), 7.45-7.6 (m, 2H), 7.25 and 7.10 (bs, 1H), 4.80 and 4.58 (s, 1H), 4.1-4.25 (m, 2H), 4.16 (d, J = 17.4 Hz, 1H), 3.81 and 3.78 (s, 3H), 3.72 (d, J = 17.4 Hz, 1H), 2.70 and 2.54 (s, 3H). |
| 1-204 | δ8.07 (s, 2H), 7.96 (s, 1H), 7.71 (t, J = 1.5 Hz, 1H), 7.45-7.6 (m, 2H), 7.24 (t, J = 6.0 Hz, 1H), 4.67 (s, 1H), 4.66 (dd, J = 15.6, 6.0 Hz, 1H), 4.56 (dd, J = 15.6, 6.0 Hz, 1H), 4.16 (d, J = 17.4 Hz, 1H), 3.82 (s, 3H), 3.73 (d, J = 17.4 Hz, 1H), 3.05 (s, 3H). |
| 1-207 | δ7.69 (s, 1H), 7.63 (s, 2H), 7.45-7.55 (m, 2H), 7.12 (bs, 1H), 4.57 (s, 2H), 4.29 (s, 1H), 4.07 (d, J = 17.4 Hz, 1H), 3.68 (d, J = 17.4 Hz, 1H), 2.15 (s, 6H). |
| 1-209 | δ8.07 (s, 2H), 7.97 (s, 1H), 7.70 (s, 1H), 7.5-7.6 (m, 2H), 7.44 and 7.35 (t, J = 6.0 Hz, 1H), 4.62 and 4.61 (d, J = 6.0 Hz, 2H), 4.17 (d, J = 17.4 Hz, 1H), 4.40 and 4.13 (s, 1H), 3.73 (d, J = 17.4 Hz, 1H), 2.68 and 2.61 (s, 3H), 2.33 and 2.27 (s, 3H). |
| 1-210 | δ7.96 (s, 1H), 7.85 (s, 1H), 7.79 (s, 1H), 7.71 (s, 1H), 7.5-7.65 (m, 3H), 4.69 and 4.62 (d, J = 6.0 Hz, 2H), 4.63 and 4.14 (d, J = 14.1 Hz, 1H), 4.11 (d, J = 17.4 Hz, 1H), 3.68 (d, J = 17.4 Hz, 1H), 2.90 and 2.88 (s, 3H), 2.83 and 2.76 (s, 3H). |
| 1-212 | δ7.95 (s, 1H), 7.84 (s, 1H), 7.79 (s, 1H), 7.69 (s, 1H), 7.54 (s, 2H), 7.51 (d, J = 6.6 Hz, 1H), 4.98 and 4.72 (s, 1H), 4.66 and 4.58 (d, J = 6.6 Hz, 2H), 4.11 (d, J = 17.4 Hz, 1H), 3.70 (d, J = 17.4 Hz, 1H), 3.23 and 3.18 (s, 3H), 2.87 and 2.84 (s, 3H). |
| 1-213 | δ8.07 (s, 2H), 7.96 (s, 1H), 7.71 (s, 1H), 7.45-7.65 (m, 2H), 7.85 and 7.44 (bs, 1H), 4.55-4.85 (m, 3H), 4.17 (d, J = 17.4 Hz, 1H), 3.72 (d, J = 17.4 Hz, 1H), 3.26 and 3.18 (s, 3H), 2.87 and 2.84 (s, 3H). |
| 1-216 | δ7.75 (d, J = 5.4 Hz, 2H), 7.68 (d, J = 1.5 Hz, 1H), 7.4-7.55 (m, 2H), 7.18 (t, J = 6.0 Hz, 1H), 4.56 (d, J = 6.0 Hz, 2H), 4.37 (s, 1H), 4.06 (d, J = 17.4 Hz, 1H), 3.68 (d, J = 17.4 Hz, 1H), 2.55-2.75 (m, 4H), 1.25 (t, J = 7.5 Hz, 6H). |
| 1-217 | δ7.82 (s, 2H), 7.69 (s, 1H), 7.45-7.55 (m, 2H), 7.16 (t, J = 6.3 Hz, 1H), 4.56 (d, J = 6.3 Hz, 2H), 4.36 (s, 1H), 4.05 (d, J = 17.4 Hz, 1H), 3.67 (d, J = 17.4 Hz, 1H), 2.66 (qd, J = 7.5, 4.8 Hz, 4H), 1.23 (t, J = 7.5 Hz, 6H). |
| 1-218 | δ7.93 (d, J = 1.8 Hz, 1H), 7.83 (s, 1H), 7.68 (s, 1H), 7.45-7.55 (m, 2H), 7.19 (t, J = 6.0 Hz, 1H), 4.56 (d, J = 60.0 Hz, 2H), 4.37 (s, 1H), 4.12 (d, J = 17.4 Hz, 1H), 3.70 (d, J = 17.4 Hz, 1H), 2.55-2.75 (m, 4H), 1.25 (t, J = 7.5 Hz, 6H). |
| 1-219 | δ8.07 (s, 2H), 7.97 (s, 1H), 7.25-7.55 (m, 3H), 7.31 (bs, 1H), 4.57 (d, J = 6.3 Hz, 2H), 4.16 (d, J = 17.4 Hz, 1H), 4.43 and 4.15 (s, 1H), 3.72 (d, J = 17.4 Hz, 1H), 2.55-3.1 (m, 4H), 1.2-1.4 (m, 6H). |
| 1-221 | δ7.75 (d, J = 5.4 Hz, 2H), 7.67 (s, 1H), 7.35-7.6 (m, 3H), 4.55-4.7 (m, 2H), 4.43 and 4.15 (s, 1H), 4.04 (d, J = 17.4 Hz, 1H), 3.66 (d, J = 17.4 Hz, 1H), 2.55-3.1 (m, 4H), 1.2-1.45 (m, 6H). |
| 1-222 | δ7.93 (d, J = 1.5 Hz, 1H), 7.82 (s, 1H), 7.67 (s, 1H), 7.35-7.6 (m, 3H), 4.5-4.7 (m, 2H), 4.44 and 4.07 (s, 1H), 4.16 (d, J = 17.4 Hz, 1H), 3.68 (d, J = 17.4 Hz, 1H), 2.55-3.1 (m, 4H), 1.2-1.45 (m, 6H). |
| 1-223 | δ8.07 (s, 2H), 7.97 (s, 1H), 7.69 (d, J = 1.8 Hz, 1H), 7.4-7.6 (m, 3H), 4.64 (dd, J = 15.6, 6.0 Hz, 1H), 4.56 (dd, J = 15.6, 6.0 Hz, 1H), 4.47 and 4.18 (s, 1H), 4.17 (d, J = 17.4 Hz, 1H), 3.73 (d, J = 17.4 Hz, 1H), 2.55-3.1 (m, 4H), 1.25-1.4 (m, 6H). |

TABLE 7-continued

| No. | $^1$H NMR (CDCl$_3$, Me$_4$Si, 300 MHz) |
|---|---|
| 1-224 | δ7.93 (s, 1H), 7.83 (s, 1H), 7.69 (s, 1H), 7.45-7.6 (m, 2H), 4.55-4.8 (m, 2H), 4.1-4.25 (m, 1H), 4.11 (d, J = 17.4 Hz, 1H), 3.69 (d, J = 17.4 Hz, 1H), 2.8-3.2 (m, 4H), 1.3-1.5 (m, 6H). |
| 1-227 | δ7.93 (d, J = 2.1 Hz, 1H), 7.89 (t, J = 6.0 Hz, 1H), 7.82 (s, 1H), 7.70 (s, 1H), 7.5-7.65 (m, 2H), 4.55-4.75 (m, 2H), 4.77 and 4.47 (s, 1H), 4.10 (d, J = 17.4 Hz, 1H), 3.67 (d, J = 17.4 Hz, 1H), 3.4-3.55 and 3.2-3.4 (m, 2H), 2.85-3.15 (m, 2H), 1.35-1.55 (m, 6H). |
| 1-230 | δ7.82 (s, 1H), 7.76 (s, 1H), 7.68 (s, 1H), 7.65 (d, J = 8.1 Hz, 2H), 7.40 (d, J = 8.1 Hz, 2H), 7.12 (d, J = 7.2 Hz, 1H), 5.15 (qui, J = 7.2 Hz, 1H), 4.11 (d, J = 17.4 Hz, 1H), 3.70 (d, J = 17.4 Hz, 1H), 3.24 (d, J = 16.2 Hz, 1H), 3.17 (d, J = 16.2 Hz, 1H), 2.09 (s, 3H), 1.53 (d, J = 7.2 Hz, 3H). |
| 1-231 | δ8.15 (s, 1H), 8.02 (s, 1H), 7.83 (s, 1H), 7.65 (d, J = 8.4 Hz, 2H), 7.39 (d, J = 8.4 Hz, 2H), 7.13 (d, J = 7.2 Hz, 1H), 5.15 (qui, J = 7.2 Hz, 1H), 4.11 (d, J = 17.4. Hz, 1H), 3.69 (d, J = 17.4 Hz, 1H), 3.23 (d, J = 16.5 Hz, 1H), 3.18 (d, J = 16.5 Hz, 1H), 2.09 (s, 3H), 1.53 (d, J = 7.2 Hz, 3H). |
| 1-233 | δ7.76 (d, J = 5.4 Hz, 2H), 7.5-7.65 (m, 2H), 7.35-7.45 (m, 2H), 5.12 (qui, J = 7.2 Hz, 1H), 4.07 and 4.06 (d, J = 17.4 Hz, 1H), 3.67 (d, J = 17.4 Hz, 1H), 3.7-3.8 and 3.3-3.5 (m, 2H), 2.76, 2.57, 2.42 and 2.09 (s, 3H), 1.4-1.6 (m, 3H). |
| 1-236 | δ7.82 (s, 1H), 7.76 (s, 1H), 7.68 (s, 1H), 7.65 (d, J = 8.1 Hz, 2H), 7.40 (d, J = 8.1 Hz, 2H), 7.16 (d, J = 7.2 Hz, 1H), 5.14 (qui, J = 7.2 Hz, 1H), 4.12 (d, J = 17.4 Hz, 1H), 3.71 (d, J = 17.4 Hz, 1H), 3.26 (d, J = 15.9 Hz, 1H), 3.20 (d, J = 15.9 Hz, 1H), 2.53 (q, J = 7.5 Hz, 2H), 1.52 (d, J = 7.2 Hz, 3H), 1.24 (t, J = 7.5 Hz, 3H). |
| 1-239 | δ7.95 (s, 1H), 7.84 (s, 1H), 7.79 (s, 1H), 7.68 (s, 1H), 7.54 (d, J = 8.1 Hz, 1H), 7.50 (d, J = 8.1 Hz, 1H), 7.44 (t, J = 6.0 Hz, 1H), 4.60 (d, J = 6.0 Hz, 2H), 4.10 (d, J = 17.1 Hz, 1H), 3.68 (d, J = 17.1 Hz, 1H), 3.67 (d, J = 14.4 Hz, 1H), 3.31 (d, J = 14.4 Hz, 1H), 2.7-2.95 (m, 2H), 1.33 (t, J = 7.7 Hz, 3H). |
| 1-240 | δ7.76 (d, J = 6.0 Hz, 2H), 7.61 (d, J = 5.4 Hz, 2H), 7.35-7.55 (m, 3H), 5.05-5.2 (m, 1H), 4.06 (d, J = 17.4 Hz, 1H), 3.66 (d, J = 17.4 Hz, 1H), 3.66 and 3.60 (d, J = 14.4 Hz, 1H), 3.32 and 3.24 (d, J = 14.4 Hz, 1H), 2.8-3.0 and 2.6-2.8 (m, 2H), 1.50 (t, J = 6.6 Hz, 3H), 1.36 and 1.26 (t, J = 7.5 Hz, 3H). |
| 1-242 | δ7.76 (d, J = 5.7 Hz, 2H), 7.63 (d, J = 8.4 Hz, 2H), 7.38 (d, J = 8.4 Hz, 2H), 6.85 (d, J = 7.2 Hz, 1H), 5.10 (qui, J = 7.2 Hz, 1H), 4.32 (s, 1H), 4.07 (d, J = 17.4 Hz, 1H), 3.67 (d, J = 17.4 Hz, 1H), 2.55-2.8 (m, 4H), 1.51 (d, J = 7.2 Hz, 3H), 1.26 (t, J = 7.5 Hz, 3H), 1.23 (t, J = 7.5 Hz, 3H). |
| 2-001 | δ8.08 (s, 2H), 7.97 (s, 1H), 7.69 and 7.61 (d, J = 1.8 Hz, 1H), 7.5-7.6 (m, 1H), 7.2-7.35 (m, 1H), 4.72 (s, 2H), 4.20 and 4.18 (d, J = 17.4 Hz, 1H), 3.75 (d, J = 17.4 Hz, 1H), 3.39 and 3.26 (s, 2H), 3.09 and 2.99 (s, 3H), 2.71 and 2.68 (q, J = 7.5 Hz, 2H), 1.32 and 1.28 (t, J = 7.5 Hz, 3H). |
| 2-003 | δ8.08 (s, 2H), 7.97 (s, 1H), 7.76 and 7.68 (s, 1H), 7.5-7.6 (m, 1H), 7.2-7.35 (m, 1H), 4.71 and 4.69 (s, 2H), 4.20 and 4.18 (d, J = 17.4 Hz, 1H), 3.74 (d, J = 17.4 Hz, 1H), 3.3-3.5 (m, 2H), 3.38 and 3.19 (s, 2H), 2.72 and 2.67 (q, J = 7.5 Hz, 2H), 1.30 and 1.24 (t, J = 7.5 Hz, 3H), 1.32 and 1.16 (t, J = 7.5 Hz, 3H). |
| 2-004 | δ8.08 (s, 2H), 7.97 (s, 1H), 7.76 and 7.69 (s, 1H), 7.5-7.6 (m, 1H), 7.25-7.4 (m, 1H), 4.89 and 4.80 (s, 2H), 4.1-4.25 (m, 3H), 3.74 (d, J = 17.4 Hz, 1H), 3.48 and 3.26 (s, 2H), 2.69 and 2.68 (q, J = 7.5 Hz, 2H), 2.33 and 2.23 (t, J = 2.4 Hz, 1H), 1.32 and 1.28 (t, J = 7.5 Hz, 3H). |
| 2-006 | δ8.09 (s, 2H), 7.97 (s, 1H), 7.77 and 7.70 (d, J = 1.5 Hz, 1H), 7.55-7.65 (m, 1H), 7.2-7.35 (m, 1H), 4.73 (s, 2H), 4.22 and 4.20 (d, J = 17.4 Hz, 1H), 3.78 (d, J = 17.4 Hz, 1H), 3.36 and 3.24 (s, 2H), 3.10 and 3.00 (s, 3H), 2.24 and 2.22 (s, 3H). |
| 2-007 | δ8.08 (s, 2H), 7.97 (s, 1H), 7.76 and 7.69 (d, J = 1.5 Hz, 1H), 7.5-7.6 (m, 1H), 7.33 and 7.26 (d, J = 7.1 Hz, 1H), 4.70 (s, 2H), 4.21 and 4.19 (d, J = 17.4 Hz, 1H), 3.76 (d, J = 17.4 Hz, 1H), 3.43 and 3.41 (q, J = 7.2 Hz, 2H), 3.35 and 3.16 (s, 2H), 2.26 and 2.21 (s, 3H), 1.26 and 1.24 (t, J = 7.2 Hz, 3H). |
| 2-008 | δ7.96 (s, 1H), 7.75-7.95 (m, 3H), 7.55-7.65 (m, 1H), 7.30 and 7.23 (d, J = 8.4 Hz, 1H), 4.67 and 4.66 (s, 2H), 4.12 and 4.11 (d, J = 17.1 Hz, 1H), 3.69 (d, J = 17.1 Hz, 1H), 3.3-3.5 (m, 2H), 3.35 and 3.24 (s, 2H), 2.27 and 2.21 (s, 3H), 1.23 and 1.19 (t, J = 7.2 Hz, 3H). |
| 2-009 | δ8.07 (s, 2H), 7.97 (s, 1H), 7.55-7.8 (m, 2H), 7.51 and 7.33 (d, J = 8.1 Hz, 1H), 4.84 and 4.82 (s, 2H), 4.37 and 4.27 (s, 2H), 4.19 (d, J = 17.4 Hz, 1H), 3.74 (d, J = 17.4 Hz, 1H), 3.41 and 3.33 (s, 2H), 2.23 (s, 3H). |
| 2-011 | δ8.07 (s, 2H), 7.97 (s, 1H), 7.76 and 7.72 (d, J = 1.5 Hz, 1H), 7.55-7.65 (m, 1H), 7.43 and 7.22 (d, J = 7.8 Hz, 1H), 4.65-4.9 (m, 2H), 4.19 and 4.17 (d, J = 17.4 Hz, 1H), 4.0-4.05 (m, 1H), 3.75-3.85 (m, 1H), 3.73 (d, J = 17.4 Hz, 1H), 3.12 and 3.01 (s, 3H), 2.81 and 2.79 (s, 3H). |
| 2-012 | δ8.07 (s, 2H), 7.97 (s, 1H), 7.75 and 7.71 (d, J = 1.5 Hz, 1H), 7.4-7.6 and 7.2-7.3 (m, 2H), 4.6-4.85 (m, 2H), 4.18 and 4.16 (d, J = 17.4 Hz, 1H), 3.75-4.05 (m, 2H), |

TABLE 7-continued

| No. | $^1$H NMR (CDCl$_3$, Me$_4$Si, 300 MHz) |
|---|---|
| | 3.78 and 3.72 (d, J = 17.4 Hz, 1H), 3.3-3.6 (m, 2H), 2.82 and 2.79 (s, 3H), 1.26 and 1.24 (t, J = 7.5 Hz, 3H). |
| 2-013 | δ8.07 (s, 2H), 7.97 (s, 1H), 7.80 and 7.74 (d, J = 1.5 Hz, 1H), 7.55-7.7 (m, 1H), 7.49 and 7.37 (d, J = 7.1 Hz, 1H), 4.65-5.1 (m, 2H), 4.17 (d, J = 17.4 Hz, 1H), 4.15-4.4 and 3.95-4.05 (m, 3H), 3.75 and 3.73 (d, J = 17.4 Hz, 1H), 3.78 and 3.60 (d, J = 13.2 Hz, 1H), 2.79 and 2.77 (s, 3H). |
| 2-014 | δ8.07 (s, 2H), 7.97 (s, 1H), 7.77 and 7.72 (s, 1H), 7.5-7.65 (m, 1H), 7.47 and 7.33 (d, J = 7.4 Hz, 1H), 4.65-5.05 (m, 2H), 4.33 (d, J = 19.2 Hz, 1H), 4.17 (d, J = 17.4 Hz, 1H), 4.0-4.25 (m, 2H), 3.7-3.85 (m, 1H), 3.74 and 3.73 (d, J = 17.4 Hz, 1H), 2.78 (s, 3H), 2.37 and 2.26 (t, J = 2.4 Hz, 1H). |
| 2-015 | δ7.96 and 7.94 (s, 1H), 7.89 (s, 1H), 7.84 (s, 1H), 7.79 (s, 1H), 7.55-7.7 (m, 1H), 7.42 and 7.21 (d, J = 8.1 Hz, 1H), 4.82 (d, J = 16.2 Hz, 1H), 4.63 (d, J = 16.2 Hz, 1H), 3.7-4.2 (m, 2H), 3.3-3.7 (m, 4H), 2.81 and 2.77 (s, 3H), 1.24 and 1.18 (t, J = 7.5 Hz, 3H). |
| 2-016 | δ8.07 (s, 2H), 7.97 (s, 1H), 7.76 and 7.73 (s, 1H), 7.55-7.65 (m, 1H), 7.38 and 7.24 (d, J = 7.2 Hz, 1H), 4.77 (s, 2H), 4.19 and 4.18 (d, J = 17.4 Hz, 1H), 4.19 and 4.04 (s, 2H), 3.75 and 3.74 (d, J = 17.4 Hz, 1H), 3.19 (s, 3H), 3.16 (s, 3H). |
| 2-017 | δ8.07 (s, 2H), 7.97 (s, 1H), 7.76 and 7.73 (d, J = 1.5 Hz, 1H), 7.5-7.65 (m, 1H), 7.38 and 7.26 (d, J = 8.4 Hz, 1H), 4.74 and 4.73 (s, 2H), 4.20 and 4.18 (d, J = 17.4 Hz, 1H), 4.17 and 3.97 (s, 2H), 3.76 and 3.74 (d, J = 17.4 Hz, 1H), 3.53 and 3.47 (q, J = 7.2 Hz, 2H), 3.19 and 3.17 (s, 3H), 1.27 and 1.18 (t, J = 7.2 Hz, 3H). |
| 2-018 | δ8.07 (s, 2H), 7.97 (s, 1H), 7.80 and 7.76 (s, 1H), 7.55-7.7 (m, 1H), 7.38 (d, J = 7.1 Hz, 1H), 4.88 (s, 2H), 4.44 and 4.26 (s, 2H), 4.28 and 4.19 (s, 2H), 4.19 and 4.17 (d, J = 17.4 Hz, 1H), 3.75 and 3.74 (d, J = 17.4 Hz, 1H), 3.19 and 3.13 (s, 3H). |
| 2-019 | δ8.07 (s, 2H), 7.97 (s, 1H), 7.77 and 7.73 (d, J = 1.8 Hz, 1H), 7.55-7.65 (m, 1H), 7.3-7.4 (m, 1H), 4.89 and 4.84 (s, 2H), 4.26 and 4.23 (d, J = 2.4 Hz, 2H), 4.18 and 4.17 (d, J = 17.4 Hz, 1H), 4.29 and 4.03 (s, 2H), 3.74 and 3.72 (d, J = 17.4 Hz, 1H), 3.19 and 3.15 (s, 3H), 2.40 and 2.26 (t, J = 2.4 Hz, 1H). |
| 2-021 | δ8.08 (s, 2H), 7.97 (s, 1H), 7.76 and 7.68 (d, J = 1.8 Hz, 1H), 7.5-7.6 (m, 1H), 7.2-7.35 (m, 1H), 4.72 and 4.69 (s, 2H), 4.19 and 4.18 (d, J = 17.4 Hz, 1H), 3.75 and 3.74 (d, J = 17.4 Hz, 1H), 3.38 and 3.18 (s, 2H), 3.25-3.4 (m, 2H), 2.73 and 2.67 (q, J = 7.5 Hz, 2H), 1.65 (sxt, J = 7.5 Hz, 2H), 1.32 and 1.28 (t, J = 7.5 Hz, 3H), 0.93 and 0.91 (t, J = 7.5 Hz, 3H). |
| 2-022 | δ8.07 (s, 2H), 7.97 (s, 1H), 7.76 and 7.68 (d, J = 1.5 Hz, 1H), 7.55 (td, J = 8.1, 1.8 Hz, 1H), 7.37 and 7.20 (d, J = 8.1 Hz, 1H), 4.73 and 4.71 (s, 2H), 4.19 and 4.17 (d, J = 17.4 Hz, 1H), 3.73 (d, J = 17.4 Hz, 1H), 3.39 and 3.16 (s, 2H), 3.21 and 3.14 (d, J = 7.5 Hz, 2H), 2.70 and 2.68 (q, J = 7.5 Hz, 2H), 1.9-2.1 (m, 1H), 1.31 and 1.28 (t, J = 7.5 Hz, 3H), 0.95 (t, J = 7.5 Hz, 6H). |
| 2-023 | δ8.08 (s, 2H), 7.97 (s, 1H), 7.75 and 7.67 (d, J = 1.2 Hz, 1H), 7.5-7.6 (m, 1H), 7.2-7.3 (m, 1H), 4.84 and 4.82 (s, 2H), 4.19 and 4.18 (d, J = 17.4 Hz, 1H), 3.75 and 3.74 (d, J = 17.4 Hz, 1H), 3.44 and 3.21 (s, 2H), 3.32 and 3.27 (d, J = 16.6 Hz, 2H), 2.73 and 2.68 (q, J = 7.2 Hz, 2H), 1.32 and 1.28 (t, J = 7.2 Hz, 3H), 0.85-1.05 (m, 1H), 0.45-0.6 (m, 2H), 0.1-0.25 (m, 2H). |
| 2-024 | δ8.07 (s, 2H), 7.97 (s, 1H), 7.78 and 7.73 (s, 1H), 7.55-7.7 (m, 1H), 7.3-7.4 (m, 1H), 4.85 (s, 2H), 4.37 and 4.27 (s, 2H), 4.18 (d, J = 17.4 Hz, 1H), 3.74 (d, J = 17.4 Hz, 1H), 3.45 and 3.36 (s, 2H), 2.69 (q, J = 7.5 Hz, 2H), 1.30 (t, J = 7.5 Hz, 3H). |
| 2-025 | δ8.07 (s, 2H), 7.97 (s, 1H), 7.75 and 7.68 (d, J = 1.5 Hz, 1H), 7.57 (td, J = 8.1, 1.8 Hz, 1H), 7.36 and 7.27 (d, J = 8.1 Hz, 1H), 7.7-7.9 (m, 1H), 5.1-5.3 (m, 2H), 4.69 (s, 2H), 4.19 and 4.17 (d, J = 17.4 Hz, 1H), 3.95-4.05 (m, 2H), 3.73 (d, J = 17.4 Hz, 1H), 3.34 and 3.21 (s, 2H), 2.71 and 2.69 (q, J = 7.5 Hz, 2H), 1.32 and 1.28 (t, J = 7.5 Hz, 3H). |
| 2-026 | δ8.08 (s, 2H), 7.97 (s, 1H), 7.73 and 7.66 (d, J = 1.5 Hz, 1H), 7.55-7.6 (m, 1H), 7.15-7.45 (m, 6H), 4.71 and 4.66 (s, 2H), 4.62 and 4.61 (s, 2H), 4.19 and 4.18 (d, J = 17.4 Hz, 1H), 3.74 (d, J = 17.4 Hz, 1H), 3.37 and 3.23 (s, 2H), 2.73 and 2.72 (q, J = 7.5 Hz, 2H), 1.32 and 1.30 (t, J = 7.5 Hz, 3H). |
| 2-027 | δ8.08 (s, 2H), 7.98 (s, 1H), 7.77 and 7.73 (d, J = 1.8 Hz, 1H), 7.55-7.65 (m, 1H), 7.43 and 7.23 (d, J = 7.8 Hz, 1H), 4.84, 4.79, 4.76 and 4.70 (s, 2H), 4.20 and 4.18 (d, J = 17.4 Hz, 1H), 3.97 (d, J = 16.8 Hz, 1H), 3.80 (d, J = 16.8 Hz, 1H), 3.75 and 3.74 (d, J = 17.4 Hz, 1H), 3.14 and 3.02 (s, 2H), 2.8-3.1 (m, 3H), 1.40 and 1.38 (t, J = 7.5 Hz, 3H). |
| 2-028 | δ8.07 (s, 2H), 7.97 (s, 1H), 7.77 and 7.71 (d, J = 1.2 Hz, 1H), 7.5-7.8 and 7.2-7.45 (m, 2H), 4.65-4.85 (m, 2H), 4.20 and 4.17 (d, J = 17.4 Hz, 1H), 3.93 and 3.79 (d, J = 13.8 Hz, 2H), |

TABLE 7-continued

| No. | $^1$H NMR (CDCl$_3$, Me$_4$Si, 300 MHz) |
|---|---|
| | 3.67 (d, J = 17.4 Hz, 1H), 3.7-3.85 and 3.35-3.6 (m, 2H), 2.8-3.1 (m, 2H), 1.40 and 1.36 (t, J = 7.5 Hz, 3H), 1.26 and 1.24 (t, J = 7.2 Hz, 3H). |
| 2-029 | δ8.07 (s, 2H), 7.97 (s, 1H), 7.76 and 7.72 (d, J = 1.5 Hz, 1H), 7.5-7.65 (m, 1H), 7.46 and 7.33 (d, J = 7.1 Hz, 1H), 4.94, 4.88, 4.80 and 4.75 (s, 2H), 4.18 and 4.16 (d, J = 17.4 Hz, 1H), 4.1-4.4 (m, 3H), 3.75-3.85 (m, 1H), 3.74 and 3.72 (d, J = 17.4 Hz, 1H), 2.8-3.1 (m, 2H), 2.36 and 2.25 (t, J = 2.4 Hz, 1H), 1.40 and 1.37 (t, J = 7.5 Hz, 3H). |
| 2-030 | δ8.08 (s, 2H), 7.98 (s, 1H), 7.77 and 7.74 (d, J = 1.8 Hz, 1H), 7.65-7.55 and 7.45-7.35 (m, 2H), 4.81 and 4.78 (s, 2H), 4.19 and 4.18 (d, J = 17.4 Hz, 1H), 4.19 and 4.04 (s, 2H), 3.74 and 3.73 (d, J = 17.4 Hz, 1H), 3.31 and 3.22 (q, J = 7.5 Hz, 2H), 3.22 and 3.03 (s, 3H), 1.46 and 1.45 (t, J = 7.5 Hz, 3H). |
| 2-031 | δ8.07 (s, 2H), 7.97 (s, 1H), 7.76 and 7.73 (d, J = 1.5 Hz, 1H), 7.5-7.65 (m, 1H), 7.39 and 7.26 (d, J = 7.1 Hz, 1H), 4.77 and 4.73 (s, 2H), 4.19 and 4.17 (d, J = 17.4 Hz, 1H), 4.13 and 3.93 (s, 2H), 3.74 and 3.73 (d, J = 17.4 Hz, 1H), 3.55 and 3.46 (q, J = 7.2 Hz, 2H), 3.35 and 3.31 (q, J = 7.5 Hz, 2H), 1.46 and 1.45 (t, J = 7.5 Hz, 3H), 1.27 and 1.26 (t, J = 7.2 Hz, 3H). |
| 2-032 | δ8.07 (s, 2H), 7.97 (s, 1H), 7.77 and 7.73 (d, J = 1.8 Hz, 1H), 7.5-7.65 (m, 1H), 7.3-7.4 (m, 1H), 4.91 and 4.83 (s, 2H), 4.25 (d, J = 2.4 Hz, 2H), 4.19 and 4.17 (d, J = 17.4 Hz, 1H), 4.27 and 4.02 (s, 2H), 3.75 and 3.73 (d, J = 17.4 Hz, 1H), 3.33 and 3.28 (q, J = 7.2 Hz, 2H), 2.40 and 2.26 (t, J = 2.4 Hz, 1H), 1.46 and 1.45 (t, J = 7.2 Hz, 3H). |
| 3-001 | δ9.27 (bs, 1H), 7.9-7.95 (m, 2H), 7.82 (s, 1H), 7.5-7.65 (m, 2H), 5.01 (d, J = 5.7 Hz, 2H), 4.11 (d, J = 17.4 Hz, 1H), 3.81 (s, 2H), 3.69 (d, J = 17.4 Hz, 1H), 2.05 (s, 3H). |

TEST EXAMPLES

Next, the usefulness of the compound of the present invention as a pest control agent is more specifically described in the following Test Examples, which should not be construed as limiting the scope of the present invention.

Test Example 1

Mortality Test for *Plutella xylostella*

A 10% emulsifiable concentrate of the compound of the present invention (depending on the type of the compound, a 10% wettable powder was subjected to the test) was diluted with water containing a spreader to prepare a drug solution in a concentration of 10 ppm. In this drug solution, a leaf of cabbage was immersed for about 10 seconds and was air-dried and then put into a petri dish. In the petri dish, five 2 instar larvae of *Plutella xylostella* per petri dish were released and the petri dish was capped and stored in a thermostatic room of 25° C. The number of killed larvae after 6 days was measured and the mortality was calculated from the following calculation formula:

Mortality (%)=(number of killed insect/number of released insect)×100.

Here, the test was carried out on the duplicate samples.

As the results of the test, among the compounds subjected to the test, the following compounds exhibited the mortality of 80% or more.

The compounds of the present invention: Nos. 1-001, 1-002, 1-003*, 1-004, 1-004(+), 1-005 to 1-011, 1-011(+), 1-012 to 1-014, 1-015*, 1-016, 1-017, 1-018*, 1-019 to 1-027, 1-028**, 1-029, 1-030*, 1-031, 1-032**, 1-033*, 1-034*, 1-035*, 1-036*, 1-037, 1-038*, 1-039*, 1-040*, 1-041**, 1-042 to 1-059, 1-060*, 1-061**, 1-062 to 1-067, 1-068*, 1-069, 1-070*, 1-071*, 1-072, 1-073*, 1-074, 1-075, 1-076*, 1-077*, 1-078*, 1-079 to 1-082, 1-083*, 1-084*, 1-085*, 1-086*, 1-087*, 1-088*, 1-089*, 1-090, 1-091, 1-092*, 1-093*, 1-094*, 1-095*, 1-096 to 1-098, 1-099*, 1-100*, 1-101, 1-102, 1-103*, 1-104*, 1-105, 1-106, 1-107*, 1-108*, 1-109, 1-110*, 1-111, 1-112*, 1-113*, 1-114*, 1-115*, 1-116 to 1-119, 1-120*, 1-121, 1-122*, 1-123, 1-124*, 1-125, 1-126*, 1-127 to 1-132, 1-133*, 1-134*, 1-135 to 1-139, 1-140*, 1-141*, 1-142, 1-143*, 1-144*, 1-145*, 1-146, 1-147, 1-148*, 1-149 to 1-151, 1-152*, 1-153, 1-154*, 1-155, 1-156*, 1-157, 1-158*, 1-159 to 1-161, 1-162*, 1-164 to 1-166, 1-167*, 1-168, 1-169*, 1-170*, 1-171, 1-172*, 1-173, 1-174*, 1-175*, 1-176*, 1-177*, 1-178*, 1-179*, 1-180*, 1-181**, 1-182*, 1-183, 1-184**, 1-185*, 1-186 to 1-189, 1-190*, 1-191*, 1-192*, 1-193*, 1-194*, 1-195, 1-196*, 1-197*, 1-198*, 1-199*, 1-200**, 1-201*, 1-202*, 1-203*, 1-204*, 1-205*, 1-206 to 1-208, 1-209*, 1-210*, 1-211*, 1-212*, 1-213*, 1-214, 1-215*, 1-216, 1-217, 1-218*, 1-219, 1-220*, 1-221, 1-222*, 1-223*, 1-224*, 1-225*, 1-226*, 1-227*, 1-228, 1-229, 1-230 to 1-242, 2-001 to 2-005, 2-006*, 2-007*, 2-008*, 2-009, 2-010, 2-011*, 2-012*, 2-013, 2-014, 2-015*, 2-016*, 2-017*, 2-018, 2-019, 2-020*, 2-021 to 2-025, 2-026*, 2-027*, 2-028*, 2-029, 2-030*, 2-031*, 2-032*, 3-001*, and 4-001*.

Here, the mark "*" indicates that the mortality test was performed using a drug solution of 100 ppm concentration, and the mark "**" indicates that the mortality test was performed using a drug solution of 500 ppm concentration.

Test Example 2

Mortality Test for *Spodoptera litura*

A 10% emulsifiable concentrate of the compound of the present invention (depending on the type of the compound, a 10% wettable powder was subjected to the test) was diluted with water containing a spreader to prepare a drug solution in a concentration of 10 ppm. In this drug solution, a leaf of cabbage was immersed for about 10 seconds and was air-dried and then put into a petri dish. In the petri dish, five 2 instar larvae of *Spodoptera litura* per petri dish were released and the petri dish was capped and stored in a thermostatic room of 25° C. The number of killed larvae after 6 days was measured and the mortality was calculated from the same calculation formula as that in Test Example 1. Here, the test was carried out on the duplicate samples.

As the results of the test, among the compounds subjected to the test, the following compounds exhibited the mortality of 80% or more.

The compounds of the present invention: Nos. 1-001, 1-002, 1-003*, 1-004, 1-004(+), 1-005 to 1-008, 1-010, 1-011, 1-011 (+), 1-012 to 1-014, 1-015*, 1-016, 1-017, 1-018*, 1-019 to 1-027, 1-028**, 1-029, 1-030*, 1-031, 1-033*, 1-034*, 1-035*, 1-036*, 1-038*, 1-039*, 1-040*, 1-041**, 1-042 to 1-059, 1-060*, 1-061**, 1-062 to 1-067, 1-068*, 1-069, 1-070*, 1-071*, 1-072, 1-073*, 1-074, 1-075, 1-076*, 1-077*, 1-078*, 1-079 to 1-082, 1-083*, 1-084*, 1-085*, 1-086*, 1-087*, 1-088*, 1-089*, 1-090, 1-091, 1-092*, 1-093*, 1-094*, 1-095*, 1-096 to 1-098, 1-099*, 1-100*, 1-101, 1-102, 1-103*, 1-104*, 1-105, 1-106, 1-107*, 1-108*, 1-109, 1-110*, 1-111, 1-112*, 1-113*, 1-114*, 1-115*, 1-116 to 1-119, 1-120*, 1-121, 1-122*, 1-123, 1-124*, 1-125, 1-126*, 1-127, 1-128, 1-130 to 1-132, 1-133*, 1-134*, 1-135 to 1-139, 1-140*, 1-141*, 1-142, 1-143*, 1-144*, 1-145*, 1-146, 1-147, 1-148*, 1-149 to 1-151, 1-152*, 1-153, 1-154*, 1-155, 1-156*, 1-157, 1-158*, 1-159 to 1-161, 1-162*, 1-164 to 1-166, 1-167*, 1-168, 1-169*, 1-170*, 1-171, 1-172*, 1-173, 1-174*, 1-175*, 1-176*, 1-177*, 1-178*, 1-179*, 1-182*, 1-183, 1-184**, 1-186 to 1-189, 1-190*, 1-191*, 1-192*, 1-193*, 1-194*, 1-195, 1-196*, 1-197*, 1-198*, 1-199*, 1-200**, 1-201*, 1-202*, 1-203*, 1-204*, 1-205*, 1-206 to 1-208, 1-209*, 1-210*, 1-211*, 1-212*, 1-213*, 1-214, 1-215*, 1-216, 1-217, 1-218*, 1-219, 1-220*, 1-221, 1-222*, 1-223*, 1-224*, 1-225*, 1-226*, 1-227*, 1-232, 1-235, 1-237 to 1-241, 2-001 to 2-005, 2-006*, 2-007*, 2-008*, 2-009, 2-010, 2-011*, 2-012*, 2-013, 2-014, 2-015*, 2-016*, 2-017*, 2-018, 2-019, 2-020*, 2-021 to 2-025, 2-027*, 2-028*, 2-029, 2-030*, 2-031*, 2-032*, 3-001*, and 4-001*.

Here, the mark "*" indicates that the mortality test was performed using a drug solution of 100 ppm concentration, and the mark "**" indicates that the mortality test was performed using a drug solution of 500 ppm concentration.

Test Example 3

Mortality Test for *Spodoptera exigua*

A 10% emulsifiable concentrate of the compound of the present invention (depending on the type of the compound, a 10% wettable powder was subjected to the test) was diluted with water containing a spreader to prepare a drug solution in a concentration of 100 ppm. In this drug solution, a leaf of cabbage was immersed for about 10 seconds and was air-dried and then put into a petri dish. In the petri dish, five 2 instar larvae of *Spodoptera exigua* per petri dish were released and the petri dish was capped and stored in a thermostatic room of 25° C. The number of killed larvae after 6 days was measured and the mortality was calculated from the same calculation formula as that in Test Example 1. Here, the test was carried out on the duplicate samples.

As the results of the test, among the compounds subjected to the test, the following compounds exhibited the mortality of 80% or more.

The compounds of the present invention: Nos. 1-001, 1-010, 1-011, 1-013, 1-015, 1-022, 1-042, 1-047, 1-054, 1-056, 1-092, 1-100, 1-102, 1-113, 1-122, 1-125, 1-128, 1-137, 1-142, 1-149, 1-155, 1-156, 1-172, 1-206, 1-209, 2-001, 2-003, 2-004, 2-012, 2-014, 2-018, 2-019, 2-021 to 2-023, 2-025, 2-027 to 2-029, and 2-031.

Test Example 4

Mortality Test for *Homona magnanima*

A 10% emulsifiable concentrate of the compound of the present invention (depending on the type of the compound, a 10% wettable powder was subjected to the test) was diluted with water containing a spreader to prepare a drug solution in a concentration of 100 ppm. In this drug solution, a leaf of cabbage was immersed for about 10 seconds and was air-dried and then put into a petri dish. In the petri dish, five 2 instar larvae of *Homona magnanima* per petri dish were released and the petri dish was capped and stored in a thermostatic room of 25° C. The number of killed larvae after 6 days was measured and the mortality was calculated from the same calculation formula as that in Test Example 1. Here, the test was carried out on the duplicate samples.

As the results of the test, among the compounds subjected to the test, the following compounds exhibited the mortality of 80% or more.

The compounds of the present invention: Nos. 1-001, 1-002, 1-004, 1-005, 1-007, 1-008, 1-010 to 1-017, 1-019, 1-020, 1-022 to 1-027, 1-029, 1-031, 1-042, 1-043, 1-044, 1-047, 1-049, 1-051, 1-053 to 1-059, 1-062, 1-064 to 1-071, 1-074, 1-076, 1-078 to 1-080, 1-082 to 1-085, 1-087 to 1-090, 1-092, 1-094 to 1-100, 1-104, 1-106 to 1-108, 1-111, 1-113, 1-115 to 1-117, 1-120 to 1-122, 1-125 to 1-128, 1-131 to 1-133, 1-136, 1-137, 1-139 to 1-144, 1-147, 1-149, 1-151 to 1-156, 1-158, 1-161, 1-162, 1-164, 1-166 to 1-173, 1-176 to 1-179, 1-186, 1-191, 1-205 to 1-213, 1-215, 1-217, 1-218, 1-220, 1-222 to 1-227, 2-001, 2-002, 2-005, 2-010, 2-011, 2-016, 2-027, 2-030, and 3-001.

Test Example 5

Mortality Test for *Helicoverpa armigera*

A 10% emulsifiable concentrate of the compound of the present invention (depending on the type of the compound, a 10% wettable powder was subjected to the test) was diluted with water containing a spreader to prepare a drug solution in a concentration of 100 ppm. In this drug solution, a leaf of cabbage was immersed for about 10 seconds and was air-dried and then put into a petri dish. In the petri dish, one 2 instar larva of *Helicoverpa armigera* per petri dish was released and the petri dish was capped and stored in a thermostatic room of 25° C. The number of killed larvae after 6 days was measured and the mortality was calculated from the same calculation formula as that in Test Example 1. Here, the test was carried out on 12 duplicate samples.

As the results of the test, among the compounds subjected to the test, the following compounds exhibited the mortality of 80% or more.

The compounds of the present invention: Nos. 1-001 to 1-031, 1-033 to 1-040, 1-042 to 1-162, 1-164 to 1-189, 1-191 to 1-227, 1-229, 2-001 to 2-032, 3-001, and 4-001.

Test Example 6

Mortality Test for *Frankliniella occidentalis*

In a styrol cup having an inner diameter of 7 cm, a wet filtration paper was laid and on the paper, a leaf of kidney bean cut out so as to have the same diameter as the inner diameter of the cup was laid, followed by inoculating ten 1 instar larvae of *Frankliniella occidentalis* per leaf with the leaf. A 10% emulsifiable concentrate of the compound of the present invention (depending on the type of the compound, a 10% wettable powder was subjected to the test) was diluted with water containing a spreader to prepare a drug solution in a concentration of 500 ppm. The drug solution was sprayed using a rotary spray tower in an amount of 2.5 mL per styrol cup, and the cup was capped and stored in a thermostatic room of 25° C. The number of killed larvae after 2 days was measured and the mortality was calculated from the same calculation formula as that in Test Example 1. Here, the test was carried out on the duplicate samples.

As the results of the test, among the compounds subjected to the test, the following compounds exhibited the mortality of 80% or more.

The compounds of the present invention: Nos. 1-001, 1-002, 1-004, 1-005, 1-007, 1-008, 1-010, 1-011, 1-013, 1-014, 1-016, 1-019, 1-020, 1-022, 1-023, 1-025, 1-027, 1-029, 1-031, 1-033 to 1-035, 1-042, 1-045, 1-051, 1-053 to 1-059, 1-061 to 1-064, 1-066 to 1-068, 1-070, 1-071, 1-073, 1-075 to 1-080, 1-082 to 1-085, 1-087 to 1-089, 1-091 to 1-101, 1-104, 1-107, 1-108, 1-112 to 1-117, 1-119, 1-120, 1-122 to 1-127, 1-130, 1-133 to 1-137, 1-139 to 1-141, 1-143, 1-144, 1-146, 1-148 to 1-156, 1-158, 1-160, 1-164 to 1-170, 1-172, 1-173, 1-177 to 1-180, 1-182, 1-191 to 1-193, 1-196 to 1-199, 1-201, 1-203, 1-205 to 1-227, 2-001, 2-002, 2-004, 2-005, 2-006, 2-008, 2-011, 2-012, 2-015 to 2-017, 2-020, 2-027, 2-028, 2-030 to 2-032, and 3-001.

Test Example 7

Mortality Test for *Thrips palmi*

In a styrol cup having an inner diameter of 7 cm, a wet filtration paper was laid and on the paper, a leaf of kidney bean cut out so as to have the same diameter as the inner diameter of the cup was laid, followed by inoculating ten imagines of *Thrips palmi* per leaf with the leaf. A 10% emulsifiable concentrate of the compound of the present invention (depending on the type of the compound, a 10% wettable powder was subjected to the test) was diluted with water containing a spreader to prepare a drug solution in a concentration of 100 ppm. The drug solution was sprayed using a rotary spray tower in an amount of 2.5 mL per styrol cup, and the cup was capped and stored in a thermostatic room of 25° C. The number of killed imagines after 2 days was measured and the mortality was calculated from the same calculation formula as that in Test Example 1. Here, the test was carried out on the duplicate samples.

As the results of the test, among the compounds subjected to the test, the following compounds exhibited the mortality of 80% or more.

The compounds of the present invention: Nos. 1-001 to 1-008, 1-010 to 1-017, 1-019 to 1-029, 1-031, 1-033 to 1-039, 1-042 to 1-059, 1-062 to 1-102, 1-104 to 1-156, 1-158, 1-160 to 1-162, 1-164 to 1-173, 1-176 to 1-179, 1-182, 1-183, 1-185 to 1-189, 1-191 to 1-194, 1-196 to 1-199, 1-202 to 1-227, 2-001 to 2-032, and 3-001.

Test Example 8

Mortality Test for *Eysarcoris lewisi*

A 10% emulsifiable concentrate of the compound of the present invention (depending on the type of the compound, a 10% wettable powder was subjected to the test) was diluted with water containing a spreader to prepare a drug solution in a concentration of 500 ppm. In this drug solution, a leaf sheath of rice was immersed for about 10 seconds and was air-dried and then put into a test tube. In the test tube, five 1 instar larvae of *Eysarcoris lewisi* per test tube were released and the test tube was capped with a sponge and stored in a thermostatic room of 25° C. The number of killed larvae after 2 days was measured and the mortality was calculated from the same calculation formula as that in Test Example 1. Here, the test was carried out on the duplicate samples.

As the results of the test, among the compounds subjected to the test, the following compounds exhibited the mortality of 80% or more.

The compounds of the present invention: Nos. 1-002, 1-005, 1-012, and 1-020.

Test Example 9

Mortality Test for *Nilaparvata lugens*

A 10% emulsifiable concentrate of the compound of the present invention (depending on the type of the compound, a 10% wettable powder was subjected to the test) was diluted with water containing a spreader to prepare a drug solution in a concentration of 500 ppm. In this drug solution, a leaf sheath of rice was immersed for about 10 seconds and was air-dried and then put into a test tube. In the test tube, five 2 instar larvae of *Nilaparvata lugens* per test tube were released and the test tube was capped with a sponge and stored in a thermostatic room of 25° C. The number of killed larvae after 6 days was measured and the mortality was calculated from the same calculation formula as that in Test Example 1. Here, the test was carried out on the duplicate samples.

As the results of the test, among the compounds subjected to the test, the following compounds exhibited the mortality of 80% or more.

The compounds of the present invention: Nos. 1-001, 1-002, 1-005, 1-008*, 1-012, 1-015*, 1-016, 1-020, 1-023*, 1-024 to 1-026, 1-029, 1-031, 1-033, 1-035, 1-038, 1-054, 1-055, 1-057, 1-059, 1-062, 1-064 to 1-066, 1-068, 1-070, 1-072*, 1-073, 1-074, 1-076*, 1-078, 1-079*, 1-080, 1-081, 1-082*, 1-083 to 1-085, 1-088, 1-092, 1-094, 1-095, 1-099, 1-109*, 1-113, 1-115, 1-120, 1-122, 1-126, 1-133, 1-136*, 1-140, 1-141, 1-152, 1-154, 1-161, 1-162, 1-205, 1-207, 1-218, 1-222, 2-002, 2-005, 2-008, and 3-001.

Here, the mark "*" indicates that the mortality test was performed using a drug solution of 100 ppm concentration.

Test Example 10

Mortality Test for *Bemisia argentifolii*

In a styrol cup having an inner diameter of 7 cm, a wet filtration paper was laid and on the paper, a cut-out leaf of tomato on which *Bemisia argentifolii* laid eggs (10 eggs/leaf) was laid. A 10% emulsifiable concentrate of the compound of the present invention (depending on the type of the compound, a 10% wettable powder was subjected to the test) was diluted with water containing a spreader to prepare a drug solution in a concentration of 500 ppm. The drug solution was sprayed using a rotary spray tower in an amount of 2.5 mL per styrol cup, and the cup was capped and stored in a thermostatic room of 25° C. The number of killed larvae after 6 days was measured and the mortality was calculated from the same calculation formula as that in Test Example 1. Here, the test was carried out on the duplicate samples.

As the results of the test, among the compounds subjected to the test, the following compounds exhibited the mortality of 80% or more.
The compounds of the present invention: Nos. 1-002, 1-005, 1-011, 1-020, 1-025, 1-027, 1-031, 1-034, 1-036, 1-051, 1-055, 1-057, 1-063, 1-068, 1-070, 1-075, 1-077 to 1-079, 1-082, 1-083, 1-091 to 1-095, 1-099, 1-107, 1-113, 1-115, 1-119, 1-120, 1-126, 1-134 to 1-137, 1-139 to 1-141, 1-148, 1-150 to 1-154, 1-165, 1-166, 1-191, 1-197, 1-208, 1-210, 1-221, 1-224, 1-227, 2-002, 2-005, and 3-001.

Test Example 11

Mortality Test for *Myzus persicae*

In a glass petri dish having an inner diameter of 3 cm, a wet absorbent cotton was laid and on the cotton, a leaf of cabbage cut out so as to have the same diameter as the inner diameter of the petri dish was laid, followed by releasing four apterous imagines of *Myzus persicae* on the leaf. After one day, a 10% emulsifiable concentrate of the compound of the present invention (depending on the type of the compound, a 10% wettable powder was subjected to the test) was diluted with water containing a spreader to prepare a drug solution in a concentration of 500 ppm. The drug solution was sprayed using a rotary spray tower (2.5 mg/cm$^2$), and the petri dish was capped and stored in a thermostatic room of 25° C. The number of killed imagines after 6 days was measured and the mortality was calculated from the same calculation formula as that in Test Example 1. Here, the test was carried out on the duplicate samples.

As the results of the test, among the compounds subjected to the test, the following compounds exhibited the mortality of 80% or more.
The compounds of the present invention: Nos. 1-001, 1-005, 1-015*, 1-016, 1-020, 1-024 to 1-026, 1-027*, 1-029, 1-031, 1-043*, 1-053, 1-055, 1-057, 1-058, 1-062, 1-064, 1-068, 1-069*, 1-070, 1-072*, 1-073, 1-074, 1-075*, 1-076, 1-078, 1-079*, 1-080, 1-083 to 1-085, 1-088, 1-092, 1-094, 1-095*, 1-097, 1-099, 1-106*, 1-107, 1-113, 1-115, 1-119*, 1-120, 1-122, 1-126, 1-128*, 1-131*, 1-132 to 1-134, 1-135*, 1-138, 1-140, 1-141, 1-144, 1-150*, 1-152, 1-154, 1-156, 1-158, 1-165% 1-178, 1-182, 1-191, 1-193, 1-197, 1-205, 1-213, 1-216*, 1-218, 1-219*, 1-220*, 1-221, 1-224, 1-225, 2-002, 2-005, 2-008, 2-011, 2-012, 2-016, 2-017, 2-019*, 2-020, 2-027, 2-028, 2-030, and 3-001.
Here, the mark "*" indicates that the mortality test was performed using a drug solution of 100 ppm concentration.

Test Example 12

Mortality Test for *Planococcus kraunhiae*

In a styrol cup having an inner diameter of 7 cm, a wet filtration paper was laid and on the paper, a leaf of kidney bean cut out so as to have the same diameter as the inner diameter of the cup was laid, followed by inoculating ten 1 instar larvae of *Planococcus kraunhiae* per leaf with the leaf. A 10% emulsifiable concentrate of the compound of the present invention (depending on the type of the compound, a 10% wettable powder was subjected to the test) was diluted with water containing a spreader to prepare a drug solution in a concentration of 500 ppm. The drug solution was sprayed using a rotary spray tower in an amount of 2.5 mL per styrol cup, and the cup was capped and stored in a thermostatic room of 25° C. The number of killed larvae after 6 days was measured and the mortality was calculated from the same calculation formula as that in Test Example 1. Here, the test was carried out on the duplicate samples.

As the results of the test, among the compounds subjected to the test, the following compounds exhibited the mortality of 80% or more.
The compounds of the present invention: Nos. 1-005 and 1-020.

Test Example 13

Mortality Test for *Aulacophora femoralis*

A 10% emulsifiable concentrate of the compound of the present invention (depending on the type of the compound, a 10% wettable powder was subjected to the test) was diluted with water containing a spreader to prepare a drug solution in a concentration of 500 ppm. In this drug solution, a leaf of cucumber was immersed for about 10 seconds and was air-dried and then put into a petri dish. In the petri dish, five 2 instar larvae of *Aulacophora femoralis* per petri dish were released and the petri dish was capped and stored in a thermostatic room of 25° C. The number of killed larvae after 6 days was measured and the mortality was calculated from the same calculation formula as that in Test Example 1. Here, the test was carried out on the duplicate samples.

As the results of the test, among the compounds subjected to the test, the following compounds exhibited the mortality of 80% or more.
The compounds of the present invention: Nos. 1-002, 1-005, 1-012, and 1-020.

Test Example 14

Mortality Test for *Liriomyza trifolii*

A 10% emulsifiable concentrate of the compound of the present invention (depending on the type of the compound, a 10% wettable powder was subjected to the test) was diluted with water containing a spreader to prepare a drug solution in a concentration of 500 ppm. In this drug solution, a leaf of kidney bean which was cut out to a diameter of 7 cm, on which *Liriomyza trifolii* laid eggs (10 eggs/leaf) was immersed for about 10 seconds and was air-dried and then laid on a wet filtration paper laid in a styrol cup having an inner diameter of 7 cm. The styrol cup was capped and stored in a thermostatic room of 25° C. The number of killed larvae after 6 days was measured and the mortality was calculated from the same calculation formula as that in Test Example 1. Here, the test was carried out on the duplicate samples.

As the results of the test, among the compounds subjected to the test, the following compounds exhibited the mortality of 80% or more.
The compounds of the present invention: Nos. 1-005, 1-011, 1-020, 1-025, 1-027, 1-051, 1-063, 1-070, 1-075, 1-076, 1-078, 1-082, 1-083, 1-085, 1-088, 1-091 to 1-096, 1-098, 1-113, 1-115, 1-116, 1-119, 1-122, 1-126, 1-133, 1-135 to 1-137, 1-139, 1-141, 1-144, 1-146, 1-148, 1-150 to 1-154, 1-156, 1-160, 1-165, 1-166, 1-173, 1-191, 1-193, 1-197, 1-199, 1-210, 1-211, 1-220, 1-221, 1-223, 1-224, 1-227, 2-005, and 3-001.

Test Example 15

Mortality Test for *Tetranychus urticae*

In a styrol cup having an inner diameter of 7 cm, a wet filtration paper was laid and on the paper, a leaf of kidney bean cut out so as to have the same diameter as the inner diameter of the cup was laid, followed by inoculating ten larvae of *Tetranychus urticae* per leaf with the leaf. A 10% emulsifiable concentrate of the compound of the present invention (depending on the type of the compound, a 10% wettable powder was subjected to the test) was diluted with water containing a spreader to prepare a drug solution in a concentration of 500 ppm. The drug solution was sprayed using a rotary spray tower in an amount of 2.5 mL per styrol cup, and the cup was capped and stored in a thermostatic room of 25° C. The number of killed larvae after 6 days was measured and the mortality was calculated from the same calculation formula as that in Test Example 1. Here, the test was carried out on the duplicate samples.

As the results of the test, among the compounds subjected to the test, the following compounds exhibited the mortality of 80% or more.

The compounds of the present invention: Nos. 1-001, 1-002, 1-003*, 1-005, 1-008, 1-010, 1-012, 1-014, 1-015, 1-016, 1-017, 1-018*, 1-019, 1-020, 1-023, 1-024 to 1-026, 1-027*, 1-028, 1-029, 1-031, 1-033 to 1-036, 1-038, 1-039, 1-042, 1-043*, 1-045*, 1-047, 1-049, 1-051*, 1-053 to 1-055, 1-057 to 1-059, 1-061, 1-062, 1-063*, 1-064 to 1-066, 1-067*, 1-068, 1-070, 1-071, 1-072*, 1-073, 1-075*, 1-076 to 1-078, 1-079*, 1-080**, 1-082*, 1-083 to 1-085, 1-088, 1-089, 1-091*, 1-092 to 1-095, 1-096*, 1-097**, 1-098*, 1-099, 1-100*, 1-101*, 1-107, 1-108, 1-109*, 1-110, 1-112 to 1-115, 1-116*, 1-117*, 1-119*, 1-120, 1-121**, 1-122, 1-123*, 1-125*, 1-126, 1-130*, 1-131*, 1-133, 1-134, 1-135*, 1-136*, 1-137*, 1-139*, 1-140, 1-141, 1-142*, 1-143*, 1-144, 1-146*, 1-148, 1-150*, 1-151*, 1-152, 1-153*, 1-154, 1-156, 1-158, 1-160*, 1-162, 1-165*, 1-166*, 1-167*, 1-168*, 1-169, 1-170, 1-171, 1-172, 1-173, 1-176 to 1-180, 1-182, 1-183, 1-191 to 1-194, 1-196 to 1-199, 1-201, 1-203*, 1-204, 1-205, 1-208*, 1-209, 1-210*, 1-211*, 1-212*, 1-213, 1-215, 1-216*, 1-217*, 1-218, 1-219*, 1-220*, 1-221, 1-222, 1-223*, 1-224, 1-225, 1-226*, 1-227, 2-002, 2-005, 2-006, 2-011, 2-012, 2-015, 2-016, 2-027, 2-028, 2-030 to 2-032, and 3-001.

Here, the mark "*" indicates that the mortality test was performed using a drug solution of 100 ppm concentration and the mark "**" indicates that the mortality test was performed using a drug solution of 10 ppm concentration.

Test Example 16

Mortality Test for *Aculops pelekassi*

In a styrol cup having an inner diameter of 7 cm, a wet filtration paper was laid and on the paper, a leaf of mandarin orange cut out so as to have the same diameter as the inner diameter of the cup was laid, followed by inoculating ten larvae of *Aculops pelekassi* per leaf with the leaf. A 10% emulsifiable concentrate of the compound of the present invention (depending on the type of the compound, a 10% wettable powder was subjected to the test) was diluted with water containing a spreader to prepare a drug solution in a concentration of 100 ppm. The drug solution was sprayed using a rotary spray tower in an amount of 2.5 mL per styrol cup, and the cup was capped and stored in a thermostatic room of 25° C. The number of killed larvae after 6 days was measured and the mortality was calculated from the same calculation formula as that in Test Example 1. Here, the test was carried out on the duplicate samples.

As the results of the test, among the compounds subjected to the test, the following compounds exhibited the mortality of 80% or more.

The compounds of the present invention: Nos. 1-002, 1-004, 1-005, 1-007, 1-008, 1-010, 1-011, 1-013, 1-014, 1-019, 1-020 to 1-023, 1-043, 1-046 to 1-048, 1-052, 1-054 to 1-058, 1-100, 1-102, 1-113, 1-122, 1-128, 1-142, 1-144, 1-149, 1-152, 1-154 to 1-157, 1-162, 1-164, 1-170, 1-178, 1-186, 1-206, 1-209, 1-215, 2-001, 2-025, 2-027, and 3-001.

Test Example 17

Mortality Test for *Polyphagotarsonemus latus*

In a styrol cup having an inner diameter of 7 cm, a wet filtration paper was laid and on the paper, a leaf of kidney bean cut out so as to have the same diameter as the inner diameter of the cup was laid, followed by inoculating ten imagines of *Polyphagotarsonemus latus* per leaf with the leaf. A 10% emulsifiable concentrate of the compound of the present invention (depending on the type of the compound, a 10% wettable powder was subjected to the test) was diluted with water containing a spreader to prepare a drug solution in a concentration of 100 ppm. The drug solution was sprayed using a rotary spray tower in an amount of 2.5 mL per styrol cup, and the cup was capped and stored in a thermostatic room of 25° C. The number of killed imagines after 2 days was measured and the mortality was calculated from the same calculation formula as that in Test Example 1. Here, the test was carried out on the duplicate samples.

As the results of the test, among the compounds subjected to the test, the following compounds exhibited the mortality of 80% or more.

The compounds of the present invention: Nos. 1-005, 1-006, 1-008, 1-010, 1-011, 1-013, 1-015, 1-019, 1-020 to 1-023, 1-046, 1-047, 1-056, 1-057, 1-100, 1-108, 1-117, 1-122, 1-125, 1-137, 1-142, 1-149, 1-152, 1-154, 1-156, 1-162, and 1-170.

Test Example 18

Mortality Test for Cat Flea

To the bottom surface and the side surface of a petri dish having an inner diameter of 5.3 cm, 400 μL of an acetone solution in which 4 mg of the compound of the present invention was dissolved in 40 mL of acetone (concentration: 100 ppm) was applied and then acetone was volatilized to form a thin film of the compound of the present invention on the inner wall of the petri dish. The inner wall of the used petri dish had an area of 40 cm$^2$, so that the amount of the applied drug became 1.0 μg/cm$^2$. In the petri dish, ten *Ctenocephalides felis* imagines (male and female were mixed) were released and the petri dish was capped and stored in a thermostat room of 25° C. The number of killed imagines after 4 days was measured and the mortality was calculated from the same calculation formula as that in Test Example 1. Here, the test was carried out on the single sample.

As the results of the test, among the compounds subjected to the test, the following compounds exhibited the mortality of 80% or more.

The compounds of the present invention: Nos. 1-072, 1-081, 1-085, 1-109, 1-118, 1-138, 1-142, 1-152, 1-206, 2-006, 2-007, 2-011, 2-017, 2-027, and 2-028.

Test Example 19

Mortality Test for American Dog Tick

To the bottom surface and the side surface of two petri dishes having an inner diameter of 5.3 cm, 400 μL of an acetone solution in which 4 mg of the compound of the present invention was dissolved in 40 mL of acetone (concentration: 100 ppm) was applied and then acetone was volatilized to form a thin film of the compound of the present invention on the inner wall of the petri dishes. The inner wall of each of the used petri dishes had an area of 40 cm², so that the amount of the applied drug became 0.1 μg/cm². In one of the petri dishes, ten American dog tick (*Dermacentor variabilis*) protonymphs (male and female were mixed) were released, and the petri dish was capped with the other petri dish. The seam of the two petri dishes was sealed with tape so that the protonymphs did not escape, and the petri dishes were stored in a thermostat room of 25° C. The number of killed protonymphs after 4 days was measured and the mortality was calculated from the same calculation formula as that in Test Example 1. Here, the test was carried out on the single sample.

As the results of the test, among the compounds subjected to the test, the following compounds exhibited the mortality of 80% or more.

The compounds of the present invention: Nos. 1-011, 1-072, 1-081, 1-085, 1-109, 1-117, 1-118, 1-122, 1-138, 1-142, 1-152, 1-191, 1-206, 1-209, 2-006, 2-007, 2-016, 2-017, 2-027, and 2-030 to 2-032.

Test Example 20

Mortality Test for *Helicoverpa armigera*
(Comparative Test)

10% emulsifiable concentrates of the compound of the present invention and a comparative compound were diluted with water containing a spreader to prepare drug solutions in a predetermined concentration. In each of the drug solutions, a leaf of cabbage was immersed for about 10 seconds and was air-dried and put into a petri dish. In the petri dish, seven 3 instar larvae of *Helicoverpa armigera* per petri dish were released and the petri dish was capped with a lid having a pore and stored in a thermostat room of 25° C. After 2 days of the treatment, an artificial fertilizer (1 cm³) was added into the petri dish. The number of killed larvae after 6 days was measured and the mortality was calculated from the calculation formula:

Mortality (%)=(number of killed insect/number of released insect)×100.

Here, the test was carried out on the duplicate samples.

The mortality of each compound subjected to the test at predetermined concentrations is shown in Table 8.

TABLE 8

| Compound subjected to test | Concentrations (ppm) | | | | | | |
|---|---|---|---|---|---|---|---|
| | 33 | 10 | 3 | 1 | 0.3 | 0.1 | 0.03 |
| Compound of present invention No. 1-011 | | | | 100 | 100 | 71.4 | 64.3 |
| Comparative compound A | 100 | 92.9 | 57.1 | 0 | | | |

Comparative compound A: International Patent Application Publication No. WO 2007/105814 specification, Compound No. 2-069

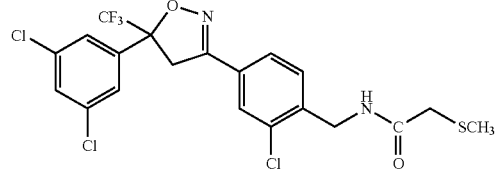

INDUSTRIAL APPLICABILITY

The substituted isoxazoline compound according to the present invention is an extremely useful compound exhibiting excellent pest control activity, particularly excellent insecticidal and miticidal activity and having substantially no adverse effect on non-target organisms such as mammals, fish and beneficial insects.

The invention claimed is:
1. A substituted isoxazoline compound of General Formula (1):

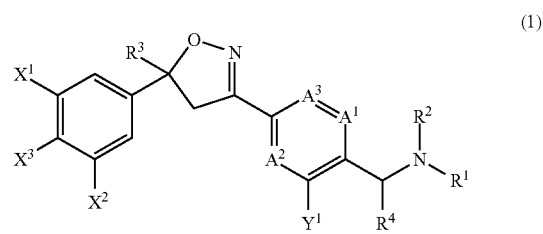

(1)

where $A^1$, $A^2$ and $A^3$ independently are $C-Y^2$, $X^1$ is a halogen atom, $-SF_5$, $C_{1-6}$ haloalkyl, hydroxy $(C_{1-4})$haloalkyl, $C_{1-4}$ alkoxy$(C_{1-4})$haloalkyl, $C_{1-6}$ haloalkoxy, $C_{1-4}$ haloalkoxy$(C_{1-4})$haloalkoxy or $C_{1-6}$ haloalkylthio, $X^2$ is a hydrogen atom, a halogen atom, cyano, nitro, $C_{1-6}$ alkyl, $C_{1-6}$ haloalkyl, $-OR^5$ or $-S(O)_rR^5$, $X^3$ is a hydrogen atom, a halogen atom, $C_{1-6}$ haloalkoxy or $-NH_2$, or $X^3$ together with $X^1$ or $X^2$ optionally forms $-CF_2OCF_2-$, $-OCF_2O-$, $-CF_2OCF_2O-$ or $-OCF_2CF_2O-$ to form together with a carbon atom to which each of $X^3$ and $X^1$ or $X^2$ is bonded, a 5- or 6-membered ring, with the proviso that when $X^1$ and $X^2$ are simultaneously a chlorine atom, $X^3$ is a halogen atom, $C_{1-6}$ haloalkoxy or $-NH_2$, $Y^1$ is a hydrogen atom, a halogen atom, cyano, nitro, $C_{1-6}$ alkyl, $C_{1-6}$ haloalkyl, $(C_{1-4})$alkyl substituted with $R^6$, $C_{2-6}$ alkenyl, $C_{2-6}$ alkynyl, $-OR^5$, $-S(O)_rR^5$, $-N(R^8)R^7$, $-C(S)NH_2$, D-1 to D-4, D-8 or D-10, $Y^2$ is a hydrogen atom, a halogen atom or methyl and further, when two $Y^2$s are adjacent to each other, the two $Y^2$s adjacent to each other optionally form $-CH_2CH_2CH_2-$, $-CH_2CH_2O-$, $-CH_2OCH_2-$, $-OCH_2O-$, $-CH_2CH_2S-$, $-CH_2SCH_2-$, $-SCH_2S-$, $-CH_2CH_2CH_2CH_2-$, $-CH_2CH_2CH_2O-$, $-CH_2CH_2OCH_2-$, $-CH_2OCH_2O-$, $-OCH_2CH_2O-$, $-OCH_2CH_2S-$, $-SCH_2CH_2S-$, $-OCH=N-$, $-SCH=N-$, $-CH=CHCH=CH-$, $-CH=CHCH=N-$, $-CH=CHN=CH-$, $-CH=NCH=CH-$ or $-N=CHCH=CH-$ to form together with carbon atoms to which each of the two $Y^2$s is bonded, a 5-membered ring or a 6-membered ring, $R^1$ is $-C(O)R^{1a}$ or $-C(S)R^{1a}$, $R^{1a}$ is $-C(R^9)(R^{9a})-S(O)_r-R^{10}$, $-C(R^9)(R^{9a})-S(O)_t(R^{10})=NR^{11}$ or E-1 to E-6, where E-1 to E-6 individually are a sulfur-containing saturated heterocycle of Structural Formulae:

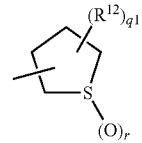

E-1

-continued

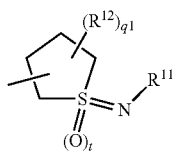
E-2

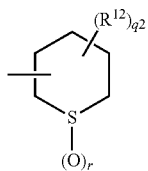
E-3

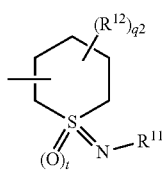
E-4

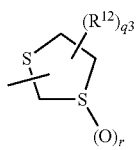
E-5

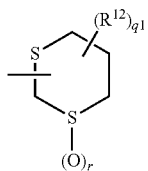
E-6

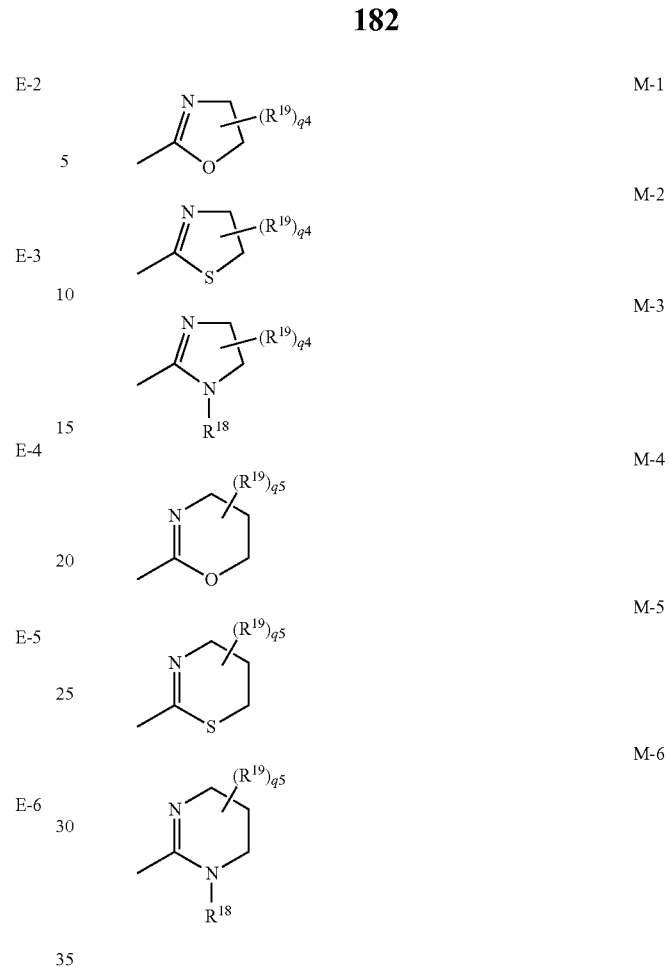

$R^2$ is a hydrogen atom, cyano, $C_{1-6}$ alkyl, $(C_{1-4})$alkyl optionally substituted with $R^{13}$, $C_{3-6}$ cycloalkyl, $C_{3-6}$ alkenyl, $C_{3-6}$ alkynyl, $C_{1-6}$ alkylcarbonyl, $C_{1-6}$ alkoxycarbonyl or $C_{1-6}$ alkoxy, $R^3$ is $C_{1-6}$ haloalkyl or $C_{3-8}$ halocycloalkyl, $R^4$ is a hydrogen atom, cyano, $C_{1-6}$ alkyl, $C_{1-6}$ haloalkyl, $C_{3-6}$ cycloalkyl, $C_{2-6}$ alkynyl, —C(O)NH$_2$, —C(S)NH$_2$, phenyl, D-6 or D-7, $R^5$ is $C_{1-6}$ alkyl or $C_{1-6}$ haloalkyl, $R^6$ is —OH, $C_{1-4}$ alkoxy, $C_{1-4}$ alkylthio, $C_{1-4}$ alkylsulfinyl or $C_{1-4}$ alkylsulfonyl, $R^7$ is a hydrogen atom, $C_{1-6}$ alkyl, —CHO, $C_{1-6}$ alkylcarbonyl or $C_{1-6}$ alkoxycarbonyl, $R^8$ is a hydrogen atom or $C_{1-6}$ alkyl, $R^9$ is a hydrogen atom, a halogen atom, $C_{1-6}$ alkyl, $C_{1-6}$ alkoxy, $C_{1-6}$ alkylthio, $C_{1-6}$ alkylsulfinyl or $C_{1-6}$ alkylsulfonyl, $R^{9a}$ is a hydrogen atom, a halogen atom or $C_{1-6}$ alkyl, or $R^{9a}$ together with $R^9$ optionally forms an ethylene chain to form together with an atom to which $R^9$ and $R^{9a}$ are bonded, a cyclopropyl ring, $R^{10}$ is cyano, $C_{1-6}$ alkyl, $(C_{1-4})$alkyl optionally substituted with $R^{14}$, $C_{3-6}$ cycloalkyl, $C_{2-6}$ alkenyl, $C_{2-6}$ haloalkenyl, $C_{2-6}$ alkynyl, $C_{2-6}$ haloalkynyl, —C(O)R$^{15}$, —C(O)OR$^{16}$, —C(O)SR$^{16}$, —C(O)N(R$^{17}$)R$^{16}$, —C(S)R$^{15}$, —C(S)OR$^{16}$, —C(S)SR$^{16}$, —C(S)N(R$^{17}$)R$^{16}$, M-1 to M-6, phenyl, D-6, D-7, D-9, D-11 or D-12 to D-14, where M-1 to M-6 individually are a partially saturated heterocycle of Structural Formulae:

$R^{11}$ is a hydrogen atom, cyano, nitro, $C_{1-6}$ alkyl, $C_{1-6}$ haloalkyl, $C_{1-6}$ alkylcarbonyl, $C_{1-6}$ haloalkylcarbonyl, $C_{1-6}$ alkoxycarbonyl, $C_{1-6}$ haloalkoxycarbonyl, $C_{1-6}$ alkylsulfonyl or $C_{1-6}$ haloalkylsulfonyl, $R^{12}$ is a fluorine atom, nitro, —OH, $C_{1-4}$ alkyl or $C_{1-4}$ haloalkyl, $R^{13}$ is a halogen atom, cyano, $C_{3-6}$ cycloalkyl, —OR$^{20}$, —S(O)$_r$R$^{21}$, —N(R$^{23}$)R$^{22}$, —C(O)R$^{24}$, —C(O)OR$^{25}$, —C(O)SR$^{25}$, —C(O)NH$_2$, —C(O)N(R$^{26}$)R$^{25}$, —C(S)OR$^{25}$, —C(S)SR$^{25}$, —C(S)NH$_2$, —C(S)N(R$^{26}$)R$^{25}$ or phenyl, $R^{14}$ is a halogen atom, cyano, $C_{3-6}$ cycloalkyl, —OR$^{20}$, —S(O)$_r$R$^{21}$, —C(O)R$^{24}$, —C(O)OR$^{25}$, —C(O)NH$_2$, —C(O)N(R$^{26}$)R$^{25}$, —C(S)NH$_2$, phenyl or D-11, $R^{15}$ is $C_{1-6}$ alkyl, $C_{1-6}$ haloalkyl, $C_{3-6}$ cycloalkyl, phenyl, phenyl substituted with $(Z)_{p1}$, D-1, D-2, D-4, D-5, D-7, D-8, D-10 or D-11, where D-1 to D-14 individually are an aromatic heterocycle of Structural Formulae:

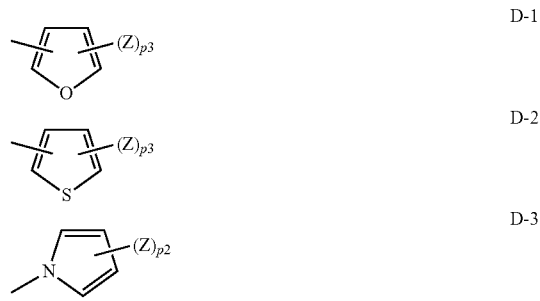

-continued

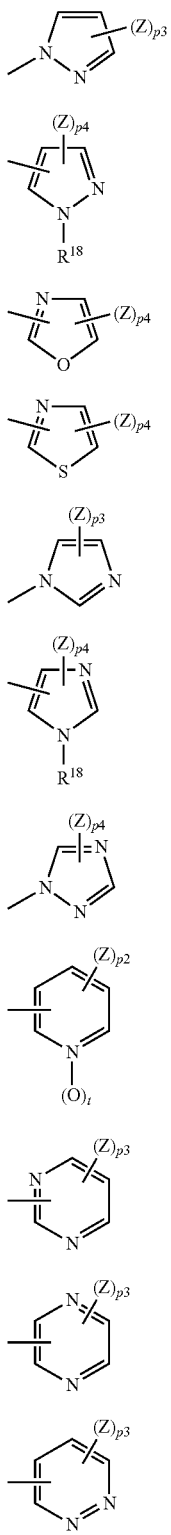

Z is a halogen atom, cyano, nitro, $C_{1-6}$ alkyl, $C_{1-6}$ haloalkyl, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, $C_{1-4}$ haloalkylthio, $C_{1-4}$ haloalkylsulfinyl or $C_{1-4}$ haloalkylsulfonyl, where when p1 and p2 are an integer of 2 or more, Zs are optionally the same as or different from each other, $R^{16}$ is $C_{1-6}$ alkyl or $C_{1-6}$ haloalkyl,
$R^{17}$ is a hydrogen atom or $C_{1-6}$ alkyl, or $R^{17}$ together with $R^{16}$ optionally forms a $C_{3-5}$ alkylene chain to form together with a nitrogen atom to which $R^{16}$ and $R^{17}$ are bonded, a 4- to 6-membered ring, and at this time, the alkylene chain optionally contains one oxygen atom, sulfur atom or nitrogen atom and is optionally substituted with a $C_{1-4}$ alkyl group, a —CHO group, a $C_{1-4}$ alkylcarbonyl group, a $C_{1-4}$ alkoxycarbonyl group or an oxo group,
$R^{18}$ is a hydrogen atom, $C_{1-4}$ alkyl or $C_{1-4}$ haloalkyl,
$R^{19}$ is a fluorine atom, $C_{1-4}$ alkyl or $C_{1-4}$ haloalkyl,
$R^{20}$ is $C_{1-4}$ alkyl, $C_{1-4}$ haloalkyl, —C(O)$R^{27}$ or —C(O)OR$^{28}$,
$R^{21}$ is $C_{1-4}$ alkyl or $C_{1-4}$ haloalkyl,
$R^{22}$ is $C_{1-4}$ alkyl, —C(O)$R^{27}$ or —C(O)OR$^{28}$,
$R^{23}$ is a hydrogen atom or $C_{1-4}$ alkyl,
$R^{24}$ is $C_{1-4}$ alkyl or $C_{1-4}$ haloalkyl,
$R^{25}$ is $C_{1-4}$ alkyl, $C_{1-4}$ haloalkyl or $C_{3-6}$ cycloalkyl,
$R^{26}$ is a hydrogen atom or $C_{1-4}$ alkyl, or $R^{26}$ together with $R^{25}$ optionally forms a $C_{3-5}$ alkylene chain to form together with a nitrogen atom to which $R^{25}$ and $R^{26}$ are bonded, a 4- to 6-membered ring, and at this time, the alkylene chain optionally contains one oxygen atom, sulfur atom or nitrogen atom and is optionally substituted with a $C_{1-4}$ alkyl group, a —CHO group, a $C_{1-4}$ alkylcarbonyl group, a $C_{1-4}$ alkoxycarbonyl group or an oxo group,
$R^{27}$ is $C_{1-4}$ alkyl, $C_{1-4}$ haloalkyl, $C_{3-6}$ cycloalkyl, phenyl, phenyl substituted with $(Z)_{p1}$, D-1, D-2, D-5, D-7 or D-11,
$R^{28}$ is $C_{1-4}$ alkyl or $C_{1-4}$ haloalkyl,
p1 is an integer of 1 to 3,
p2 is an integer of 0 to 2,
p3 and p4 are an integer of 0 or 1,
q1 is an integer of 0 to 7,
q2 is an integer of 0 to 9,
q3 is an integer of 0 to 5,
q4 and q5 are an integer of 0 to 2,
r is an integer of 0 to 2, and
t is an integer of 0 or 1; or
a salt of the substituted isoxazoline compound.

2. The substituted isoxazoline compound or the salt of the substituted isoxazoline compound according to claim 1, wherein
$A^1$ is CH,
$A^2$ and $A^3$ are CH,
$X^1$ is a halogen atom, —SF$_5$, $C_{1-4}$ haloalkyl, $C_{1-4}$ haloalkoxy or $C_{1-4}$ haloalkylthio,
$X^2$ is a hydrogen atom, a halogen atom, cyano, nitro, $C_{1-4}$ alkyl, $C_{1-4}$ haloalkyl, $C_{1-4}$ alkoxy, $C_{1-4}$ haloalkoxy, $C_{1-4}$ alkylthio or $C_{1-4}$ haloalkylthio,
$X^3$ is a hydrogen atom, a halogen atom or $C_{1-4}$ haloalkoxy, with the proviso that when $X^1$ and $X^2$ are simultaneously a chlorine atom, $X^3$ is a halogen atom or $C_{1-4}$ haloalkoxy,
$Y^1$ is a hydrogen atom, a halogen atom, cyano, nitro, $C_{1-4}$ alkyl, $C_{1-4}$ haloalkyl, $C_{2-4}$ alkynyl, $C_{1-4}$ alkoxy, $C_{1-4}$ haloalkoxy, $C_{1-4}$ alkylthio, $C_{1-4}$ haloalkylthio or —C(S)NH$_2$,
$R^{1a}$ is —C($R^9$)($R^{9a}$)—S(O)$_r$—$R^{10}$, —C($R^9$)($R^{9a}$)—S(O)$_t$($R^{10}$)=NR$^{11}$, E-1 to E-3 or E-5,
$R^2$ is a hydrogen atom, $C_{1-4}$ alkyl, $C_{1-4}$ haloalkyl, ($C_{1-2}$) alkyl substituted with $R^{13}$, $C_{3-4}$ alkenyl, $C_{3-4}$ alkynyl or $C_{1-4}$ alkoxy,
$R^3$ is $C_{1-4}$ haloalkyl,
$R^4$ is a hydrogen atom, cyano, $C_{1-2}$ alkyl, $C_{1-2}$ haloalkyl, ethynyl, —C(S)NH$_2$ or D-7, $R^9$ is a hydrogen atom, a fluorine atom, $C_{1-4}$ alkyl, $C_{1-4}$ alkoxy, $C_{1-4}$ alkylthio or $C_{1-4}$ alkylsulfinyl, $R^{9a}$ is a hydrogen atom, a fluorine atom or methyl, $R^{10}$ is $C_{1-4}$ alkyl, $C_{1-4}$ haloalkyl, $(C_{1-2})$alkyl substituted with $R^{14}$, $(C_{1-2})$ haloalkyl substituted with $R^{14}$, $C_{3-4}$ cycloalkyl, $C_{3-4}$ alkenyl, $C_{3-4}$ alkynyl, $-C(O)R^{15}$, $-C(O)OR^{16}$ or $-C(O)N(R^{17})R^{16}$, $R^{11}$ is a hydrogen atom, cyano or $C_{1-4}$ haloalkylcarbonyl, $R^{13}$ is cyano, $C_{3-4}$ cycloalkyl, $-OR^{20}$, $C_{1-2}$ alkylthio, $-N(R^{23})R^{22}$, $-C(O)OR^{25}$, $-C(O)NH_2$, $-C(O)N(R^{26})R^{25}$, $-C(S)NH_2$ or phenyl, $R^{14}$ is cyano or $-C(O)N(R^{26})R^{25}$, $R^{15}$ is $C_{1-4}$ alkyl, D-4, D-8 or D-10, $R^{16}$ is $C_{1-4}$ alkyl, $R^{17}$ is a hydrogen atom or $C_{1-4}$ alkyl, $R^{20}$ is $C_{1-2}$ alkyl or $C_{1-2}$ haloalkyl, $R^{22}$ is $C_{1-2}$ alkylcarbonyl or $C_{1-2}$ alkoxycarbonyl, $R^{23}$ is a hydrogen atom, $R^{25}$ is $C_{1-2}$ alkyl or $C_{1-2}$ haloalkyl, $R^{26}$ is a hydrogen atom or $C_{1-2}$ alkyl, p3 and p4 are 0, and q1, q2 and q3 are 0.

3. The substituted isoxazoline compound or the salt of the substituted isoxazoline compound according to claim 2, wherein $X^1$ is a halogen atom, $-SF_5$, $C_{1-2}$ haloalkyl, $C_{1-2}$ haloalkoxy or $C_{1-2}$ haloalkylthio, $X^2$ is a hydrogen atom, a halogen atom, cyano, $C_{1-2}$ haloalkyl, $C_{1-2}$ haloalkoxy or $C_{1-2}$ haloalkylthio, $X^3$ is a hydrogen atom, a halogen atom or $C_{1-2}$ haloalkoxy, with the proviso that when $X^1$ and $X^2$ are simultaneously a chlorine atom, $X^3$ is a halogen atom or $C_{1-2}$ haloalkoxy, $Y^1$ is a hydrogen atom, a halogen atom, cyano, nitro, $C_{1-2}$ alkyl, $C_{1-2}$ haloalkyl, $C_{1-2}$ haloalkoxy, $C_{1-2}$ haloalkylthio or $-C(S)NH_2$, $R^{1a}$ is $-C(R^9)(R^{9a})-S(O)_rR^{10}$, $-C(R^9)(R^{9a})-S(O)_r(R^{10})=NR^{11}$ or E-1, $R^2$ is a hydrogen atom, $C_{1-2}$ alkyl, methyl substituted with $R^{13}$, allyl or propargyl, $R^3$ is $C_{1-2}$ haloalkyl, $R^4$ is a hydrogen atom, cyano, methyl, ethynyl or $-C(S)NH_2$, $R^9$ is a hydrogen atom, a fluorine atom, $C_{1-2}$ alkyl, $C_{1-2}$ alkylthio or $C_{1-2}$ alkylsulfinyl, $R^{9a}$ is a hydrogen atom or a fluorine atom, $R^{10}$ is $C_{1-2}$ alkyl, $C_{1-2}$ haloalkyl or cyanomethyl, $R^{11}$ is a hydrogen atom or $C_{1-2}$ haloalkylcarbonyl, $R^{13}$ is cyano, cyclopropyl, $C_{1-2}$ alkoxy, $-C(O)OR^{25}$, $-C(O)NH_2$, $-C(O)N(R^{26})R^{25}$ or $-C(S)NH_2$, $R^{25}$ is $C_{1-2}$ alkyl, and $R^{26}$ is a hydrogen atom or methyl.

4. The substituted isoxazoline compound or the salt of the substituted isoxazoline compound according to claim 3, wherein $A^1$ is CH, $X^1$ is a chlorine atom, a bromine atom or trifluoromethyl, $X^2$ is a fluorine atom, a chlorine atom, a bromine atom, an iodine atom or trifluoromethyl, $X^3$ is a hydrogen atom, a fluorine atom or a chlorine atom, with the proviso that when $X^1$ and $X^2$ are simultaneously a chlorine atom, $X^3$ is a fluorine atom or a chlorine atom, $Y^1$ is a hydrogen atom, a halogen atom, nitro or methyl, $R^{1a}$ is $-C(R^9)(R^{9a})-S(O)_r-R^{10}$ or E-1, $R^2$ is a hydrogen atom, $C_{1-2}$ alkyl or propargyl, $R^3$ is trifluoromethyl or chlorodifluoromethyl, $R^4$ is a hydrogen atom or methyl, $R^9$ is a hydrogen atom, $C_{1-2}$ alkyl, $C_{1-2}$ alkylthio or $C_{1-2}$ alkylsulfinyl, $R^{9a}$ is a hydrogen atom, and $R^{10}$ is $C_{1-2}$ alkyl or $C_{1-2}$ haloalkyl.

5. The substituted isoxazoline compound or the salt of the substituted isoxazoline compound according to claim 4, wherein $Y^1$ is a halogen atom, $R^{1a}$ is $-CH(R^9)-S(O)_r-R^{10}$, $R^2$ is a hydrogen atom, $R^4$ is a hydrogen atom, $R^9$ is a hydrogen atom or $C_{1-2}$ alkylthio, and $R^{10}$ is $C_{1-2}$ alkyl.

6. A pest control agent comprising as active ingredient(s), one or two or more selected from the substituted isoxazoline compounds and the salts of the substituted isoxazoline compounds as claimed in claim 1.

7. An agricultural chemical comprising as active ingredient(s), one or two or more selected from the substituted isoxazoline compounds and the salts of the substituted isoxazoline compounds as claimed in claim 1.

8. A control agent against internal or external parasites of mammals or birds comprising as active ingredient(s), one or two or more selected from the substituted isoxazoline compounds and the salts of the substituted isoxazoline compounds as claimed in claim 1.

9. An insecticide or a miticide comprising as active ingredient(s), one or two or more selected from the substituted isoxazoline compounds and the salts of the substituted isoxazoline compounds as claimed in claim 1.

* * * * *